US007943340B2

(12) United States Patent
Monod et al.

(10) Patent No.: US 7,943,340 B2
(45) Date of Patent: *May 17, 2011

(54) FUNGAL DIPEPTIDYL PEPTIDASE IV (DPPIV) ENZYME FOR REAGENT USE

(75) Inventors: Michel Monod, Lausanne (CH); Reto Stocklin, Plan-les-Ouates (CH); Eric Grouzmann, La Conversion (CH)

(73) Assignee: Funzyme Biotechnologies SA, Plan-les-Ouates (CH)

(*) Notice: Subject to any disclaimer, the term of this patent is extended or adjusted under 35 U.S.C. 154(b) by 0 days.

This patent is subject to a terminal disclaimer.

(21) Appl. No.: 12/217,470

(22) Filed: Jul. 3, 2008

(65) Prior Publication Data

US 2009/0130737 A1 May 21, 2009

Related U.S. Application Data

(62) Division of application No. 10/569,908, filed as application No. PCT/IB2004/002963 on Aug. 25, 2004, now Pat. No. 7,468,267.

(60) Provisional application No. 60/498,318, filed on Aug. 25, 2003.

(51) Int. Cl.
*C12P 21/06* (2006.01)
(52) U.S. Cl. .................................................. 435/68.1
(58) Field of Classification Search .................... None
See application file for complete search history.

(56) References Cited

U.S. PATENT DOCUMENTS

| | | | |
|---|---|---|---|
| 4,522,811 A | 6/1985 | Eppstein et al. |
| 4,736,866 A | 4/1988 | Leder et al. |
| 4,855,231 A | 8/1989 | Stroman et al. |
| 4,857,467 A | 8/1989 | Sreekrishna et al. |
| 4,870,009 A | 9/1989 | Evans et al. |
| 4,873,191 A | 10/1989 | Wagner et al. |
| 4,879,231 A | 11/1989 | Stroman et al. |
| 4,929,555 A | 5/1990 | Cregg et al. |
| 5,328,470 A | 7/1994 | Nabel et al. |
| 5,603,793 A | 2/1997 | Yoshida et al. |
| 5,811,238 A | 9/1998 | Stemmer et al. |
| 5,830,721 A | 11/1998 | Stemmer et al. |
| 5,994,113 A | 11/1999 | Kauppinen et al. |
| 6,127,161 A | 10/2000 | Umitsuki et al. |
| 2005/0158298 A1 | 7/2005 | Monod et al. |

FOREIGN PATENT DOCUMENTS

| | | | |
|---|---|---|---|
| WO | 95/22625 A1 | 8/1995 |
| WO | 96/33207 A1 | 10/1996 |
| WO | 97/20078 A1 | 6/1997 |
| WO | 97/33957 A1 | 9/1997 |
| WO | 97/35966 A1 | 10/1997 |
| WO | 98/13485 A1 | 4/1998 |
| WO | 98/13487 A1 | 4/1998 |
| WO | 98/27230 A1 | 6/1998 |
| WO | 98/31837 A1 | 7/1998 |
| WO | 98/42832 A1 | 10/1998 |

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Brenda; definition of dipeptidyl-peptidase IV, downloaded Jun. 18, 2010.*
ExPASy Proteomics Server; definition of dipeptidyl-peptidase IV, downloaded Jun. 18, 2010.*
GenBank AC AAC34310, Beauvais, A. et al., "Dipeptidyl-peptidase IV secreted by *Aspergillus fumigatus*, a fungus pathogenic to humans," Infect. Immun., vol. 65(8):3042-3047 (Sep. 4, 1998).
GenBank AC CAA05343, Doumas, A. et al., "Characterisation of the prolyl dipeptidyl peptidase-encoding gene (dppIV) from the koji mould *Aspergillus oryzae*," (Mar. 2, 1998).
GenBank AC CAA33512, Roberts, C.J. et al., "Structure, biosynthesis, and localization of dipeptidyl aminopeptidase B, an integral membrane glycoprotein of the yeast vacuole," J. Cell Biol., vol. 108(4):1363-1373 (Feb. 17, 1997).
GenBank AC CAC41019, Jalving, R. et al., "Cloning of an *Aspergillus niger* vacuolar dipeptidyl peptidase," (Jun. 6, 2001).
GenBank AC NP_593970, Wood, V. et al., "The genome sequence of *Schizosaccharomyces pombe*," Nature, vol. 415 (6874):871-880 (Mar. 5, 2002).
Stemmer, Willem P.C., "DNA shuffling by random fragmentation and reassembly: In vitro recombination for molecular evolution," Proc. Natl. Acad. Sci. USA, vol. 91:10747-10751 (1994).
Stemmer, Willem P.C., "Rapid evolution of a protein in vitro by DNA shuffling," Nature, vol. 370:389-391 (1994).
Stoeckel, Angela et al., "Specific Inhibitors of Aminopeptidase P, Peptides and Pseudopeptides of 2-Hydroxy-3-Amino Acids," Cellular Peptidases in Immune Functions and Diseases, edited by Ansorge and Langner, Plenum Press, New York, Chapt. 5, pp. 31-35 (1997).
Stoecklin, Reto et al., "A new affinity tag-removal system (TRS) in protein expression and peptide synthesis," The First International Congress on Natural Peptides to Drugs (NP2D), pp. 98-99 (2004).
Stoecklin, Reto et al., "Creation of a Spin-off to Industrialise Novel Fungal Enzymes," retrieved online at: http://www.bioalps.ch/Bioalps/FHomePageBioalps.aspx?tokenPage=XDDC744ZODyQwaiuV89j9fFJMQ9nN_MtVGNkBVCVMm8%29%29 (2005).
Vader, Willemun et al., "The Gluten Response in Children With Celiac Disease Is Directed Toward Multiple Gliadin and Glutenin Peptides," Gastroenterology, vol. 122:1729-1737 (2002).
Vanbreuseghem, R. et al., "The Dermatophytia or Ringworms," Practical Guide to Medical and Veterinary Mycology, 2nd Edition, Masson Publishing USA, Inc., pp. 8-13, 81-150 and 242-249 (1978).
Villain, Matteo et al., "Covalent capture: a new tool for the purification of synthetic and recombinant polypeptides," Chemistry & Biology, vol. 8:673-679 (2001).

(Continued)

*Primary Examiner* — Sheridan Swope
(74) *Attorney, Agent, or Firm* — Nelson Mullins Riley & Scarborough LLP; Debra J. Milasincic

(57) ABSTRACT

Disclosed herein are fungal nucleic acid sequences that encode novel dipetidyl peptidase IV (DPPIV) polypeptides. Also disclosed are polypeptides encoded by these nucleic acid sequences, as well as derivatives, variants, mutants, or fragments of the aforementioned polypeptide, polynucleotide, or antibody. The aminopeptidase polypeptides, referred to herein as DPPIV proteins of the invention are useful in a variety of medical, research, and commercial applications.

18 Claims, 18 Drawing Sheets

OTHER PUBLICATIONS

Weitzman, Irene et al., "The Dermatophytes," Clinical Microbiology Reviews, vol. 8(2):240-259 (1995).

Woodfolk, Judith A. et al., "Trichophyton Antigens Associated with IgE Antibodies and Delayed Type Hypersensitivity," The Journal of Biological Chemistyr, vol. 273(45):29489-29496 (1998).

Yelton, M. Melanie et al., "Transformation of *Aspergillus nidulans* by using a trpC plasmid," Proc. Natl. Acad. Sci. USA, vol. 81:1470-1474 (1984).

Arentz-Hansen, Helene et al., "Celiac Lesion T Cells Recognize Epitopes That Cluster in Regions of Gliadins Rich in Proline Residues," Gastroenterology, vol. 123:803-809 (2002).

Arkin, Adam P. et al., "An algorithm for protein engineering: Stimulations of recursive ensemble mutagenesis," Proc. Natl. Acad. Sci. USA, vol. 89:7811-7815 (1992).

Ausubel, Frederick M., "Hybridization with Radioactive Probes," Current Protocols in Molecular Biology, vol. 1, Section II, John Wiley & Sons, N.Y., pp. 6.3.1-6.3.6 (1989).

Beauvais, Anne et al., "Biochemical and Antigenic Characterization of a New Dipeptidyl-Peptidase Isolated from *Aspergillus fumigatus*," The Journal of Biological Chemistry, vol. 272(10):6238-6244 (1997).

Beauvais, A. et al., "Dipeptidyl-Peptidase IV Secreted by *Aspergillus fumigatus*, a Fungus Pathogenic to Humans," Infection and Immunity, vol. 65(8):3042-3047 (1997).

Ben-Meir, Daniella et al., "Specificity of *Streptomyces griseus* aminopeptidase and modulation of activity by divalent metal ion binding and substitution," Eur. J. Biochem., vol. 212:107-112 (1993).

Borg-von Zepelin, M. et al., "The expression of the secreted aspartyl proteinases Sap4 to Sap6 from *Candida albicans* in murine macrophages," Molecular Microbiology, vol. 28(3):543-554 (1998).

Brouta, F. et al., "Purification and characterization of a 43-5 kDa keratinolytic metalloprotease from *Microsporum canis*," Medical Mycology, vol. 39:269-275 (2000).

Brouta, Frederic et al., "Secreted Metalloprotease Gene Family of *Microsporum canis*," Infection and Immunity, vol. 70 (10):5676-5683 (2002).

Chambers, Steve P. et al., "The pMTLnic-cloning vectors. I. Improved pUC polylinker revions to facilitate the use of sonicated DNA for nucleotide sequencing," Gene, vol. 68:139-149 (1988).

Chen, Shu-Hsia et al., "Gene therapy for brain tumors: Regression of experimental gliomas by adenovirus-mediated gene transfer in vivo," Proc. Natl. Acad. Sci. USA, vol. 91:3054-3057 (1994).

Crameri, Andreas et al., "Construction and evolution of antibody-phage libraries by DNA shuffling," Nature Medicine, vol. 2(1):100-103 (1996).

Danew, P. et al., "Untersuchungen zur Peptidaseaktivitat hautpathogener Pilze," mykosen, vol. 23(9):502-511 (1980).

De Bersaques, J. et al., "Proteolytic and Leucylnaphthlamidase Activity in some Dermatophytes," Archives Belges de Dermatologic, vol. 28(2):135-140 (1973).

Delagrave, Simon et al., "Recursive ensemble mutagenesis," Protein Engineering, vol. 6(3):327-331 (1993).

Descamps, Frederic et al., "Isolation of a *Microsporum canis* Gene Family Encoding Three Subtilisin-like Proteases Expressed in vivo," J. Invest. Dermatol., vol. 119:830-835 (2002).

Doumas, Agnes et al., "Characterization of the Prolyl Dipeptidyl Peptidase Gene (dppIV) from the Koji Mold *Aspergillus oryzae*," Applied and Environmental Microbiology, vol. 64(12):4809-4815 (1998).

Doumas, Agnes et al., "Cloning of the gene encoding neutral protease I of the koji mold *Aspergillus oryzae* and its expression in *Pichia pastoris*," J. Food Mycol., vol. 2(1):271-279 (1999).

Ellis, Keith J. et al., "Buffers of Constant Ionic Strength for Studying pH-Dependent Processes," Methods in Enzymology, vol. 87:405-426 (1982).

Greenblatt, H.M. et al., "*Streptomyces griseus* Aminopeptidase: X-ray Crystallographic Structure at 1.75 A Resolution," J. Mol. Biol., vol. 265:620-636 (1997).

Grossberger, Dario, "Minipreps of DNA from bacteriophage lambda," Nucleic Acids Research, vol. 15(16):6737 (1987).

Hasselgren, Catrin et al., "Metal ion binding and activation of *Streptomyces griseus* dinuclear aminopeptidase: cadmium(II) binding as a model," J. Biol. Inorg. Chem., vol. 6:120-127 (2001).

Hausch, Felix et al., "Intestinal digestive resistance of immunodominant gliadin peptides," Am. J. Phsiol. Gastrointest. Liver Physiol., vol. 283:G996-G1003 (2002).

Hauser, Melinda et al., "Multiplicity and regulation of genes encoding peptide transporters in *Saccharomyces cerevisiae*," Molecular Membrane Biology, vol. 18:105-112 (2001).

Ike, Yoshimasa et al., "Solid phase synthesis of polynucleotides. VII. Synthesis of mixed oligodeoxyribonucleotides by the phosphotriester solid phase method," Nucleic Acids Research, vol. 11(2):477-488 (1983).

Itakura, Keiichi et al., "Expression in *Escherichia coli* of a Chemically Synthesized Gene for the Hormone Somatostatin," Science, vol. 198:1056-1063 (1977).

Itakura, Keiichi et al., "Synthesis and Use of Synthetic Oligonucleotides," Ann. Rev. Biochem., vol. 53:323-356 (1984).

Kwon-Chung, K.J. et al., "Cryptococcosis, Torulosis, European blastomycosis, Busse-Buschke disease," Medical Mycology, Carroll Cann ed., Lea& Febiger, Chpt. 16, pp. 397-446 (1992).

Lin, Lung-Yu et al., "Metal-binding and active-site structure of di-zinc *Streptomyces griseus* aminopeptidase," JBIC, vol. 2:744-749 (1997).

Lubkowitz, Mark A. et al., "An oligopeptide transport gene from *Candida albicans*," Microbiology, vol. 143:387-396 (1997).

Luckow, Verne A. et al., "High Level Expression of Nonfused Foreign Genes with *Autographa californica* Nuclear Polyhedrosis Virus Expression Vectors," Virology, vol. 170:31-39 (1989).

Ma, Julian K-C. et al., "The Production of Recombinant Pharmaceutical Proteins in Plants," Nature, vol. 4(10):794-802 (2003).

McAdam, S. et al., "Getting to grips with gluten," Gut, vol. 47:743-745 (2000).

Mignon, B. et al., "Purification and characterization of a 315 kDa keratinolytic subtilisin-like serine protease from *Microsporum canis* and evidence of its secretion in naturally infected cats," Medical Mycology, vol. 36:395-404 (1998).

Molberg, Oyvind et al., "Tissue transglutiminase selectively modifies gliadin peptides that are recognized by gut-derived T cells in celiac disease," Nature Medicine, vol. 4(6):713-717 (1998).

Monod, Michel et al., "Aminopeptidases and dipeptidyl-peptidases secreted by the dermatophyte *Trichophyton rubrum*," Microbiology, vol. 151:145-155 (2005).

Monod, Michel et al., "Multiplicity of genes encoding secreted aspartic proteinases in *Candida* species," Molecular Microbiology, vol. 13(2):357-368 (1994).

Monod, Michel et al., "Secreted proteases from pathogenic fungi," Int. J. Med. Microbiol., vol. 292:405-419 (2002).

Monod, Michel et al., "Survey of Dermatophyte Infections in the Lausanne Area (Switzerland)," Dermatology, vol. 205:201-203 (2002).

Narang, Saran A., "Tetrahedron Report No. 40, DNA Synthesis," Tetrahedron, vol. 39(1):3:22 (1983).

Needleman, Saul B. et al., "A General Method Applicable to the Search for Similarities in the Amino Acid Sequence of Two Proteins," J. Mol. Biol., vol. 48:443-453 (1970).

Nishizawa, Mayumi et al., "Molecular Cloning of the Aminopeptidase Y Gene of *Saccharomyces cerevisiae*," The Journal of Biological Chemistry, vol. 269(18):13651-13655 (1994).

O'Cuinn, G. et al., "Generation of non-bitter casein hydrolysates by using combination of a proteinase and aminopeptidases," Biochemical Society Transactions, vol. 27(4):730-734 (1999).

Rubio-Aliaga, Isabel et al., "Mammalian peptide transporters as targets for drug delivery," TRENDS in Pharmacological Sciences, vol. 23(9):434-440 (2002).

Schnoelzer, Martina et al., "In situ neutralization in Boc-chemistry solid phase peptide synthesis," Int. J. Peptide Protein Res., vol. 40:180-193 (1992).

Shan, Li et al., "Structural Basis for Gluten Intolerance in Celiac Sprue," Science, vol. 297:2275-2279 (2002).

Shilo, Ben-Zion et al., "DNA sequences homologous to vertebrate oncogenes are conserved in *Drosophila melanogaster*," Proc. Natl. Acad. Sci. USA, vol. 78(11):6789-6792 (1981).

Smith, Gale E. et al., "Production of Human Beta Interferon in Insect Cells Infected with a Baculovirus Expression Vector," Molecular and Cellular Biology, vol. 3(12):2156-2165 (1983).

Sollid, Ludvig M., "Doeliac Disease: Dissecting a Complex Inflammatory Disorder," Nature Review Immunol., vol. 2 (9):647-655 (2002).

Stacey, Gary et al., "Peptide transport in plants," TRENDS in Plant Science, vol. 7(6):257-263 (2002).

* cited by examiner

Digestion of gliadin 14mer without (A) or with
(B) ruLAP2 over 4h at 37°C with a E/S ration of 1/50 (w:w).

Digestion of gliadin 33mer at 37°C over 4h with a mixture of ruLAP2 and ruDPPIV at an E/S ratio of 1:50 (w:w) each.

Mass spectrum of Gly-Ser-proNPY (calculated molecular mass at 8203.12 Da) before (A) and after digestion (B) with ruLAP2 which results in the cleavage of Gly-Ser (-144.1 Da)

Mass spectrum of Gly-Ser-proNPY (calculated molecular mass at 8203.12 Da) before (A) and after digestion (B) with ruLAP2 which results in the cleavage of Gly-Ser (-144.1 Da)

Characterisation by ESI-MS of the digestion product of desMET-G-CSF without (A) or with (B) ruDPPIV.

```
                           SEQUENCE LISTING

<160> NUMBER OF SEQ ID NOS: 87

<210> SEQ ID NO 1
<211> LENGTH: 1757
<212> TYPE: DNA
<213> ORGANISM: Trichophyton rubrum

<400> SEQUENCE: 1
atgaagtcgc aactgttgag cctggctgtg gccgtcacaa ccatctccca gggcgttgtt     60
ggtcaagagc ccttcggatg gcctttcaag cctatggtca ctcaggtgag ttgctctcaa    120
cagatcgatc gatcgatcta cctttgtccc tgtcacatca aactccagca gagccaaaga    180
aacagacaca atgttcctgg ggaattctta tgggctaatg taaatgtata ggatgacctg    240
caaaacaaga taaagctcaa ggatatcatg gcaggcgtcg agaagctgca aagcttttct    300
gatgctcatc ctgaaaagaa ccgagtgttt ggtggtaatg ccacaagga cactgtagag     360 tggatctaca atgagatcaa ggccactggc tactacgatg tgaagaagca ggagcaagta    420
cacctgtggt ctcatgccga ggctgctctc aatgccaatg caaggacct caaggccagc     480 gccatgtcct acagccctcc tgccagcaag atcatgctg agcttgttgt tgccaagaac     540
aatggctgca atgctgtatg tgccatacac tttctatacg tcacattctc tctagaatga    600
agagcacggg agaactaact ttatgtatac agactgatta cccagcgaac actcagggca    660
agatcgtcct cgttgagcgt ggtgtctgca gcttcggcga gaagtctgct caggctggtg    720
atgcaaaggc tgctggtgcc attgtctaca acaacgtccc cggatccctt gctggcactc    780
ttggtggcct tgacaagcgc catgtcccaa ccgctggtct ttcccaggag gatggaaaga    840
accttgctac cctcgttgct tctggtaaga ttgatgtcac catgaacgtt atcagtctgt    900
ttgagaaccg aaccacgtaa gtagctcaac ggctgatcca gcatcaattg tctcgagtat    960
atactaaatc gatacctcat agctggaacg tcattgctga ccaagggga ggagaccaca    1020 acaacgttat catgctcggt gctcactccg actccgtcga tgccggccct ggtattaacg   1080
acaacggctc gggctccatt ggtatcatga ccgttgccaa agccctcacc aacttcaagc   1140
tcaacaacgc cgtccgcttt gcctggtgga ccgctgagga attcggtctc cttggaagca   1200
ccttctacgt caacagcctc gatgaccgtg agctgcacaa ggtcaagttg tacctcaact   1260
tcgacatgat cggctctccc aacttcgcca accagatcta cgacggtgac ggttcggcct   1320
acaacatgac cggccccgct ggctctgctg aaatcgagta cctgttcgag aagttctttg   1380
acgaccaggg tatcccacac cagcccactg ccttcactgg ccgatccgac tactctgctt   1440
tcatcaagcg caacgtgccc gctggcggcc tcttcactgg agccgaggtt gtcaagaccc   1500
ccgagcaagt caagttgttc ggtggtgagg ctggcgttgc ctatgacaag aactaccatc   1560
gcaagggcga caccgttgcc aacatcaaca agggagctat cttccttaac actcgagcca   1620
tcgcctacgc tatcgccgag tatgcccgat ccctcaaggg attcccaacc cgcccaaaga   1680
ccggcaagcg tgacgtcaac ccccagtatt ctaagatgcc tggtggtggc tgcggacacc   1740
acactgtctt catgtaa                                                  1757

<210> SEQ ID NO 2
<211> LENGTH: 1488
```

```
<212> TYPE: DNA
<213> ORGANISM: Trichophyton rubrum

<400> SEQUENCE: 2
atgaagtcgc aactgttgag cctggctgtg gccgtcacaa ccatctccca gggcgttgtt      60
ggtcaagagc ccttcggatg gccttcaag cctatggtca ctcaggatga cctgcaaaac     120
aagataaagc tcaaggatat catggcaggc gtcgagaagc tgcaaagctt ttctgatgct     180
catcctgaaa agaaccgagt gtttggtggt aatggccaca aggacactgt agagtggatc     240
tacaatgaga tcaaggccac tggctactac gatgtgaaga agcaggagca agtacacctg     300
tggtctcatg ccgaggctgc tctcaatgcc aatggcaagg acctcaaggc cagcgccatg     360
tcctacagcc ctcctgccag caagatcatg gctgagcttg ttgttgccaa gaacaatggc     420
tgcaatgcta ctgattaccc agcgaacact cagggcaaga tcgtcctcgt tgagcgtggt     480
gtctgcagct cggcgagaa gtctgctcag gctggtgatg caaaggctgc tggtgccatt     540
gtctacaaca acgtccccgg atcccttgct ggcactcttg gtggccttga caagcgccat     600
gtcccaaccg ctggtctttc ccaggaggat ggaagaacc ttgctaccct cgttgcttct     660
ggtaagattg atgtcaccat gaacgttatc agtctgtttg agaaccgaac cacctggaac     720
gtcattgctg agaccaaggg aggagaccac aacaacgtta tcatgctcgg tgctcactcc     780
gactccgtcg atgccggccc tggtattaac gacaacggct cgggctccat ggtatcatg      840 accgttgcca agccctcac caacttcaag ctcaacaacg ccgtccgctt tgcctggtgg     900
accgctgaga attcggtct ccttggaagc accttctacg tcaacagcct cgatgaccgt     960
gagctgcaca aggtcaagtt gtacctcaac ttcgacatga tcggctctcc caacttcgcc    1020
aaccagatct acgacggtga cggttcggcc tacaacatga ccggcccgc tggctctgct    1080 gaaatcgagt acctgttcga gaagttcttt gacgaccagg gtatcccaca ccagcccact    1140
gccttcactg ccgatccga ctactctgct ttcatcaagc gcaacgtgcc cgctggcggc    1200
ctcttcactg gagccgaggt tgtcaagacc cccgagcaag tcaagttgtt cggtggtgag    1260
gctggcgttg cctatgacaa gaactaccat cgcaagggcg acaccgttgc aacatcaac     1320 aagggagcta tcttccttaa cactcgagcc atcgcctacg ctatcgccga gtatgcccga    1380
tccctcaagg gattcccaac ccgcccaaag accggcaagc gtgacgtcaa ccccagtat     1440 tctaagatgc ctggtggtgg ctgcggacac cacactgtct catgtaa                  1488

<210> SEQ ID NO 3
<211> LENGTH: 495
<212> TYPE: PRT
<213> ORGANISM: Trichophyton rubrum

<400> SEQUENCE: 3

Met Lys Ser Gln Leu Leu Ser Leu Ala Val Ala Val Thr Thr Ile Ser
  1               5                  10                  15

Gln Gly Val Val Gly Gln Glu Pro Phe Gly Trp Pro Phe Lys Pro Met
                 20                  25                  30

Val Thr Gln Asp Asp Leu Gln Asn Lys Ile Lys Leu Lys Asp Ile Met
             35                  40                  45

Ala Gly Val Glu Lys Leu Gln Ser Phe Ser Asp Ala His Pro Glu Lys
         50                  55                  60

Asn Arg Val Phe Gly Gly Asn Gly His Lys Asp Thr Val Glu Trp Ile
 65                  70                  75                  80

Tyr Asn Glu Ile Lys Ala Thr Gly Tyr Tyr Asp Val Lys Lys Gln Glu
                 85                  90                  95
```

Gln Val His Leu Trp Ser His Ala Glu Ala Leu Asn Ala Asn Gly
                100                 105                 110

Lys Asp Leu Lys Ala Ser Ala Met Ser Tyr Ser Pro Ala Ser Lys
            115                 120                 125

Ile Met Ala Glu Leu Val Ala Lys Asn Asn Gly Cys Asn Ala Thr
130                 135                 140

Asp Tyr Pro Ala Asn Thr Gln Gly Lys Ile Val Leu Glu Arg Gly
145                 150                 155                 160

Val Cys Ser Phe Gly Glu Lys Ser Ala Gln Ala Gly Asp Ala Lys Ala
                165                 170                 175

Ala Gly Ala Ile Val Tyr Asn Asn Val Pro Gly Ser Leu Ala Gly Thr
            180                 185                 190

Leu Gly Gly Leu Asp Lys Arg His Val Pro Thr Ala Gly Leu Ser Gln
            195                 200                 205

Glu Asp Gly Lys Asn Leu Ala Thr Leu Val Ala Ser Gly Lys Ile Asp
210                 215                 220

Val Thr Met Asn Val Ile Ser Leu Phe Glu Asn Arg Thr Thr Trp Asn
225                 230                 235                 240

Val Ile Ala Glu Thr Lys Gly Gly Asp His Asn Asn Val Ile Met Leu
                245                 250                 255

Gly Ala His Ser Asp Ser Val Asp Ala Gly Pro Gly Ile Asn Asp Asn
            260                 265                 270

Gly Ser Gly Ser Ile Gly Ile Met Thr Val Ala Lys Ala Leu Thr Asn
            275                 280                 285

Phe Lys Leu Asn Asn Ala Val Arg Phe Ala Trp Trp Thr Ala Glu Glu
290                 295                 300

Phe Gly Leu Leu Gly Ser Thr Phe Tyr Val Asn Ser Leu Asp Asp Arg
305                 310                 315                 320

Glu Leu His Lys Val Lys Leu Tyr Leu Asn Phe Asp Met Ile Gly Ser
                325                 330                 335

Pro Asn Phe Ala Asn Gln Ile Tyr Asp Gly Asp Gly Ser Ala Tyr Asn
            340                 345                 350

Met Thr Gly Pro Ala Gly Ser Ala Glu Ile Glu Tyr Leu Phe Glu Lys
            355                 360                 365

Phe Phe Asp Asp Gln Gly Ile Pro His Gln Pro Thr Ala Phe Thr Gly
370                 375                 380

Arg Ser Asp Tyr Ser Ala Phe Ile Lys Arg Asn Val Pro Ala Gly Gly
385                 390                 395                 400

Leu Phe Thr Gly Ala Glu Val Val Lys Thr Pro Glu Gln Val Lys Leu
                405                 410                 415

Phe Gly Gly Glu Ala Gly Val Ala Tyr Asp Lys Asn Tyr His Arg Lys
            420                 425                 430

Gly Asp Thr Val Ala Asn Ile Asn Lys Gly Ala Ile Phe Leu Asn Thr
            435                 440                 445

Arg Ala Ile Ala Tyr Ala Ile Ala Glu Tyr Ala Arg Ser Leu Lys Gly
450                 455                 460

Phe Pro Thr Arg Pro Lys Thr Gly Lys Arg Asp Val Asn Pro Gln Tyr
465                 470                 475                 480

Ser Lys Met Pro Gly Gly Cys Gly His His Thr Val Phe Met
                485                 490                 495

<210> SEQ ID NO 4
<211> LENGTH: 1256
<212> TYPE: DNA

<213> ORGANISM: Trichophyton rubrum

<400> SEQUENCE: 4

| | | | | | |
|---|---|---|---|---|---|
| atgaagctcc | tctctgttct | tgcgctgagc | gctaccgcta | cctccgtcct | cggagctagc | 60 |
| attcctgttg | atgcccgggc | cgagaagttc | ctcatcgaac | ttgcccctgg | tgagactcgc | 120 |
| tgggttaccg | aggaggagaa | gtgggagctt | aagcgggtat | gtaccactat | cctacgcaaa | 180 |
| agttgtattt | tcactagata | atattggtta | ttaacaccca | ttctagaagg | gtcaagactt | 240 |
| ctttgacatc | actgacgagg | aggttggatt | cactgctgct | gttgcacagc | cagccattgc | 300 |
| ctacccaacc | tccatccgcc | atgctaatgc | tgttaacgcc | atgattgcta | ccctctccaa | 360 |
| ggagaacatg | cagcgcgatc | tgaccaagct | cagctcgttc | caaaccgctt | actataaggt | 420 |
| tgactttggc | aagcagtctg | ccacctggct | ccaggagcaa | gtccaggctg | ccatcaatac | 480 |
| cgctggtgcc | aatcgctacg | gagccaaggt | cgccagcttc | cgacacaact | cgctcagca | 540 |
| cagcatcatt | gccactattc | ccggccgctc | ccctgaagtc | gttgtcgtcg | gtgctcacca | 600 |
| agacagcatc | aaccaacgca | gccccatgac | cggccgcgct | ccaggtgccg | atgacaacgg | 660 |
| cagtggctcc | gtcaccatcc | ttgaggccct | ccgtggtgtt | ctccgggacc | agaccatcct | 720 |
| ccagggcaag | gctgccaaca | ccattgagtt | ccactggtac | gccggtgagg | aagctggtct | 780 |
| tctgggctcc | caggccatct | tcgccaacta | caaacagacc | ggcaagaagg | tcaagggcat | 840 |
| gctcaaccag | gacatgaccg | gttacatcaa | gggaatggtc | gacaagggtc | tcaaggtgtc | 900 |
| cttcggtatc | atcaccgaca | acgtcaacgc | taacttgacc | aagttcgtcc | gcatggtcat | 960 |
| caccaaggta | agcttcaact | cttgataaat | atattttca | tcgatgaaat | gatgtcctaa | 1020 |
| taatgcttaa | gtactgctca | atcccaacca | tcgacacccg | ctgcggctat | gcttgctctg | 1080 |
| accacgcctc | tgccaaccgc | aatggctacc | catctgccat | ggttgccgag | tctcccatcg | 1140 |
| atctcctcga | ccctcacctc | cacactgact | ctgacaacat | tagctacctc | gacttcgacc | 1200 |
| acatgatcga | gcacgctaag | ctcattgtcg | gcttcgtcac | tgagctcgct | aagtaa | 1256 |

<210> SEQ ID NO 5
<211> LENGTH: 1122
<212> TYPE: DNA
<213> ORGANISM: Trichophyton rubrum

<400> SEQUENCE: 5

| | | | | | |
|---|---|---|---|---|---|
| atgaagctcc | tctctgttct | tgcgctgagc | gctaccgcta | cctccgtcct | cggagctagc | 60 |
| attcctgttg | atgcccgggc | cgagaagttc | ctcatcgaac | ttgcccctgg | tgagactcgc | 120 |
| tgggttaccg | aggaggagaa | gtgggagctt | aagcggaagg | gtcaagactt | ctttgacatc | 180 |
| actgacgagg | aggttggatt | cactgctgct | gttgcacagc | cagccattgc | ctacccaacc | 240 |
| tccatccgcc | atgctaatgc | tgttaacgcc | atgattgcta | ccctctccaa | ggagaacatg | 300 |
| cagcgcgatc | tgaccaagct | cagctcgttc | caaaccgctt | actataaggt | tgactttggc | 360 |
| aagcagtctg | ccacctggct | ccaggagcaa | gtccaggctg | ccatcaatac | cgctggtgcc | 420 |
| aatcgctacg | gagccaaggt | cgccagcttc | cgacacaact | cgctcagca | cagcatcatt | 480 |
| gccactattc | ccggccgctc | ccctgaagtc | gttgtcgtcg | gtgctcacca | agacagcatc | 540 |
| aaccaacgca | gccccatgac | cggccgcgct | ccaggtgccg | atgacaacgg | cagtggctcc | 600 |
| gtcaccatcc | ttgaggccct | ccgtggtgtt | ctccgggacc | agaccatcct | ccagggcaag | 660 |
| gctgccaaca | ccattgagtt | ccactggtac | gccggtgagg | aagctggtct | tctgggctcc | 720 |
| caggccatct | tcgccaacta | caaacagacc | ggcaagaagg | tcaagggcat | gctcaaccag | 780 |

```
gacatgaccg gttacatcaa gggaatggtc gacaagggtc tcaaggtgtc cttcggtatc    840
atcaccgaca acgtcaacgc taacttgacc aagttcgtcc gcatggtcat caccaagtac    900
tgctcaatcc caaccatcga cacccgctgc ggctatgctt gctctgacca cgcctctgcc    960
aaccgcaatg ctacccatc tgccatggtt gccgagtctc ccatcgatct cctcgacccet   1020 cacctccaca ctgactctga acacattagc tacctcgact tcgaccacat gatcgagcac   1080
gctaagctca ttgtcggctt cgtcactgag ctcgctaagt aa                      1122
```

<210> SEQ ID NO 6
<211> LENGTH: 373
<212> TYPE: PRT
<213> ORGANISM: Trichophyton rubrum

<400> SEQUENCE: 6

```
Met Lys Leu Leu Ser Val Leu Ala Leu Ser Ala Thr Ala Thr Ser Val
 1               5                  10                  15

Leu Gly Ala Ser Ile Pro Val Asp Ala Arg Ala Glu Lys Phe Leu Ile
            20                  25                  30

Glu Leu Ala Pro Gly Glu Thr Arg Trp Val Thr Glu Glu Lys Trp
        35                  40                  45

Glu Leu Lys Arg Lys Gly Gln Asp Phe Phe Asp Ile Thr Asp Glu Glu
    50                  55                  60

Val Gly Phe Thr Ala Ala Val Ala Gln Pro Ala Ile Ala Tyr Pro Thr
65                  70                  75                  80

Ser Ile Arg His Ala Asn Ala Val Asn Ala Met Ile Ala Thr Leu Ser
                85                  90                  95

Lys Glu Asn Met Gln Arg Asp Leu Thr Lys Leu Ser Ser Phe Gln Thr
           100                 105                 110

Ala Tyr Tyr Lys Val Asp Phe Gly Lys Gln Ser Ala Thr Trp Leu Gln
       115                 120                 125

Glu Gln Val Gln Ala Ala Ile Asn Thr Ala Gly Ala Asn Arg Tyr Gly
    130                 135                 140

Ala Lys Val Ala Ser Phe Arg His Asn Phe Ala Gln His Ser Ile Ile
145                 150                 155                 160

Ala Thr Ile Pro Gly Arg Ser Pro Glu Val Val Val Gly Ala His
                165                 170                 175

Gln Asp Ser Ile Asn Gln Arg Ser Pro Met Thr Gly Arg Ala Pro Gly
           180                 185                 190

Ala Asp Asp Asn Gly Ser Gly Ser Val Thr Ile Leu Glu Ala Leu Arg
       195                 200                 205

Gly Val Leu Arg Asp Gln Thr Ile Leu Gln Gly Lys Ala Ala Asn Thr
    210                 215                 220

Ile Glu Phe His Trp Tyr Ala Gly Glu Glu Ala Gly Leu Leu Gly Ser
225                 230                 235                 240

Gln Ala Ile Phe Ala Asn Tyr Lys Gln Thr Gly Lys Lys Val Lys Gly
                245                 250                 255

Met Leu Asn Gln Asp Met Thr Gly Tyr Ile Lys Gly Met Val Asp Lys
           260                 265                 270

Gly Leu Lys Val Ser Phe Gly Ile Ile Thr Asp Asn Val Asn Ala Asn
       275                 280                 285

Leu Thr Lys Phe Val Arg Met Val Ile Thr Lys Tyr Cys Ser Ile Pro
    290                 295                 300

Thr Ile Asp Thr Arg Cys Gly Tyr Ala Cys Ser Asp His Ala Ser Ala
305                 310                 315                 320
```

```
Asn Arg Asn Gly Tyr Pro Ser Ala Met Val Ala Glu Ser Pro Ile Asp
            325                 330                 335

Leu Leu Asp Pro His Leu His Thr Asp Ser Asp Asn Ile Ser Tyr Leu
        340                 345                 350

Asp Phe Asp His Met Ile Glu His Ala Lys Leu Ile Val Gly Phe Val
        355                 360                 365

Thr Glu Leu Ala Lys
    370

<210> SEQ ID NO 7
<211> LENGTH: 1557
<212> TYPE: DNA
<213> ORGANISM: Aspergillus fumigatus

<400> SEQUENCE: 7
atgaagctgc tctacctcac atcgtttgcc tctctggccg tggccaatgg cccaggatgg      60
gactggaagc cccgagttca tccggttagt gttcctctcg ccgggtttgt ctgctgtatg     120
ctaacagcat cctgtctatt acagaaagtc ctgccccaaa tgatccattt gtgggatctt     180
ctgcagggcg ctcaacagct ggaagacttc gcctatgcct accccgagcg caaccgcgtc     240
tttggtggac gggcccacga ggacaccgtc aactacctct accgtgagtt gaagaaaacc     300
ggctactacg acgtttacaa gcagcccag gttcaccagt ggacccgagc cgaccaggct      360
ctcaccgtcg acggccagtc ctatgacgcc acaaccatga cttacagccc cagcgtaaac     420 gccacgcgc cgctggcagt ggtgaacaac ctgggctgcg tcgaggctga ctatcccgcc      480
gatctgacgg gcaagattgc tctgatctcg cggggcgagt gcacctttgc gaccaaatcc     540
gtcttgagcg ccaaggccgg ggcggcggcg cactcgtgt acaacaatat cgagggttcg      600
atggcgggaa ctctgggcgg cgcgaccagc gagctgggtg cctacgctcc catcgccggc     660
atcagcctcg cggacggaca ggcgctgatc cagatgatcc aggcgggcac ggtgacagcc     720
aacctgtgga tcgacagcca ggtcgagaac cgtaccacct caacgtgat cgcgcagacc      780 aagggcggcg accccaacaa cgtcgtcgcg ctgggtggcc acacggactc ggtcgaggcc     840
gggcccggca tcaacgacga cggctccggc atcatcagca acctcgtcgt cgccaaggcg     900
ctgacccgct ctcggtcaa gaacgcggtg cgcttctgct tctggacggc ggaggagttc      960
ggcctgctgg cagcaacta ctacgtcaac agcctcaatg ccaccgagca ggccaagatc     1020
cgcctgtatc tcaacttcga catgatcgcc tcccccaact acgccctgat gatctatgac    1080
ggcgacggct cggccttcaa cctgacgggg ccggccggct cggcgcagat cgagcggctc    1140
ttcgaggact actacacgtc gatccgcaag ccgttcgtgc cgaccgagtt caacggccgc    1200
tccgactacc aggcctttat tctcaacggc atccccgcgg aggcctcttc accggcgcg    1260 gaggcgatca agaccgagga acaggcccaa ttgtttggcg gccaggccgg cgtggctctg    1320
gacgccaact accacgccaa gggtgacaac atgactaatc tcaaccgcga ggctttcctg    1380
atcaattcca gggcgacggc ctttgccgtg gcgacgtacg ccaacagcct tgactcgatc    1440
cccccacgca acatgaccac cgtggtcaag cggtcgcagc tggagcaagc catgaagagg    1500
accccgcaca cgcacaccgg cggaacagga tgctacaagg accgggttga gcagtag       1557

<210> SEQ ID NO 8
<211> LENGTH: 1497
<212> TYPE: DNA
<213> ORGANISM: Aspergillus fumigatus

<400> SEQUENCE: 8
```

-continued

```
atgaagctgc tctacctcac atcgtttgcc tctctggccg tggccaatgg cccaggatgg    60
gactggaagc cccgagttca tccgaaagtc ctgccccaaa tgatccattt gtgggatctt   120
ctgcagggcg ctcaacagct ggaagacttc gcctatgcct accccgagcg caaccgcgtc   180
tttggtggac gggcccacga ggacaccgtc aactacctct accgtgagtt gaagaaaacc   240
ggctactacg acgtttacaa gcagccccag gttcaccagt ggaccccgag cgaccaggct   300
ctcaccgtcg acggccagtc ctatgacgcc acaaccatga cttacagccc cagcgtaaac   360
gccacggcgc cgctggcagt ggtgaacaac ctgggctgcg tcgaggctga ctatcccgcc   420
gatctgacgg gcaagattgc tctgatctcg cggggcgagt gcacctttgc gaccaaatcc   480
gtcttgagcg ccaaggccgg ggcggcggcg gcactcgtgt acaacaatat cgagggttcg   540
atggcgggaa ctctgggcgg cgcgaccagc gagctgggtg cctacgctcc catcgccggc   600
atcagcctcg cggacggaca ggcgctgatc agatgatcc aggcgggcac ggtgacagcc   660
aacctgtgga tcgacagcca ggtcgagaac cgtaccacct acaacgtgat cgcgcagacc   720
aagggcggcg accccaacaa cgtcgtcgcg ctgggtggcc acacggactc ggtcgaggcc   780
gggcccggca tcaacgacga cggctccggc atcatcagca acctcgtcgt cgccaaggcg   840
ctgacccgct ctcggtcaa gaacgcggtg cgcttctgct tctggacggc ggaggagttc   900
ggcctgctgg cagcaacta ctacgtcaac agcctcaatg ccaccgagca ggccaagatc   960
cgcctgtatc tcaacttcga catgatcgcc tcccccaact acgccctgat gatctatgac  1020
ggcgacggct cggccttcaa cctgacgggg ccggccggct cggcgcagat cgagcggctc  1080
ttcgaggact actacacgtc gatccgcaag ccgttcgtgc cgaccgagtt caacggccgc  1140
tccgactacc aggcctttat tctcaacggc atccccgcgg gaggcctctt caccggcgcg  1200
gaggcgatca agaccgagga acaggcccaa ttgtttggcg ccaggccgg cgtggctctg  1260
gacgccaact accacgccaa gggtgacaac atgactaatc tcaaccgcga ggctttcctg  1320
atcaattcca gggcgacggc ctttgccgtg gcgacgtacg ccaacagcct tgactcgatc  1380
cccccacgca acatgaccac cgtggtcaag cggtcgcagc tggagcaagc catgaagagg  1440
accccgcaca cgcacaccgg cggaacagga tgctacaagg accgggttga gcagtag    1497
```

<210> SEQ ID NO 9
<211> LENGTH: 498
<212> TYPE: PRT
<213> ORGANISM: Aspergillus fumigatus

<400> SEQUENCE: 9

```
Met Lys Leu Leu Tyr Leu Thr Ser Phe Ala Ser Leu Ala Val Ala Asn
  1               5                  10                  15

Gly Pro Gly Trp Asp Trp Lys Pro Arg Val His Pro Lys Val Leu Pro
             20                  25                  30

Gln Met Ile His Leu Trp Asp Leu Leu Gln Gly Ala Gln Gln Leu Glu
         35                  40                  45

Asp Phe Ala Tyr Ala Tyr Pro Glu Arg Asn Arg Val Phe Gly Gly Arg
     50                  55                  60

Ala His Glu Asp Thr Val Asn Tyr Leu Tyr Arg Glu Leu Lys Lys Thr
 65                  70                  75                  80

Gly Tyr Tyr Asp Val Tyr Lys Gln Pro Gln Val His Gln Trp Thr Arg
                 85                  90                  95

Ala Asp Gln Ala Leu Thr Val Asp Gly Gln Ser Tyr Asp Ala Thr Thr
            100                 105                 110

Met Thr Tyr Ser Pro Ser Val Asn Ala Thr Ala Pro Leu Ala Val Val
```

```
                115                 120                 125
Asn Asn Leu Gly Cys Val Glu Ala Asp Tyr Pro Ala Asp Leu Thr Gly
    130                 135                 140

Lys Ile Ala Leu Ile Ser Arg Gly Glu Cys Thr Phe Ala Thr Lys Ser
145                 150                 155                 160

Val Leu Ser Ala Lys Ala Gly Ala Ala Ala Leu Val Tyr Asn Asn
                165                 170                 175

Ile Glu Gly Ser Met Ala Gly Thr Leu Gly Ala Thr Ser Glu Leu
                180                 185                 190

Gly Ala Tyr Ala Pro Ile Ala Gly Ile Ser Leu Ala Asp Gly Gln Ala
                195                 200                 205

Leu Ile Gln Met Ile Gln Ala Gly Thr Val Thr Ala Asn Leu Trp Ile
    210                 215                 220

Asp Ser Gln Val Glu Asn Arg Thr Thr Tyr Asn Val Ile Ala Gln Thr
225                 230                 235                 240

Lys Gly Gly Asp Pro Asn Asn Val Val Ala Leu Gly Gly His Thr Asp
                245                 250                 255

Ser Val Glu Ala Gly Pro Gly Ile Asn Asp Asp Gly Ser Gly Ile Ile
                260                 265                 270

Ser Asn Leu Val Val Ala Lys Ala Leu Thr Arg Phe Ser Val Lys Asn
    275                 280                 285

Ala Val Arg Phe Cys Phe Trp Thr Ala Glu Glu Phe Gly Leu Leu Gly
    290                 295                 300

Ser Asn Tyr Tyr Val Asn Ser Leu Asn Ala Thr Glu Gln Ala Lys Ile
305                 310                 315                 320

Arg Leu Tyr Leu Asn Phe Asp Met Ile Ala Ser Pro Asn Tyr Ala Leu
                325                 330                 335

Met Ile Tyr Asp Gly Asp Gly Ser Ala Phe Asn Leu Thr Gly Pro Ala
                340                 345                 350

Gly Ser Ala Gln Ile Glu Arg Leu Phe Glu Asp Tyr Tyr Thr Ser Ile
                355                 360                 365

Arg Lys Pro Phe Val Pro Thr Glu Phe Asn Gly Arg Ser Asp Tyr Gln
370                 375                 380

Ala Phe Ile Leu Asn Gly Ile Pro Ala Gly Gly Leu Phe Thr Gly Ala
385                 390                 395                 400

Glu Ala Ile Lys Thr Glu Glu Gln Ala Gln Leu Phe Gly Gly Gln Ala
                405                 410                 415

Gly Val Ala Leu Asp Ala Asn Tyr His Ala Lys Gly Asp Asn Met Thr
                420                 425                 430

Asn Leu Asn Arg Glu Ala Phe Leu Ile Asn Ser Arg Ala Thr Ala Phe
    435                 440                 445

Ala Val Ala Thr Tyr Ala Asn Ser Leu Asp Ser Ile Pro Pro Arg Asn
    450                 455                 460

Met Thr Thr Val Val Lys Arg Ser Gln Leu Glu Gln Ala Met Lys Arg
465                 470                 475                 480

Thr Pro His Thr His Thr Gly Gly Thr Gly Cys Tyr Lys Asp Arg Val
                485                 490                 495

Glu Gln

<210> SEQ ID NO 10
<211> LENGTH: 1298
<212> TYPE: DNA
<213> ORGANISM: Aspergillus fumigatus

<400> SEQUENCE: 10
```

```
atgaaagttc ttacagctat tgcgctgagc gcaatagctt tcacaggggc tgtagctgca      60
gtgattactc aggaagcatt cttaaacaac ccccgcatcc atcatgacca ggagaagtac     120
ttgatcgaac tggcccctta tcgaacacga tgggtgactg aagaggagaa atgggcattg     180
aaattggtac catacttccc caaaatttgg gtctccaagt ccacgggcga ctaactgcac     240
gattgcttga aggacggcgt gaattttatc gatatcacag aagagcacaa caccggattt     300
tacccgactc tccacagcgc cagctatgtg aaatatccac cgaagatgca gtatgcagaa     360
gaagtggctg ctcttaacaa gaattttatcg aaagaaaaca tgaaggccaa cctggaacga     420
ttcacatcat ttcatactcg ctattacaaa tctcagacgg gaatccgatc ggcaacgtgg     480
ctgttcgacc aagttcagag agttgtctct gagtctggag ccgctgagta tggtgcaact     540
gttgagcgat tctctcatcc atggggtcag ttcagcatta ttgcccgaat acccggccga     600
acgaacaaga ctgtggtgct gggcgcccat caggacagca tcaatttgtt tctcccgtca     660
atcttggctg ctcccggtgc tgatgacgat ggaagtggaa ctgtcaccat tcttgaagcg     720
ttgcgcggtc tgctgcagtc agacgccatt gccaagggta atgcatccaa tactgtcgag     780
ttccactggt actctgcaga gaaggcggaa atgctgggct cccaggcaat atttccaat     840 tacaagcgga ataggcggga aatcaaagcc atgctccagc aagacatgac tggctacgtc     900
cagggagctt gaacgccgg tgttgaggaa gccataggaa ttatggtcga ttatgtcgac     960
cagggcctca cacagtttct caaggacgtt gttacagcgg taagcctcag ttgtccccca    1020
cgaaaagctg tttagtcgac aaatgaaatt gacggctgca ttagtactgc tctgtgggtt    1080
acctggagac gaagtgcgga tatgcctgct ccgaccacac ctcggccagt aaatatggtt    1140
atcccgcggc tatggcgaca gaagcagaga tggaaaatac caataagaag atacatacta    1200
ccgacgacaa gatcaagtat ttgagcttcg atcatatgtt ggagcatgcc aagttgagtc    1260
ttggcttcgc tttcgaattg gcatttgcgc cgttttaa                             1298

<210> SEQ ID NO 11
<211> LENGTH: 1167
<212> TYPE: DNA
<213> ORGANISM: Aspergillus fumigatus

<400> SEQUENCE: 11
atgaaagttc ttacagctat tgcgctgagc gcaatagctt tcacaggggc tgtagctgca      60
gtgattactc aggaagcatt cttaaacaac ccccgcatcc atcatgacca ggagaagtac     120
ttgatcgaac tggcccctta tcgaacacga tgggtgactg aagaggagaa atgggcattg     180
aaattggacg gcgtgaattt tatcgatatc acagaagagc acaacaccgg attttacccg     240
actctccaca gcgccagcta tgtgaaatat ccaccgaaga tgcagtatgc agaagaagtg     300
gctgctctta acaagaattt atcgaaagaa aacatgaagg ccaacctgga acgattcaca     360
tcatttcata ctcgctatta caaatctcag acgggaatcc gatcggcaac gtggctgttc     420
gaccaagttc agagagttgt ctctgagtct ggagccgctg agtatggtgc aactgttgag     480
cgattctctc atccatgggg tcagttcagc attattgccc gaatacccgg ccgaacgaac     540
aagactgtgg tgctgggcgc ccatcaggac agcatcaatt tgtttctccc gtcaatcttg     600
gctgctcccg gtgctgatga cgatggaagt ggaactgtca ccattcttga gcgttgcgc     660 ggtctgctgc agtcagacgc cattgccaag ggtaatgcat ccaatactgt cgagttccac     720
tggtactctg cagaagaagg cggaatgctg ggctcccagg caatattttc caattacaag     780
cggaataggc gggaaatcaa agccatgctc cagcaagaca tgactggcta cgtccaggga     840
```

```
gctttgaacg ccggtgttga ggaagccata ggaattatgg tcgattatgt cgaccagggc      900
ctcacacagt ttctcaagga cgttgttaca gcgtactgct ctgtgggtta cctggagacg      960
aagtgcggat atgcctgctc cgaccacacc tcggccagta aatatggtta tcccgcggct     1020
atggcgacag aagcagagat ggaaaatacc aataagaaga tacatactac cgacgacaag     1080
atcaagtatt tgagcttcga tcatatgttg gagcatgcca agttgagtct tggcttcgct     1140
ttcgaattgg catttgcgcc gttttaa                                         1167
```

<210> SEQ ID NO 12
<211> LENGTH: 388
<212> TYPE: PRT
<213> ORGANISM: Aspergillus fumigatus

<400> SEQUENCE: 12

```
Met Lys Val Leu Thr Ala Ile Ala Leu Ser Ala Ile Ala Phe Thr Gly
  1               5                  10                  15

Ala Val Ala Ala Val Ile Thr Gln Glu Ala Phe Leu Asn Asn Pro Arg
                 20                  25                  30

Ile His His Asp Gln Glu Lys Tyr Leu Ile Glu Leu Ala Pro Tyr Arg
             35                  40                  45

Thr Arg Trp Val Thr Glu Glu Lys Trp Ala Leu Lys Leu Asp Gly
         50                  55                  60

Val Asn Phe Ile Asp Ile Thr Glu Glu His Asn Thr Gly Phe Tyr Pro
 65                  70                  75                  80

Thr Leu His Ser Ala Ser Tyr Val Lys Tyr Pro Pro Lys Met Gln Tyr
                 85                  90                  95

Ala Glu Glu Val Ala Ala Leu Asn Lys Asn Leu Ser Lys Glu Asn Met
            100                 105                 110

Lys Ala Asn Leu Glu Arg Phe Thr Ser Phe His Thr Arg Tyr Tyr Lys
        115                 120                 125

Ser Gln Thr Gly Ile Arg Ser Ala Thr Trp Leu Phe Asp Gln Val Gln
    130                 135                 140

Arg Val Val Ser Glu Ser Gly Ala Ala Glu Tyr Gly Ala Thr Val Glu
145                 150                 155                 160

Arg Phe Ser His Pro Trp Gly Gln Phe Ser Ile Ile Ala Arg Ile Pro
                165                 170                 175

Gly Arg Thr Asn Lys Thr Val Val Leu Gly Ala His Gln Asp Ser Ile
            180                 185                 190

Asn Leu Phe Leu Pro Ser Ile Leu Ala Ala Pro Gly Ala Asp Asp Asp
        195                 200                 205

Gly Ser Gly Thr Val Thr Ile Leu Glu Ala Leu Arg Gly Leu Leu Gln
    210                 215                 220

Ser Asp Ala Ile Ala Lys Gly Asn Ala Ser Asn Thr Val Glu Phe His
225                 230                 235                 240

Trp Tyr Ser Ala Glu Glu Gly Gly Met Leu Gly Ser Gln Ala Ile Phe
                245                 250                 255

Ser Asn Tyr Lys Arg Asn Arg Glu Ile Lys Ala Met Leu Gln Gln
            260                 265                 270

Asp Met Thr Gly Tyr Val Gln Gly Ala Leu Asn Ala Gly Val Glu Glu
        275                 280                 285

Ala Ile Gly Ile Met Val Asp Tyr Val Asp Gln Gly Leu Thr Gln Phe
    290                 295                 300

Leu Lys Asp Val Val Thr Ala Tyr Cys Ser Val Gly Tyr Leu Glu Thr
305                 310                 315                 320
```

```
Lys Cys Gly Tyr Ala Cys Ser Asp His Thr Ser Ala Ser Lys Tyr Gly
                325                 330                 335

Tyr Pro Ala Ala Met Ala Thr Glu Ala Glu Met Glu Asn Thr Asn Lys
            340                 345                 350

Lys Ile His Thr Thr Asp Asp Lys Ile Lys Tyr Leu Ser Phe Asp His
        355                 360                 365

Met Leu Glu His Ala Lys Leu Ser Leu Gly Phe Ala Phe Glu Leu Ala
    370                 375                 380

Phe Ala Pro Phe
385

<210> SEQ ID NO 13
<211> LENGTH: 2106
<212> TYPE: DNA
<213> ORGANISM: Trichophyton rubrum

<400> SEQUENCE: 13
```

| | | |
|---|---|---|
| atggtgtcat tctgcggagt ggcagcctgc ctgctgacag ttgctggcca tcttgcgcag | 60 |
| gctcagttcc caccaaaacc ggagggagtc actgtcctgg agtcgaaatt cggcagcggt | 120 |
| gctcgcatca cttataagga ggtccgttag ctgcatagaa agtccacgtg aagacgctgt | 180 |
| agctaacaat ccactagcct ggcctctgtg agacgacaga gggcgtcaag tcgtacgccg | 240 |
| gatatgtcca tctgcctcca ggcacgctca gggacttcgg tgtcgagcag gactacccta | 300 |
| tcaacacctt ttttttggttc tttgaggcaa gaaaggaccc tgaaaatgcc cctctcggca | 360 |
| tctggatgaa cggtggcccg gtagctcgt cgatgtttgg aatgatgact gagaacgggc | 420 |
| cttgcttcgt caatgcagac tccaattcta ctcgcctgaa ccctcattct tggaacaatg | 480 |
| aaggtatgcc atcagcttct gatggaaaac taaatattgc taacattgta ctttctgtga | 540 |
| ctagtcaata tgctgtatat agaccagcca gtgcaggtcg gtctgtccta cgacactttg | 600 |
| gccaacttca ccaggaatct agtcacggat gagatcacga aactgaaacc cggagaacct | 660 |
| attccggaac agaatgccac tttcctggta ggtacatatg caagccgcaa tatgaacacc | 720 |
| actgcacacg gaactaggca tgctgccatg gctctctggc acttcgccca agtctggttc | 780 |
| caagagttcc caggatatca ccctaggaac aacaagatca gcattgctac cgaatcctac | 840 |
| ggcggccgtt atgcccggc ctttactgcc ttctttgaag agcagaacca agatcaag | 900 |
| aacggcacat ggaagggaca cgagggaact atgcacgtgc tgcatctcga caccctcatg | 960 |
| atcgtcaacg gatgcatcga ccgtcttgtc aatggccgg catatccgca aatggcgtac | 1020 |
| aacaacacat atagcatcga ggcagtcaac gccagcattc atgcaggaat gctggatgcc | 1080 |
| ctctaccgcg acgtggctg tcgagacaag attaaccact gccgctccct ctcttctgtg | 1140 |
| ttcgatcctg agaatctcgg catcaactca accgtcaatg atgtctgcaa ggatgccgag | 1200 |
| acattctgct ccaatgatgt tcgcgatccc tacctcaagt tctctggccg caactactat | 1260 |
| gacatcggac agcttgaccc cagcccattc ccagcaccat tttacatggc ctggctaaat | 1320 |
| cagccgcatg tgcaggcagc actgggtgtg ccacttaact ggacacagtc aaacgatgtt | 1380 |
| gtgtctaccg cattccgtgc aattggtgac taccctcggc cagggtggct ggagaacctg | 1440 |
| gcttatttgc tggagaatgg catcaaggtt tcgcttgttt acggtgatcg ggactacgca | 1500 |
| tgcaactggt tcggtggtga gctctcaagt ctgggaatca actacactga cacccacgaa | 1560 |
| ttccataatg ccggctatgc aggtatccag atcaatagca gctacatcgg tggacaggtg | 1620 |
| aggcagtacg gcaacctctc cttcgcccgc gtctacgagg ccggccatga ggtgccatcg | 1680 |

```
taccaacccg agactgcact gcagatattc caccgttccc tgttcaacaa ggatatcgct    1740
actggaacca aggacacgtc atcgcgcatg gacggaggca gtttttacgg cacctcgggc    1800
cctgcggact cgtttggttt caagaacaaa cctccaccgc agcacgtcca cttctgtcat    1860
atcttagaca ccagcacctg caccaaggag cagatccagt cagttgagaa cggcactgcc    1920
gccgtacgca gctggatcat tgtcgactcc aactcgacct ctctgttccc cgaggtagtt    1980
ggctcagggg aacccacgcc aaccccctatg cctggagggg ctactacact atctgctcac    2040
gggttcttgt atggcgtgac attatgggct gttattgttg tagctgttat agagctggca    2100
atgtaa                                                                2106

<210> SEQ ID NO 14
<211> LENGTH: 1989
<212> TYPE: DNA
<213> ORGANISM: Trichophyton rubrum

<400> SEQUENCE: 14
atggtgtcat tctgcggagt ggcagcctgc ctgctgacag ttgctggcca tcttgcgcag     60
gctcagttcc caccaaaacc ggagggagtc actgtcctgg agtcgaaatt cggcagcggt    120
gctcgcatca cttataagga gcctggcctc tgtgagacga cagagggcgt caagtcgtac    180
gccggatatg tccatctgcc tccaggcacg ctcaggggact tcggtgtcga gcaggactac    240
cctatcaaca ccttttttg gttctttgag gcaagaaagg accctgaaaa tgcccctctc    300
ggcatctgga tgaacggtgg cccgggtagc tcgtcgatgt ttggaatgat gactgagaac    360
gggccttgct tcgtcaatgc agactccaat tctactcgcc tgaaccctca ttcttggaac    420
aatgaagtca atatgctgta tatagaccag ccagtgcagg tcggtctgtc ctacgacact    480
ttggccaact tcaccaggaa tctagtcacg gatgagatca cgaaactgaa acccggagaa    540
cctattccgg aacagaatgc cactttcctg gtaggtacat atgcaagccg caatatgaac    600
accactgcac acggaactag gcatgctgcc atggctctct ggcacttcgc caagtctgg     660 ttccaagagt tcccaggata tcaccctagg aacaacaaga tcagcattgc taccgaatcc    720
tacggcggcc gttatggccc ggcctttact gccttctttg aagagcagaa ccagaagatc    780
aagaacggca catggaaggg acacgaggga actatgcacg tgctgcatct cgacaccctc    840
atgatcgtca acggatgcat cgaccgtctt gtccaatggc cggcatatcc gcaaatggcg    900
tacaacaaca catatagcat cgaggcagtc aacgccagca ttcatgcagg aatgctggat    960
gccctctacc gcgacggtgg ctgtcgagac aagattaacc actgccgctc cctctcttct   1020
gtgttcgatc ctgagaatct cggcatcaac tcaaccgtca atgatgtctg caaggatgcc   1080
gagacattct gctccaatga tgttcgcgat ccctacctca agttctctgg ccgcaactac   1140
tatgacatcg acagcttga ccccagccca ttcccagcac cattttacat ggcctggcta   1200
aatcagccgc atgtgcaggc agcactgggt gtgccactta ctggacacag tcaaacgat    1260 gttgtgtcta ccgcattccg tgcaattggt gactaccctc ggccagggtg ctggagaac    1320 ctggcttatt tgctggagaa tggcatcaag gtttcgcttg tttacggtga tcggactac    1380 gcatgcaact ggttcggtgg tgagctctca agtctgggaa tcaactacac tgacacccac    1440
gaattccata tgccggcta tgcaggtatc cagatcaata gcagctacat cggtggacag    1500
gtgaggcagt acggcaacct ctccttcgcc cgcgtctacg aggccggcca tgaggtgcca    1560
tcgtaccaac ccgagactgc actgcagata ttccaccgtt ccctgttcaa caaggatatc    1620
gctactggaa ccaaggacac gtcatcgcgc atggacggag gcaagtttta cggcacctcg    1680
```

-continued

```
ggccctgcgg actcgtttgg tttcaagaac aaacctccac cgcagcacgt ccacttctgt    1740
catatcttag acaccagcac ctgcaccaag gagcagatcc agtcagttga gaacggcact    1800
gccgccgtac gcagctggat cattgtcgac tccaactcga cctctctgtt ccccgaggta    1860
gttggctcag gggaacccac gccaacccct atgcctggag gggctactac actatctgct    1920
cacgggttct tgtatggcgt gacattatgg gctgttattg ttgtagctgt tatagagctg    1980
gcaatgtaa                                                            1989
```

<210> SEQ ID NO 15
<211> LENGTH: 662
<212> TYPE: PRT
<213> ORGANISM: Trichophyton rubrum

<400> SEQUENCE: 15

```
Met Val Ser Phe Cys Gly Val Ala Ala Cys Leu Leu Thr Val Ala Gly
  1               5                  10                  15

His Leu Ala Gln Ala Gln Phe Pro Pro Lys Pro Glu Gly Val Thr Val
                 20                  25                  30

Leu Glu Ser Lys Phe Gly Ser Gly Ala Arg Ile Thr Tyr Lys Glu Pro
             35                  40                  45

Gly Leu Cys Glu Thr Thr Glu Gly Val Lys Ser Tyr Ala Gly Tyr Val
         50                  55                  60

His Leu Pro Pro Gly Thr Leu Arg Asp Phe Gly Val Glu Gln Asp Tyr
 65                  70                  75                  80

Pro Ile Asn Thr Phe Phe Trp Phe Phe Glu Ala Arg Lys Asp Pro Glu
                 85                  90                  95

Asn Ala Pro Leu Gly Ile Trp Met Asn Gly Gly Pro Gly Ser Ser Ser
                100                 105                 110

Met Phe Gly Met Met Thr Glu Asn Gly Pro Cys Phe Val Asn Ala Asp
            115                 120                 125

Ser Asn Ser Thr Arg Leu Asn Pro His Ser Trp Asn Asn Glu Val Asn
        130                 135                 140

Met Leu Tyr Ile Asp Gln Pro Val Gln Val Gly Leu Ser Tyr Asp Thr
145                 150                 155                 160

Leu Ala Asn Phe Thr Arg Asn Leu Val Thr Asp Glu Ile Thr Lys Leu
                165                 170                 175

Lys Pro Gly Glu Pro Ile Pro Glu Gln Asn Ala Thr Phe Leu Val Gly
            180                 185                 190

Thr Tyr Ala Ser Arg Asn Met Asn Thr Thr Ala His Gly Thr Arg His
        195                 200                 205

Ala Ala Met Ala Leu Trp His Phe Ala Gln Val Trp Phe Gln Glu Phe
    210                 215                 220

Pro Gly Tyr His Pro Arg Asn Asn Lys Ile Ser Ile Ala Thr Glu Ser
225                 230                 235                 240

Tyr Gly Gly Arg Tyr Gly Pro Ala Phe Thr Ala Phe Phe Glu Glu Gln
                245                 250                 255

Asn Gln Lys Ile Lys Asn Gly Thr Trp Lys Gly His Glu Gly Thr Met
            260                 265                 270

His Val Leu His Leu Asp Thr Leu Met Ile Val Asn Gly Cys Ile Asp
        275                 280                 285

Arg Leu Val Gln Trp Pro Ala Tyr Pro Gln Met Ala Tyr Asn Asn Thr
    290                 295                 300

Tyr Ser Ile Glu Ala Val Asn Ala Ser Ile His Ala Gly Met Leu Asp
305                 310                 315                 320
```

```
Ala Leu Tyr Arg Asp Gly Gly Cys Arg Asp Lys Ile Asn His Cys Arg
            325                 330                 335

Ser Leu Ser Ser Val Phe Asp Pro Glu Asn Leu Gly Ile Asn Ser Thr
            340                 345                 350

Val Asn Asp Val Cys Lys Asp Ala Glu Thr Phe Cys Ser Asn Asp Val
            355                 360                 365

Arg Asp Pro Tyr Leu Lys Phe Ser Gly Arg Asn Tyr Tyr Asp Ile Gly
            370                 375                 380

Gln Leu Asp Pro Ser Pro Phe Pro Ala Pro Phe Tyr Met Ala Trp Leu
385                 390                 395                 400

Asn Gln Pro His Val Gln Ala Ala Leu Gly Val Pro Leu Asn Trp Thr
            405                 410                 415

Gln Ser Asn Asp Val Val Ser Thr Ala Phe Arg Ala Ile Gly Asp Tyr
            420                 425                 430

Pro Arg Pro Gly Trp Leu Glu Asn Leu Ala Tyr Leu Leu Glu Asn Gly
            435                 440                 445

Ile Lys Val Ser Leu Val Tyr Gly Asp Arg Asp Tyr Ala Cys Asn Trp
            450                 455                 460

Phe Gly Gly Glu Leu Ser Ser Leu Gly Ile Asn Tyr Thr Asp Thr His
465                 470                 475                 480

Glu Phe His Asn Ala Gly Tyr Ala Gly Ile Gln Ile Asn Ser Ser Tyr
            485                 490                 495

Ile Gly Gly Gln Val Arg Gln Tyr Gly Asn Leu Ser Phe Ala Arg Val
            500                 505                 510

Tyr Glu Ala Gly His Glu Val Pro Ser Tyr Gln Pro Glu Thr Ala Leu
            515                 520                 525

Gln Ile Phe His Arg Ser Leu Phe Asn Lys Asp Ile Ala Thr Gly Thr
            530                 535                 540

Lys Asp Thr Ser Ser Arg Met Asp Gly Lys Phe Tyr Gly Thr Ser
545                 550                 555                 560

Gly Pro Ala Asp Ser Phe Gly Phe Lys Asn Lys Pro Pro Gln His
            565                 570                 575

Val His Phe Cys His Ile Leu Asp Thr Ser Thr Cys Thr Lys Glu Gln
            580                 585                 590

Ile Gln Ser Val Glu Asn Gly Thr Ala Ala Val Arg Ser Trp Ile Ile
            595                 600                 605

Val Asp Ser Asn Ser Thr Ser Leu Phe Pro Glu Val Val Gly Ser Gly
            610                 615                 620

Glu Pro Thr Pro Thr Pro Met Pro Gly Gly Ala Thr Thr Leu Ser Ala
625                 630                 635                 640

His Gly Phe Leu Tyr Gly Val Thr Leu Trp Ala Val Ile Val Val Ala
            645                 650                 655

Val Ile Glu Leu Ala Met
            660

<210> SEQ ID NO 16
<211> LENGTH: 2030
<212> TYPE: DNA
<213> ORGANISM: Trichophyton rubrum

<400> SEQUENCE: 16
atgcgctttg ctgctagcat tgccgtggcc ctgccagtca ttcacgcggc gagtgctcaa      60
ggcttccctc cacccgttaa gggcgtcacc gtggtcaaat ccaagttcga cgaaaacgta     120
aagatcacat acaaggaggt atgtgtttac atcattttca catccagatc ttatatcctt     180
```

| | |
|---|---:|
| acaataaatc tggctaactc actggataga atgacatatg tgaaaccact caaggagtta | 240 |
| gatcattcac cggtcatgtc caccttcctc cagacaacga tgactttggt gtctaccgga | 300 |
| actactccat caacacattc ttctggttct ttgaagctcg tgaagaccct aagaatgctc | 360 |
| ctctctccat ctggctgaac ggtggtccgg gatcgtcatc catgattgga ctcttccagg | 420 |
| aaaacggtcc atgctgggtc aatgaagact ctaaatctac caccaacaat tcattttcat | 480 |
| ggaacaataa agtaaatatg ctctacattg atcagccaaa ccaagtcggt ttcagttatg | 540 |
| acgtacctac caacatcact tactctacca tcaatgatac aatatctgtt gcggacttct | 600 |
| ctaacggtgt ccctgcgcaa aatctttcta cgttggttgg aaccggcagc agccagaacc | 660 |
| cttgggcaac tgccaataac actgtgaacg ctgctcgttc tatctggcac tttgcacaag | 720 |
| tgtggttcca ggaattccct gaacacaagc ctaacaataa caagatcagt atttggacag | 780 |
| agtcctatgg aggaagatat ggtccctcat tcgcctctta cttccaggaa cagaacgaaa | 840 |
| agatcaaaaa ccataccatt actgaagaag gagagatgca tattctgaac ctcgacaccc | 900 |
| tcggtatcat caacggctgc atcgatctta tgttccaagc agaaagttat gctgaattcc | 960 |
| catacaacaa cacctatggc atcaaagctt ataccaagga gaagcgtgac gctatattac | 1020 |
| acgacatcca ccgtcctgac ggctgcttcg acaaggttac caagtgccgt gaggccgcga | 1080 |
| aagaaggaga ccctcacttc tacagcaaca atgcaaccgt caacacaatc tgtgcggatg | 1140 |
| ctaactctgc ctgcgacaaa tatctaatgg atcctttcca agagaccaat cttggttact | 1200 |
| atgatattgc tcatcctctt caggatccct tcccccacc attctataag ggcttcctca | 1260 |
| gccaatccag cgttctatct gacatgggat cgccagtcaa cttctcccaa tacgcccaag | 1320 |
| ctgtgggaaa atcattccat ggagttggcg actacgctcg ccctgatgtg cgcggcttca | 1380 |
| ccggtgacat tgcttatctt ctcgagagcg gagtcaaggt tgctctcgtc tatggtgaca | 1440 |
| gagactacat ctgcaattgg ttcggtggtg agcaggtcag tcttggcttg aactacactg | 1500 |
| gcacccaaga cttccacagg gcaaaatatg ccgatgtcaa ggtcaactct tcatacgtcg | 1560 |
| gaggcgtagt gcgtcaacat ggaaacttct cttcaccag agttttcgag gccggtcatg | 1620 |
| aagtccctgg ttaccaaccc gagactgccc tcaagatctt tgagcgcatc atgttcaaca | 1680 |
| aggatatttc taccggtgag atcgacattg ctcagaaacc agactacggt accactggaa | 1740 |
| ctgagtctac gttccatatc aaaaacgata ccctccttc gcctgagccg acctgctacc | 1800 |
| tcctcagtgc tgacggaacc tgtaccccgg agcagcttaa tgctattaag gatggaactg | 1860 |
| cagttgttga gaactacatt attaagagcc ctgctgcgtc gaaggggaac cctccaccaa | 1920 |
| ccacgacctc atctcccaca gcagccccta ccgctggaag tgccatgcta aaggctcctg | 1980 |
| tggcaatgct agcaatatca gctctcactg tccttgcttt cttcttgtag | 2030 |

<210> SEQ ID NO 17
<211> LENGTH: 1959
<212> TYPE: DNA
<213> ORGANISM: Trichophyton rubrum

<400> SEQUENCE: 17

| | |
|---|---:|
| atgcgctttg ctgctagcat tgccgtggcc ctgccagtca ttcacgcggc gagtgctcaa | 60 |
| ggcttccctc cacccgttaa gggcgtcacc gtggtcaaat ccaagttcga cgaaaacgta | 120 |
| aagatcacat acaaggagaa tgacatatgt gaaaccactc aaggagttag atcattcacc | 180 |
| ggtcatgtcc accttcctcc agacaacgat gactttggtg tctaccggaa ctactccatc | 240 |
| aacacattct tctggttctt tgaagctcgt gaagaccta agaatgctcc tctctccatc | 300 |

-continued

```
tggctgaacg gtggtccggg atcgtcatcc atgattggac tcttccagga aaacggtcca   360
tgctgggtca atgaagactc taaatctacc accaacaatt cattttcatg aacaataaa    420
gtaaatatgc tctacattga tcagccaaac caagtcggtt tcagttatga cgtacctacc   480
aacatcactt actctaccat caatgataca atatctgttg cggacttctc taacggtgtc   540
cctgcgcaaa atctttctac gttggttgga accggcagca gccagaaccc ttgggcaact   600
gccaataaca ctgtgaacgc tgctcgttct atctggcact tgcacaagt gtggttccag    660
gaattccctg aacacaagcc taacaataac aagatcagta tttggacaga gtcctatgga   720
ggaagatatg gtccctcatt cgcctcttac ttccaggaac agaacgaaaa gatcaaaaac   780
cataccatta ctgaagaagg agagatgcat attctgaacc tcgacaccct cggtatcatc   840
aacggctgca tcgatcttat gttccaagca gaaagttatg ctgaattccc atacaacaac   900
acctatggca tcaaagctta taccaaggag aagcgtgacg ctatattaca cgacatccac   960
cgtcctgacg gctgcttcga caaggttacc aagtgccgtg aggccgcgaa agaaggagac  1020
cctcacttct acagcaacaa tgcaaccgtc aacacaatct gtgcggatgc taactctgcc  1080
tgcgacaaat atctaatgga tccttttccaa gagaccaatc ttggttacta tgatattgct  1140
catcctcttc aggatccctt cccccccacca ttctataagg gcttcctcag ccaatccagc  1200
gttctatctg acatgggatc gccagtcaac ttctcccaat acgcccaagc tgtgggaaaa  1260
tcattccatg gagttggcga ctacgctcgc cctgatgtgc gcggcttcac cggtgacatt  1320
gcttatcttc tcgagagcgg agtcaaggtt gctctcgtct atggtgacag agactacatc  1380
tgcaattggt tcggtggtga gcaggtcagt cttggcttga actacactgg cacccaagac  1440
ttccacaggg caaaatatgc cgatgtcaag gtcaactctt catacgtcgg aggcgtagtg  1500
cgtcaacatg gaaacttctc ttttcaccaga gttttcgagg ccggtcatga agtccctggt  1560
taccaacccg agactgccct caagatcttt gagcgcatca tgttcaacaa ggatatttct  1620
accggtgaga tcgacattgc tcagaaacca gactacggta ccactggaac tgagtctacg  1680
ttccatatca aaacgatat ccctccttcg cctgagccga cctgctacct cctcagtgct  1740
gacggaacct gtaccccgga gcagcttaat gctattaagg atggaactgc agttgttgag  1800
aactacatta ttaagagccc tgctgcgtcg aagggggaacc ctccaccaac cacgacctca  1860
tctcccacag cagcccctac cgctggaagt gccatgctaa aggctcctgt ggcaatgcta  1920
gcaatatcag ctctcactgt ccttgctttc ttcttgtag                         1959
```

<210> SEQ ID NO 18
<211> LENGTH: 652
<212> TYPE: PRT
<213> ORGANISM: Trichophyton rubrum

<400> SEQUENCE: 18

Met Arg Phe Ala Ala Ser Ile Ala Val Ala Leu Pro Val Ile His Ala
 1               5                  10                  15

Ala Ser Ala Gln Gly Phe Pro Pro Val Lys Gly Val Thr Val Val
                20                  25                  30

Lys Ser Lys Phe Asp Glu Asn Val Lys Ile Thr Tyr Lys Glu Asn Asp
             35                  40                  45

Ile Cys Glu Thr Thr Gln Gly Val Arg Ser Phe Thr Gly His Val His
         50                  55                  60

Leu Pro Pro Asp Asn Asp Asp Phe Gly Val Tyr Arg Asn Tyr Ser Ile
 65                  70                  75                  80

Asn Thr Phe Phe Trp Phe Phe Glu Ala Arg Glu Asp Pro Lys Asn Ala

-continued

```
                85                  90                  95
Pro Leu Ser Ile Trp Leu Asn Gly Gly Pro Gly Ser Ser Ser Met Ile
            100                 105                 110
Gly Leu Phe Gln Glu Asn Gly Pro Cys Trp Val Asn Glu Asp Ser Lys
            115                 120                 125
Ser Thr Thr Asn Asn Ser Phe Ser Trp Asn Asn Lys Val Asn Met Leu
            130                 135                 140
Tyr Ile Asp Gln Pro Asn Gln Val Gly Phe Ser Tyr Asp Val Pro Thr
145                 150                 155                 160
Asn Ile Thr Tyr Ser Thr Ile Asn Asp Thr Ile Ser Val Ala Asp Phe
                165                 170                 175
Ser Asn Gly Val Pro Ala Gln Asn Leu Ser Thr Leu Val Gly Thr Gly
            180                 185                 190
Ser Ser Gln Asn Pro Trp Ala Thr Ala Asn Asn Thr Val Asn Ala Ala
            195                 200                 205
Arg Ser Ile Trp His Phe Ala Gln Val Trp Phe Gln Glu Phe Pro Glu
210                 215                 220
His Lys Pro Asn Asn Asn Lys Ile Ser Ile Trp Thr Glu Ser Tyr Gly
225                 230                 235                 240
Gly Arg Tyr Gly Pro Ser Phe Ala Ser Tyr Phe Gln Glu Gln Asn Glu
                245                 250                 255
Lys Ile Lys Asn His Thr Ile Thr Glu Gly Glu Met His Ile Leu
            260                 265                 270
Asn Leu Asp Thr Leu Gly Ile Ile Asn Gly Cys Ile Asp Leu Met Phe
            275                 280                 285
Gln Ala Glu Ser Tyr Ala Glu Phe Pro Tyr Asn Asn Thr Tyr Gly Ile
            290                 295                 300
Lys Ala Tyr Thr Lys Glu Lys Arg Asp Ala Ile Leu His Asp Ile His
305                 310                 315                 320
Arg Pro Asp Gly Cys Phe Asp Lys Val Thr Lys Cys Arg Glu Ala Ala
                325                 330                 335
Lys Glu Gly Asp Pro His Phe Tyr Ser Asn Asn Ala Thr Val Asn Thr
            340                 345                 350
Ile Cys Ala Asp Ala Asn Ser Ala Cys Asp Lys Tyr Leu Met Asp Pro
            355                 360                 365
Phe Gln Glu Thr Asn Leu Gly Tyr Tyr Asp Ile Ala His Pro Leu Gln
            370                 375                 380
Asp Pro Phe Pro Pro Phe Tyr Lys Gly Phe Leu Ser Gln Ser Ser
385                 390                 395                 400
Val Leu Ser Asp Met Gly Ser Pro Val Asn Phe Ser Gln Tyr Ala Gln
                405                 410                 415
Ala Val Gly Lys Ser Phe His Gly Val Gly Asp Tyr Ala Arg Pro Asp
            420                 425                 430
Val Arg Gly Phe Thr Gly Asp Ile Ala Tyr Leu Leu Glu Ser Gly Val
            435                 440                 445
Lys Val Ala Leu Val Tyr Gly Asp Arg Asp Tyr Ile Cys Asn Trp Phe
450                 455                 460
Gly Gly Glu Gln Val Ser Leu Gly Leu Asn Tyr Thr Gly Thr Gln Asp
465                 470                 475                 480
Phe His Arg Ala Lys Tyr Ala Asp Val Lys Val Asn Ser Ser Tyr Val
                485                 490                 495
Gly Gly Val Val Arg Gln His Gly Asn Phe Ser Phe Thr Arg Val Phe
            500                 505                 510
```

```
Glu Ala Gly His Glu Val Pro Gly Tyr Gln Pro Glu Thr Ala Leu Lys
        515                 520                 525

Ile Phe Glu Arg Ile Met Phe Asn Lys Asp Ile Ser Thr Gly Glu Ile
    530                 535                 540

Asp Ile Ala Gln Lys Pro Asp Tyr Gly Thr Thr Gly Thr Glu Ser Thr
545                 550                 555                 560

Phe His Ile Lys Asn Asp Ile Pro Pro Ser Pro Glu Pro Thr Cys Tyr
                565                 570                 575

Leu Leu Ser Ala Asp Gly Thr Cys Thr Pro Glu Gln Leu Asn Ala Ile
            580                 585                 590

Lys Asp Gly Thr Ala Val Val Glu Asn Tyr Ile Ile Lys Ser Pro Ala
        595                 600                 605

Ala Ser Lys Gly Asn Pro Pro Pro Thr Thr Thr Ser Ser Pro Thr Ala
    610                 615                 620

Ala Pro Thr Ala Gly Ser Ala Met Leu Lys Ala Pro Val Ala Met Leu
625                 630                 635                 640

Ala Ile Ser Ala Leu Thr Val Leu Ala Phe Phe Leu
                645                 650
```

```
<210> SEQ ID NO 19
<211> LENGTH: 1795
<212> TYPE: DNA
<213> ORGANISM: Trichophyton rubrum
<220> FEATURE:
<221> NAME/KEY: modified_base
<222> LOCATION: (283)
<223> OTHER INFORMATION: a, c, g, t, unknown or other

<400> SEQUENCE: 19
atgcaagcag caaaattgtt gagccggtac tggcaaaatg tacctggtta gtgcagctaa      60
tcttgagtca catcatgcat agttaaccga gtatcacaac acaatctact attgcgtttt     120
tgctaatggc taccatagga agactgaggg tatctgagct cctttcgat gtcccttttag     180 actactcaaa cccgtcttcc acttcgctcc ggttgttcgc caggagtgtg cagcggcgaa     240
ttccagggtc ctctctcgat gataaagaca gacagctacc ctngattgt tttcctgcag     300 ggtggaccag gaggagcttg cccacaacct caggaggtag gctgggttgg gccattgctg     360
gatcgaggat tccaggtgag tctccagaat cgggatgagt aactgtagaa cacccttgttg    420 aatttcttga ttagatcctt ctccttgacc agcgaggaac agggctttca accctataa      480 ccgctgcgac gcttgctctt cagggaaacg cagtaaagca agccgaatat cttaggctat    540
tccgtgccga taatatcgtg cgagactgtg aagcagtgcg taaactattg actgcttatt   600
accctccaga taagcagaaa tggagcgtcc ttggccagag ttttggagga ttctgtgccg   660
tcacgtatgt ttctaagtag tgagtaacta ctccttcaaa tccacctgct atagattgtc   720
gtgcaaatct aaccttcatc atctagtcct gagggactta agaagtcttc acaactggt    780 ggattacccc ctcttgtgtc aaagcctgat cctgtgtacg agaggaccta cggtaagttg   840
ggatagattg ggctattttt agtttaatat acagctgaca tctacagaca aggtccagtc    900
ccggaataaa gtgtactatt ccactttccc cgaagacgaa gatcgagtgc ggattatact    960
caagcatctc caaacccacg atgttaagct ccccgatggc tcaccgttaa ctccggaacg   1020 cttctccag ctaggaattc attttggaat gaaaggtacg ccatacttcg caggtgactt    1080
ctcgtaacca atgactaaca tatgcatata gggggcatcg gcttagttca tagtatgata    1140
ccatcaataa cttacattat acttattcac tgactaacaa tgtcgaaata tcaggcataa    1200
ttttgaagtg cattaatgaa ctggaatact ttggcttcct cacacgacct actttatctc    1260
```

```
tgattgagaa cgacacgagt gcagacaacg gcattctata tgccataatg catgaatcta    1320
tctactgcca agggtaaaac gtctctcctg atcgagtcaa tatcagaatc taacgtgata    1380
ccgtagggag gcctcaaact gggctgccga aagactacta ccaaagttct ctggcttccg    1440
aggcgctcat aatcctgatg gcatctactt cactggggag atggtataca aacactggtt    1500
tgagtcgtcc acagaactcg gccagctcaa agaggtagcc gatattcttg cttcctacaa    1560
tgactggccg cagttgtatg ataaggaaca gctcgcgcgc aacgaggtgc cagtgtattc    1620
cgctacatat gtcgaggata tgtacgtgca cttcagctac gccaacgaaa cagctgccac    1680
tattcacaat tgcaaacagt tcatcaccaa cacgatgtac cacaacggac tgcgttcaga    1740
ttccgctgaa cttattgcgc agctgtttgc tcttcgtgat gatacgattg actag         1795
```

<210> SEQ ID NO 20
<211> LENGTH: 1326
<212> TYPE: DNA
<213> ORGANISM: Trichophyton rubrum

<400> SEQUENCE: 20

```
atgcaagcag caaaattgtt gagccggtac tggcaaaatg tacctggaag actgagggta      60
tctgagctcc ttttcgatgt ccctttagac tactcaaacc cgtcttccac ttcgctccgg     120
ttgttcgcca ggagtgtgca gcggcgaatt ccagggtcct ctctcgatga taagacaga     180 cagctaccct ggattgtttt cctgcagggt ggaccaggag gagcttgccc acaacctcag    240
gaggtaggct gggttgggcc attgctggat cgaggattcc agatccttct ccttgaccag    300
cgaggaacag ggctttcaac ccctataacc gctgcgacgc ttgctcttca gggaaacgca    360
gtaaagcaag ccgaatatct taggctattc cgtgccgata atatcgtgcg agactgtgaa    420
gcagtgcgta aactattgac tgcttattac cctccagata gcagaaatg gagcgtcctt     480 ggccagagtt ttggaggatt ctgtgccgtc acgtatgttt ctaatcctga gggacttaaa    540
gaagtcttca caactggtgg attacccct cttgtgtcaa agcctgatcc tgtgtacgag     600
aggacctacg acaaggtcca gtcccggaat aaagtgtact attccacttt ccccgaagac    660
gaagatcgag tgcggattat actcaagcat ctccaaaccc acgatgttaa gctccccgat    720
ggctcaccgt taactccgga acgctttctc cagctaggaa ttcattttgg aatgaaaggc    780 ataatttga agtgcattaa tgaactggaa tactttggct tcctcacacg acctacttta    840
tctctgattg agaacgacac gagtgcagac aacggcattc tatatgccat aatgcatgaa    900
tctatctact gccaagggga ggcctcaaac tgggctgccg aaagactact accaaagttc    960
tctggcttcc gaggcgctca taatcctgat ggcatctact tcactgggga gatggtatac    1020
aaacactggt ttgagtcgtc cacagaactc ggccagctca agaggtagc cgatattctt    1080 gcttcctaca tgactggcc gcagttgtat gataaggaac agctcgcgcg caacgaggtg    1140
ccagtgtatt ccgctacata tgtcgaggat atgtacgtgc acttcagcta cgccaacgaa    1200
acagctgcca ctattcacaa ttgcaaacag ttcatcacca acacgatgta ccacaacgga    1260
ctgcgttcag attccgctga acttattgcg cagctgtttg ctcttcgtga tgatacgatt   1320
gactag                                                                1326
```

<210> SEQ ID NO 21
<211> LENGTH: 441
<212> TYPE: PRT
<213> ORGANISM: Trichophyton rubrum

<400> SEQUENCE: 21

Met Gln Ala Ala Lys Leu Leu Ser Arg Tyr Trp Gln Asn Val Pro Gly
1               5                   10                  15

Arg Leu Arg Val Ser Glu Leu Leu Phe Asp Val Pro Leu Asp Tyr Ser
            20                  25                  30

Asn Pro Ser Ser Thr Ser Leu Arg Leu Phe Ala Arg Ser Val Gln Arg
        35                  40                  45

Arg Ile Pro Gly Ser Ser Leu Asp Asp Lys Asp Arg Gln Leu Pro Trp
    50                  55                  60

Ile Val Phe Leu Gln Gly Gly Pro Gly Gly Ala Cys Pro Gln Pro Gln
65                  70                  75                  80

Glu Val Gly Trp Val Gly Pro Leu Leu Asp Arg Gly Phe Gln Ile Leu
                85                  90                  95

Leu Leu Asp Gln Arg Gly Thr Gly Leu Ser Thr Pro Ile Thr Ala Ala
            100                 105                 110

Thr Leu Ala Leu Gln Gly Asn Ala Val Lys Gln Ala Glu Tyr Leu Arg
        115                 120                 125

Leu Phe Arg Ala Asp Asn Ile Val Arg Asp Cys Glu Ala Val Arg Lys
    130                 135                 140

Leu Leu Thr Ala Tyr Tyr Pro Pro Asp Lys Gln Lys Trp Ser Val Leu
145                 150                 155                 160

Gly Gln Ser Phe Gly Gly Phe Cys Ala Val Thr Tyr Val Ser Asn Pro
                165                 170                 175

Glu Gly Leu Lys Glu Val Phe Thr Thr Gly Gly Leu Pro Pro Leu Val
            180                 185                 190

Ser Lys Pro Asp Pro Val Tyr Glu Arg Thr Tyr Asp Lys Val Gln Ser
        195                 200                 205

Arg Asn Lys Val Tyr Tyr Ser Thr Phe Pro Glu Asp Glu Asp Arg Val
    210                 215                 220

Arg Ile Ile Leu Lys His Leu Gln Thr His Asp Val Lys Leu Pro Asp
225                 230                 235                 240

Gly Ser Pro Leu Thr Pro Glu Arg Phe Leu Gln Leu Gly Ile His Phe
                245                 250                 255

Gly Met Lys Gly Ile Ile Leu Lys Cys Ile Asn Glu Leu Glu Tyr Phe
            260                 265                 270

Gly Phe Leu Thr Arg Pro Thr Leu Ser Leu Ile Glu Asn Asp Thr Ser
        275                 280                 285

Ala Asp Asn Gly Ile Leu Tyr Ala Ile Met His Glu Ser Ile Tyr Cys
    290                 295                 300

Gln Gly Glu Ala Ser Asn Trp Ala Ala Glu Arg Leu Leu Pro Lys Phe
305                 310                 315                 320

Ser Gly Phe Arg Gly Ala His Asn Pro Asp Gly Ile Tyr Phe Thr Gly
                325                 330                 335

Glu Met Val Tyr Lys His Trp Phe Glu Ser Ser Thr Glu Leu Gly Gln
            340                 345                 350

Leu Lys Glu Val Ala Asp Ile Leu Ala Ser Tyr Asn Asp Trp Pro Gln
        355                 360                 365

Leu Tyr Asp Lys Glu Gln Leu Ala Arg Asn Glu Val Pro Val Tyr Ser
    370                 375                 380

Ala Thr Tyr Val Glu Asp Met Tyr Val His Phe Ser Tyr Ala Asn Glu
385                 390                 395                 400

Thr Ala Ala Thr Ile His Asn Cys Lys Gln Phe Ile Thr Asn Thr Met
                405                 410                 415

Tyr His Asn Gly Leu Arg Ser Asp Ser Ala Glu Leu Ile Ala Gln Leu

| | | 420 | | | 425 | | | 430 | |
|---|---|---|---|---|---|---|---|---|---|

Phe Ala Leu Arg Asp Asp Thr Ile Asp
435 440

<210> SEQ ID NO 22
<211> LENGTH: 2418
<212> TYPE: DNA
<213> ORGANISM: Trichophyton rubrum

<400> SEQUENCE: 22

| atgccgccac | caccggttga | cacgacccag | cgtctcgcaa | agctgcgaga | gctgatggct | 60 |
|---|---|---|---|---|---|---|
| cagaacaagg | tcgatgtata | tagtatgcaa | ttcagataca | ccattaaagc | tcccttgata | 120 |
| ataacagtcg | tatactcatt | cttctttctt | ctactcctcg | ccttaaagtt | gtgccttcgg | 180 |
| aagacagcca | tcagtcggag | tacattgctc | catgtgatgg | gcgtcgaggt | tagacctgtc | 240 |
| cctccataaa | agaataccta | cccgtaatac | cagccggcag | acgctcatac | gtatcactgc | 300 |
| agctttcata | tccagcttca | ctggctcggc | aggatgtgcc | atcgtctcta | tgagtaaagc | 360 |
| tgctctgtct | acagacggca | gatacttcag | ccaagctgca | aaacagctcg | atgccaactg | 420 |
| gatcctgttg | aagcgaggtg | tcgagggtgt | cccaacctgg | aagaatggt | atatctgccc | 480 |
| ctggtatcga | cttttccggt | ataatggttg | acaggctgga | tataggaccg | ctgagcaggc | 540 |
| cgagacacgg | caaggttgtg | ggtgttgacc | cgtcacttat | tacggcaggt | gagaatctac | 600 |
| agtatgcgtc | tcttacaagt | gtcatcgtga | ctaactgtat | gttatagcgg | atgcacgaaa | 660 |
| gctttctcag | acgttgaaga | ccaccggagg | ctccttggtt | ggaattgatc | agaacctgat | 720 |
| tgatgccgtc | tggggagatg | aacgtcctgc | acggcctgcc | aaccaaatta | cggtacagcc | 780 |
| tgttgagcgc | gcgggaaagt | cattcgagga | gaaagtggaa | gacctgcgaa | aggaattgac | 840 |
| tgcgaagaag | aggtctgcta | tggttatttg | tatgacgcta | gatctatttt | tgatcaaaca | 900 |
| tatactaaca | aacgcaatat | agccaccttg | gatgagattg | catggctctt | caacctccgt | 960 |
| ggaagcgagt | aagtttctat | ataaatggta | tctttcactt | tatacaaaaa | gccatgctga | 1020 |
| ctggtgtagt | attccatata | accccgtctt | tttctcgtac | gcaattgtga | cgccctcagt | 1080 |
| tgcggaactc | tatgtcgatg | agagcaagct | gtctccagaa | gccagaaaac | atctcgaagg | 1140 |
| caaggtcgtt | ctcaagccat | acgagtccat | cttccaagct | tccaaagtcc | tgccgaatc | 1200 |
| aaaggcatcg | gctagcagcg | gttcctctgg | gaagttcttg | ttgtctaaca | aggcttcgtg | 1260 |
| gtctttgagc | ctcgcccctcg | gtggggaaca | gaacgtcgtt | gaggttcgaa | gtcccatcac | 1320 |
| tgacgccaaa | gccatcaaga | acgaagttga | actggaagga | ttcagaaaat | gccatatccg | 1380 |
| agacggtgca | gctctgatcg | agtacttcgc | ctggcttgaa | aatgcattga | tcaaagaagg | 1440 |
| tgccaagcta | gacgaagtag | atggagccga | caaactcttc | gagatccgca | agaaatatga | 1500 |
| cctcttcgtc | ggcaactcct | tcgacaccat | ctcttctacc | ggtgctaacg | gtgctaccat | 1560 |
| tcattacaaa | cccgagaagt | caacttgcgc | tatcattgac | ccgaaggcta | tgtacctgtg | 1620 |
| tgactctggt | ggccaatacc | ttgatggtac | tactgatact | acccgaactc | tccactttgg | 1680 |
| agagcccacg | gagttccaga | agaaggctta | tgcacttgtt | ctaaagggac | atatcagcat | 1740 |
| tgacaatgcc | attttcccca | aaggaaccac | cggatacgcc | attgactcgt | tgctcgaca | 1800 |
| gcatttgtga | aaggagggtc | tggattacct | ccacggcacc | ggtcatggtg | ttggctcatt | 1860 |
| tttggtacgg | ggtttccttt | ttctttttttt | ttctttttttt | tattttatt | attacttctc | 1920 |
| ttaggctaac | acattctctc | taagaacgtc | catgagggac | ctatgggcat | aggaagccgt | 1980 |
| gctcagtacg | ctgaagttcc | tctctctgcc | agcaatgttc | tttccaacgg | taggatttct | 2040 |

```
gcatctcatc tttcttgaat cctactaatt gcaaaataga gcctggatat tatgaagacg    2100
gcaacttcgg cattcgtctc gagagtaagt tcaatgactg cgtattctag ttttttcata    2160
ctgacggcct ctttagacct cgtaatctgc aaggaggtcc agactgcaca caaattcggc    2220
gacaagccct tcctcggatt tgagtccatc accctggtac ctttctgcca aaaactcctt    2280
gatgcttctc tcttgaccga agctgagaga aagtgggtga atgattacca tgcgaaagtc    2340
tgggagaaga ccagtccctt ctttgagaag gacgagttaa caaccgcctg gctaaagcgc    2400
gagacacaac ctatttaa                                                  2418

<210> SEQ ID NO 23
<211> LENGTH: 1878
<212> TYPE: DNA
<213> ORGANISM: Trichophyton rubrum

<400> SEQUENCE: 23
atgccgccac caccggttga cacgacccag cgtctcgcaa agctgcgaga gctgatggct      60
cagaacaagg tcgatgtata tattgtgcct tcggaagaca gccatcagtc ggagtacatt     120
gctccatgtg atgggcgtcg agctttcata tccagcttca ctggctcggc aggatgtgcc     180
atcgtctcta tgagtaaagc tgctctgtct acagacggca gatacttcag ccaagctgca     240
aaacagctcg atgccaactg gatcctgttg aagcgaggtg tcgagggtgt cccaacctgg     300
gaagaatgga ccgctgagca ggccgagaca cggcaaggtt gtgggtcgga tgcacgaaag     360
ctttctcaga cgttgaagac caccggaggc tccttggttg gaattgatca gaaccctgat     420
gatgccgtct ggggagatga acgtcctgca cggcctgcca accaaattac ggtacagcct     480
gttgagcgcg cgggaaagtc attcgaggag aaagtggaag acctgcgaaa ggaattgact     540
gcgaagaaga ggtctgctat ggttatttcg agtaagtttc tatataaatg gtatctttca     600
ctttatacaa aaagccatgc tgactggtgt agtattccat ataacccgt cttttttctcg      660 tacgcaattg tgacgccctc agttgcggaa ctctatgtcg atgagagcaa gctgtctcca     720
gaagccagaa acatctcga aggcaaggtc gttctcaagc catacgagtc catcttccaa      780
gcttccaaag tcctcgccga atcaaaggca tcggctagca gcggttcctc tgggaagttc     840
ttgttgtcta acaaggcttc gtggtctttg agcctcgccc tcggtgggga acagaacgtc     900
gttgaggttc gaagtcccat cactgacgcc aaagccatca gaacgaagt tgaactggaa      960 ggattcagaa aatgccatat ccgagacggt gcagctctga tcgagtactt cgcctggctt    1020
gaaaatgcat tgatcaaaga aggtgccaag ctagacgaag tagatggagc cgacaaactc    1080
ttcgagatcc gcaagaaata tgacctcttc gtcggcaact ccttcgacac catctcttct    1140
accggtgcta acggtgctac cattcattac aaacccgaga agtcaacttg cgctatcatt    1200
gacccgaagg ctatgtacct gtgtgactct ggtggccaat accttgatgg tactactgat    1260
actacccgaa ctctccactt ggagagccc acggagttcc agaagaaggc ttatgcactt     1320
gttctaaagg gacatatcag cattgacaat gccattttcc ccaaaggaac caccggatac    1380
gccattgact cgtttgctcg acagcatttg tggaaggagg gtctggatta cctccacggc    1440
accggtcatg tgttggctc attttttgaac gtccatgagg gacctatggg cataggaagc     1500
cgtgctcagt acgctgaagt tcctctctct gccagcaata gcctggatat tatgaagacg    1560
gcaacttcgg cattcgtctc gagagtaagt tcaatgactg cgtattctag ttttttcata    1620
ctgacggcct ctttagacct cgtaatctgc aaggaggtcc agactgcaca caaattcggc    1680
gacaagccct tcctcggatt tgagtccatc accctggtac ctttctgcca aaaactcctt    1740
```

```
gatgcttctc tcttgaccga agctgagaga aagtgggtga atgattacca tgcgaaagtc   1800
tgggagaaga ccagtcccct ctttgagaag gacgagttaa caaccgcctg gctaaagcgc   1860
gagacacaac ctatttaa                                                 1878
```

<210> SEQ ID NO 24
<211> LENGTH: 625
<212> TYPE: PRT
<213> ORGANISM: Trichophyton rubrum

<400> SEQUENCE: 24

```
Met Pro Pro Pro Val Asp Thr Thr Gln Arg Leu Ala Lys Leu Arg
 1               5                  10                  15

Glu Leu Met Ala Gln Asn Lys Val Asp Val Tyr Ile Val Pro Ser Glu
                20                  25                  30

Asp Ser His Gln Ser Glu Tyr Ile Ala Pro Cys Asp Gly Arg Arg Ala
            35                  40                  45

Phe Ile Ser Ser Phe Thr Gly Ser Ala Gly Cys Ala Ile Val Ser Met
        50                  55                  60

Ser Lys Ala Ala Leu Ser Thr Asp Gly Arg Tyr Phe Ser Gln Ala Ala
 65                  70                  75                  80

Lys Gln Leu Asp Ala Asn Trp Ile Leu Leu Lys Arg Gly Val Glu Gly
                85                  90                  95

Val Pro Thr Trp Glu Glu Trp Thr Ala Glu Gln Ala Glu Thr Arg Gln
            100                 105                 110

Gly Cys Gly Ser Asp Ala Arg Lys Leu Ser Gln Thr Leu Lys Thr Thr
        115                 120                 125

Gly Gly Ser Leu Val Gly Ile Asp Gln Asn Leu Ile Asp Ala Val Trp
    130                 135                 140

Gly Asp Glu Arg Pro Ala Arg Pro Ala Asn Gln Ile Thr Val Gln Pro
145                 150                 155                 160

Val Glu Arg Ala Gly Lys Ser Phe Glu Glu Lys Val Glu Asp Leu Arg
                165                 170                 175

Lys Glu Leu Thr Ala Lys Lys Arg Ser Ala Met Val Ile Ser Ser Lys
            180                 185                 190

Phe Leu Tyr Lys Trp Tyr Leu Ser Leu Tyr Thr Lys Ser His Ala Asp
        195                 200                 205

Trp Cys Ser Ile Pro Tyr Asn Pro Val Phe Phe Ser Tyr Ala Ile Val
    210                 215                 220

Thr Pro Ser Val Ala Glu Leu Tyr Val Asp Glu Ser Lys Leu Ser Pro
225                 230                 235                 240

Glu Ala Arg Lys His Leu Glu Gly Lys Val Val Leu Lys Pro Tyr Glu
                245                 250                 255

Ser Ile Phe Gln Ala Ser Lys Val Leu Ala Glu Ser Lys Ala Ser Ala
            260                 265                 270

Ser Ser Gly Ser Ser Gly Lys Phe Leu Leu Ser Asn Lys Ala Ser Trp
        275                 280                 285

Ser Leu Ser Leu Ala Leu Gly Gly Glu Gln Asn Val Val Glu Val Arg
    290                 295                 300

Ser Pro Ile Thr Asp Ala Lys Ala Ile Lys Asn Glu Val Glu Leu Glu
305                 310                 315                 320

Gly Phe Arg Lys Cys His Ile Arg Asp Gly Ala Ala Leu Ile Glu Tyr
                325                 330                 335

Phe Ala Trp Leu Glu Asn Ala Leu Ile Lys Glu Gly Ala Lys Leu Asp
            340                 345                 350
```

```
Glu Val Asp Gly Ala Asp Lys Leu Phe Glu Ile Arg Lys Lys Tyr Asp
            355                 360                 365

Leu Phe Val Gly Asn Ser Phe Asp Thr Ile Ser Ser Thr Gly Ala Asn
    370                 375                 380

Gly Ala Thr Ile His Tyr Lys Pro Glu Lys Ser Thr Cys Ala Ile Ile
385                 390                 395                 400

Asp Pro Lys Ala Met Tyr Leu Cys Asp Ser Gly Gly Gln Tyr Leu Asp
                405                 410                 415

Gly Thr Thr Asp Thr Thr Arg Thr Leu His Phe Gly Glu Pro Thr Glu
            420                 425                 430

Phe Gln Lys Lys Ala Tyr Ala Leu Val Leu Lys Gly His Ile Ser Ile
        435                 440                 445

Asp Asn Ala Ile Phe Pro Lys Gly Thr Thr Gly Tyr Ala Ile Asp Ser
    450                 455                 460

Phe Ala Arg Gln His Leu Trp Lys Glu Gly Leu Asp Tyr Leu His Gly
465                 470                 475                 480

Thr Gly His Gly Val Gly Ser Phe Leu Asn Val His Glu Gly Pro Met
                485                 490                 495

Gly Ile Gly Ser Arg Ala Gln Tyr Ala Glu Val Pro Leu Ser Ala Ser
            500                 505                 510

Asn Ser Leu Asp Ile Met Lys Thr Ala Thr Ser Ala Phe Val Ser Arg
        515                 520                 525

Val Ser Ser Met Thr Ala Tyr Ser Ser Phe Phe Ile Leu Thr Ala Ser
    530                 535                 540

Leu Asp Leu Val Ile Cys Lys Glu Val Gln Thr Ala His Lys Phe Gly
545                 550                 555                 560

Asp Lys Pro Phe Leu Gly Phe Glu Ser Ile Thr Leu Val Pro Phe Cys
                565                 570                 575

Gln Lys Leu Leu Asp Ala Ser Leu Leu Thr Glu Ala Glu Arg Lys Trp
            580                 585                 590

Val Asn Asp Tyr His Ala Lys Val Trp Glu Lys Thr Ser Pro Phe Phe
        595                 600                 605

Glu Lys Asp Glu Leu Thr Thr Ala Trp Leu Lys Arg Glu Thr Gln Pro
    610                 615                 620

Ile
625

<210> SEQ ID NO 25
<211> LENGTH: 2344
<212> TYPE: DNA
<213> ORGANISM: Trichophyton rubrum

<400> SEQUENCE: 25
atcaacctca cctcttcacc gtctcacgcc cttcgtcccg tccaactctt catttcgccc      60
tctctatgat aaccaacaaa catccgctgt tatgtaatcg aacccgccgt tagccatccc    120
tagccccgcg ttttctccca gcatcaatac gaccgaaatg aagacagacg gggaagacga    180
ggcaaaacaa taacacatca acaatttaac ccgttgccgt cttctaccca tcttgtctac    240
gcatcgtcca acctttctt gccctatatc agccgaactc ggccatcatg gatatccacg    300
tcgacaaata cccggctaag agtcacgcca ggcgcgtcgc cgagaagctc aaggccgcgg    360
ggcacggctc taccggcatc atcttcgtcg aaggccaaaa ggagcatatt atcgatgata    420
gcgacgagcc gtttcacttc cggtgagccg tgggaataca ctcgactggg cggaataagc    480
taacaaaagg gtgtgatagt caacgccgaa acttcctcta tctgtccggc tgtcttgagg    540
```

```
ccgagtgctc cgttgcatac aacatcgaga aagatgagct tacattgttc attccaccag      600
tcgacccagc ctcggttatg tggtccggcc tccctcttga gcccgccgaa gccttgaagc      660
agttcgatgt tgatgccgtg ctcctcacaa ctgagataaa caactatctc gcgaagtgtg      720
ggggcgagaa ggtcttcacc attgcagaca gagtttgccc ggaggtctcc ttctcatcct      780
tcaagcacaa cgacaccgat gccctgaagc ttgccatcga gtcctgccgt atagtgaaag      840
acgagtatga aattggtctt ctccgacgtg ctaatgaggt ctccagccaa gctcatattg      900
aagtgatgaa agccgcaacc aagtcaaaga cgagagaga gctctatgct actctcaact      960
atgtctgcat gtctaatggc tgctccgacc agtcttacca tccaattctt gcatgtggcc     1020
ccaatgctgc cactctccac tacaccaaga acaacggtga cctaactaac ccggctaccg     1080
ggattaagga ccagctcgta cttatcgacg ctggatgcca gtacaaggcg tactgtgcag     1140
atatcactcg tgcattcccc ttgtccggca aattcaccac ggagggccgc cagatctatg     1200
atattgcctt ggagatgcag aaagtcgcgt ttggcatgat caaacctaat gttttgttcg     1260
acgacatgca tgctgcggtc caccgggttg cgatcaaggg gctgctcaag attggcattc     1320
tcactggctc tgaggatgag attttcgata agggaatcag cactgccttt ttcccacatg     1380
gtctaggcca ccatctcggc atggacactc acgatgttgg aggaaaccct aacccggctg     1440
acccgaatcg catgtttaaa tacttgcgtc tgcgaggcac tgttccagag ggatccgtca     1500
ttacaattga gcccggtgta agtgttgaat cgagtagttg ctccgccgaa tgtttcacat     1560
acatttacta acccttgctc taggtctact tctgccgtta catcattgag ccattcctta     1620
ctaaccccga gaccagcaag tacatcaact ccgaagttct agacaagtac tgggctgttg     1680
gaggtgtacg tatcgaggac aacgtcgtcg tccgcgccaa tggctttgag aacctgacca     1740
cggtgccaaa ggagcccgag gaggtcgaac gcattgtcca ggagggtgct aaataattat     1800 gttttattc agtacaccga gtggtcgac acacgcagga gcatgtacat atttatgatc     1860
tacccagttg atttgctacc aaaaaagaac cgaccacagc cctatttatt gatattacat     1920
agtaggaata aaggccactt tgcccaccgc gaataataac aataagaaaa gcaactactc     1980
gtacaaccag cctagaaagc tctagacctc tttctcgctg ggcccttgaa tgccgggcta     2040
ctggtgttat cacgctccct ggccctcttc tccttcatgt ccaacacccg attaagcaaa     2100
tcgaaactga actggggatg ctcaagacac aatgccttga actgctcttc agcatcatga     2160
cgcagcacat cactcatctt agcccagaag cgagcaaccg gtcctctgat gcagtgtct      2220 tccggcgtgg tatggctgta cacgtatctc gcatactcga tctcacccgt agcactactc     2280
tcgatgctac caatcttgtt ctgagcaagc agtttgagtt tttcgtttcc gagcttttcg     2340
gcca                                                                  2344
```

<210> SEQ ID NO 26
<211> LENGTH: 1401
<212> TYPE: DNA
<213> ORGANISM: Trichophyton rubrum

<400> SEQUENCE: 26

```
ccgaactcgg ccatcatgga tatccacgtc gacaaatacc cggctaagag tcacgccagg       60
cgcgtcgccg agaagctcaa ggccgcgggg cacggctcta ccggcatcat cttcgtcgaa      120
ggccaaaagg agcatattat cgatgatagc gacgagccgt ttcacttccg tcaacgccga      180
aacttcctct atctgtccgg ctgtcttgag gccgagtgct ccgttgcata caacatcgag      240
aaagatgagc ttacattgtt cattccacca gtcgacccag cctcggttat gtggtccggc      300
```

```
ctccctcttg agcccgccga agccttgaag cagttcgatg ttgatgccgt gctcctcaca    360
actgagataa acaactatct cgcgaagtgt gggggcgaga aggtcttcac cattgcagac    420
agagtttgcc cggaggtctc cttctcatcc ttcaagcaca acgacaccga tgccctgaag    480
cttgccatcg agtcctgccg tatagtgaaa gacgagtatg aaattggtct tctccgacgt    540
gctaatgagg tctccagcca agctcatatt gaagtgatga agccgcaac caagtcaaag    600 aacgagagag agctctatgc tactctcaac tatgtctgca tgtctaatgg ctgctccgac    660
cagtcttacc atccaattct tgcatgtggc cccaatgctg ccactctcca ctacaccaag    720
aacaacggtg acctaactaa cccggctacc gggattaagg accagctcgt acttatcgac    780
gctggatgcc agtacaaggc gtactgtgca gatatcactc gtgcattccc cttgtccggc    840
aaattcacca cggagggccg ccagatctat gatattgcct tggagatgca gaaagtcgcg    900
tttggcatga tcaaacctaa tgttttgttc gacgacatgc atgctgcggt ccaccgggtt    960
gcgatcaagg ggctgctcaa gattggcatt ctcactggct ctgaggatga gattttcgat   1020
aagggaatca gcactgcctt tttcccacat ggtctaggcc accatctcgg catggacact   1080
cacgatgttg gaggaaaccc taacccggct gacccgaatc gcatgtttaa atacttgcgt   1140
ctgcgaggca ctgttccaga gggatccgtc attacaattg agcccggtgt ctacttctgc   1200
cgttacatca ttgagccatt ccttactaac cccgagacca gcaagtacat caactccgaa   1260
gttctagaca agtactgggc tgttggaggt gtacgtatcg aggacaacgt cgtcgtccgc   1320
gccaatggct ttgagaacct gaccacggtg ccaaaggagc ccgaggaggt cgaacgcatt   1380
gtccaggagg gtgctaaata a                                             1401
```

<210> SEQ ID NO 27
<211> LENGTH: 466
<212> TYPE: PRT
<213> ORGANISM: Trichophyton rubrum

<400> SEQUENCE: 27

```
Pro Asn Ser Ala Ile Met Asp Ile His Val Asp Lys Tyr Pro Ala Lys
  1               5                  10                  15

Ser His Ala Arg Arg Val Ala Glu Lys Leu Lys Ala Ala Gly His Gly
                 20                  25                  30

Ser Thr Gly Ile Ile Phe Val Glu Gly Gln Lys Glu His Ile Ile Asp
             35                  40                  45

Asp Ser Asp Glu Pro Phe His Phe Arg Gln Arg Arg Asn Phe Leu Tyr
         50                  55                  60

Leu Ser Gly Cys Leu Glu Ala Glu Cys Ser Val Ala Tyr Asn Ile Glu
 65                  70                  75                  80

Lys Asp Glu Leu Thr Leu Phe Ile Pro Pro Val Asp Pro Ala Ser Val
                 85                  90                  95

Met Trp Ser Gly Leu Pro Leu Glu Pro Ala Ala Leu Lys Gln Phe
                100                 105                 110

Asp Val Asp Ala Val Leu Leu Thr Thr Glu Ile Asn Asn Tyr Leu Ala
            115                 120                 125

Lys Cys Gly Gly Glu Lys Val Phe Thr Ile Ala Asp Arg Val Cys Pro
        130                 135                 140

Glu Val Ser Phe Ser Ser Phe Lys His Asn Asp Thr Asp Ala Leu Lys
145                 150                 155                 160

Leu Ala Ile Glu Ser Cys Arg Ile Val Lys Asp Glu Tyr Glu Ile Gly
                165                 170                 175
```

```
Leu Leu Arg Arg Ala Asn Glu Val Ser Ser Gln Ala His Ile Glu Val
                180                 185                 190
Met Lys Ala Ala Thr Lys Ser Lys Asn Glu Arg Glu Leu Tyr Ala Thr
            195                 200                 205
Leu Asn Tyr Val Cys Met Ser Asn Gly Cys Ser Asp Gln Ser Tyr His
        210                 215                 220
Pro Ile Leu Ala Cys Gly Pro Asn Ala Ala Thr Leu His Tyr Thr Lys
225                 230                 235                 240
Asn Asn Gly Asp Leu Thr Asn Pro Ala Thr Gly Ile Lys Asp Gln Leu
                245                 250                 255
Val Leu Ile Asp Ala Gly Cys Gln Tyr Lys Ala Tyr Cys Ala Asp Ile
            260                 265                 270
Thr Arg Ala Phe Pro Leu Ser Gly Lys Phe Thr Thr Glu Gly Arg Gln
        275                 280                 285
Ile Tyr Asp Ile Ala Leu Glu Met Gln Lys Val Ala Phe Gly Met Ile
290                 295                 300
Lys Pro Asn Val Leu Phe Asp Asp Met His Ala Ala Val His Arg Val
305                 310                 315                 320
Ala Ile Lys Gly Leu Leu Lys Ile Gly Ile Leu Thr Gly Ser Glu Asp
                325                 330                 335
Glu Ile Phe Asp Lys Gly Ile Ser Thr Ala Phe Phe Pro His Gly Leu
            340                 345                 350
Gly His His Leu Gly Met Asp Thr His Asp Val Gly Gly Asn Pro Asn
        355                 360                 365
Pro Ala Asp Pro Asn Arg Met Phe Lys Tyr Leu Arg Leu Arg Gly Thr
370                 375                 380
Val Pro Glu Gly Ser Val Ile Thr Ile Glu Pro Gly Val Tyr Phe Cys
385                 390                 395                 400
Arg Tyr Ile Ile Glu Pro Phe Leu Thr Asn Pro Glu Thr Ser Lys Tyr
                405                 410                 415
Ile Asn Ser Glu Val Leu Asp Lys Tyr Trp Ala Val Gly Gly Val Arg
            420                 425                 430
Ile Glu Asp Asn Val Val Val Arg Ala Asn Gly Phe Glu Asn Leu Thr
        435                 440                 445
Thr Val Pro Lys Glu Pro Glu Glu Val Glu Arg Ile Val Gln Glu Gly
    450                 455                 460
Ala Lys
465

<210> SEQ ID NO 28
<211> LENGTH: 1730
<212> TYPE: DNA
<213> ORGANISM: Microsporum canis

<400> SEQUENCE: 28
atgaagacac agttgttgag tctgggagtt gccctcacgg ccatctctca gggcgttatt      60
gctgaggatg ccttgaactg gccattcaag ccgttggtta atgctgtgag tatatacaca     120
agatcgatcg atcgtcctct tgtccctgtc acttatcgct ctacagtaag caaaaatact     180
ggagaatcat gtgctgatgt aaatgtatag gatgacctgc aaaacaagat taagctcaag     240
gatcttatgc ctggcgtaca gaaactccaa gacttcgcct acgctcaccc tgagaagaat     300
cgagtattcg gtggtgctgg ccacaaggat accgtcgact ggatctacaa tgagctcaag     360
gctaccggct actacgatgt gaagatgcag ccacaagtcc acctgtggtc tcatgctgag     420
gcagctgtca atgccaatgg caaggatctc actgccagtg ccatgtccta cagcccttca     480
```

```
gccgacaaga tcactgccga gcttgtcctg gccaagaaca tgggatgcaa tgctgtatgt      540
gcgccccttt tccattctat atatcgactg gtcgcttgga aattcagaag agctgacaat      600
tgcaaacaga ctgattaccc agagggtacc aagggcaaga ttgtcctcat cgagcgtggt      660
gtctgcagct ttggcgagaa gtccgctcag gctggcgatg caaaggctat tggtgccatc      720
gtctacaaca acgtccctgg aagcttggcc ggcaccctgg gtggccttga caaccgccat      780
gctccaactg ctggaatctc tcaggctgat ggaaagaacc tcgctagcct tgtcgcctct      840
ggcaaggtta ccgtcaccat gaacgttatc agcaagtttg agaacaggac tacgtgagta      900
ttgttccata cttttggtcaa caatgatata tacacgtact aacactgctc tatagctgga     960
acgtcattgc cgagaccaag ggaggagacc acaacaacgt catcatgctc ggttctcact     1020
ctgactctgt cgacgccggc cctggtatca acgacaacgg ctccggtacc attggtatca     1080
tgaccgttgc caaagccctc accaacttca aggtcaacaa cgccgtccgc ttcggctggt     1140
ggaccgccga ggagttcggc cttctcggca gcactttcta cgtcgacagc cttgacgacc     1200
gtgaactgca aaggtcaag ctgtacctca acttcgacat gattggctcc cccaacttcg      1260
ccaaccagat ctacgacgga gacggctccg cctacaacat gactggcccc gccggatctg     1320
ctgaaatcga gtacctgttc gagaagttct tcgatgacca gggaatccca caccagccca     1380
ccgccttcac cggccgctcc gactactctg ccttcatcaa gcgcaacgtc cctgccggag     1440
gtctgtttac tggtgctgag gtcgtcaaga ccgccgagca ggctaagcta tttggcggcg     1500
aggctggcgt tgcttatgac aagaactacc acggcaaggg cgacactgta gacaacatca     1560
acaagggtgc tatctacctc aacactcgag gaatcgcgta tgccactgct cagtatgcta     1620
gttcgctgcg cggattccca acccgcccaa agacgggtaa gcgtgacgtg agccccgtg      1680 gccagtctat gcctggtggt ggatgcggac accacagcgt cttcatgtaa                 1730

<210> SEQ ID NO 29
<211> LENGTH: 1488
<212> TYPE: DNA
<213> ORGANISM: Microsporum canis

<400> SEQUENCE: 29
atgaagacac agttgttgag tctgggagtt gccctcacgg ccatctctca gggcgttatt       60
gctgaggatg ccttgaactg gccattcaag ccgttggtta atgctgatga cctgcaaaac      120
aagattaagc tcaaggatct tatggctggc gtacagaaac tccaagactt cgcctacgct      180
caccctgaga gaatcgagt attcggtggt gctggccaca aggataccgt cgactggatc      240
tacaatgagc tcaaggctac cggctactac gatgtgaaga tgcagccaca agtccacctg      300
tggtctcatg ctgaggcagc tgtcaatgcc aatggcaagg atctcactgc cagtgccatg      360
tcctacagcc ctccagccga caagatcact gccgagcttg tcctggccaa gaacatggga      420
tgcaatgcta ctgattaccc agagggtacc aagggcaaga ttgtcctcat cgagcgtggt      480
gtctgcagct ttggcgagaa gtccgctcag gctggcgatg caaaggctat tggtgccatc      540
gtctacaaca acgtccctgg aagcttggcc ggcaccctgg gtggccttga caaccgccat      600
gctccaactg ctggaatctc tcaggctgat ggaaagaacc tcgctagcct tgtcgcctct      660
ggcaaggtta ccgtcaccat gaacgttatc agcaagtttg agaacaggac tacctggaac     720
gtcattgccg agaccaaggg aggagaccac aacaacgtca tcatgctcgg ttctcactct     780
gactctgtcg acgccggccc tggtatcaac gacaacggct ccggtaccat ggtatcatg      840 accgttgcca aagccctcac caacttcaag gtcaacaacg ccgtccgctt cggctggtgg     900
```

```
accgccgagg agttcggcct tctcggcagc actttctacg tcgacagcct tgacgaccgt        960
gaactgcaca aggtcaagct gtacctcaac ttcgacatga ttggctcccc caacttcgcc       1020
aaccagatct acgacggaga cggctccgcc tacaacatga ctggcccgc cggatctgct        1080 gaaatcgagt acctgttcga aagttcttc gatgaccagg gaatcccaca ccagcccacc       1140
gccttcaccg gccgctccga ctactctgcc ttcatcaagc gcaacgtccc tgccggaggt       1200
ctgtttactg gtgctgaggt cgtcaagacc gccgagcagg ctaagctatt tggcggcgag      1260
gctggcgttg cttatgacaa gaactaccac ggcaagggcg acactgtaga caacatcaac      1320
aagggtgcta tctacctcaa cactcgagga atcgcgtatg ccactgctca gtatgctagt     1380
tcgctgcgcg gattcccaac ccgcccaaag acgggtaagc gtgacgtgag cccccgtggc      1440
cagtctatgc ctggtggtgg atgcggacac cacagcgtct tcatgtaa                   1488
```

```
<210> SEQ ID NO 30
<211> LENGTH: 495
<212> TYPE: PRT
<213> ORGANISM: Microsporum canis

<400> SEQUENCE: 30

Met Lys Thr Gln Leu Leu Ser Leu Gly Val Ala Leu Thr Ala Ile Ser
 1               5                  10                  15

Gln Gly Val Ile Ala Glu Asp Ala Leu Asn Trp Pro Phe Lys Pro Leu
             20                  25                  30

Val Asn Ala Asp Asp Leu Gln Asn Lys Ile Lys Leu Lys Asp Leu Met
         35                  40                  45

Ala Gly Val Gln Lys Leu Gln Asp Phe Ala Tyr Ala His Pro Glu Lys
     50                  55                  60

Asn Arg Val Phe Gly Gly Ala Gly His Lys Asp Thr Val Asp Trp Ile
 65                  70                  75                  80

Tyr Asn Glu Leu Lys Ala Thr Gly Tyr Tyr Asp Val Lys Met Gln Pro
                 85                  90                  95

Gln Val His Leu Trp Ser His Ala Glu Ala Ala Val Asn Ala Asn Gly
            100                 105                 110

Lys Asp Leu Thr Ala Ser Ala Met Ser Tyr Ser Pro Pro Ala Asp Lys
        115                 120                 125

Ile Thr Ala Glu Leu Val Leu Ala Lys Asn Met Gly Cys Asn Ala Thr
    130                 135                 140

Asp Tyr Pro Glu Gly Thr Lys Gly Lys Ile Val Leu Ile Glu Arg Gly
145                 150                 155                 160

Val Cys Ser Phe Gly Glu Lys Ser Ala Gln Ala Gly Asp Ala Lys Ala
                165                 170                 175

Ile Gly Ala Ile Val Tyr Asn Asn Val Pro Gly Ser Leu Ala Gly Thr
            180                 185                 190

Leu Gly Gly Leu Asp Asn Arg His Ala Pro Thr Ala Gly Ile Ser Gln
        195                 200                 205

Ala Asp Gly Lys Asn Leu Ala Ser Leu Val Ala Ser Gly Lys Val Thr
    210                 215                 220

Val Thr Met Asn Val Ile Ser Lys Phe Glu Asn Arg Thr Thr Trp Asn
225                 230                 235                 240

Val Ile Ala Glu Thr Lys Gly Gly Asp His Asn Asn Val Ile Met Leu
                245                 250                 255

Gly Ser His Ser Asp Ser Val Asp Ala Gly Pro Gly Ile Asn Asp Asn
            260                 265                 270
```

```
Gly Ser Gly Thr Ile Gly Ile Met Thr Val Ala Lys Ala Leu Thr Asn
            275                 280                 285
Phe Lys Val Asn Asn Ala Val Arg Phe Gly Trp Trp Thr Ala Glu Glu
            290                 295                 300
Phe Gly Leu Leu Gly Ser Thr Phe Tyr Val Asp Ser Leu Asp Asp Arg
305                 310                 315                 320
Glu Leu His Lys Val Lys Leu Tyr Leu Asn Phe Asp Met Ile Gly Ser
                325                 330                 335
Pro Asn Phe Ala Asn Gln Ile Tyr Asp Gly Asp Gly Ser Ala Tyr Asn
            340                 345                 350
Met Thr Gly Pro Ala Gly Ser Ala Glu Ile Glu Tyr Leu Phe Glu Lys
            355                 360                 365
Phe Phe Asp Asp Gln Gly Ile Pro His Gln Pro Thr Ala Phe Thr Gly
            370                 375                 380
Arg Ser Asp Tyr Ser Ala Phe Ile Lys Arg Asn Val Pro Ala Gly Gly
385                 390                 395                 400
Leu Phe Thr Gly Ala Glu Val Val Lys Thr Ala Glu Gln Ala Lys Leu
                405                 410                 415
Phe Gly Gly Glu Ala Gly Val Ala Tyr Asp Lys Asn Tyr His Gly Lys
            420                 425                 430
Gly Asp Thr Val Asp Asn Ile Asn Lys Gly Ala Ile Tyr Leu Asn Thr
            435                 440                 445
Arg Gly Ile Ala Tyr Ala Thr Ala Gln Tyr Ala Ser Ser Leu Arg Gly
            450                 455                 460
Phe Pro Thr Arg Pro Lys Thr Gly Lys Arg Asp Val Ser Pro Arg Gly
465                 470                 475                 480
Gln Ser Met Pro Gly Gly Gly Cys Gly His His Ser Val Phe Met
                485                 490                 495

<210> SEQ ID NO 31
<211> LENGTH: 1775
<212> TYPE: DNA
<213> ORGANISM: Trichophyton mentagrophytes

<400> SEQUENCE: 31
atgaagtcgc aactgttgag cctagccgtg gccgtcacca ccatttccca gggcgttgtt      60
ggtcaagagc cctttggatg gcccttcaag cctatggtca ctcaggtgag ttgctgtcaa     120
cagatcgatc gatcgatcta ccttcgtccc tgtcacctat aactccacag caggaccaag     180
aaaacacaag ttttccgggg aattcttatg tgctgatgta aatgtatagg atgacctgca     240
aaacaagatt aagctcaagg atatcatggc aggtgtcgag aagctgcaaa gcttttctga     300
tgctcatcct gaaagaacc gagtgttcgg tggtaatggc cacaaggaca ctgtcgagtg     360
gatctacaat gagctcaagg ccaccggcta ctacaatgtg aagaagcagg agcaggtaca     420
cctgtggtct cacgctgagg ccgctctcag tgccaatggc aaggacctca aggccagcgc     480
catgtcgtac agccctcctg ccaacaagat catggccgag cttgtcgttg ccaagaacaa     540
tggctgcaat gctgtaagtg ccatacactt cctatacatc acattcactt tagaatgaag     600
agcgcgggag aactgatttt tttttttttt tttttttttt tgtaacagac cgattaccca     660
gagaacactc agggaaagat agtcctcatt cagcgtggtg tctgcagctt cggcgagaag     720
tcttctcagg ctggtgatgc gaaggctatt ggtgccgttg tctacaacaa cgtccccgga     780
tcccttgctg gcactcttgg tggccttgac aagcgccatg tcccaaccgc tggtctttcc     840
caggaggatg gaaagaatct tgctagcctc gttgcttctg gcaaggttga tgtcaccatg     900
```

-continued

| | |
|---|---|
| aacgttgtca gtctgtttga gaaccgaacc acgtaagtaa ctcaacgtca tatccagcat | 960 |
| taatcttcag gagtatatat actaattcgg tatctcacag ctggaacgtc attgctgaga | 1020 |
| ccaagggagg agaccacaac aatgttgtca tgcttggtgc tcactccgac tccgtcgatg | 1080 |
| ccggccccgg tatcaacgac aacggctccg gctccattgg tatcatgacc gttgccaaag | 1140 |
| cccttactaa cttcaagctc aacaacgccg ttcgctttgc ctggtggacc gctgaggaat | 1200 |
| tcggtctcct tggaagcacc ttctacgtcg acagccttga tgaccgtgag ctgcacaagg | 1260 |
| tcaagctgta cctcaacttc gacatgatcg gctctcccaa cttcgccaac cagatctacg | 1320 |
| acggtgacgg ttcggcctac aacatgactg gtcccgctgg ctctgctgaa atcgagtacc | 1380 |
| tgttcgagaa gttctttgac gaccagggtc tcccacacca gcccactgcc ttcaccggcc | 1440 |
| gatccgacta ctctgcattc atcaagcgca acgtccccgc tggaggtctt ttcactggtg | 1500 |
| ccgaggttgt caagaccccc gagcaagtta agctgttcgg tggtgaggct ggcgttgcct | 1560 |
| atgacaagaa ctaccatggc aagggtgaca ccgttgccaa catcaacaag ggagctatct | 1620 |
| tccttaacac tcgagcaatc gcctactctg tggccgagta tgctcgatcc ctcaagggct | 1680 |
| tcccaacccg cccaaagacc ggcaagcgtg ccgtcaaccc tcagtatgct aagatgcctg | 1740 |
| gtggtggttg cggacaccac actgtcttca tgtaa | 1775 |

<210> SEQ ID NO 32
<211> LENGTH: 1488
<212> TYPE: DNA
<213> ORGANISM: Trichophyton mentagrophytes

<400> SEQUENCE: 32

| | |
|---|---|
| atgaagtcgc aactgttgag cctagccgtg gccgtcacca ccatttccca gggcgttgtt | 60 |
| ggtcaagagc cctttggatg gcccttcaag cctatggtca ctcaggatga cctgcaaaac | 120 |
| aagattaagc tcaaggatat catggcaggt gtcgagaagc tgcaaagctt ttctgatgct | 180 |
| catcctgaaa agaaccgagt gttcggtggt aatggccaca aggacactgt cgagtggatc | 240 |
| tacaatgagc tcaaggccac cggctactac aatgtgaaga agcaggagca ggtacacctg | 300 |
| tggtctcacg ctgaggccgc tctcagtgcc aatggcaagg acctcaaggc cagcgccatg | 360 |
| tcgtacagcc ctcctgccaa caagatcatg gccgagcttg tcgttgccaa gaacaatggc | 420 |
| tgcaatgcta ccgattaccc agagaacact cagggaaaga tagtcctcat tcagcgtggt | 480 |
| gtctgcagct tcggcgagaa gtcttctcag gctggtgatg cgaaggctat tggtgccgtt | 540 |
| gtctacaaca acgtccccgg atcccttgct ggcactcttg gtggccttga caagcgccat | 600 |
| gtcccaaccg ctggtctttc ccaggaggat ggaaagaatc ttgctagcct cgttgcttct | 660 |
| ggcaaggttg atgtcaccat gaacgttgtc agtctgtttg agaaccgaac cacctggaac | 720 |
| gtcattgctg agaccaaggg aggagaccac aacaatgttg tcatgcttgg tgctcactcc | 780 |
| gactccgtcg atgccggccc cggtatcaac gacaacggct ccggctccat ggtatcatg | 840 |
| accgttgcca aagcccttac taacttcaag ctcaacaacg ccgttcgctt tgcctggtgg | 900 |
| accgctgagg aattcggtct ccttggaagc accttctacg tcgacagcct tgatgaccgt | 960 |
| gagctgcaca aggtcaagct gtacctcaac ttcgacatga tcggctctcc caacttcgcc | 1020 |
| aaccagatct acgacggtga cggttcggcc tacaacatga ctggtcccgc tggctctgct | 1080 |
| gaaatcgagt acctgttcga agttcttt gacgaccagg gtctcccaca ccagcccact | 1140 |
| gccttcaccg gccgatccga ctactctgca ttcatcaagc gcaacgtccc cgctggaggt | 1200 |
| cttttcactg gtgccgaggt tgtcaagacc cccgagcaag ttaagctgtt cggtggtgag | 1260 |

-continued

```
gctggcgttg cctatgacaa gaactaccat ggcaagggtg acaccgttgc caacatcaac    1320
aagggagcta tcttccttaa cactcgagca atcgcctact ctgtggccga gtatgctcga    1380
tccctcaagg gcttcccaac ccgcccaaag accggcaagc gtgccgtcaa ccctcagtat    1440
gctaagatgc ctggtggtgg ttgcggacac cacactgtct tcatgtaa                1488
```

```
<210> SEQ ID NO 33
<211> LENGTH: 495
<212> TYPE: PRT
<213> ORGANISM: Trichophyton mentagrophytes

<400> SEQUENCE: 33
```

| Met | Lys | Ser | Gln | Leu | Leu | Ser | Leu | Ala | Val | Ala | Val | Thr | Thr | Ile | Ser |
|---|---|---|---|---|---|---|---|---|---|---|---|---|---|---|---|
| 1 | | | | 5 | | | | | 10 | | | | | 15 | |

| Gln | Gly | Val | Val | Gly | Gln | Glu | Pro | Phe | Gly | Trp | Pro | Phe | Lys | Pro | Met |
|---|---|---|---|---|---|---|---|---|---|---|---|---|---|---|---|
| | | | 20 | | | | | 25 | | | | | 30 | | |

| Val | Thr | Gln | Asp | Asp | Leu | Gln | Asn | Lys | Ile | Lys | Leu | Lys | Asp | Ile | Met |
|---|---|---|---|---|---|---|---|---|---|---|---|---|---|---|---|
| | 35 | | | | | 40 | | | | | 45 | | | | |

| Ala | Gly | Val | Glu | Lys | Leu | Gln | Ser | Phe | Ser | Asp | Ala | His | Pro | Glu | Lys |
|---|---|---|---|---|---|---|---|---|---|---|---|---|---|---|---|
| 50 | | | | | 55 | | | | | 60 | | | | | |

| Asn | Arg | Val | Phe | Gly | Gly | Asn | Gly | His | Lys | Asp | Thr | Val | Glu | Trp | Ile |
|---|---|---|---|---|---|---|---|---|---|---|---|---|---|---|---|
| 65 | | | | | 70 | | | | | 75 | | | | | 80 |

| Tyr | Asn | Glu | Leu | Lys | Ala | Thr | Gly | Tyr | Tyr | Asn | Val | Lys | Lys | Gln | Glu |
|---|---|---|---|---|---|---|---|---|---|---|---|---|---|---|---|
| | | | | 85 | | | | | 90 | | | | | 95 | |

| Gln | Val | His | Leu | Trp | Ser | His | Ala | Glu | Ala | Ala | Leu | Ser | Ala | Asn | Gly |
|---|---|---|---|---|---|---|---|---|---|---|---|---|---|---|---|
| | | | 100 | | | | | 105 | | | | | 110 | | |

| Lys | Asp | Leu | Lys | Ala | Ser | Ala | Met | Ser | Tyr | Ser | Pro | Pro | Ala | Asn | Lys |
|---|---|---|---|---|---|---|---|---|---|---|---|---|---|---|---|
| | | 115 | | | | | 120 | | | | | 125 | | | |

| Ile | Met | Ala | Glu | Leu | Val | Val | Ala | Lys | Asn | Asn | Gly | Cys | Asn | Ala | Thr |
|---|---|---|---|---|---|---|---|---|---|---|---|---|---|---|---|
| | 130 | | | | | 135 | | | | | 140 | | | | |

| Asp | Tyr | Pro | Glu | Asn | Thr | Gln | Gly | Lys | Ile | Val | Leu | Ile | Gln | Arg | Gly |
|---|---|---|---|---|---|---|---|---|---|---|---|---|---|---|---|
| 145 | | | | | 150 | | | | | 155 | | | | | 160 |

| Val | Cys | Ser | Phe | Gly | Glu | Lys | Ser | Ser | Gln | Ala | Gly | Asp | Ala | Lys | Ala |
|---|---|---|---|---|---|---|---|---|---|---|---|---|---|---|---|
| | | | | 165 | | | | | 170 | | | | | 175 | |

| Ile | Gly | Ala | Val | Val | Tyr | Asn | Asn | Val | Pro | Gly | Ser | Leu | Ala | Gly | Thr |
|---|---|---|---|---|---|---|---|---|---|---|---|---|---|---|---|
| | | | 180 | | | | | 185 | | | | | 190 | | |

| Leu | Gly | Gly | Leu | Asp | Lys | Arg | His | Val | Pro | Thr | Ala | Gly | Leu | Ser | Gln |
|---|---|---|---|---|---|---|---|---|---|---|---|---|---|---|---|
| | | 195 | | | | | 200 | | | | | 205 | | | |

| Glu | Asp | Gly | Lys | Asn | Leu | Ala | Ser | Leu | Val | Ala | Ser | Gly | Lys | Val | Asp |
|---|---|---|---|---|---|---|---|---|---|---|---|---|---|---|---|
| | 210 | | | | | 215 | | | | | 220 | | | | |

| Val | Thr | Met | Asn | Val | Val | Ser | Leu | Phe | Glu | Asn | Arg | Thr | Thr | Trp | Asn |
|---|---|---|---|---|---|---|---|---|---|---|---|---|---|---|---|
| 225 | | | | | 230 | | | | | 235 | | | | | 240 |

| Val | Ile | Ala | Glu | Thr | Lys | Gly | Gly | Asp | His | Asn | Asn | Val | Val | Met | Leu |
|---|---|---|---|---|---|---|---|---|---|---|---|---|---|---|---|
| | | | | 245 | | | | | 250 | | | | | 255 | |

| Gly | Ala | His | Ser | Asp | Ser | Val | Asp | Ala | Gly | Pro | Gly | Ile | Asn | Asp | Asn |
|---|---|---|---|---|---|---|---|---|---|---|---|---|---|---|---|
| | | | 260 | | | | | 265 | | | | | 270 | | |

| Gly | Ser | Gly | Ser | Ile | Gly | Ile | Met | Thr | Val | Ala | Lys | Ala | Leu | Thr | Asn |
|---|---|---|---|---|---|---|---|---|---|---|---|---|---|---|---|
| | | 275 | | | | | 280 | | | | | 285 | | | |

| Phe | Lys | Leu | Asn | Asn | Ala | Val | Arg | Phe | Ala | Trp | Trp | Thr | Ala | Glu | Glu |
|---|---|---|---|---|---|---|---|---|---|---|---|---|---|---|---|
| | 290 | | | | | 295 | | | | | 300 | | | | |

| Phe | Gly | Leu | Leu | Gly | Ser | Thr | Phe | Tyr | Val | Asp | Ser | Leu | Asp | Asp | Arg |
|---|---|---|---|---|---|---|---|---|---|---|---|---|---|---|---|
| 305 | | | | | 310 | | | | | 315 | | | | | 320 |

| Glu | Leu | His | Lys | Val | Lys | Leu | Tyr | Leu | Asn | Phe | Asp | Met | Ile | Gly | Ser |
|---|---|---|---|---|---|---|---|---|---|---|---|---|---|---|---|
| | | | | 325 | | | | | 330 | | | | | 335 | |

| Pro | Asn | Phe | Ala | Asn | Gln | Ile | Tyr | Asp | Gly | Asp | Gly | Ser | Ala | Tyr | Asn |

```
              340             345             350
Met Thr Gly Pro Ala Gly Ser Ala Glu Ile Glu Tyr Leu Phe Glu Lys
        355                 360                 365

Phe Phe Asp Asp Gln Gly Leu Pro His Gln Pro Thr Ala Phe Thr Gly
    370                 375                 380

Arg Ser Asp Tyr Ser Ala Phe Ile Lys Arg Asn Val Pro Ala Gly Gly
385                 390                 395                 400

Leu Phe Thr Gly Ala Glu Val Val Lys Thr Pro Glu Gln Val Lys Leu
                405                 410                 415

Phe Gly Gly Glu Ala Gly Val Ala Tyr Asp Lys Asn Tyr His Gly Lys
            420                 425                 430

Gly Asp Thr Val Ala Asn Ile Asn Lys Gly Ala Ile Phe Leu Asn Thr
        435                 440                 445

Arg Ala Ile Ala Tyr Ser Val Ala Glu Tyr Ala Arg Ser Leu Lys Gly
    450                 455                 460

Phe Pro Thr Arg Pro Lys Thr Gly Lys Arg Ala Val Asn Pro Gln Tyr
465                 470                 475                 480

Ala Lys Met Pro Gly Gly Gly Cys Gly His His Thr Val Phe Met
                485                 490                 495

<210> SEQ ID NO 34
<211> LENGTH: 2326
<212> TYPE: DNA
<213> ORGANISM: Trichophyton rubrum
<220> FEATURE:
<221> NAME/KEY: modified_base
<222> LOCATION: (1835)
<223> OTHER INFORMATION: a, c, g, t, unknown or other

<400> SEQUENCE: 34
atgaagctcc tctcgctact tatgctggcg ggcatcgccc aagccatcgt tcctcctcgt      60
gagccccgtt caccaactgg tggcggcaac aagctgttga cctacaagga gtgtgtccct     120
agagctacta tctctccaag gtcgacgtcc cttgcctgga ttaacagtga agaagatggc     180
cggtacatct cccagtccga cgatggagca ttgatcctcc agaacatcgt cacgaacacc     240
aacaagactc tcgtggccgc agacaaggta cccaagggtt actatgacta ctggttcaag     300
ccagaccttt ctgctgtctt atgggcaacc aattacacca gcagtaccg tcactcttac      360 tttgccaact acttcattct agacatcaaa aagggatcgt tgacccctct agcccaggac     420
caggctggtg acatccagta tgctcaatgg agccccatga caactctat cgcctatgtc      480 cgtgraaacg acctgtatat ctggaacaat ggcaagacca agcgtattac cgaaaatggc     540
ggcccggata tcttcaatgg tgtccctgac tgggtatacg aggaagaaat cttcggggac     600
cggttcgctc tttggttctc acctgacggt gaataccttg cgtacctccg ctttaacgag     660
actggagtcc cgacctacac tattccgtac tacaagaaca gcaaaagat tgccctgcc      720 tacccaaggg agctggagat ccgttaccct aaagtctctg cgaagaaccc aaccgtgcag     780
ttccacctgt taaacattgc ttcatcccag gagacaacta tcccagttac tgcgttcccg     840
gaaaacgatc ttgtgatcgg tgaggttgct ggctcagca gtggccatga tagtgtagca     900
tatcgtgctt tcaaccgtgt ccaggataga gaaaagattg tcagcgtcaa ggttgagtcc     960
aaggaatcca aggttattcg cgaaagagat ggcaccgacg gctggatcga caaccttctc    1020
tcatgtcata tatcggaaac gttaacggca aggagtacta cgtcgatata tctgatgctt    1080
ctggctgggc acatatctac ctctacccgg ttgatggagg aaaggagatt gcactaacaa    1140
agggagaatg ggaagtcgtt gccattctca aggttgacac gaagaagaag ctgatctact    1200
```

```
tcacctctac caaatatcac agcaccactc gacacgtcta ctctgtctcg tatgacacaa   1260
aggtcatgac ccctctcgtc aacgataagg aggctgcgta ctacactgca tccttctcgg   1320
ccaagggtgg ttactatatc ttgtcctacc aaggtccaaa tgttccatac caagaacttt   1380
actccaccaa ggacagtaag aagcctctca agacaatcac tagcaatgat gcattgctcg   1440
agaagctgaa ggagtacaag ctccccaagg ttagcttctt tgagatcaag cttccatctg   1500
gtgaaaccct taatgttaag caacgcctac cacctaactt caacccacac aagaagtacc   1560
ccgtcctctt cactccgtat ggtggccctg gtgcccaaga ggtaagccag gcatggaatt   1620
cattggactt caagtcctac attacatctg accctgagct tgaatacgtt acctggactg   1680
ttgacaaccg tggaaccggc tacaagggcc gcaagttccg cagcgccgta gctaagcgtc   1740
tcggtttcct cgaagcccag gaccaggtct ttgctgctaa ggaggtgctg aaaaaccgtt   1800
gggctgataa ggaccatatt ggaatctggg gctgnagcta tggcggcttc ctgaccgcta   1860
agaccctcga gaccgacagt ggtgtattca cttttggtat cagtactgct cctgtctctg   1920
atttcagact ctacgacagc atgtacactg agcgttacat gaagaccgtt gaactaaacg   1980
ctgacggcta cagtgagacc gccgtgcaca aggttgatgg ctttaagaac ctcaaaggtc   2040
attactcatc cagcatggaa ccggtgacga caacgtccac ttccaaaacg ccgctgtcct   2100
ttccaacacc ctgatgaacg gcggtgtaac tgcagacaag ttgactactc agtggtttac   2160
tgactcggac cacggcatca gatacgatat ggactccact taccagtaca gcagctttc    2220 taagatggtc tacgaccaga agcaacgaag gccagaaagc ccaccaatgc accaatggag   2280
caagagagtt ttggctgccc tgtttggtga gagggcagag gaatga               2326
```

```
<210> SEQ ID NO 35
<211> LENGTH: 775
<212> TYPE: PRT
<213> ORGANISM: Trichophyton rubrum
<220> FEATURE:
<221> NAME/KEY: MOD_RES
<222> LOCATION: (162)
<223> OTHER INFORMATION: Variable amino acid
<220> FEATURE:
<221> NAME/KEY: MOD_RES
<222> LOCATION: (612)
<223> OTHER INFORMATION: Variable amino acid

<400> SEQUENCE: 35
```

```
Met Lys Leu Leu Ser Leu Leu Met Leu Ala Gly Ile Ala Gln Ala Ile
 1               5                  10                  15

Val Pro Pro Arg Glu Pro Arg Ser Pro Thr Gly Gly Gly Asn Lys Leu
            20                  25                  30

Leu Thr Tyr Lys Glu Cys Val Pro Arg Ala Thr Ile Ser Pro Arg Ser
        35                  40                  45

Thr Ser Leu Ala Trp Ile Asn Ser Glu Glu Asp Gly Arg Tyr Ile Ser
    50                  55                  60

Gln Ser Asp Asp Gly Ala Leu Ile Leu Gln Asn Ile Val Thr Asn Thr
65                  70                  75                  80

Asn Lys Thr Leu Val Ala Ala Asp Lys Val Pro Lys Gly Tyr Tyr Asp
                85                  90                  95

Tyr Trp Phe Lys Pro Asp Leu Ser Ala Val Leu Trp Ala Thr Asn Tyr
            100                 105                 110

Thr Lys Gln Tyr Arg His Ser Tyr Phe Ala Asn Tyr Phe Ile Leu Asp
        115                 120                 125

Ile Lys Lys Gly Ser Leu Thr Pro Leu Ala Gln Asp Gln Ala Gly Asp
```

```
                130                 135                 140
Ile Gln Tyr Ala Gln Trp Ser Pro Met Asn Asn Ser Ile Ala Tyr Val
145                 150                 155                 160

Arg Xaa Asn Asp Leu Tyr Ile Trp Asn Asn Gly Lys Thr Lys Arg Ile
                165                 170                 175

Thr Glu Asn Gly Gly Pro Asp Ile Phe Asn Gly Val Pro Asp Trp Val
                180                 185                 190

Tyr Glu Glu Ile Phe Gly Asp Arg Phe Ala Leu Trp Phe Ser Pro
                195                 200                 205

Asp Gly Glu Tyr Leu Ala Tyr Leu Arg Phe Asn Glu Thr Gly Val Pro
210                 215                 220

Thr Tyr Thr Ile Pro Tyr Tyr Lys Asn Lys Gln Lys Ile Ala Pro Ala
225                 230                 235                 240

Tyr Pro Arg Glu Leu Glu Ile Arg Tyr Pro Lys Val Ser Ala Lys Asn
                245                 250                 255

Pro Thr Val Gln Phe His Leu Leu Asn Ile Ala Ser Ser Gln Glu Thr
                260                 265                 270

Thr Ile Pro Val Thr Ala Phe Pro Glu Asn Asp Leu Val Ile Gly Glu
                275                 280                 285

Val Ala Trp Leu Ser Ser Gly His Asp Ser Val Ala Tyr Arg Ala Phe
290                 295                 300

Asn Arg Val Gln Asp Arg Glu Lys Ile Val Ser Val Lys Val Glu Ser
305                 310                 315                 320

Lys Glu Ser Lys Val Ile Arg Glu Arg Asp Gly Thr Asp Gly Trp Ile
                325                 330                 335

Asp Asn Leu Leu Ser Met Ser Tyr Ile Gly Asn Val Asn Gly Lys Glu
                340                 345                 350

Tyr Tyr Val Asp Ile Ser Asp Ala Ser Gly Trp Ala His Ile Tyr Leu
                355                 360                 365

Tyr Pro Val Asp Gly Gly Lys Glu Ile Ala Leu Thr Lys Gly Glu Trp
                370                 375                 380

Glu Val Val Ala Ile Leu Lys Val Asp Thr Lys Lys Lys Leu Ile Tyr
385                 390                 395                 400

Phe Thr Ser Thr Lys Tyr His Ser Thr Thr Arg His Val Tyr Ser Val
                405                 410                 415

Ser Tyr Asp Thr Lys Val Met Thr Pro Leu Val Asn Asp Lys Glu Ala
                420                 425                 430

Ala Tyr Tyr Thr Ala Ser Phe Ser Ala Lys Gly Gly Tyr Tyr Ile Leu
                435                 440                 445

Ser Tyr Gln Gly Pro Asn Val Pro Tyr Gln Glu Leu Tyr Ser Thr Lys
450                 455                 460

Asp Ser Lys Lys Pro Leu Lys Thr Ile Thr Ser Asn Asp Ala Leu Leu
465                 470                 475                 480

Glu Lys Leu Lys Glu Tyr Lys Leu Pro Lys Val Ser Phe Phe Glu Ile
                485                 490                 495

Lys Leu Pro Ser Gly Glu Thr Leu Asn Val Lys Gln Arg Leu Pro Pro
                500                 505                 510

Asn Phe Asn Pro His Lys Lys Tyr Pro Val Leu Phe Thr Pro Tyr Gly
                515                 520                 525

Gly Pro Gly Ala Gln Glu Val Ser Gln Ala Trp Asn Ser Leu Asp Phe
                530                 535                 540

Lys Ser Tyr Ile Thr Ser Asp Pro Glu Leu Glu Tyr Val Thr Trp Thr
545                 550                 555                 560
```

-continued

```
Val Asp Asn Arg Gly Thr Gly Tyr Lys Gly Arg Lys Phe Arg Ser Ala
            565                 570                 575

Val Ala Lys Arg Leu Gly Phe Leu Glu Ala Gln Asp Gln Val Phe Ala
        580                 585                 590

Ala Lys Glu Val Leu Lys Asn Arg Trp Ala Asp Lys Asp His Ile Gly
    595                 600                 605

Ile Trp Gly Xaa Ser Tyr Gly Gly Phe Leu Thr Ala Lys Thr Leu Glu
610                 615                 620

Thr Asp Ser Gly Val Phe Thr Phe Gly Ile Ser Thr Ala Pro Val Ser
625                 630                 635                 640

Asp Phe Arg Leu Tyr Asp Ser Met Tyr Thr Glu Arg Tyr Met Lys Thr
                645                 650                 655

Val Glu Leu Asn Ala Asp Gly Tyr Ser Glu Thr Ala Val His Lys Val
            660                 665                 670

Asp Gly Phe Lys Asn Leu Lys Gly His Tyr Leu Ile Gln His Gly Thr
        675                 680                 685

Gly Asp Asp Asn Val His Phe Gln Asn Ala Ala Val Leu Ser Asn Thr
    690                 695                 700

Leu Met Asn Gly Gly Val Thr Ala Asp Lys Leu Thr Thr Gln Trp Phe
705                 710                 715                 720

Thr Asp Ser Asp His Gly Ile Arg Tyr Asp Met Asp Ser Thr Tyr Gln
                725                 730                 735

Tyr Lys Gln Leu Ser Lys Met Val Tyr Asp Gln Lys Gln Arg Arg Pro
            740                 745                 750

Glu Ser Pro Pro Met His Gln Trp Ser Lys Arg Val Leu Ala Ala Leu
        755                 760                 765

Phe Gly Glu Arg Ala Glu Glu
    770                 775
```

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

```
Gly Pro Gly Ile Asn Asp Asp Gly Ser Gly
  1               5                  10
```

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Gln or Met

<400> SEQUENCE: 37

```
Asp Met Xaa Ala Ser Pro Asn
  1               5
```

<210> SEQ ID NO 38
<211> LENGTH: 23
<212> TYPE: DNA
<213> ORGANISM: Artificial Sequence
<220> FEATURE:

```
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: a, c, g, t, unknown or other
<220> FEATURE:
<221> NAME/KEY: modified_base
<222> LOCATION: (6)
<223> OTHER INFORMATION: a, c, g, t, unknown or other
<220> FEATURE:
<221> NAME/KEY: modified_base
<222> LOCATION: (18)
<223> OTHER INFORMATION: a, c, g, t, unknown or other
<220> FEATURE:
<221> NAME/KEY: modified_base
<222> LOCATION: (21)
<223> OTHER INFORMATION: a, c, g, t, unknown or other

<400> SEQUENCE: 38
ggnatnaayg aygayggntc ngg                                           23

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: a, c, g, t, unknown or other
<220> FEATURE:
<221> NAME/KEY: modified_base
<222> LOCATION: (6)
<223> OTHER INFORMATION: a, c, g, t, unknown or other
<220> FEATURE:
<221> NAME/KEY: modified_base
<222> LOCATION: (9)
<223> OTHER INFORMATION: a, c, g, t, unknown or other
<220> FEATURE:
<221> NAME/KEY: modified_base
<222> LOCATION: (12)
<223> OTHER INFORMATION: a, c, g, t, unknown or other

<400> SEQUENCE: 39
ttnggngang cnatcatrtc                                               20

<210> SEQ ID NO 40
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 40
gcattcctgu gatgcccggg ccg                                           23

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
ttacttagca agctcagtga cgaagccgac                                    30
```

```
<210> SEQ ID NO 42
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Pro Gln Pro Gln Leu Pro Tyr Pro Gln Pro Gln Leu Pro Tyr
 1               5                  10

<210> SEQ ID NO 43
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Leu Gln Leu Gln Pro Phe Pro Gln Pro Gln Leu Pro Tyr Pro Gln Pro
 1               5                  10                  15

Gln Leu Pro Tyr Pro Gln Pro Gln Leu Pro Tyr Pro Gln Pro Gln Pro
            20                  25                  30

Phe

<210> SEQ ID NO 44
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Leu Val Pro Arg Gly Ser
 1               5

<210> SEQ ID NO 45
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Asp Asp Asp Asp Lys
 1               5

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ile Glu Gly Arg
 1

<210> SEQ ID NO 47
<211> LENGTH: 35
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 47
gttgtcgact tgttggtcaa gagcccttcg gatgg                              35

<210> SEQ ID NO 48
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
cttgcggccg cttacatgaa gacagtgtgg tgtcc                              35

<210> SEQ ID NO 49
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gttctcgagg cccaggatgg gactggaag                                    29

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
cgcaaaggtg cactcgcccc gcga                                         24

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
tcgcggggcg agtgcacctt tgcg                                         24

<210> SEQ ID NO 52
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cttagatctc tactgctcaa cccggtcctt                                   30

<210> SEQ ID NO 53
<211> LENGTH: 33
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 53
gttctcgagg cattcctgtt gatgcccggg ccg                                   33

<210> SEQ ID NO 54
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
cttagatctt tacttagcaa gctcagtgac gaagccgac                             39

<210> SEQ ID NO 55
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
gttctcgagg ggctgtagct gcagtgatt                                        29

<210> SEQ ID NO 56
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
cttagatctt taaaacggcg caaatgccaa                                       30

<210> SEQ ID NO 57
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
cttctcgagt cgttcctcct cgtgagcccc g                                     31

<210> SEQ ID NO 58
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gttccatggt catgaccttt gtgtcatacg agacag                                36

<210> SEQ ID NO 59
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 59
gttccatggt catgacccct ctcgtcaacg ataagg                              36

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
cttggatcct cattcctctg ccctctcacc                                     30

<210> SEQ ID NO 61
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ccggaattct ttaccccaga ggacttc                                        27

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gagtctagac tagtagtcga agtaagagtg                                     30

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Leu Val Gly Gln Glu Pro Phe Gly Trp
 1               5                  10

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Gly His His Thr Val Phe Met
 1               5

<210> SEQ ID NO 65
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 65

Arg Gly Pro Gly Trp Asp Trp Lys
 1               5

<210> SEQ ID NO 66
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ser Arg Gly Glu Cys Thr Phe Ala
 1               5

<210> SEQ ID NO 67
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ser Arg Gly Glu Cys Thr Phe Ala
 1               5

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Asp Arg Val Glu Gln
 1               5

<210> SEQ ID NO 69
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Arg Gly Ile Pro Val Asp Ala Arg Ala
 1               5

<210> SEQ ID NO 70
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Val Gly Phe Val Thr Glu Leu Ala Lys
 1               5

<210> SEQ ID NO 71
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 71

Arg Gly Ala Val Ala Ala Val Ile
  1               5

<210> SEQ ID NO 72
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Leu Ala Phe Ala Pro Phe
  1               5

<210> SEQ ID NO 73
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Arg Val Val Pro Pro Arg Glu Pro Arg
  1               5

<210> SEQ ID NO 74
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Val Ser Tyr Asp Thr Lys Val Met
  1               5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Val Met Thr Pro Leu Val Asn Asp Lys
  1               5

<210> SEQ ID NO 76
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Glu Arg Ala Glu Glu
  1               5
```

```
<210> SEQ ID NO 77
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Glu Phe Phe Thr Pro Glu Asp Phe
  1               5

<210> SEQ ID NO 78
<211> LENGTH: 373
<212> TYPE: PRT
<213> ORGANISM: Trichophyton rubrum

<400> SEQUENCE: 78

Met Lys Leu Leu Ser Val Leu Ala Leu Ser Ala Thr Ala Thr Ser Val
  1               5                  10                  15

Leu Gly Ala Ser Ile Pro Val Asp Ala Arg Ala Glu Lys Phe Leu Ile
                 20                  25                  30

Glu Leu Ala Pro Gly Glu Thr Arg Trp Val Thr Glu Glu Lys Trp
             35                  40                  45

Glu Leu Lys Arg Lys Gly Gln Asp Phe Phe Asp Ile Thr Asp Glu Glu
     50                  55                  60

Val Gly Phe Thr Ala Ala Val Ala Gln Pro Ala Ile Ala Tyr Pro Thr
 65                  70                  75                  80

Ser Ile Arg His Ala Asn Ala Val Asn Ala Met Ile Ala Thr Leu Ser
                 85                  90                  95

Lys Glu Asn Met Gln Arg Asp Leu Thr Lys Leu Ser Ser Phe Gln Thr
            100                 105                 110

Ala Tyr Tyr Lys Val Asp Phe Gly Lys Gln Ser Ala Thr Trp Leu Gln
        115                 120                 125

Glu Gln Val Gln Ala Ala Ile Asn Thr Ala Gly Ala Asn Arg Tyr Gly
    130                 135                 140

Ala Lys Val Ala Ser Phe Arg His Asn Phe Ala Gln His Ser Ile Ile
145                 150                 155                 160

Ala Thr Ile Pro Gly Arg Ser Pro Glu Val Val Val Gly Ala His
                165                 170                 175

Gln Asp Ser Ile Asn Gln Arg Ser Pro Met Thr Gly Arg Ala Pro Gly
            180                 185                 190

Ala Asp Asp Asn Gly Ser Gly Ser Val Thr Ile Leu Glu Ala Leu Arg
        195                 200                 205

Gly Val Leu Arg Asp Gln Thr Ile Leu Gln Gly Lys Ala Ala Asn Thr
    210                 215                 220

Ile Glu Phe His Trp Tyr Ala Gly Glu Glu Ala Gly Leu Leu Gly Ser
225                 230                 235                 240

Gln Ala Ile Phe Ala Asn Tyr Lys Gln Thr Gly Lys Lys Val Lys Gly
                245                 250                 255

Met Leu Asn Gln Asp Met Thr Gly Tyr Ile Lys Gly Met Val Asp Lys
            260                 265                 270

Gly Leu Lys Val Ser Phe Gly Ile Ile Thr Asp Asn Val Asn Ala Asn
        275                 280                 285

Leu Thr Lys Phe Val Arg Met Val Ile Thr Lys Tyr Cys Ser Ile Pro
    290                 295                 300

Thr Ile Asp Thr Arg Cys Gly Tyr Ala Cys Ser Asp His Ala Ser Ala
```

```
                305                 310                 315                 320
Asn Arg Asn Gly Tyr Pro Ser Ala Met Val Ala Glu Ser Pro Ile Asp
            325                 330                 335

Leu Leu Asp Pro His Leu His Thr Asp Ser Asp Asn Ile Ser Tyr Leu
            340                 345                 350

Asp Phe Asp His Met Ile Glu His Ala Lys Leu Ile Val Gly Phe Val
            355                 360                 365

Thr Glu Leu Ala Lys
    370

<210> SEQ ID NO 79
<211> LENGTH: 388
<212> TYPE: PRT
<213> ORGANISM: Aspergillus fumigatus

<400> SEQUENCE: 79

Met Lys Val Leu Thr Ala Ile Ala Leu Ser Ala Ile Ala Phe Thr Gly
  1               5                  10                  15

Ala Val Ala Ala Val Ile Thr Gln Glu Ala Phe Leu Asn Asn Pro Arg
             20                  25                  30

Ile His His Asp Gln Glu Lys Tyr Leu Ile Glu Leu Ala Pro Tyr Arg
         35                  40                  45

Thr Arg Trp Val Thr Glu Glu Lys Trp Ala Leu Lys Leu Asp Gly
     50                  55                  60

Val Asn Phe Ile Asp Ile Thr Glu Glu His Asn Thr Gly Phe Tyr Pro
 65                  70                  75                  80

Thr Leu His Ser Ala Ser Tyr Val Lys Tyr Pro Pro Lys Met Gln Tyr
                 85                  90                  95

Ala Glu Glu Val Ala Ala Leu Asn Lys Asn Leu Ser Lys Glu Asn Met
            100                 105                 110

Lys Ala Asn Leu Glu Arg Phe Thr Ser Phe His Thr Arg Tyr Tyr Lys
        115                 120                 125

Ser Gln Thr Gly Ile Arg Ser Ala Thr Trp Leu Phe Asp Gln Val Gln
    130                 135                 140

Arg Val Val Ser Glu Ser Gly Ala Ala Glu Tyr Gly Ala Thr Val Glu
145                 150                 155                 160

Arg Phe Ser His Pro Trp Gly Gln Phe Ser Ile Ile Ala Arg Ile Pro
                165                 170                 175

Gly Arg Thr Asn Lys Thr Val Val Leu Gly Ala His Gln Asp Ser Ile
            180                 185                 190

Asn Leu Phe Leu Pro Ser Ile Leu Ala Ala Pro Gly Ala Asp Asp Asp
        195                 200                 205

Gly Ser Gly Thr Val Thr Ile Leu Glu Ala Leu Arg Gly Leu Leu Gln
    210                 215                 220

Ser Asp Ala Ile Ala Lys Gly Asn Ala Ser Asn Thr Val Glu Phe His
225                 230                 235                 240

Trp Tyr Ser Ala Glu Glu Gly Gly Met Leu Gly Ser Gln Ala Ile Phe
                245                 250                 255

Ser Asn Tyr Lys Arg Asn Arg Arg Glu Ile Lys Ala Met Leu Gln Gln
            260                 265                 270

Asp Met Thr Gly Tyr Val Gln Gly Ala Leu Asn Ala Gly Val Glu Glu
        275                 280                 285

Ala Ile Gly Ile Met Val Asp Tyr Val Asp Gln Gly Leu Thr Gln Phe
    290                 295                 300

Leu Lys Asp Val Val Thr Ala Tyr Cys Ser Val Gly Tyr Leu Glu Thr
```

```
                305                 310                 315                 320
Lys Cys Gly Tyr Ala Cys Ser Asp His Thr Ser Ala Ser Lys Tyr Gly
                    325                 330                 335

Tyr Pro Ala Ala Met Ala Thr Glu Ala Glu Met Glu Asn Thr Asn Lys
                340                 345                 350

Lys Ile His Thr Thr Asp Asp Lys Ile Lys Tyr Leu Ser Phe Asp His
            355                 360                 365

Met Leu Glu His Ala Lys Leu Ser Leu Gly Phe Ala Phe Glu Leu Ala
370                 375                 380

Phe Ala Pro Phe
385

<210> SEQ ID NO 80
<211> LENGTH: 376
<212> TYPE: PRT
<213> ORGANISM: Aspergillus oryzae

<400> SEQUENCE: 80

Met Arg Pro Leu Pro Cys Ile Ala Thr Leu Ala Ala Thr Ala Ser Ala
1               5                   10                  15

Leu Ala Ile Gly Asp His Val Arg Ser Asp Asp Gln Tyr Val Leu Glu
                20                  25                  30

Leu Ala Pro Gly Gln Thr Lys Val Val Thr Glu Ala Glu Lys Trp Ala
            35                  40                  45

Leu Arg Ala Glu Gly Lys Arg Phe Phe Asp Ile Thr Glu Arg Ala Ser
        50                  55                  60

Ser Leu Glu Leu Ala Ser Asn Lys Lys Gln Lys Leu Ala Val Thr Tyr
65                  70                  75                  80

Pro Asp Ser Val Gln His Asn Glu Thr Val Gln Asn Leu Ile Lys Ser
                85                  90                  95

Leu Asp Lys Lys Asn Phe Glu Thr Val Leu Gln Pro Phe Ser Glu Phe
                100                 105                 110

His Asn Arg Tyr Tyr Lys Ser Asp Asn Gly Lys Lys Ser Ser Glu Trp
            115                 120                 125

Leu Gln Gly Lys Ile Gln Glu Ile Ile Ser Ala Ser Gly Ala Lys Gly
        130                 135                 140

Val Thr Val Glu Pro Phe Lys His Ser Phe Pro Gln Ser Ser Leu Ile
145                 150                 155                 160

Ala Lys Ile Pro Gly Lys Ser Asp Lys Thr Ile Val Leu Gly Ala His
                165                 170                 175

Gln Asp Ser Ile Asn Leu Asp Ser Pro Ser Glu Gly Arg Ala Pro Gly
            180                 185                 190

Ala Asp Asp Asp Gly Ser Gly Val Val Thr Ile Leu Glu Ala Phe Arg
        195                 200                 205

Val Leu Leu Thr Asp Glu Lys Val Ala Ala Gly Glu Ala Pro Asn Thr
210                 215                 220

Val Glu Phe His Phe Tyr Ala Gly Glu Glu Gly Leu Leu Gly Ser Gln
225                 230                 235                 240

Asp Ile Phe Glu Gln Tyr Ser Gln Lys Ser Arg Asp Val Lys Ala Met
                245                 250                 255

Leu Gln Gln Asp Met Thr Gly Tyr Thr Lys Gly Thr Thr Asp Ala Gly
            260                 265                 270

Lys Pro Glu Ser Ile Gly Ile Ile Thr Asp Asn Val Asp Glu Asn Leu
        275                 280                 285

Thr Lys Phe Leu Lys Val Ile Val Asp Ala Tyr Cys Thr Ile Pro Thr
```

```
                290                 295                 300
Val Asp Ser Lys Cys Gly Tyr Gly Cys Ser Asp His Ala Ser Ala Thr
305                 310                 315                 320

Lys Tyr Gly Tyr Pro Ala Ala Phe Ala Phe Glu Ser Ala Phe Gly Asp
                325                 330                 335

Asp Ser Pro Tyr Ile His Ser Ala Asp Asp Thr Ile Glu Thr Val Asn
                340                 345                 350

Phe Asp His Val Leu Gln His Gly Lys Leu Thr Leu Gly Phe Ala Tyr
                355                 360                 365

Glu Leu Ala Phe Ala Asp Ser Leu
                370                 375

<210> SEQ ID NO 81
<211> LENGTH: 384
<212> TYPE: PRT
<213> ORGANISM: Agaricus bisporus

<400> SEQUENCE: 81

Met Lys Phe Gln Leu Ala Leu Leu Lys Ala Leu Ile Ala Ala Ala Val
1               5                   10                  15

Phe Val His Ala Val Pro Ile Ser Arg Asp Glu Leu Val Glu Asn Ser
                20                  25                  30

Ala Lys Gly Leu Arg Leu Leu Gln Leu Ser Glu Asp Gly Leu Pro Val
            35                  40                  45

Trp Lys Thr Glu Asp Glu Val Leu Gln Leu Leu Arg Ser Gly Ala Arg
    50                  55                  60

Phe Phe Asp Val Thr Glu Thr Tyr Glu Ile Gln Gln Glu Leu Asp Lys
65                  70                  75                  80

Thr Ser Ala Glu Ser Lys Asn Ala Gly Glu Phe Ser Thr Ala Ala Thr
                85                  90                  95

Phe Ser Pro Pro Ser His Gln Ser Gln Val Thr Pro Leu Leu Ser Arg
            100                 105                 110

Leu Ser Ile Ser Asn Met Gln Ser Tyr Leu Ser Ser Leu Ser Gly Phe
        115                 120                 125

Asn Asn Arg Tyr Tyr Arg Ser Gln Ser Gly Ala Asp Ala Ser Ala Trp
130                 135                 140

Leu Leu Asp Thr Val Gln Asp Ile Thr Arg Gly Arg Ser Asp Ile Thr
145                 150                 155                 160

Ala Ser Ala Phe Thr His Gly Trp Pro Gln Ser Ser Thr Ile Val Lys
                165                 170                 175

Ile Ala Gly Ser Ser Ser Ser Gly Pro Val Thr Ile Leu Gly Ala His
            180                 185                 190

Met Asp Ser Ile Asn Leu Ser Asn Pro Met Asn Gly Arg Ala Pro Gly
        195                 200                 205

Ser Asp Asp Asp Gly Thr Gly Thr Val Asn Leu Ile Glu Thr Leu Arg
    210                 215                 220

Val Leu Val Ser Ser Gly Phe Arg Pro Ser Thr Pro Leu Glu Phe His
225                 230                 235                 240

Trp Tyr Ser Gly Glu Glu Gly Gly Leu Leu Gly Ser Asn Ala Ile Ala
                245                 250                 255

Thr Ser Tyr Lys Arg Ala Gly Thr Gln Val Lys Ala Phe Leu Gln Leu
            260                 265                 270

Asp Met Thr Gly Tyr Val Lys Pro Gly Thr Pro Glu Val Val Ala Ile
        275                 280                 285

Met Pro Asp Phe Ile Asp Gln Gly Leu Asn Asn Phe Leu Lys Gln Leu
```

```
                290                 295                 300
Val Thr Thr Tyr Ser Arg Leu Pro Val Val Asn Val Pro Cys Gly
305                 310                 315                 320

Tyr Ala Cys Ser Asp His Ala Ser Trp Phe Arg Gln Gly Tyr Pro Thr
                325                 330                 335

Ala Leu Pro Phe Glu Gly Ile Phe Gly Glu Asp Pro Phe Ile His
                340                 345                 350

Ser Ser Gly Asp Thr Thr Ser Val Asn Gly Phe Ser Trp Ser His Ser
                355                 360                 365

Leu Glu Phe Ala Lys Ile Ala Val Ala Phe Ala Tyr Glu Leu Thr Ala
370                 375                 380

<210> SEQ ID NO 82
<211> LENGTH: 395
<212> TYPE: PRT
<213> ORGANISM: Vibrio cholerae

<400> SEQUENCE: 82

Met Asn Lys Leu Phe Ala Met Ala Leu Met Ser Ala Ala Leu Ser Ala
1               5                   10                  15

Asn Ala Glu Asp Lys Val Trp Ile Ser Met Gly Ala Asp Ala Val Gly
                20                  25                  30

Ser Leu Asn Pro Ala Leu Ser Glu Ser Leu Leu Pro His Ser Phe Ala
            35                  40                  45

Ser Gly Ser Gln Val Trp Ile Gly Glu Val Ala Ile Asp Glu Leu Ala
        50                  55                  60

Glu Leu Ser His Thr Met His Glu Gln His Asn Arg Cys Gly Gly Tyr
65                  70                  75                  80

Met Val His Thr Ser Ala Gln Gly Ala Met Ala Ala Leu Met Met Pro
                85                  90                  95

Glu Ser Ile Ala Asn Phe Thr Ile Pro Ala Pro Ser Gln Gln Asp Leu
            100                 105                 110

Val Asn Ala Trp Leu Pro Gln Val Ser Ala Asp Gln Ile Thr Asn Thr
        115                 120                 125

Ile Arg Ala Leu Ser Ser Phe Asn Asn Arg Phe Tyr Thr Thr Ala Ser
    130                 135                 140

Gly Ala Gln Ala Ser Asp Trp Leu Ala Asn Glu Trp Arg Ser Leu Ile
145                 150                 155                 160

Ser Ser Leu Pro Gly Ser Arg Ile Glu Gln Ile Lys His Ser Gly Tyr
                165                 170                 175

Asn Gln Lys Ser Val Val Leu Thr Ile Gln Gly Ser Glu Lys Pro Asp
            180                 185                 190

Glu Trp Val Ile Val Gly Gly His Leu Asp Ser Thr Leu Gly Ser His
        195                 200                 205

Thr Asn Glu Gln Ser Ile Ala Pro Gly Ala Asp Asp Ala Ser Gly
    210                 215                 220

Ile Ala Ser Leu Ser Glu Ile Ile Arg Val Leu Arg Asp Asn Asn Phe
225                 230                 235                 240

Arg Pro Lys Arg Ser Ala Ala Leu Met Ala Tyr Ala Ala Glu Glu Val
                245                 250                 255

Gly Leu Arg Gly Ser Gln Asp Pro Ala Asn Gln Tyr Lys Ala Gln Gly
            260                 265                 270

Lys Lys Val Val Ser Val Leu Gln Leu Asp Met Thr Asn Tyr Arg Gly
        275                 280                 285

Ser Ala Glu Asp Ile Val Phe Ile Thr Asp Tyr Thr Asp Ser Asn Leu
```

```
              290                 295                 300
Thr Gln Phe Leu Thr Thr Leu Ile Asp Glu Tyr Leu Pro Glu Leu Thr
305                 310                 315                 320

Tyr Gly Tyr Asp Arg Cys Gly Tyr Ala Cys Ser Asp His Ala Ser Trp
                325                 330                 335

His Lys Ala Gly Phe Ser Ala Ala Met Pro Phe Glu Ser Lys Phe Lys
                340                 345                 350

Asp Tyr Asn Pro Lys Ile His Thr Ser Gln Asp Thr Leu Ala Asn Ser
                355                 360                 365

Asp Pro Thr Gly Asn His Ala Val Thr Phe Thr Lys Leu Gly Leu Ala
370                 375                 380

Tyr Val Ile Glu Met Ala Asn Ala Gly Ser Ser
385                 390                 395

<210> SEQ ID NO 83
<211> LENGTH: 495
<212> TYPE: PRT
<213> ORGANISM: Trichophyton rubrum

<400> SEQUENCE: 83

Met Lys Ser Gln Leu Leu Ser Leu Ala Val Ala Val Thr Thr Ile Ser
 1               5                  10                  15

Gln Gly Val Val Gly Gln Glu Pro Phe Gly Trp Pro Phe Lys Pro Met
                20                  25                  30

Val Thr Gln Asp Asp Leu Gln Asn Lys Ile Lys Leu Lys Asp Ile Met
                35                  40                  45

Ala Gly Val Glu Lys Leu Gln Ser Phe Ser Asp Ala His Pro Glu Lys
        50                  55                  60

Asn Arg Val Phe Gly Gly Asn Gly His Lys Asp Thr Val Glu Trp Ile
65                  70                  75                  80

Tyr Asn Glu Ile Lys Ala Thr Gly Tyr Tyr Asp Val Lys Lys Gln Glu
                85                  90                  95

Gln Val His Leu Trp Ser His Ala Glu Ala Ala Leu Asn Ala Asn Gly
                100                 105                 110

Lys Asp Leu Lys Ala Ser Ala Met Ser Tyr Ser Pro Pro Ala Ser Lys
        115                 120                 125

Ile Met Ala Glu Leu Val Val Ala Lys Asn Asn Gly Cys Asn Ala Thr
130                 135                 140

Asp Tyr Pro Ala Asn Thr Gln Gly Lys Ile Val Leu Val Glu Arg Gly
145                 150                 155                 160

Val Cys Ser Phe Gly Glu Lys Ser Ala Gln Ala Gly Asp Ala Lys Ala
                165                 170                 175

Ala Gly Ala Ile Val Tyr Asn Asn Val Pro Gly Ser Leu Ala Gly Thr
                180                 185                 190

Leu Gly Gly Leu Asp Lys Arg His Val Pro Thr Ala Gly Leu Ser Gln
        195                 200                 205

Glu Asp Gly Lys Asn Leu Ala Thr Leu Val Ala Ser Gly Lys Ile Asp
210                 215                 220

Val Thr Met Asn Val Ile Ser Leu Phe Glu Asn Arg Thr Thr Trp Asn
225                 230                 235                 240

Val Ile Ala Glu Thr Lys Gly Gly Asp His Asn Asn Val Ile Met Leu
                245                 250                 255

Gly Ala His Ser Asp Ser Val Asp Ala Gly Pro Gly Ile Asn Asp Asn
                260                 265                 270

Gly Ser Gly Ser Ile Gly Ile Met Thr Val Ala Lys Ala Leu Thr Asn
```

```
              275                 280                 285
Phe Lys Leu Asn Asn Ala Val Arg Phe Ala Trp Trp Thr Ala Glu Glu
        290                 295                 300

Phe Gly Leu Leu Gly Ser Thr Phe Tyr Val Asn Ser Leu Asp Asp Arg
305                 310                 315                 320

Glu Leu His Lys Val Lys Leu Tyr Leu Asn Phe Asp Met Ile Gly Ser
                325                 330                 335

Pro Asn Phe Ala Asn Gln Ile Tyr Asp Gly Asp Ser Ala Tyr Asn
        340                 345                 350

Met Thr Gly Pro Ala Gly Ser Ala Glu Ile Glu Tyr Leu Phe Glu Lys
                355                 360                 365

Phe Phe Asp Asp Gln Gly Ile Pro His Gln Pro Thr Ala Phe Thr Gly
        370                 375                 380

Arg Ser Asp Tyr Ser Ala Phe Ile Lys Arg Asn Val Pro Ala Gly Gly
385                 390                 395                 400

Leu Phe Thr Gly Ala Glu Val Val Lys Thr Pro Glu Gln Val Lys Leu
                405                 410                 415

Phe Gly Gly Glu Ala Gly Val Ala Tyr Asp Lys Asn Tyr His Arg Lys
                420                 425                 430

Gly Asp Thr Val Ala Asn Ile Asn Lys Gly Ala Ile Phe Leu Asn Thr
                435                 440                 445

Arg Ala Ile Ala Tyr Ala Ile Ala Glu Tyr Ala Arg Ser Leu Lys Gly
        450                 455                 460

Phe Pro Thr Arg Pro Lys Thr Gly Lys Arg Asp Val Asn Pro Gln Tyr
465                 470                 475                 480

Ser Lys Met Pro Gly Gly Gly Cys Gly His His Thr Val Phe Met
                485                 490                 495

<210> SEQ ID NO 84
<211> LENGTH: 498
<212> TYPE: PRT
<213> ORGANISM: Aspergillus fumigatus

<400> SEQUENCE: 84

Met Lys Leu Leu Tyr Leu Thr Ser Phe Ala Ser Leu Ala Val Ala Asn
  1               5                  10                  15

Gly Pro Gly Trp Asp Trp Lys Pro Arg Val His Pro Lys Val Leu Pro
            20                  25                  30

Gln Met Ile His Leu Trp Asp Leu Leu Gln Gly Ala Gln Gln Leu Glu
        35                  40                  45

Asp Phe Ala Tyr Ala Tyr Pro Glu Arg Asn Arg Val Phe Gly Gly Arg
    50                  55                  60

Ala His Glu Asp Thr Val Asn Tyr Leu Tyr Arg Glu Leu Lys Lys Thr
65                  70                  75                  80

Gly Tyr Tyr Asp Val Tyr Lys Gln Pro Gln Val His Gln Trp Thr Arg
                85                  90                  95

Ala Asp Gln Ala Leu Thr Val Asp Gly Gln Ser Tyr Asp Ala Thr Thr
            100                 105                 110

Met Thr Tyr Ser Pro Ser Val Asn Ala Thr Ala Pro Leu Ala Val Val
        115                 120                 125

Asn Asn Leu Gly Cys Val Glu Ala Asp Tyr Pro Ala Asp Leu Thr Gly
    130                 135                 140

Lys Ile Ala Leu Ile Ser Arg Gly Glu Cys Thr Phe Ala Thr Lys Ser
145                 150                 155                 160

Val Leu Ser Ala Lys Ala Gly Ala Ala Ala Ala Leu Val Tyr Asn Asn
```

```
              165                 170                 175
Ile Glu Gly Ser Met Ala Gly Thr Leu Gly Gly Ala Thr Ser Glu Leu
            180                 185                 190

Gly Ala Tyr Ala Pro Ile Ala Gly Ile Ser Leu Ala Asp Gly Gln Ala
            195                 200                 205

Leu Ile Gln Met Ile Gln Ala Gly Thr Val Thr Ala Asn Leu Trp Ile
            210                 215                 220

Asp Ser Gln Val Glu Asn Arg Thr Thr Tyr Asn Val Ile Ala Gln Thr
225                 230                 235                 240

Lys Gly Gly Asp Pro Asn Asn Val Val Ala Leu Gly Gly His Thr Asp
                245                 250                 255

Ser Val Glu Ala Gly Pro Gly Ile Asn Asp Asp Gly Ser Gly Ile Ile
            260                 265                 270

Ser Asn Leu Val Val Ala Lys Ala Leu Thr Arg Phe Ser Val Lys Asn
            275                 280                 285

Ala Val Arg Phe Cys Phe Trp Thr Ala Glu Glu Phe Gly Leu Leu Gly
            290                 295                 300

Ser Asn Tyr Tyr Val Asn Ser Leu Asn Ala Thr Glu Gln Ala Lys Ile
305                 310                 315                 320

Arg Leu Tyr Leu Asn Phe Asp Met Ile Ala Ser Pro Asn Tyr Ala Leu
                325                 330                 335

Met Ile Tyr Asp Gly Asp Gly Ser Ala Phe Asn Leu Thr Gly Pro Ala
                340                 345                 350

Gly Ser Ala Gln Ile Glu Arg Leu Phe Glu Asp Tyr Tyr Thr Ser Ile
            355                 360                 365

Arg Lys Pro Phe Val Pro Thr Glu Phe Asn Gly Arg Ser Asp Tyr Gln
            370                 375                 380

Ala Phe Ile Leu Asn Gly Ile Pro Ala Gly Gly Leu Phe Thr Gly Ala
385                 390                 395                 400

Glu Ala Ile Lys Thr Glu Glu Gln Ala Gln Leu Phe Gly Gly Gln Ala
                405                 410                 415

Gly Val Ala Leu Asp Ala Asn Tyr His Ala Lys Gly Asp Asn Met Thr
            420                 425                 430

Asn Leu Asn Arg Glu Ala Phe Leu Ile Asn Ser Arg Ala Thr Ala Phe
            435                 440                 445

Ala Val Ala Thr Tyr Ala Asn Ser Leu Asp Ser Ile Pro Pro Arg Asn
            450                 455                 460

Met Thr Thr Val Val Lys Arg Ser Gln Leu Glu Gln Ala Met Lys Arg
465                 470                 475                 480

Thr Pro His Thr His Thr Gly Gly Thr Gly Cys Tyr Lys Asp Arg Val
                485                 490                 495

Glu Gln

<210> SEQ ID NO 85
<211> LENGTH: 496
<212> TYPE: PRT
<213> ORGANISM: Aspergillus oryzae

<400> SEQUENCE: 85

Met Arg Ser Leu Leu Trp Ala Ser Leu Leu Ser Gly Ala Leu Ala Gly
1               5                   10                  15

Arg Ala Leu Val Ser Pro Asp Glu Phe Pro Glu Asp Ile Gln Leu Glu
            20                  25                  30

Asp Leu Leu Glu Gly Ser Gln Gln Leu Glu Asp Phe Ala Tyr Ala Tyr
        35                  40                  45
```

```
Pro Glu Arg Asn Arg Val Phe Gly Gly Lys Ala His Asp Asp Thr Val
    50                  55                  60
Asn Tyr Leu Tyr Lys Glu Leu Lys Lys Thr Gly Tyr Asp Val Tyr
 65                  70                  75                  80
Lys Gln Pro Gln Val His Leu Trp Ser Asn Ala Asp Gln Thr Leu Lys
                 85                  90                  95
Val Gly Asp Glu Glu Ile Glu Ala Lys Thr Met Thr Tyr Ser Pro Ser
                100                 105                 110
Val Glu Val Thr Ala Asp Val Ala Val Lys Asn Leu Gly Cys Ser
                115                 120                 125
Glu Ala Asp Tyr Pro Ser Asp Val Glu Gly Lys Val Ala Leu Ile Lys
        130                 135                 140
Arg Gly Glu Cys Ala Phe Gly Asp Lys Ser Val Leu Ala Ala Lys Ala
145                 150                 155                 160
Lys Ala Ala Ala Ser Ile Val Tyr Asn Asn Val Ala Gly Ser Met Ala
                165                 170                 175
Gly Thr Leu Gly Ala Ala Gln Ser Asp Lys Gly Pro Tyr Ser Ala Ile
            180                 185                 190
Val Gly Ile Ser Leu Glu Asp Gly Gln Lys Leu Ile Lys Leu Ala Glu
        195                 200                 205
Ala Gly Ser Val Ser Val Asp Leu Trp Val Asp Ser Lys Gln Glu Asn
    210                 215                 220
Arg Thr Thr Tyr Asn Val Ile Ala Gln Thr Lys Gly Gly Asp Pro Asn
225                 230                 235                 240
Asn Val Val Ala Leu Gly Gly His Thr Asp Ser Val Glu Ala Gly Pro
                245                 250                 255
Gly Ile Asn Asp Asp Gly Ser Gly Ile Ile Ser Asn Leu Val Val Ala
                260                 265                 270
Lys Ala Leu Thr Gln Tyr Ser Val Lys Asn Ala Val Arg Phe Leu Phe
            275                 280                 285
Trp Thr Ala Glu Glu Phe Gly Leu Leu Gly Ser Asn Tyr Tyr Val Ser
    290                 295                 300
His Leu Asn Ala Thr Glu Leu Asn Lys Ile Arg Leu Tyr Leu Asn Phe
305                 310                 315                 320
Asp Met Ile Ala Ser Pro Asn Tyr Ala Leu Met Ile Tyr Asp Gly Asp
                325                 330                 335
Gly Ser Ala Phe Asn Gln Ser Gly Pro Ala Gly Ser Ala Gln Ile Glu
                340                 345                 350
Lys Leu Phe Glu Asp Tyr Tyr Asp Ser Ile Asp Leu Pro His Ile Pro
            355                 360                 365
Thr Gln Phe Asp Gly Arg Ser Asp Tyr Glu Ala Phe Ile Leu Asn Gly
        370                 375                 380
Ile Pro Ala Gly Gly Leu Phe Thr Gly Ala Glu Gly Ile Met Ser Glu
385                 390                 395                 400
Glu Asn Ala Ser Arg Trp Gly Gly Gln Ala Gly Val Ala Tyr Asp Ala
                405                 410                 415
Asn Tyr His Ala Ala Gly Asp Asn Met Thr Asn Leu Asn His Glu Ala
                420                 425                 430
Phe Leu Ile Asn Ser Lys Ala Thr Ala Phe Ala Val Ala Thr Tyr Ala
            435                 440                 445
Asn Asp Leu Ser Ser Ile Pro Lys Arg Asn Thr Thr Ser Ser Leu His
        450                 455                 460
Arg Arg Ala Arg Thr Met Arg Pro Phe Gly Lys Arg Ala Pro Lys Thr
```

```
                465             470             475             480
                His Ala His Val Ser Gly Ser Gly Cys Trp His Ser Gln Val Glu Ala
                                485             490             495

<210> SEQ ID NO 86
<211> LENGTH: 537
<212> TYPE: PRT
<213> ORGANISM: Saccharomyces cerevisiae

<400> SEQUENCE: 86

Met His Phe Ser Leu Lys Gln Leu Ala Val Ala Ala Phe Tyr Ala Thr
  1               5                  10                  15

Asn Leu Gly Ser Ala Tyr Val Ile Pro Gln Phe Phe Gln Glu Ala Phe
                 20                  25                  30

Gln Gln Glu Glu Pro Ile Glu Asn Tyr Leu Pro Gln Leu Asn Asp Asp
             35                  40                  45

Asp Ser Ser Ala Val Ala Ala Asn Ile Pro Lys Pro His Ile Pro Tyr
        50                  55                  60

Phe Met Lys Pro His Val Glu Ser Glu Lys Leu Gln Asp Lys Ile Lys
 65                  70                  75                  80

Val Asp Asp Leu Asn Ala Thr Ala Trp Asp Leu Tyr Arg Leu Ala Asn
                 85                  90                  95

Tyr Ser Thr Pro Asp Tyr Gly His Pro Thr Arg Val Ile Gly Ser Lys
            100                 105                 110

Gly His Asn Lys Thr Met Glu Tyr Ile Leu Asn Val Phe Asp Asp Met
        115                 120                 125

Gln Asp Tyr Tyr Asp Val Ser Leu Gln Glu Phe Glu Ala Leu Ser Gly
    130                 135                 140

Lys Ile Ile Ser Phe Asn Leu Ser Asp Ala Glu Thr Gly Lys Ser Phe
145                 150                 155                 160

Ala Asn Thr Thr Ala Phe Ala Leu Ser Pro Pro Val Asp Gly Phe Val
                165                 170                 175

Gly Lys Leu Val Glu Ile Pro Asn Leu Gly Cys Glu Glu Lys Asp Tyr
            180                 185                 190

Ala Ser Val Val Pro Pro Arg His Asn Glu Lys Gln Ile Ala Leu Ile
        195                 200                 205

Glu Arg Gly Lys Cys Pro Phe Gly Asp Lys Ser Asn Leu Ala Gly Lys
    210                 215                 220

Phe Gly Phe Thr Ala Val Val Ile Tyr Asp Asn Glu Pro Lys Ser Lys
225                 230                 235                 240

Glu Gly Leu His Gly Thr Leu Gly Glu Pro Thr Lys His Thr Val Ala
                245                 250                 255

Thr Val Gly Val Pro Tyr Lys Val Gly Lys Lys Leu Ile Ala Asn Ile
            260                 265                 270

Ala Leu Asn Ile Asp Tyr Ser Leu Tyr Phe Ala Met Asp Ser Tyr Val
        275                 280                 285

Glu Phe Ile Lys Thr Gln Asn Ile Ile Ala Asp Thr Lys His Gly Asp
    290                 295                 300

Pro Asp Asn Ile Val Ala Leu Gly Ala His Ser Asp Ser Val Glu Glu
305                 310                 315                 320

Gly Pro Gly Ile Asn Asp Asp Gly Ser Gly Thr Ile Ser Leu Leu Asn
                325                 330                 335

Val Ala Lys Gln Leu Thr His Phe Lys Ile Asn Asn Lys Val Arg Phe
            340                 345                 350

Ala Trp Trp Ala Ala Glu Glu Glu Gly Leu Leu Gly Ser Asn Phe Tyr
```

|    |     |     |     |     | 355 |     |     |     | 360 |     |     |     |     | 365 |
|----|-----|-----|-----|-----|-----|-----|-----|-----|-----|-----|-----|-----|-----|-----|

Ala Tyr Asn Leu Thr Lys Glu Glu Asn Ser Lys Ile Arg Val Phe Met
     370                             375                     380

Asp Tyr Asp Met Met Ala Ser Pro Asn Tyr Glu Tyr Glu Ile Tyr Asp
385                           390                     395                   400

Ala Asn Asn Lys Glu Asn Pro Lys Gly Ser Glu Glu Leu Lys Asn Leu
              405                   410                   415

Tyr Val Asp Tyr Tyr Lys Ala His His Leu Asn Tyr Thr Leu Val Pro
          420                   425                 430

Phe Asp Gly Arg Ser Asp Tyr Val Gly Phe Ile Asn Asn Gly Ile Pro
          435                 440                 445

Ala Gly Gly Ile Ala Thr Gly Ala Glu Lys Asn Asn Val Asn Asn Gly
    450                    455                 460

Lys Val Leu Asp Arg Cys Tyr His Gln Leu Cys Asp Asp Val Ser Asn
465                       470                     475                   480

Leu Ser Trp Asp Ala Phe Ile Thr Asn Thr Lys Leu Ile Ala His Ser
          485                 490                   495

Val Ala Thr Tyr Ala Asp Ser Phe Glu Gly Phe Pro Lys Arg Glu Thr
          500                 505                 510

Gln Lys His Lys Glu Val Asp Ile Leu Asn Ala Gln Gln Pro Gln Phe
    515                    520                 525

Lys Tyr Arg Ala Asp Phe Leu Ile Ile
    530                    535

```
<210> SEQ ID NO 87
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87
```

His Ser Tyr Phe Asp Tyr
 1               5

FUNGAL DIPEPTIDYL PEPTIDASE IV (DPPIV) ENZYME FOR REAGENT USE

RELATED APPLICATIONS

This application is a divisional of U.S. application Ser. No. 10/569,908, filed Sep. 19, 2006, now issued as U.S. Pat. No. 7,468,267, which is a 35 USC §371 filing of international application number PCT/IB/2004/002963 which was filed Aug. 25, 2004. PCT/IB/2004/002963 claims priority to U.S. Provisional Application No. 60/498,318, filed on Aug. 25, 2003. The contents of the aforementioned applications are hereby incorporated herein by reference.

FIELD OF THE INVENTION

The present invention relates to novel polypeptides, and the nucleic acids encoding them, having unique catalytic properties. More particularly, the invention relates to nucleic acids encoding novel leucine aminopeptidase (LAP) and other amino- and carboxy-peptidases polypeptides, which will be herein collectively referred to as EXOX, as well as vectors, host cells, antibodies, and recombinant methods for producing these nucleic acids and polypeptides. These genes have been identified in two different fungal species, *Trichophyton rubrum* and *Aspergillus fumigatus*.

BACKGROUND OF THE INVENTION

Bacteria, yeast and filamentous fungi, as well as specialized cells of plants, invertebrates and vertebrates express membrane proteins useful for the uptake of amino acids, dipeptides and tripeptides. Lubkowitz et al., Microbiology 143:387-396 (1997); Hauser et al., Mol. Membr. Biol. 18(1): 105-112 (2001); Stacey et al., Trends Plant Sci. 7(6):257-263 (2002); Rubio-Aliaga & Daniel, Trends Pharmacol. Sci. 23(9):434-440 (2002). Transporters that also accept larger oligopeptides (4-5 amino acid residues) are known in yeast, filamentous fungi and plants. Protein digestion into amino acids has been investigated in microorganisms used in food fermentation industry. Bacteria of the genus *Lactobacillus* (O'Cuinn et al., Biochem. Soc. Trans. 27(4):730-734 (1999)) and fungi of the genus *Aspergillus* (Doumas et al., Appl. Environ. Microbiol. 64:4809-4815 (1998)) secrete endoproteases and exoproteases, which cooperate very efficiently in protein digestion.

Aminopeptidase activity, which may also play a role in the development of fungus during infection, has been detected in the mycelium and culture supernatant of a species of fungi (De Bersaques & Dockx, Arch. Belg. Dermatol. Syphiligr. 29:135-140 (1973); Danew & Friedrich, Mykosen 23:502-511 (1980)), however, no aminopeptidase or carboxypeptidase has been isolated and characterized from dermatophytes to date.

SUMMARY OF THE INVENTION

The invention is based in part upon the discovery of isolated polypeptides containing the mature form of an amino acid sequence selected from SEQ ID NOs: 3, 6, 9, 12, 15, 18, 21, 24, 27, 30, 33, and 35. The invention also provides isolated polypeptides containing an amino acid sequence selected from SEQ ID NOs. 3, 6, 9, 12, 15, 18, 21, 24, 27, 30, 33, and 35, as well as isolated polypeptides that are at least 90% identical to polypeptides having these sequences, wherein the polypeptide optionally has aminopeptidase or carboxypeptidase activity. For example, the polypeptide may be a leucine aminopeptidase such as ruLAP2.

Also provided are isolated polypeptides having one or more conservative amino acid substitutions. Such polypeptides may possess aminopeptidase activity.

The invention also encompasses polypeptides that are naturally occurring allelic variants of the sequence selected from the group consisting of SEQ ID NOs: 3, 6, 9, 12, 15, 18, 21, 24, 27, 30, 33, and 35. These allelic variants include amino acid sequences that are the translations of nucleic acid sequences differing by one or more nucleotides from nucleic acid sequences selected from the group consisting of SEQ ID NOs: 3, 6, 9, 12, 15, 18, 21, 24, 27, 30, 33, and 35. The variant polypeptide where any amino acid changed in the chosen sequence is changed to provide a conservative substitution.

The invention also involves a method of removing particular amino acids from peptides, for instance tags from recombinant proteins, wherein the active polypeptide removing amino acid is a polypeptide having an amino acid sequence at least 90% identical to a polypeptide having the amino acid sequence selected from the group consisting of SEQ ID NOs: 3, 6, 9, 12, 15, 18, 21, 24, 27, 30, 33, and 35, or a biologically active fragment thereof.

Any of the polypeptides of the invention may be naturally occurring. Further, any of these polypeptides can be in a composition including a carrier, and the composition can be in a kit including one or more containers.

Also provided are dermatophytes containing the polypeptides of the invention. For example, suitable dermatophytes include *Epidermophyton floccosum*, *Microsporum audouinii*, *Microsporum ferrugineum*, *Trichophyton concentricum*, *Trichophyton kanei*, *Trichophyton megninii*, *Trichophyton mentagrophytes*, *Trichophyton raubitschekii*, *Trichophyton rubrum*, *Trichophyton schoenleinii*, *Trichophyton soudanense*, *Trichophyton tonsurans*, *Trichophyton violaceum*, *Trichophyton yaoundei*, *Microsporum canis*, *Microsporum equinum*, *Microsporum nanum*, *Microsporum persicolor*, *Trichophyton equinum*, *Trichophyton simii*, *Trichophyton verrucosum*, *Microsporum gypseum*, *Trichophyton ajelloi*, and *Trichophyton terrestre*.

The invention also provides microbial culture supernatants containing the polypeptides of the invention.

The invention also relates to the use of therapeutics in the manufacture of a medicament for treating a syndrome associated with a human disease, where the therapeutic includes the polypeptides of the invention and the disease is selected from a pathology associated with these polypeptides.

The invention also relates to methods of degrading a polypeptide substrate. Such methods include contacting the polypeptide substrate with one or more of the polypeptides, which have been isolated. For example, the polypeptide substrate can be a full-length protein. Further, the one or more isolated polypeptides can be used to sequentially digest the polypeptide substrate. The polypeptide substrate can be selected from denatured casein, gliadin, gluten, bovine serum albumin or fragments thereof. For example, the isolated polypeptide can be an aminopeptidase, which can be a leucine aminopeptidase such as ruLAP2.

The invention further relates to methods for identifying a potential therapeutic agent for use in treatment of fungal infections, wherein the fungal infection is related to aberrant expression or aberrant physiological interactions of the polypeptides of the invention. Such methods include providing a cell expressing the polypeptide and having a property or function ascribable to the polypeptide, contacting the cell with a composition comprising a candidate substance, and determining whether the substance alters the property or function ascribable to the polypeptide. If no alteration is observed in the presence of the substance when the cell is contacted with a composition in the absence of the substance, the substance is identified as a potential therapeutic agent. For example, the property or function ascribable to the polypeptide can be aminopeptidase or carboxypeptidase activity.

The invention further relates to methods of treating a pathological state in a mammal by administering a polypeptide to the mammal in an amount that is sufficient to alleviate the pathological state. Typically, the polypeptide has an amino acid sequence at least 90% identical to a polypeptide containing the amino acid sequence selected from SEQ ID NOs: 3, 6, 9, 12, 15, 18, 21, 24, 27, 30, 33, and 35, or a biologically active fragment thereof. The pathological state to be treated include a fungal infection, celiac disease, digestive tract malabsorption, sprue, an allergic reaction and an enzyme deficiency. For example, the allergic reaction can be a reaction to gluten.

The invention additionally relates to methods of treating a pathological state in a mammal by administering a protease inhibitor to the mammal in an amount that is sufficient to alleviate the pathological state. The protease inhibitor includes an amino acid sequence at least 90% identical to a polypeptide having the amino acid sequence selected from SEQ ID NOs:3, 6, 9, 12, 15, 18, 21, 24, 27, 30, 33, and 35, or a biologically active fragment thereof. For example, the pathological state can be a fungal infection.

The invention further relates to isolated polypeptides having an amino acid sequence selected from SEQ ID NOs: 3, 6, 9, 12, 15, 18, 21, 24, 27, 30, 33, and 35. These polypeptides can be produced by culturing a cell under conditions that lead to expression of the polypeptide. In some embodiments, the cell includes a vector containing an isolated nucleic acid molecule having a nucleic acid sequence selected from the group consisting of SEQ ID NOs: 2, 5, 8, 11, 14, 17, 20, 23, 26, 29, 32, and 34. Optionally, the cell may be a fungal cell, a bacterial cell, an insect cell (with or without a baculovirus), a plant cell and a mammalian cell.

The invention also provides isolated nucleic acid molecules containing a nucleic acid sequence selected from SEQ ID NOs: 2, 5, 8, 11, 14, 17, 20, 23, 26, 29, 32, and 34. For example, such nucleic acid molecules can be naturally occurring.

The invention also relates to nucleic acid molecules that differ by a single nucleotide from a nucleic acid sequence selected from SEQ ID NOs: 2, 5, 8, 11, 14, 17, 20, 23, 26, 29, 32, and 34 as well as to isolated nucleic acid molecules encoding the mature form of a polypeptide having an amino acid sequence selected from the group consisting of SEQ ID NOs: 3, 6, 9, 12, 15, 18, 21, 24, 27, 30, 33, and 35. Further, the nucleic acid molecules can be ones that hybridizes under stringent conditions to the nucleotide sequence selected from the group consisting of SEQ ID NOs: 2, 5, 8, 11, 14, 17, 20, 23, 26, 29, 32, and 34 or a complement of that nucleotide sequence. In some embodiments, the nucleic acid molecules can be included in a vector, that further includes a promoter operably linked to said nucleic acid molecule. Also provided are cells that include the vector.

The invention also provides methods of producing polypeptides of the invention. The methods include culturing a cell under conditions that lead to expression of the polypeptide and the cell includes a vector having an isolated nucleic acid molecule containing a nucleic acid sequence selected from SEQ ID NOs: 2, 5, 8, 11, 14, 17, 20, 23, 26, 29, 32, and 34. In some instances, the cell is selected from a fungal cell, a bacterial cell, an insect cell, a plant cell or mammalian cell.

The invention also relates to methods for producing a protein by culturing a dermatophyte containing the polypeptide under conditions sufficient for the production of the protein and isolating the protein from the dermatophyte culture. For example, the protein can be a secreted protein. Likewise, the protein can also be an aminopeptidase or a carboxypeptidase. Specifically, the aminopeptidase can be a leucine aminopeptidase, such as ruLAP2. Additionally, the dermatophyte can be selected from *Epidermophyton floccosum, Microsporum audouinii, Microsporum ferrugineum, Trichophyton concentricum, Trichophyton kanei, Trichophyton megninii, Trichophyton mentagrophytes, Trichophyton raubitschekii, Trichophyton rubrum, Trichophyton schoenleinii, Trichophyton soudanense, Trichophyton tonsurans, Trichophyton violaceum, Trichophyton yaoundei, Microsporum canis, Microsporum equinum, Microsporum nanum, Microsporum persicolor, Trichophyton equinum, Trichophyton mentagrophytes, Trichophyton simii, Trichophyton verrucosum, Microsporum gypseum, Trichophyton ajelloi,* and *Trichophyton terrestre.*

The produced proteins can be applied to polypeptide substrates. In some instances, the produced protein can degrade the polypeptide or can sequentially digests a full-length polypeptide substance. Optionally, the polypeptide substrate length can be from 2 to 200 amino acids.

In some instances, the produced protein adds one or more amino acids to the polypeptide substrate. In other instances, the produced protein removes one or more amino acids from the polypeptide substrate to form a modified polypeptide substrate, and the produced protein subsequently adds one or more amino acids to the modified polypeptide substrate, thereby forming a polypeptide product comprising a different amino acid sequence than the polypeptide substrate.

The invention also provides methods for treating mycoses in a patient suffering therefrom. Such methods include administering an effective amount of an inhibitor with the activity of an EXOX protein selected from SEQ ID NOS:3, 6, 9, 12, 15, 18, 21, 24, 27, 30, 33, and 35. For example, the EXOX protein can include SEQ ID NO: 2.

The invention further provides methods of degrading a polypeptide substrate. These methods include contacting the polypeptide substrate with one or more of the isolated polypeptides of the invention. Optionally, the polypeptide substrate is a full-length protein, and the one or more isolated polypeptides can be polypeptides that sequentially digest the polypeptide substrate. The polypeptide substrate can be selected from denatured casein, gliadin, gluten, bovine serum albumin or fragments thereof. Further, in some instances, the isolated polypeptide is an aminopeptidase. The aminopeptidase can be a leucine aminopeptidase, such as ruLAP2.

Additionally, the method optionally contacting the polypeptide substrate with one or more proteases. In some instances, the proteases are selected from trypsin, pronase, chymotrypsin, and proteinaseK.

The invention further provides methods of removing amino acids from the amino terminus of a protein. The methods include contacting the protein with one or more of the isolated polypeptides of the invention. In some instances, the amino terminus of a protein includes a His tag. In other instances the amino terminus of a protein includes an Xaa-Pro tag. Optionally, Xaa is an amino acid including at least two vicinal nucleophilic groups, with examples including serine, threonine or cysteine.

The invention further provides isolated polypeptides of the invention that can have reverse proteolytic activity.

The invention further provides methods of adding one or more amino acids to a polypeptide substrate. The method includes contacting the polypeptide substrate with one or more of the isolated polypeptides of the invention.

Unless otherwise defined, all technical and scientific terms used herein have the same meaning as commonly understood by one of ordinary skill in the art to which this invention belongs. Although methods and materials similar or equivalent to those described herein can be used in the practice of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

BRIEF DESCRIPTION OF THE DRAWINGS

FIG. 14 is an alignment of deduced amino acid sequences of aminopeptidases of the M28E subfamily, including ruLAP1 (SEQ ID NO: 6), fuLAP1 (SEQ ID NO: 12), orLAP1 (SEQ ID NO: 80), AbispLAP1 (SEQ ID NO: 81), and VibrioLap (SEQ ID NO: 82).

FIG. 15 is an alignment of deduced amino acid sequences of aminopeptidases of the M28A subfamily, including ruLAP2 (SEQ ID NO: 3), fuLAP2 (SEQ ID NO: 9), orLAP2 (SEQ ID NO: 85), and ScerY (SEQ ID NO: 86).

DETAILED DESCRIPTION OF THE INVENTION

Figure 1:
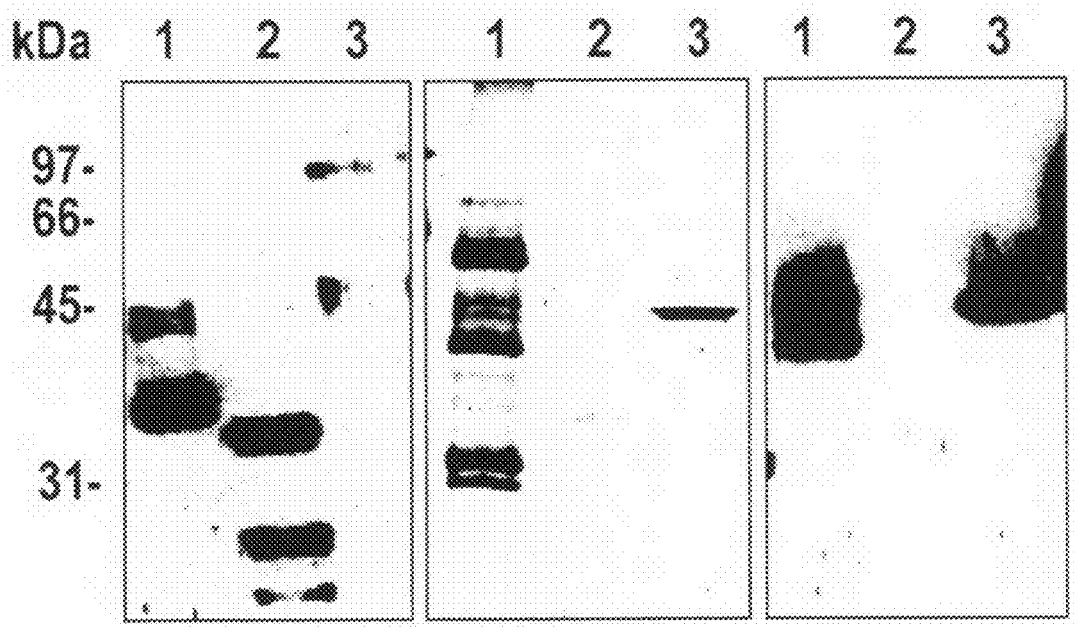
FIG. 1 is a photograph of a Western blot of *T. rubrum* supernatant preparation probed with anti-*A. oryzae* Alp (Panel A, left) and Mep antisera (Panel C, right). Panel B shows a 10% SDS-PAGE gel stained with Coomassie blue. In lane 1, the proteins of 0.25 ml of *T. rubrum* culture supernatant were precipitated with TCA before loading on the SDS-PAGE gel. 0.2 g of purified recombinant *A. oryzae* ALP and MEP were loaded on lane 2 and lane 3, respectively. The molecular mass of protein standards are shown in the left margin.

As used herein, the term protease is synonymous with peptidase, proteolytic enzyme and peptide hydrolase. The proteases include all enzymes that catalyse the cleavage of the peptide bonds (CO—NH) of proteins, digesting these proteins into peptides or free amino acids. Exopeptidases act near the ends of polypeptide chains at the amino (N) or carboxy (C) terminus. Those acting at a free N terminus liberate a single amino acid residue and are termed aminopeptidases. A large variety of highly specific proteases are involved in a number of different biological and physiological processes. Thus, these represent targets of choice for new drug applications as well as for controlled peptidic and/or proteic degradations.

Dermatophytes are human and animal pathogenic fungi, which cause cutaneous infections. Vanbreuseghem et al., GUIDE PRATIQUE DE MYCOLOGIE MEDICALE ET VETERINAIRE. (1978); Kwong-Chong & Bennet, MEDICAL MYCOLOGY (1992); Weitzman & Summerbell, Clin. Microbiol. Rev. 8:240-259 (1995). Examples of dermatophytes include, but are note limited to, *T. ajelloi, A. uncinatum, K. ajelloi, T. asteroides, T. mentagrophytes, T. concentricum, T. cruris, E. floccosum, T. dankalienese, G. dankaliensis, T. equinum, T. equinum var. autotrophicum, T. equinum var. equinum, T. erinacei, T. fischeri, T. flavescens, T. floccosum, E. floccosum, T. gloriae, T. gourvilii, T. granulare, T. granulosum, T. gypseum, T. inguinale, T. interdigitale, T. intertriginis, T. kanei, T. krajdenii, T. long fusum, T. megninii, A. quinckanum, A. benhamiae, A. vanbreuseghemii, T. pedis, T. proliferans, T. quickaneum, T. radiolatum, T. mentrophytes var. erinacei, T. mentagrophytes var. interdigitale, T. mentagrophytes var. mentagrophytes, T. mentagrophytes var. nodulare, T. mentagrophytes var. quinnckeanum, T. niveum, T. nodulare, T. persicolor, M. persicolor, T. phaseolforme, T. proliferans, T. purpureum, T. quinckeanum, T. radiolatum, T. raubitschekii, T. rubrum, S. ruber, T. schoenleinii, T. simii, A. simii, T. soudanense, T. sulphureum, T. tonsurans, A. insingulare, A. lenticularum, A. quadrifidum, T. tonsurans, T. sulphureum, T. terrestre, T. tonsurans var. sulphureum, T. tonsurans var tonsurans subvar. perforans, T. vanbreuseghemii, T. verrucosum, T. violaceum, T. yaoundei, E. floccosum, M. audouinii, M. ferrugineum, T. kanei, T. megninii, T. mentragrophytes, T. raubitschekii, T. schoenleinii, T. soudanese, T. violaceum, M. canis, M. equinum, M. nanum, M. persicolor, T. verrucosum*, and *M. gypseum*. Among the pathogenic species isolated in hospitals and private practices in Europe, *Trichophyton rubrum, T. mentagrophytes* and *Microsporum canis* are most commonly observed. Monod et al., Dermatology, 205:201-203 (2002). In fact, dermatophytes can grow exclusively in the stratum corneum, nails or hair, and digest components of the cornified cell envelope. To date, all investigated dermatophytes produce proteolytic activity in vitro and many investigators report the isolation and characterization of one or two secreted endoproteases from an individual species. For a review, see Monod et al., Int. J. Med. Microbiol. 292:405-419 (2002). In particular, *M. canis* was shown to possess two gene families encoding endoproteases of the S8 (subtilisins) and M36 (fungalysins) family as classified in the MEROPS proteolytic enzyme database (at Merops at The Sanger Institute, UK). Brouta et al., Infect. Immun. 70:5676-5683 (2002); Descamps et al., J Invest. Dermatol. 70:830-835 (2002). One member of each isolated M. canis gene family encoded one of the two previously characterized endoproteases from culture supernatants. Mignon et al., Med. Mycol. 36:395-404 (1998); Brouta et al., Med. Mycol. 39:269-275 (2001). Both enzymes were shown to be keratinolytic and produced during infection in cats. Mignon et al., Med. Mycol. 36:395-404 (1998); Brouta et al., Med. Mycol. 39:269-275 (2001). This proteolytic activity enables dermatophytes to grow exclusively in the stratum corneum, nails or hair, and to use digested components of the cornified cell envelope, i.e., single amino acids or short peptides, as nutrients for in vivo growing.

Two new leucine aminopeptidases (LAP) from the dermatophyte *T. rubrum*, ruLAP1 and ruLAP2 are described herein. *T. rubrum* is a species of the genus *Trichophyton*, which includes, e.g., *T. ajelloi, T. asteroides, T. mentagrophytes, T. concentricum, T. cruris, T. dankalienese, T. equinum, T. equinum* var. *autotrophicum, T. equinum* var. *equinum, T. erinacei, T. fischeri, T. flavescens, T. floccosum, T. gloriae, T. gourvilii, T. granulare, T. granulosum, T. gypseum, T. inguinale, T. interdigitale, T. intertriginis, T. kanei, T. krajdenii, T. long fusum, T. megninii, T. pedis, T. proliferans, T. quickaneum, T. radiolatum, T. mentrophytes* var. *erinacei, T. mentagrophytes* var. *interdigitale, T. mentagrophytes* var. *mentagrophytes, T. mentagrophytes* var. *nodulare, T. mentagrophytes* var. *quinnckeanum, T. niveum, T. nodulare, T. persicolor, T. phaseolforme, T. proliferans, T. purpureum, T. quinckeanum, T. radiolatum, T. raubitschekii, T. schoenleinii, T. simii, T. soudanense, T. sulphureum, T. tonsurans, T. sulphureum, T. terrestre, T. tonsurans* var. *sulphureum, T. tonsurans* var *tonsurans* subvar. *perforans, T. vanbreuseghemii, T. verrucosum, T. violaceum, T. yaoundei, T. kanei, T. raubitschekii, T. soudanese*. The properties of both LAPs were compared to those of the secreted enzymes encoded by the orthologue genes of the opportunistic fungus *Aspergillus fumigatus*, fuLAP1 and fuLAP2, and the commercially available microsomal LAP from porcine kidney (pkLAP) (MEROPS>M1 family). All of these enzymes exhibit a leucine aminopeptidase activity. Also; the *A. fumigatus*, aminopepeptidases fuLAP1 and fuLAP2 display about 70% amino acid identity with the *A. oryzae* orthologues reported in U.S. Pat. Nos. 6,127,161 and 5,994,113, which are incorporated herein by reference. Furthermore, ruLAP2 appears to be unique because (i) ruLAP1 and ruLAP2 display about 50% amino acid identity with the *A. fumigatus* orthologues fuLAP1 and fuLAP2 and with the *A. oryzae* orthologues reported U.S. Pat. Nos. 6,127,161 and 5,994,113; (ii) a cocktail of ruLAP2 and a trypsin-like endoprotease originating from the *P. pastoris* expression system. sequentially digests a full length polypeptide chain such as denatured casein; (iii) a cocktail of ruLAP2 and ruDPPIV (another exoprotease of *T. rubrum*) degrades a fragment of gliadin known to be resistant to protease action, thereby providing evidence that ruLAP2 alone or in combination with ruDPPIV could be used for the treatment of celiac disease or any disease of the digestive tract such as malabsorption; (iv) ruLAP2 in combination with other proteases (cocktails) is useful in the food industry, such as degrading substrates for bitterness, theves degradation, treatment of meat, soap industry, degrading prions, degrading viruses, and degrading toxic or contaminant proteins; (v) and, since ruLAP2 and/or other proteases secreted by the fungi is necessary for dermatophytes to grow on the cornified substrate of the nail, inhibitors of ruLAP2 and/or other proteases secreted by the fungi would be a new method of treatment for mycoses.

This invention provides novel fungal nucleic acids and proteins, which have leucine aminopeptidase activity. LAPs play a role in diverse functions including, but not limited to blood clotting, controlled cell death, tissue differentiation, tumor invasion, and in the infection cycle of a number of pathogenic microorganisms and viruses making these enzymes a valuable target and a powerful tool for new pharmaceuticals. Besides having a function in physiology, aminopeptidases also have commercial applications, mainly in the detergent and food industries. Microorganisms, such as fungi, are an excellent source of these enzymes due to their broad biochemical diversity and their susceptibility to genetic manipulation. Microorganisms degrade proteins and utilize the degradation products as nutrients for their growth. Thus, the novel LAPs identified herein are useful in a multitude of industrial applications including but not limited to hydrolysis of proteins in the food industry, degradation of by-products (e.g., feathers); degradation of prions; degradation of proteins for proteomics; hydrolysis of polypeptides for amino acid analysis; wound cleaning (e.g., attacking the dead tissue); prothesis cleaning and/or preparation; fabric softeners; soaps; cleaning or disinfection of septic tanks or any container (such as vats of retention, bottles, etc.) containing proteins that should be removed or sterilized; and cleaning of surgical instruments.

This invention provides novel enzymes and enzyme cocktails, i.e. a mixture of more than one enzyme that digest insoluble protein structures, such as the cornified cell envelope into short peptides and free amino acids. In fact, in addition to endoproteases of the S8 and M36 family, *T. rubrum* secretes two LAPs each with different substrate activity. RuLAP1 and ruLAP2 each belong to the same family of LAPs (MEROPS>M28). The properties of both LAPs were compared to those of the secreted enzymes encoded by the orthologue genes of the opportunistic fungus *A. fumigatus*, fuLAP1 and fuLAP2, and the commercially available microsomal LAP from porcine kidney (pkLAP) (MEROPS>M1 family). All of these enzymes exhibit leucine aminopeptidase activity. Furthermore, ruLAP2 has an original primary structure and is unique in that it is able, in the presence of ruDPPIV, to sequentially digest a polypeptide chain, such as a fragment of gliadin known to be resistant to other proteases. Partially purified ruLAP2 is also able, in the presence of a trypsin-like endoprotease originating from the *P. pastoris* expression system, to sequentially digest a full-length polypeptide chain, such as denatured casein.

The invention is based, in part, upon the isolation of novel nucleic acid sequences that encode novel polypeptides. The novel nucleic acids and their encoded polypeptides are referred to individually as ruLAP1, ruLAP2, fuLAP1 and fuLAP2. The nucleic acids, and their encoded polypeptides, are collectively designated herein as "EXOX".

The novel EXOX nucleic acids of the invention include the nucleic acids whose sequences are provided in Tables 1A, 1B, 2A, 2B, 3A, 3B, 4A, 4B, 5A, 5B, 6A, 6B, 7A, 7B, 8A, 8B, 9A, 9B, 10A, 10B, 11A, 11B, and 12A, or a fragment, derivative, analog or homolog thereof. The novel EXOX proteins of the invention include the protein fragments whose sequences are provided in Tables 1C, 2C, 3C, 4C, 5C, 6C, 7C, 8C, 9C, 10C, 11C, and 12B. The individual EXOX nucleic acids and proteins are described below.

Also, within the scope of this invention is a method of using protease inhibitors in the treatment or prevention of a fungal infection and/or opportunistic infection due to fungi, yeast cells and/or bacteria.

Using a reverse genetic approach, two aminopeptidases secreted by *T. rubrum* have been characterized in comparison with orthologues from *A. fumigatus* and the microsomal aminopeptidase pkLAP from porcine kidney. The four fungal enzymes identified herein (ruLAP1, fuLAP1, ruLAP2 and fuLAP2) as well as pkLAP share a common preference for Leu-AMC as a substrate, and function as leucine aminopeptidases. In addition, the aminopeptidase pkLAP, which acts also with an extremely high efficiency towards Ala-AMC, is also called alanine aminopeptidase (MEROPS>M1.001).

The EXOX nucleic acids of the invention, encoding EXOX proteins, include the nucleic acids whose sequences are provided herein or fragments thereof. The invention also includes mutant or variant nucleic acids any of whose bases may be changed from the corresponding base shown herein, while still encoding a protein that maintains its EXOX-like activities and physiological functions, or a fragment of such a nucleic acid. The invention further includes nucleic acids whose sequences are complementary to those described herein, including nucleic acid fragments that are complementary to any of the nucleic acids just described. The invention additionally includes nucleic acids or nucleic acid fragments, or complements thereto, whose structures include chemical modifications. Such modifications include, by way of non-limiting example, modified bases and nucleic acids whose sugar phosphate backbones are modified or derivatized. These modifications are carried out at least in part to enhance the chemical stability of the modified nucleic acid, such that they may be used, for example, as antisense binding nucleic acids in therapeutic applications in a subject.

The EXOX proteins of the invention include the EXO proteins whose sequences are provided herein. The invention also includes mutant or variant proteins any of whose residues may be changed from the corresponding residue shown herein, while still encoding a protein that maintains its EXO-like activities and physiological functions, or a functional fragment thereof. The invention further encompasses antibodies and antibody fragments, such as $F_{ab}$ or $(F_{ab})_2$, that bind immunospecifically to any of the proteins of the invention.

EXOX nucleic acids and proteins are useful in potential therapeutic applications such as the treatment of fungal infections. The EXOX nucleic acids, proteins and inhibitors also have other functions that include but are not limited to: (i) biotechnology reagent for improved protein production, e.g., tag removal, production of rare amino acids; (ii) drug development for certain disease indications, e.g., celiac disease (gluten intolerance); (iii) drug development for dermatological conditions, e.g., anti-mycosis agents, wart treatment, wound healing; (iv) cosmetology, e.g., with peeling tools, depilation, dermabrasion and dermaplaning; (v) food industry, e.g., production of nutrition supplements, sweeteners, generating hypoallergenic foods by predigestion; (vi) disinfecting agent, e.g., decontaminating protein-based contaminants such as prions or viruses (by digesting coat protein), cleaning surgery instruments or preparing items for surgery such as prosthesis or medical devices; (vii) sanitizing or recycling certain wastes, e.g., feathers, bones, hair and fur; (viii) cleaning agent, e.g., shampoo or liquid detergent.

Inhibitors of the EXOs, specifically of ruLAP2, may also be used as fungal anti-mycotic agents to treat mycoses. The LAPs themselves may also be used to treat diseases of the digestive tract, such as malabsorption or celiac disease, which is caused by wheat gluten. Gluten is the characteristic term for the protein mixture of glutelins and gliadins (prolamines) found in cereals. Due to its inherent physicochemical properties such as acting as a binding and extending agent, gluten is commonly used as an additive in food. Detection of gluten is important in the quality control and selection of food for individuals with diseases related to or caused by gluten intolerance including, gluten intolerance enteropathy, celiac disease, sprue and related allergic reactions, where a diet free from the gluten contained in wheat, rye barley, and in some cases oat is necessary.

Exoprotease Nucleic Acids and Polypeptides

*T. rubrum* aminopeptidase activity demonstrated here and previous studies on subtilisins and metalloproteases secreted by *M. canis* show that dermatophytes secrete a battery of proteases similar to those of the *Aspergillus* species in a medium containing protein as sole carbon and nitrogen source. Moreover, two genes, ruDPPIV and ruDPPV: EMBL AF082514 for ruDPPV, coding for dipeptidyl-aminopeptidases highly similar to DPPIV and DPPV from both *A. fumigatus* and *A. oryzae* (Beauvais et al., J. Biol. Chem. 272:6238-6244 (1997); Beauvais et al., Infec. Immun. 65:3042-3047 (1997); Doumas et al., Appl. Environ. Microbiol. 64:4809-4815 (1998); Doumas et al., J. Food Mycol. 2:271-279 (1999)) were isolated from genomic and cDNA libraries of *T. rubrum*. The intron-exon structures of the *T. rubrum* genes encoding these proteases are similar to the homologous genes isolated from *A. fumigatus* and *A. oryzae*. These results are not surprising since the teleomorphs of *Aspergillus* species and the teleomorphs of dermatophyte species are closely related, as they belong to the same taxonomic group of Ascomycetes producing prototunicate asci in cleistothecia (class Eurotiomycetes). In contrast to the genes encoding subtilisins and fungalysins, ruLAP1 and ruLAP2 are not members of large gene families in the *T. rubrum* genome.

Figure 14:
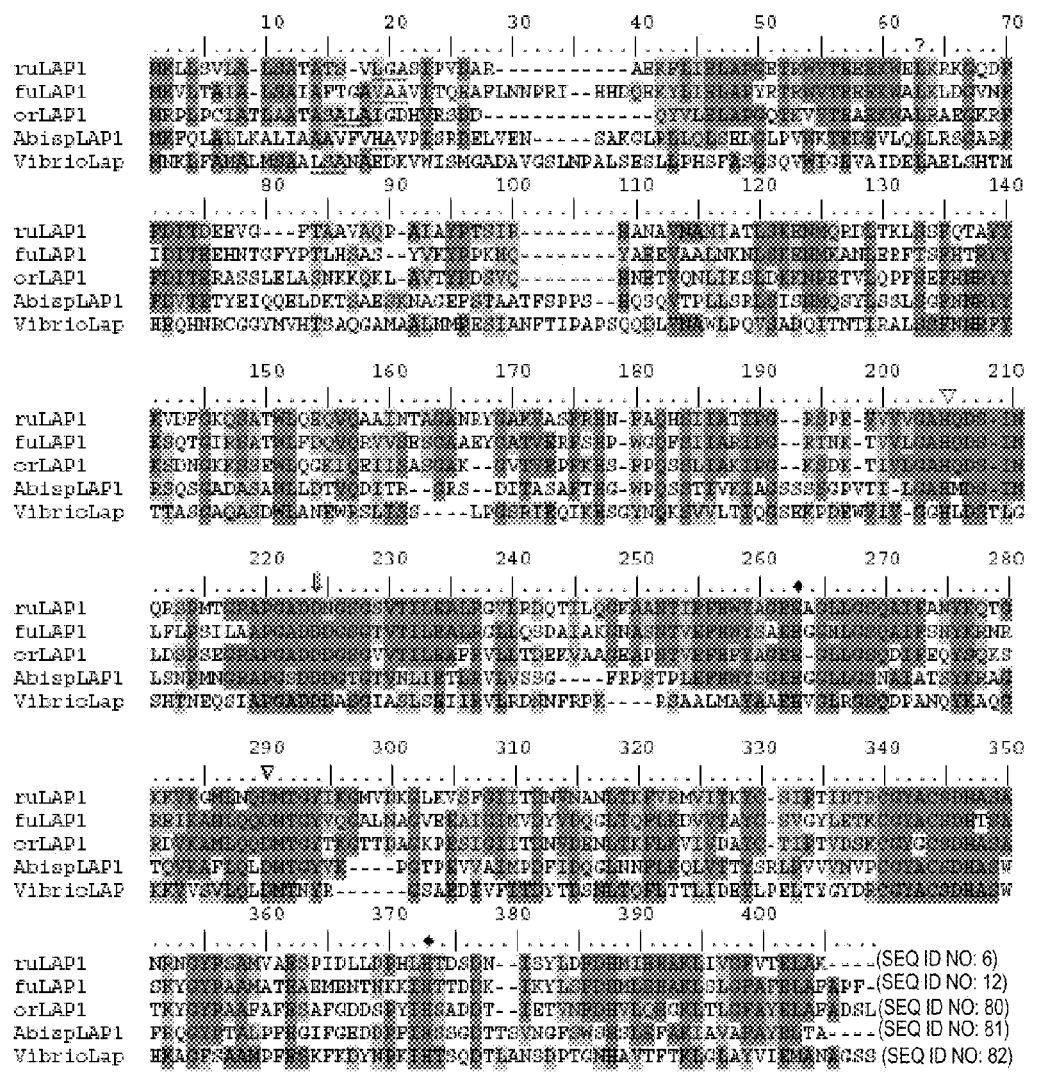

RuLAP1 displays about 50% amino acid identity with fuLAP1 and/or LAP1 (See Tables 19A and FIG. 14. These three enzymes structurally belong to the same subfamily M28E as *Aeromonas* and *Vibrio* leucyl aminopeptidases (MEROPS>M28.002). In addition, ruLAP2 displays about 50% amino acid identity with fuLAP2 and/or LAP2 (See Tables 19B and FIG. 15). These three enzymes structurally belong to the same subfamily M28A as the vacuolar protease Y of *S. cerevisiae* (MEROPS>M28.001) and the *Streptomyces griseus* secreted aminopeptidase (MEROPS>M28.00X). In addition, the members of the M28A and M28E subfamilies share low similarities. However, the amino acids of the two $Zn^{++}$ binding sites in these aminopeptidases are conserved and were identified in the fungal LAPs characterized herein (See Tables 20 and 21). In *S. griseus* and *Aeromonas proteolytica* secreted aminopeptidases, the two amino acid residues His and Asp bind a first $Zn^{++}$ ion and two additional residues His and Glu bind a second $Zn^{++}$ ion, while a second Asp residue bridges the two $Zn^{++}$ ions. Greenblatt et al., J. Mol. Biol. 265:620-636 (1997); Hasselgren et al., J. Biol. Inorg. Chem. 6:120-127 (2001). Substitution of $Zn^{++}$ by different divalent ions in *S. griseus* secreted aminopeptidase is affected by $Ca^{++}$ and has variable effects. Ben-Meir et al., Eur. J. Biochem 212:107-112 (1993); Lin et al., J. Biol. Inorg. Chem. 2:744-749 (1997); Hasselgren et al., J. Biol. Inorg. Chem. 6:120-127 (2001). The aminopeptidases of this invention were found to be sensitive to different ions. Like the *S. griseus* aminopeptidase, ruLAP2 and fuLAP2 are highly activated by $Co^{++}$.

RuLAP2 and fuLAP2 possess substantially different proteolytic activities despite a high percentage of sequence identity. In particular, ruLAP2 is able to efficiently hydrolyze Aspand Glu-7-amine-4-methylcoumarin (AMC), and ruLAP2 is the sole LAP identified so far that is able, first in the presence of ruDPPIV, to digest a peptide of gliadin known to be resistant to digestion by gastric and pancreatic proteases, or second, in the form of a partially purified extract that contains a trypsin-like endoprotease originating from the *P. pastoris* expression system, to digest a full length polypeptide chain such as denatured casein. The ability of a LAP to degrade a long polypeptide is not predictable solely on the basis of its capacity to cleave aminoacyl-AMC residues. Particular properties of dermatophyte enzymes have been observed with endoproteases secreted by *M. canis*. The 31.5 kDa *M. canis* subtilisin and the 43.5 kDa *M. canis* metalloprotease are both able to digest keratine azure in contrast to homologous secreted proteases from *A. fumigatus* and *A. oryzae*. As dermatophytes evolved from their natural habitat in soil, they have developed a strategy of infection using particular proteases to degrade the keratinized tissues. The unique properties of ruLAP2 could reflect highly specialized organisms parasiting the *stratum corneum* and the nails.

In addition to the LAPs disclosed herein, a series of novel proteases have also been isolated from the pathogenic fungi *T. rubrum* and are disclosed below. Like the LAPs these proteases are all characterised as exoproteases. They include: two carboxypeptidases, a prolylaminopeptidase, an amino peptidase P, a prolidase, and a dipeptidylpeptidase IV. Two additional novel proteases have been also characterized: a leucine aminopeptidase (caLAP1) from *Microsporum canis* and meLAP1, a *Trichophyton mentagrophytes* leucine aminopeptidase.

ruLAP2 ruLAP2 is a *T. rubrum* leucine aminopeptidase. A ruLAP2 nucleic acid of 1757 nucleotides (SEQ ID NO:1) is shown in Table 1A.

TABLE 1A

| ruLAP2 genomic nucleotide sequence (SEQ ID NO: 1). |
|---|
| ATGAAGTCGCAACTGTTGAGCCTGGCTGTGGCCGTCACAACCATCTCCCA |
| GGGCGTTGTTGGTCAAGAGCCCTTCGGATGGCCTTTCAAGCCTATGGTCA |
| CTCAGGTGAGTTGCTCTCAACAGATCGATCGATCGATCTACCTTTGTCCC |
| TGTCACATCAAACTCCAGCAGAGCCAAAGAAACAGACACAATGTTCCTGG |
| GGAATTCTTATGGGCTAATGTAAATGTATAGGATGACCTGCAAAACAAGA |
| TAAAGCTCAAGGATATCATGGCAGGCGTCGAGAAGCTGCAAAGCTTTTCT |
| GATGCTCATCCTGAAAAGAACCGAGTGTTTGGTGGTAATGGCCACAAGGA |
| CACTGTAGAGTGGATCTACAATGAGATCAAGGCCACTGGCTACTACGATG |
| TGAAGAAGCAGGAGCAAGTACACCTGTGGTCTCATGCCGAGGCTGCTCTC |
| AATGCCAATGGCAAGGACCTCAAGGCCAGCGCCATGTCCTACAGCCCTCC |
| TGCCAGCAAGATCATGGCTGAGCTTGTTGTTGCCAAGAACAATGGCTGCA |
| ATGCTGTATGTGCCATACACTTTCTATACGTCACATTCTCTCTAGAATGA |
| AGAGCACGGGAGAACTAACTTTATGTATACAGACTGATTACCCAGCGAAC |
| ACTCAGGGCAAGATCGTCCTCGTTGAGCGTGGTGTCTGCAGCTTCGGCGA |
| GAAGTCTGCTCAGGCTGGTGATGCAAAGGCTGCTGGTGCCATTGTCTACA |
| ACAACGTCCCCGGATCCCTTGCTGGCACTCTTGGTGGCCTTGACAAGCGC |
| CATGTCCCAACCGCTGGTCTTTCCCAGGAGGATGGAAAGAACCTTGCTAC |

TABLE 1A-continued

| ruLAP2 genomic nucleotide sequence (SEQ ID NO: 1). |
|---|
| CCTCGTTGCTTCTGGTAAGATTGATGTCACCATGAACGTTATCAGTCTGT |
| TTGAGAACCGAACCACGTAAGTAGCTCAACGGCTGATCCAGCATCAATTG |
| TCTCGAGTATATACTAAATCGATACCTCATAGCTGGAACGTCATTGCTGA |
| GACCAAGGGAGGAGACCACAACAACGTTATCATGCTCGGTGCTCACTCCG |
| ACTCCGTCGATGCCGGCCCTGGTATTAACGACAACGGCTCGGGCTCCATT |
| GGTATCATGACCGTTGCCAAAGCCCTCACCAACTTCAAGCTCAACAACGC |
| CGTCCGCTTTGCCTGGTGGACCGCTGAGGAATTCGGTCTCCTTGGAAGCA |
| CCTTCTACGTCAACAGCCTCGATGACCGTGAGCTGCACAAGGTCAAGTTG |
| TACCTCAACTTCGACATGATCGGCTCTCCCAACTTCGCCAACCAGATCTA |
| CGACGGTGACGGTTCGGCCTACAACATGACCGGCCCCGCTGGCTCTGCTG |
| AAATCGAGTACCTGTTCGAGAAGTTCTTTGACGACCAGGGTATCCCACAC |
| CAGCCCACTGCCTTCACTGGCCGATCCGACTACTCTGCTTTCATCAAGCG |
| CAACGTGCCCGCTGGCGGCCTCTTCACTGGAGCCGAGGTTGTCAAGACCC |
| CCGAGCAAGTCAAGTTGTTCGGTGGTGAGGCTGGCGTTGCCTATGACAAG |
| AACTACCATCGCAAGGGCGACACCGTTGCCAACATCAACAAGGGAGCTAT |
| CTTCCTTAACACTCGAGCCATCGCCTACGCTATCGCCGAGTATGCCCGAT |
| CCCTCAAGGGATTCCCAACCCGCCCAAAGACCGGCAAGCGTGACGTCAAC |
| CCCCAGTATTCTAAGATGCCTGGTGGTGGCTGCGGACACCACACTGTCTT |
| CATGTAA |

A disclosed ruLAP2 open reading frame ("ORF") of 1488 nucleotides begins with an ATG start codon at position 1 (underlined in Table 1B).

TABLE 1B

| ruLAP2 nucleotide sequence (SEQ ID NO: 2). |
|---|
| <u>ATG</u>AAGTCGCAACTGTTGAGCCTGGCTGTGGCCGTCACAACCATCTCCCA |
| GGGCGTTGTTGGTCAAGAGCCCTTCGGATGGCCTTTCAAGCCTATGGTCA |
| CTCAGGATGACCTGCAAAACAAGATAAAGCTCAAGGATATCATGGCAGGC |
| GTCGAGAAGCTGCAAAGCTTTTCTGATGCTCATCCTGAAAAGAACCGAGT |
| GTTTGGTGGTAATGGCCACAAGGACACTGTAGAGTGGATCTACAATGAGA |
| TCAAGGCCACTGGCTACTACGATGTGAAGAAGCAGGAGCAAGTACACCTG |
| TGGTCTCATGCCGAGGCTGCTCTCAATGCCAATGCCAAGGACCTCAAGGC |
| CAGCGCCATGTCCTACAGCCCTCCTGCCAGCAAGATCATGGCTGAGCTTG |
| TTGTTGCCAAGAACAATGGCTGCAATGCTACTGATTACCCAGCGAACACT |
| CAGGGCAAGATCGTCCTCGTTGAGCGTGGTGTCTGCAGCTTCGGCGAGAA |
| GTCTGCTCAGGCTGGTGATGCAAAGGCTGCTGGTGCCATTGTCTACAACA |
| ACGTCCCCGGATCCCTTGCTGGCACTCTTGGTGGCCTTGACAAGCGCCAT |
| GTCCCAACCGCTGGTCTTTCCCAGGAGGATGGAAAGAACCTTGCTACCCT |
| CGTTGCTTCTGGTAAGATTGATGTCACCATGAACGTTATCAGTCTGTTTG |
| AGAACCGAACCACCTGGAACGTCATTGCTGAGACCAAGGGAGGAGACCAC |

TABLE 1B-continued ruLAP2 nucleotide sequence (SEQ ID NO: 2).

AACAACGTTATCATGCTCGGTGCTCACTCCGACTCCGTCGATGCCGGCCC
TGGTATTAACGACAACGGCTCGGGCTCCATTGGTATCATGACCGTTGCCA
AAGCCCTCACCAACTTCAAGCTCAACAACGCCGTCCGCTTTGCCTGGTGG
ACCGCTGAGGAATTCGGTCTCCTTGGAAGCACCTTCTACGTCAACAGCCT
CGATGACCGTGAGCTGCACAAGGTCAAGTTGTACCTCAACTTCGACATGA
TCGGCTCTCCCAACTTCGCCAACCAGATCTACGACGGTGACGGTTCGGCC
TACAACATGACCGGCCCCGCTGGCTCTGCTGAAATCGAGTACCTGTTCGA
GAAGTTCTTTGACGACCAGGGTATCCCACACCAGCCCACTGCCTTCACTG
GCCGATCCGACTACTCTGCTTTCATCAAGCGCAACGTGCCCGCTGGCGGC
CTCTTCACTGGAGCCGAGGTTGTCAAGACCCCCGAGCAAGTCAAGTTGTT
CGGTGGTGAGGCTGGCGTTGCCTATGACAAGAACTACCATCGCAAGGGCG
ACACCGTTGCCAACATCAACAAGGGAGCTATCTTCCTTAACACTCGAGCC
ATCGCCTACGCTATCGCCGAGTATGCCCGATCCCTCAAGGGATTCCCAAC
CCGCCCAAAGACCGGCAAGCGTGACGTCAACCCCCAGTATTCTAAGATGC
CTGGTGGTGGCTGCGGACACCACACTGTCTTCATGTAA

A disclosed ruLAP2 nucleic acid (SEQ ID NO: 2) encodes a protein having 495 amino acid residues (SEQ ID NO: 3), which is presented in Table 1C using the one-letter amino acid code.

TABLE 1C

Encoded ruLAP2 protein sequence (SEQ ID NO: 3).

MKSQLLSLAVAVTTISQGVVGQEPFGWPFKPMVTQDDLQNKIKLKDIMAG
VEKLQSFSDAHPEKNRVFGGNGHKDTVEWIYNEIKATGYYDVKKQEQVHL

TABLE 1C-continued

Encoded ruLAP2 protein sequence (SEQ ID NO: 3).

WSHAEAALNANGKDLKASAMSYSPPASKIMAELVVAKNNGCNATDYPANT
QGKIVLVERGVCSFGEKSAQAGDAKAAGAIVYNNVPGSLAGTLGGLDKRH
VPTAGLSQEDGKNLATLVASGKIDVTMNVISLFENRTTWNVIAETKGGDH
NNVIMLGAHSDSVDAGPGINDNGSGSIGIMTVAKALTNFKLNNAVRFAWW
TAEEFGLLGSTFYVNSLDDRELHKVKLYLNFDMIGSPNFANQIYDGDGSA
YNMTGPAGSAEIEYLFEKFFDDQGIPHQPTAFTGRSDYSAFIKRNVPAGG
LFTGAEVVKTPEQVKLFGGEAGVAYDKNYHRKGDTVANINKGAIFLNTRA
IAYAIAEYARSLKGFPTRPKTGKRDVNPQYSKMPGGGCGHHTVFM

The disclosed ruLAP2 has homology to the amino acid sequences shown in the BLAST data listed in Table 1D, 1E, and 1F.

The following program options were used:

tblastn—compares the protein "Sequence 1" against the nucleotide "Sequence 2" which has been translated in all six reading frames blastx—compares the nucleotide "Sequence 1" against the protein "Sequence 2"

blastp—for protein-protein comparisons

In all BLAST alignments herein, the "E-value" or "Expect" value is a numeric indication of the probability that the aligned sequences could have achieved their similarity to the BLAST query sequence by chance alone, within the database that was searched. The Expect value (E) is a parameter that describes the number of hits one can "expect" to see just by chance when searching a database of a particular size. It decreases exponentially with the Score (S) that is assigned to a match between two sequences. Essentially, the E value describes the random background noise that exists for matches between sequences.

TABLE 1D

TBLASTN results for ruLAP2

| Gene Index/Identifier | Protein/Organism | Length (aa) | Identity (%) | Positives (%) | Expect |
|---|---|---|---|---|---|
| gi469363 | *Saccharomyces cerevisiae* aminopeptidase Y gene | 32421 | 170/477 (35%) | 239/437 (55%) | 8e-65 |
| gi15839805 | *Mycobacterium tuberculosis* CDC15551, section 33 of 280 of the complete genome | 18857 | 152/424 (35%) | 225/424 (53%) | 5e-57 |
| gi9949032 | *Pseudomonas aeruginosa* PAO1, section of 281 of 529 of the complete genome | 12547 | 129/317 (40%) | 180/317 (56%) | 1e-56 |

TABLE 1E

BLASTX results for ruLAP2

| Gene Index/Identifier | Protein/Organism | Length (aa) | Identity (%) | Positives (%) | Expect |
|---|---|---|---|---|---|
| gi28918599 | Hypothetical protein/ *Neurospora crassa* | 508 | 219/467 (46%) | 287/467 (61%) | e-112 |
| gi584764 | APE3 YEAST; Aminopeptidase precursor/ *Saccharomyces cerevisiae* | 537 | 170/477 (35%) | 239/437 (55%) | 1e-65 |
| gi23017467 | Hypothetical protein/ *Thermobifida fusca* | 514 | 151/460 (32%) | 237/460 (51%) | 5e-61 |

TABLE 1E-continued

BLASTX results for ruLAP2

| Gene Index/Identifier | Protein/Organism | Length (aa) | Identity (%) | Positives (%) | Expect |
|---|---|---|---|---|---|
| gi15839805 | Hydrolase/ *Mycobacterium tuberculosis* CDC15551 | 493 | 152/424 (35%) | 225/424 (53%) | 6e−58 |

TABLE 1F

BLASTP results for ruLAP2

| Gene Index/Identifier | Protein/Organism | Length (aa) | Identity (%) | Positives (%) | Expect |
|---|---|---|---|---|---|
| Gi28918599 | Hypothetical protein/ *Neurospora crassa* | 508 | 219/467 (46%) | 287/467 (61%) | e−105 |
| Gi584764 | APE3 YEAST; Aminopeptidase precursor/ *Saccharomyces cerevisiae* | 537 | 169/477 (35%) | 237/477 (49%) | 2e−64 |
| Gi15839805 | Hydrolase/ *Mycobacterium tuberculosis* CDC15551 | 493 | 152/424 (35%) | 225/424 (53%) | 5e−57 |
| Gi23017467 | Hypothetical protein/ *Thermobifida fusca* | 514 | 150/460 (32%) | 237/460 (51%) | 1e−56 | ruLAP1 ruLAP1 is a *T. rubrum* leucine aminopeptidase. A ruLAP1 nucleic acid of 1256 nucleotides is shown in Table 2A (SEQ ID NO: 4).

TABLE 2A ruLAP1 genomic nucleotide sequence (SEQ ID NO: 4).

ATGAAGCTCCTCTCTGTTCTTGCGCTGAGCGCTACCGCTACCTCCGTCCT

CGGAGCTAGCATTCCTGTTGATGCCCGGGCCGAGAAGTTCCTCATCGAAC

TTGCCCCTGGTGAGACTCGCTGGGTTACCGAGGAGGAGAAGTGGGAGCTT

AAGCGGGTATGTACCACTATCCTACGCAAAAGTTGTATTTTCACTAGATA

ATATTGGTTATTAACACCCATTCTAGAAGGGTCAAGACTTCTTTGACATC

ACTGACGAGGAGGTTGGATTCACTGCTGCTGTTGCACAGCCAGCCATTGC

CTACCCAACCTCCATCCGCCATGCTAATGCTGTTAACGCCATGATTGCTA

CCCTCTCCAAGGAGAACATGCAGCGCGATCTGACCAAGCTCAGCTCGTTC

CAAACCGCTTACTATAAGGTTGACTTTGGCAAGCAGTCTGCCACCTGGCT

CCAGGAGCAAGTCCAGGCTGCCATCAATACCGCTGGTGCCAATCGCTACG

GAGCCAAGGTCGCCAGCTTCCGACACAACTTCGCTCAGCACAGCATCATT

GCCACTATTCCCGGCCGCTCCCCTGAAGTCGTTGTCGTCGGTGCTCACCA

AGACAGCATCAACCAACGCAGCCCCATGACCGGCCGCGCTCCAGGTGCCG

ATGACAACGGCAGTGGCTCCGTCACCATCCTTGAGGCCCTCCGTGGTGTT

CTCCGGGACCAGACCATCCTCCAGGGCAAGGCTGCCAACACCATTGAGTT

CCACTGGTACGCCGGTGAGGAAGCTGGTCTTCTGGGCTCCCAGGCCATCT

TCGCCAACTACAAACAGACCGGCAAGAAGGTCAAGGGCATGCTCAACCAG

GACATGACCGGTTACATCAAGGGAATGGTCGACAAGGGTCTCAAGGTGTC

TABLE 2A-continued ruLAP1 genomic nucleotide sequence (SEQ ID NO: 4).

CTTCGGTATCATCACCGACAACGTCAACGCTAACTTGACCAAGTTCGTCC

GCATGGTCATCACCAAGGTAAGCTTCAACTCTTGATAAATATATTTTTCA

TCGATGAAATGATGTCCTAATAATGCTTAAGTACTGCTCAATCCCAACCA

TCGACACCCGCTGCGGCTATGCTTGCTCTGACCACGCCTCTGCCAACCGC

AATGGCTACCCATCTGCCATGGTTGCCGAGTCTCCCATCGATCTCCTCGA

CCCTCACCTCCACACTGACTCTGACAACATTAGCTACCTCGACTTCGACC

ACATGATCGAGCACGCTAAGCTCATTGTCGGCTTCGTCACTGAGCTCGCT

AAGTAA

A disclosed ruLAP1 open reading frame ("ORF") of 1122 nucleotides begins with an ATG codon (underlined in Table 2B) at position 1.

TABLE 2B ruLAP1 nucleotide sequence (SEQ ID NO: 5).

<u>ATG</u>AAGCTCCTCTCTGTTCTTGCGCTGAGCGCTACCGCTACCTCCGTCCT

CGGAGCTAGCATTCCTGTTGATGCCCGGGCCGAGAAGTTCCTCATCGAAC

TTGCCCCTGGTGAGACTCGCTGGGTTACCGAGGAGGAGAAGTGGGAGCTT

AAGCGGAAGGGTCAAGACTTCTTTGACATCACTGACGAGGAGGTTGGATT

CACTGCTGCTGTTGCACAGCCAGCCATTGCCTACCCAACCTCCATCCGCC

ATGCTAATGCTGTTAACGCCATGATTGCTACCCTCTCCAAGGAGAACATG

CAGCGCGATCTGACCAAGCTCAGCTCGTTCCAAACCGCTTACTATAAGGT

TGACTTTGGCAAGCAGTCTGCCACCTGGCTCCAGGAGCAAGTCCAGGCTG

TABLE 2B-continued ruLAP1 nucleotide sequence (SEQ ID NO: 5).

CCATCAATACCGCTGGTGCCAATCGCTACGGAGCCAAGGTCGCCAGCTTC

CGACACAACTTCGCTCAGCACAGCATCATTGCCACTATTCCCGGCCGCTC

CCCTGAAGTCGTTGTCGTCGGTGCTCACCAAGACAGCATCAACCAACGCA

GCCCCATGACCGGCCGCGCTCCAGGTGCCGATGACAACGGCAGTGGCTCC

GTCACCATCCTTGAGGCCCTCCGTGGTGTTCTCCGGGACCAGACCATCCT

CCAGGGCAAGGCTGCCAACACCATTGAGTTCCACTGGTACGCCGGTGAGG

AAGCTGGTCTTCTGGGCTCCCAGGCCATCTTCGCCAACTACAAACAGACC

GGCAAGAAGGTCAAGGGCATGCTCAACCAGGACATGACCGGTTACATCAA

GGGAATGGTCGACAAGGGTCTCAAGGTGTCCTTCGGTATCATCACCGACA

ACGTCAACGCTAACTTGACCAAGTTCGTCCGCATGGTCATCACCAAGTAC

TGCTCAATCCCAACCATCGACACCCGCTGCGGCTATGCTTGCTCTGACCA

CGCCTCTGCCAACCGCAATGGCTACCCATCTGCCATGGTTGCCGAGTCTC

CCATCGATCCTCGACCCTCACCTCCACACTGACTCTGACAACATTAGC

TACCTCGACTTCGACCACATGATCGAGCACGCTAAGCTCATTGTCGGCTT

CGTCACTGAGCTCGCTAAGTAA

A disclosed ruLAP1 nucleic acid (SEQ ID NO: 5) encodes a protein having 377 amino acid residues (SEQ ID NO: 6), which is presented in Table 2C using the one-letter amino acid code.

TABLE 2C

Encoded ruLAP1 protein sequence (SEQ ID NO: 6).

MKLLSVLALSATATSVLGASIPVDARAEKFLIELAPGETRWVTEEEKWEL

KRKGQDFFDITDEEVGFTAAVAQPAIAYPTSIRHANAVNAMIATLSKENM

QRDLTKLSSFQTAYYKVDFGKQSATWLQEQVQAAINTAGANRYGAKVASF

RHNFAQHSIIATIPGRSPEVVVVGAHQDSINQRSPMTGRAPGADDNGSGS

VTILEALRGVLRDQTILQGKAANTIEFHWYAGEEAGLLGSQAIFANYKQT

GKKVKGMLNQDMTGYIKGMVDKGLKVSFGIITDNVNANLTKFVRMVITKY

CSIPTIDTRCGYACSDHASANRNGYPSAMVAESPIDLLDPHLHTDSDNIS

YLDFDHMIEHAKLIVGFVTELAK

The disclosed ruLAP1 has homology to the amino acid sequences shown in the blast data listed in Table 2D, 2E, and 2F. This data was analyzed by the program pairwise blast.

TABLE 2D

TBLASTN results for ruLAP1

| Gene Index/Identifier | Protein/Organism | Length (aa) | Identity (%) | Positives (%) | Expect |
|---|---|---|---|---|---|
| >gi1762234 | Polyketide synthase PKSL2/ *Aspergillus parasiticus* | 9894 | 131/247 (53%) 40/76 (52%) 20/24 (83%) | 171/247 (69%) 57/76 (75%) 22/24 (91%) | 1e-95 |
| >gi23393798 | Leucine aminopeptidase (Lap1)/ *Aspergillus sojae* | 2547 | 77/159 (48%) 63/148 (42%) 14/30 (46%) | 97/159 (61%) 89/148 (60%) 23/30 (76%) | 4e-64 |
| >gi927685 | *Saccharomyces cerevisiae* chromosome IV lambda3641 and cosmid 9831, and 9410 | 78500 | 137/350 (39%) | 201/350 (57%) | 3e-62 |
| >gi7413486 | *Agaricus* partial mRNA for aminopeptidase | 1089 | 130/346 (37%) | 189/346 (54%) | 2e-55 |

TABLE 2E

BLASTX results for ruLAP1

| Gene Index/Identifier | Protein/Organism | Length (aa) | Identity (%) | Positives (%) | Expect |
|---|---|---|---|---|---|
| >gi23393799 | Leucine aminopeptidase/ *Aspergillus sojae* | 377 | 126/248 (50%) 37/78 (47%) 13/24 (54%) | 162/248 (65%) 55/78 (70%) 20/24 (83%) | 5e-87 |

TABLE 2E-continued

BLASTX results for ruLAP1

| Gene Index/Identifier | Protein/Organism | Length (aa) | Identity (%) | Positives (%) | Expect |
|---|---|---|---|---|---|
| >gi28918132 | Hypothetical protein/ Neurospora crassa | 402 | 115/247 (46%) 43/77 (55%) 18/24 (75%) | 153/247 (61%) 58/77 (75%) 23/24 (95%) | 8e−86 |
| >gi6320623 | Hypothetical ORF; ydr415 cp/ Saccharomyces cerevisiae | 374 | 96/254 (37%) 36/77 (46%) 96/226 (42%) | 143/254 (56%) 49/77 (63%) 135/226 (59%) | 7e−55 |
| >gi28916832 | Hypothetical protein/ Neurospora crassa | 409 | 31/66 (46%) | 41/66 (62%) | 4e−54 |

TABLE 2F

BLASTP results for ruLAP1

| Gene Index/Identifier | Protein/Organism | Length (aa) | Identity (%) | Positives (%) | Expect |
|---|---|---|---|---|---|
| >gi23393799 | Leucine aminopeptidase/ Aspergillus sojae | 377 | 175/348 (50%) | 234/348 (67%) | 4e−99 |
| >gi28918132 | Hypothetical protein/ Neurospora crassa | 402 | 175/345 (50%) | 230/345 (66%) | 2e−97 |
| >gi6320623 | Hypothetical ORF; ydr415cp/ Saccharomyces cerevisiae | 374 | 140/351 (39%) | 201/351 (57%) | 7e−65 |
| >gi28916832 | Hypothetical protein/ Neurospora crassa | 409 | 129/296 (43%) | 178/296 (60%) | 3e−58 | fuLAP2 fuLAP2 is an *A. fumigatus* leucine aminopeptidase. A fuLAP2 nucleic acid of 1557 nucleotides is shown in Table 3A (SEQ ID NO: 7).

TABLE 3A fuLAP2 genomic nucleotide sequence (SEQ ID NO: 7).

ATGAAGCTGCTCTACCTCACATCGTTTGCCTCTCTGGCCGTGGCCAATGG

CCCAGGATGGGACTGGAAGCCCCGAGTTCATCCGGTTAGTGTTCCTCTCG

CCGGGTTTGTCTGCTGTATGCTAACAGCATCCTGTCTATTACAGAAAGTC

CTGCCCCAAATGATCCATTTGTGGGATCTTCTGCAGGGCGCTCAACAGCT

GGAAGACTTCGCCTATGCCTACCCCGAGCGCAACCGCGTCTTTGGTGGAC

GGGCCCACGAGGACACCGTCAACTACCTCTACCGTGAGTTGAAGAAAACC

GGCTACTACGACGTTTACAAGCAGCCCCAGGTTCACCAGTGGACCCGAGC

CGACCAGGCTCTCACCGTCGACGGCCAGTCCTATGACGCCACAACCATGA

CTTACAGCCCCAGCGTAAACGCCACGGCGCCGCTGGCAGTGGTGAACAAC

CTGGGCTGCGTCGAGGCTGACTATCCCGCCGATCTGACGGGCAAGATTGC

TCTGATCTCGCGGGGCGAGTGCACCTTTGCGACCAAATCCGTCTTGAGCG

CCAAGGCCGGGCGGCGGCGGCACTCGTGTACAACAATATCGAGGGTTCG

ATGGCGGGAACTCTGGGCGGCGCGACCAGCGAGCTGGGTGCCTACGCTCC

CATCGCCGGCATCAGCCTCGCGGACGGACAGGCGCTGATCCAGATGATCC

TABLE 3A-continued fuLAP2 genomic nucleotide sequence (SEQ ID NO: 7).

AGGCGGGCACGGTGACAGCCAACCTGTGGATCGACAGCCAGGTCGAGAAC

CGTACCACCTACAACGTGATCGCGCAGACCAAGGGCGGCGACCCCAACAA

CGTCGTCGCGCTGGGTGGCCACACGGACTCGGTCGAGGCCGGGCCCGGCA

TCAACGACGACGGCTCCGGCATCATCAGCAACCTCGTCGTCGCCAAGGCG

CTGACCCGCTTCTCGGTCAAGAACGCGGTGCGCTTCTGCTTCTGGACGGC

GGAGGAGTTCGGCCTGCTGGGCAGCAACTACTACGTCAACAGCCTCAATG

CCACCGAGCAGGCCAAGATCCGCCTGTATCTCAACTTCGACATGATCGCC

TCCCCCAACTACGCCCTGATGATCTATGACGGCGACGGCTCGGCCTTCAA

CCTGACGGGGCCGGCCGGCTCGGCGCAGATCGAGCGGCTCTTCGAGGACT

ACTACACGTCGATCCGCAAGCCGTTCGTGCCGACCGAGTTCAACGGCCGC

TCCGACTACCAGGCCTTTATTCTCAACGGCATCCCCGCGGGAGGCCTCTT

CACCGGCGCGGAGGCGATCAAGACCGAGGAACAGGCCCAATTGTTTGGCG

GCCAGGCCGGCGTGGCTCTGGACGCCAACTACCACGCCAAGGGTGACAAC

ATGACTAATCTCAACCGCGAGGCTTTCCTGATCAATTCCAGGGCGACGGC

CTTTGCCGTGGCGACGTACGCCAACAGCCTTGACTCGATCCCCCCACGCA

ACATGACCACCGTGGTCAAGCGGTCGCAGCTGGAGCAAGCCATGAAGAGG

TABLE 3A-continued fuLAP2 genomic nucleotide sequence (SEQ ID NO: 7).

ACCCCGCACACGCACACCGGCGGAACAGGATGCTACAAGGACCGGGTTGA

GCAGTAG

A disclosed fuLAP2 open reading frame ("ORF") of 1497 nucleotides begins with an ATG codon (underlined in Table 3B) at position 1.

TABLE 3B fuLAP2 nucleotide sequence (SEQ ID NO: 8).

ATGAAGCTGCTCTACCTCACATCGTTTGCCTCTCTGGCCGTGGCCAATGG

CCCAGGATGGGACTGGAAGCCCCGAGTTCATCCGAAAGTCCTGCCCCAAA

TGATCCATTTGTGGGATCTTCTGCAGGGCGCTCAACAGCTGGAAGACTTC

GCCTATGCCTACCCCGAGCGCAACCGCGTCTTTGGTGGACGGGCCCACGA

GGACACCGTCAACTACCTCTACCGTGAGTTGAAGAAAACCGGCTACTACG

ACGTTTACAAGCAGCCCCAGGTTCACCAGTGGACCCGAGCCGACCAGGC

TCTCACCGTCGACGGCCAGTCCTATGACGCCACAACCATGACTTACAGCC

CCAGCGTAAACGCCACGGCGCCGCTGGCAGTGGTGAACAACCTGGGCTGC

GTCGAGGCTGACTATCCCGCCGATCTGACGGGCAAGATTGCTCTGATCTC

GCGGGGCGAGTGCACCTTTGCGACCAAATCCGTCTTGAGCGCCAAGGCCG

GGGCGGCGGCGGCACTCGTGTACAACAATATCGAGGGTTCGATGGCGGGA

ACTCTGGGCGGCGCGACCAGCGAGCTGGGTGCCTACGCTCCCATCGCCGG

CATCAGCCTCGCGGACGGACAGGCGCTGATCCAGATGATCCAGGCGGGCA

CGGTGACAGCCAACCTGTGGATCGACAGCCAGGTCGAGAACCGTACCACC

TACAACGTGATCGCGCAGACCAAGGGCGGCGACCCCAACAACGTCGTCGC

GCTGGGTGGCCACACGGACTCGGTCGAGGCCGGGCCCGGCATCAACGACG

ACGGCTCCGGCATCATCAGCAACCTCGTCGTCGCCAAGGCGCTGACCCGC

TTCTCGGTCAAGAACGCGGTGCGCTTCTGCTTCTGGACGGCGGAGGAGTT

CGGCCTGCTGGGCAGCAACTACTACGTCAACAGCCTCAATGCCACCGAGC

AGGCCAAGATCCGCCTGTATCTCAACTTCGACATGATCGCCTCCCCCAAC

TACGCCCTGATGATCTATGACGGCGACGGCTCGGCCTTCAACCTGACGGG

GCCGGCCGGCTCGGCGCAGATCGAGCGGCTCTTCGAGGACTACTACACGT

CGATCCGCAAGCCGTTCGTGCCGACCGAGTTCAACGGCCGCTCCGACTAC

CAGGCCTTTATTCTCAACGGCATCCCCGCGGGAGGCCTCTTCACCGGCGC

GGAGGCGATCAAGACCGAGGAACAGGCCCAATTGTTTGGCGGCCAGGCCG

GCGTGGCTCTGGACGCCAACTACCACGCCAAGGGTGACAACATGACTAAT

CTCAACCGCGAGGCTTTCCTGATCAATTCCAGGGCGACGGCCTTTGCCGT

GGCGACGTACGCCAACAGCCTTGACTCGATCCCCCCACGCAACATGACCA

CCGTGGTCAAGCGGTCGCAGCTGGAGCAAGCCATGAAGAGGACCCCGCAC

ACGCACACCGGCGGAACAGGATGCTACAAGGACCGGGTTGAGCAGTAG

A disclosed fuLAP2 nucleic acid (SEQ ID NO: 8) encodes a protein having 498 amino acid residues (SEQ ID NO: 9), which is presented in Table 3C using the one-letter amino acid code.

TABLE 3C

Encoded fuLAP2 protein sequence (SEQ ID NO: 9).

MKLLYLTSFASLAVANGPGWDWKPRVHPKVLPQMIHLWDLLQGAQQLEDF

AYAYPERNRVFGGRAHEDTVNYLYRELKKTGYYDVYKQPQVHQWTRADQA

LTVDGQSYDATTMTYSPSVNATAPLAVVNNLGCVEADYPADLTGKIALIS

RGECTFATKSVLSAKAGAAAALVYNNIEGSMAGTLGGATSELGAYAPIAG

ISLADGQALIQMIQAGTVTANLWIDSQVENRTTYNVIAQTKGGDPNNVVA

LGGHTDSVEAGPGINDDGSGIISNLVVAKALTRFSVKNAVRFCFWTAEEF

GLLGSNYYVNSLNATEQAKIRLYLNFDMIASPNYALMIYDGDGSAFNLTG

PAGSAQIERLFEDYYTSIRKPFVPTEFNGRSDYQAFILNGIPAGGLFTGA

EAIKTEEQAQLFGGQAGVALDANYHAKGDNMTNLNREAFLINSRATAFAV

ATYANSLDSIPPRNMTTVVKRSQLEQAMKRTPHTHTGGTGCYKDRVEQ

The disclosed fuLAP2 has homology to the amino acid sequences shown in the BLAST data listed in Table 3D, 3E, and 3F. This data was analyzed by the program PAIRWISE BLAST.

TABLE 3D

TBLASTN results for fuLAP2

| Gene Index/Identifier | Protein/Organism | Length (aa) | Identity (%) | Positives (%) | Expect |
|---|---|---|---|---|---|
| >gi469463 | *Saccharomyces cerevisiae*/ aminopeptidase Y gene | 2272 | 184/464 (39%) | 243/464 (52%) | 7e-69 |
| >gi9949032 | *Pseudomonas aeruginosa* PAO1, section of 281 of 529 of the complete genome | 12547 | 165/445 (37%) | 231/445 (51%) | 9e-67 |
| >gi23017467 | *Mycobacterium tuberculosis* CDC15551, section 33 of 280 of complete genome | 18857 | 166/426 (38%) | 218/426 (51%) | 2e-62 |

TABLE 3E

BLASTX results for fuLAP2

| Gene Index/Identifier | Protein/Organism | Length (aa) | Identity (%) | Positives (%) | Expect |
|---|---|---|---|---|---|
| >gi28918599 | Hypothetical protein/ *Neurospora crassa* | 508 | 250/479 (52%) | 314/479 (65%) | e−131 |
| >gi23017467 | Hypothetical protein/ *Thermobifida fusca* | 514 | 173/465 (37%) | 251/465 (53%) | 4e−74 |
| >gi584764 | APE3 YEAST; Aminopeptidase precursor/ *Saccharomyces cerevisiae* | 537 | 184/464 (39%) | 243/464 (52%) | 8e−70 |
| >gi15598135 | Probable aminopeptidase/ *Pseudomonas aeruginosa* PAO1 | 536 | 165/445 (37%) | 231/445 (51%) | 1e−67 |
| >gi15839805 | Hydrolase/ *Mycobacterium tuberculosis* CDC15551 | 493 | 166/426 (38%) | 218/426 (51%) | 3e−63 |

TABLE 3F

BLASTP results for fuLAP2

| Gene Index/Identifier | Protein/Organism | Length (aa) | Identity (%) | Positives (%) | Expect |
|---|---|---|---|---|---|
| >gi28918599 | Hypothetical protein/ *Neurospora crassa* | 508 | 250/469 (52%) | 314/479 (65%) | e−128 |
| >gi23017467 | Hypothetical protein/ *Thermobifida fusca* | 514 | 173/465 (37%) | 251/465 (53%) | 3e−71 |
| >gi584764 | APE3 YEAST; Aminopeptidase precursor/ *Saccharomyces cerevisiae* | 537 | 183/464 (39%) | 243/464 (52%) | 6e−70 |
| >gi15598135 | Probable aminopeptidase/ *Pseudomonas aeruginosa* PA01 | 536 | 164/445 (36%) | 230/445 (51%) | 3e−65 | fuLAP1 fuLAP1 is an *A. fumigatus* leucine aminopeptidase. A fuLAP1 nucleic acid of 1298 nucleotides is shown in Table 4A (SEQ ID NO: 10).

TABLE 4A fuLAP1 genomic nucleotide sequence (SEQ ID NO: 10).

ATGAAAGTTCTTACAGCTATTGCGCTGAGCGCAATAGCTTTCACAGGGGC

TGTAGCTGCAGTGATTACTCAGGAAGCATTCTTAAACAACCCCCGCATCC

ATCATGACCAGGAGAAGTACTTGATCGAACTGGCCCCTTATCGAACACGA

TGGGTGACTGAAGAGGAGAAATGGGCATTGAAATTGGTACCATACTTCCC

CAAAATTTGGGTCTCCAAGTCCACGGGCGACTAACTGCACGATTGCTTGA

AGGACGGCGTGAATTTTATCGATATCACAGAAGAGCACAACACCGGATTT

TACCCGACTCTCCACAGCGCCAGCTATGTGAAATATCCACCGAAGATGCA

GTATGCAGAAGAAGTGGCTGCTCTTAACAAGAATTTATCGAAAGAAAACA

TGAAGGCCAACCTGGAACGATTCACATCATTTCATACTCGCTATTACAAA

TCTCAGACGGGAATCCGATCGGCAACGTGGCTGTTCGACCAAGTTCAGAG

AGTTGTCTCTGAGTCTGGAGCCGCTGAGTATGGTGCAACTGTTGAGCGAT

TCTCTCATCCATGGGGTCAGTTCAGCATTATTGCCCGAATACCCGGCCGA

ACGAACAAGACTGTGGTGCTGGGCGCCCATCAGGACAGCATCAATTTGTT

TABLE 4A-continued fuLAP1 genomic nucleotide sequence (SEQ ID NO: 10).

TCTCCCGTCAATCTTGGCTGCTCCCGGTGCTGATGACGATGGAAGTGGAA

CTGTCACCATTCTTGAAGCGTTGCGCGGTCTGCTGCAGTCAGACGCCATT

GCCAAGGGTAATGCATCCAATACTGTCGAGTTCCACTGGTACTCTGCAGA

AGAAGGCGGAATGCTGGGCTCCCAGGCAATATTTTCCAATTACAAGCGGA

ATAGGCGGGAAATCAAAGCCATGCTCCAGCAAGACATGACTGGCTACGTC

CAGGGAGCTTTGAACGCCGGTGTTGAGGAAGCCATAGGAATTATGGTCGA

TTATGTCGACCAGGGCCTCACACAGTTTCTCAAGGACGTTGTTACAGCGG

TAAGCCTCAGTTGTCCCCCACGAAAAGCTGTTTAGTCGACAAATGAAATT

GACGGCTGCATTAGTACTGCTCTGTGGGTTACCTGGAGACGAAGTGCGGA

TATGCCTGCTCCGACCACACCTCGGCCAGTAAATATGGTTATCCCGCGGC

TATGGCGACAGAAGCAGAGATGGAAAATACCAATAAGAAGATACATACTA

CCGACGACAAGATCAAGTATTTGAGCTTCGATCATATGTTGGAGCATGCC

AAGTTGAGTCTTGGCTTCGCTTTCGAATTGGCATTTGCGCCGTTTTAA

A disclosed fuLAP1 open reading frame ("ORF") of 1167 nucleotides begins with an ATG codon at position 1 (underlined in Table 4B).

TABLE 4B fuLAP1 nucleotide sequence (SEQ ID NO: 11).

ATGAAAGTTCTTACAGCTATTGCGCTGAGCGCAATAGCTTTCACAGGGGC

TGTAGCTGCAGTGATTACTCAGGAAGCATTCTTAAACAACCCCCGCATCC

ATCATGACCAGGAGAAGTACTTGATCGAACTGGCCCCTTATCGAACACGA

TGGGTGACTGAAGAGGAGAAATGGGCATTGAAATTGGACGGCGTGAATTT

TATCGATATCACAGAAGAGCACAACACCGGATTTTACCCGACTCTCCACA

GCGCCAGCTATGTGAAATATCCACCGAAGATGCAGTATGCAGAAGAAGTG

GCTGCTCTTAACAAGAATTTATCGAAAGAAACATGAAGGCCAACCTGGA

ACGATTCACATCATTTCATACTCGCTATTACAAATCTCAGACGGGAATCC

GATCGGCAACGTGGCTGTTCGACCAAGTTCAGAGAGTTGTCTCTGAGTCT

GGAGCCGCTGAGTATGGTGCAACTGTTGAGCGATTCTCTCATCCATGGGG

TCAGTTCAGCATTATTGCCCGAATACCCGGCCGAACGAACAAGACTGTGG

TGCTGGGCGCCCATCAGGACAGCATCAATTTGTTTCTCCCGTCAATCTTG

GCTGCTCCCGGTGCTGATGACGATGGAAGTGGAACTGTCACCATTCTTGA

AGCGTTGCGCGGTCTGCTGCAGTCAGACGCCATTGCCAAGGGTAATGCAT

CCAATACTGTCGAGTTCCACTGGTACTCTGCAGAAGAAGGCGGAATGCTG

GGCTCCCAGGCAATATTTTCCAATTACAAGCGGAATAGGCGGGAAATCAA

AGCCATGCTCCAGCAAGACATGACTGGCTACGTCCAGGGAGCTTTGAACG

CCGGTGTTGAGGAAGCCATAGGAATTATGGTCGATTATGTCGACCAGGGC

CTCACACAGTTTCTCAAGGACGTTGTTACAGCGTACTGCTCTGTGGGTTA

CCTGGAGACGAAGTGCGGATATGCCTGCTCCGACCACACCTCGGCCAGTA

AATATGGTTATCCCGCGGCTATGGCGACAGAAGCAGAGATGGAAAATACC

AATAAGAAGATACATACTACCGACGACAAGATCAAGTATTTGAGCTTCGA

TCATATGTTGGAGCATGCCAAGTTGAGTCTTGGCTTCGCTTTCGAATTGG

CATTTGCGCCGTTTTAA

A disclosed fuLAP1 nucleic acid (SEQ ID NO: 11) encodes a protein having 388 amino acid residues (SEQ ID NO: 12), which is presented in Table 4C using the one-letter amino acid code.

TABLE 4C

Encoded fuLAP1 protein sequence (SEQ ID NO: 12).

MKVLTAIALSAIAFTGAVAAVITQEAFLNNPRIHHDQEKYLIELAPYRTR

WVTEEEKWALKLDGVNFIDITEEHNTGFYPTLHSASYVKYPPKMQYAEEV

AALNKNLSKENMKANLERFTSFHTRYYKSQTGIRSATWLFDQVQRVVSES

GAAEYGATVERFSHPWGQFSIIARIPGRTNKTVVLGAHQDSINLFLPSIL

AAPGADDDGSGTVTILEALRGLLQSDAIAKGNASNTVEFHWYSAEEGGML

GSQAIFSNYKRNRREIKAMLQQDMTGYVQGALNAGVEEAIGIMIDYVDQG

LTQFLKDVVTAYCSVGYLETKCGYACSDHTSASKYGYPAAMATEAEMENT

NKKIHTTDDKIKYLSFDHMLEHAKLSLGFAFELAFAPF

The disclosed fuLAP1 has homology to the amino acid sequences shown in the BLAST data listed in Table 4D, 4E, and 4F. This data was analyzed by the program PAIRWISE BLAST.

TABLE 4D

| TBLASTN results for fuLAP1 | | | | |
|---|---|---|---|---|
| Gene Index/Identifier | Protein/Organism | Length (aa) | Identity (%) | Positives (%) | Expect |
| >gi1762234 | Polyketide synthase PKSL2/ Aspergillus parasiticus | 9894 | 208/249 (80%) 61/84 (72%) 46/62 (74%) | 226/249 (90%) 67/84 (79%) 55/62 (88%) | e−169 |

TABLE 4D-continued

TBLASTN results for fuLAP1

| Gene Index/Identifier | Protein/Organism | Length (aa) | Identity (%) | Positives (%) | Expect |
|---|---|---|---|---|---|
| >gi23393798 | Leucine aminopeptidase (LAP1)/ Aspergillus sojae | 2547 | 66/110 (60%) 68/152 (44%) 37/75 (49%) 15/30 (50%) | 82/110 (74%) 92/152 (60%) 52/75 (69%) 21/30 (70%) | 7e-82 |
| >gi927685 | Saccharomyces cerevisiae chromosome IV lambda3641 and cosmid 9831, and 9410 | 78500 | 152/341 (44%) | 207/341 (60%) | 1e-71 |
| >gi5832144 | Botrytis cinerea strain T4 cDNA library under condition of nitrogen deprivation | 780 | 89/134 (66%) 27/53 (50%) | 106/134 (79%) 33/53 (62%) | 7e-58 |

TABLE 4E

BLASTX results for fuLAP1

| Gene Index/Identifier | Protein/Organism | Length (aa) | Identity (%) | Positives (%) | Expect |
|---|---|---|---|---|---|
| >gi28918132 | Hypothetical protein/ Neurospora crassa | 402 | 208/352 (59%) | 255/352 (72%) | e-116 |
| >gi23393799 | Leucine aminopeptidase/ Aspergillus sojae | 377 | 183/355 (51%) | 241/355 (67%) | 3e-97 |
| >gi6320623 | Hypothetical ORF; Ydr415cp/ Saccharomyces cerevisiae | 374 | 152/341 (44%) | 207/341 (60%) | 2e-72 |
| >gi18250467 | Aminopeptidase/ Agaricus bisporus | 384 | 139/352 (39%) | 186/352 (52%) | 1e-58 |

TABLE 4F

BLASTP results for fuLAP1

| Gene Index/Identifier | Protein/Organism | Length (aa) | Identity (%) | Positives (%) | Expect |
|---|---|---|---|---|---|
| >gi28918132 | Hypothetical protein/ Neurospora crassa | 402 | 208/352 (59%) | 255/352 (72%) | e-116 |
| >gi23393799 | Leucine aminopeptidase (LAP1)/ Aspergillus sojae | 377 | 183/355 (51%) | 241/355 (67%) | 6e-98 |
| >gi6320623 | Hypothetical ORF Ydr415cp/ Saccharomyces cerevisiae | 374 | 152/341 (44%) | 207/341 (60%) | 3e-73 |
| >gi18250467 | Aminopeptidase/ Agaricus bisporus | 384 | 140/352 (39%) | 190/352 (53%) | 7e-59 | ruCBPS1 ruCBPS1 is a *T. rubrum* carboxypeptidase. Genomic DNA sequence of a ruCBPS1 nucleic acid of 2106 nucleotides (SEQ ID NO: 13) is shown in Table 5A.

TABLE 5A ruCBPS1 genomic nucleotide sequence (SEQ ID NO: 13).

ATGGTGTCATTCTGCGGAGTGGCAGCCTGCCTGCTGACAGTTGCTGGCCA

TCTTGCGCAGGCTCAGTTCCCACCAAAACCGGAGGGAGTCACTGTCCTGG

AGTCGAAATTCGGCAGCGGTGCTCGCATCACTTATAAGGAGGTCCGTTAG

CTGCATAGAAAGTCCACGTGAAGACGCTGTAGCTAACAATCCACTAGCCT

GGCCTCTGTGAGACGACAGAGGGCGTCAAGTCGTACGCCGGATATGTCCA

TCTGCCTCCAGGCACGCTCAGGGACTTCGGTGTCGAGCAGGACTACCCTA

TCAACACCTTTTTTTGGTTCTTTGAGGCAAGAAAGGACCCTGAAAATGCC

TABLE 5A-continued ruCBPS1 genomic nucleotide sequence (SEQ ID NO: 13).

CCTCTCGGCATCTGGATGAACGGTGGCCCGGGTAGCTCGTCGATGTTTGG

AATGATGACTGAGAACGGGCCTTGCTTCGTCAATGCAGACTCCAATTCTA

CTCGCCTGAACCCTCATTCTTGGAACAATGAAGGTATGCCATCAGCTTCT

GATGGAAAACTAAATATTGCTAACATTGTACTTTCTGTGACTAGTCAATA

TGCTGTATATAGACCAGCCAGTGCAGGTCGGTCTGTCCTACGACACTTTG

GCCAACTTCACCAGGAATCTAGTCACGGATGAGATCACGAAACTGAAACC

CGGAGAACCTATTCCGGAACAGAATGCCACTTTCCTGGTAGGTACATATG

CAAGCCGCAATATGAACACCACTGCACACGGAACTAGGCATGCTGCCATG

GCTCTCTGGCACTTCGCCCAAGTCTGGTTCCAAGAGTTCCCAGGATATCA

CCCTAGGAACAACAAGATCAGCATTGCTACCGAATCCTACGGCGGCCGTT

ATGGCCCGGCCTTTACTGCCTTCTTTGAAGAGCAGAACCAGAAGATCAAG

AACGGCACATGGAAGGGACACGAGGGAACTATGCACGTGCTGCATCTCGA

CACCCTCATGATCGTCAACGGATGCATCGACCGTCTTGTCCAATGGCCGG

CATATCCGCAAATGGCGTACAACAACACATATAGCATCGAGGCAGTCAAC

GCCAGCATTCATGCAGGAATGCTGGATGCCCTCTACCGCGACGGTGGCTG

TCGAGACAAGATTAACCACTGCCGCTCCCTCTCTTCTGTGTTCGATCCTG

AGAATCTCGGCATCAACTCAACCGTC1ATGATGTCTGCAAGGATGCCGAG

ACATTCTGCTCCAATGATGTTCGCGATCCCTACCTCAAGTTCTCTGGCCG

CAACTACTATGACATCGGACAGCTTGACCCCAGCCCATTCCCAGCACCAT

TTTACATGGCCTGGCTAAATCAGCCGCATGTGCAGGCAGCACTGGGTGTG

CCACTTAACTGGACACAGTCAAACGATGTTGTGTCTACCGCATTCCGTGC

AATTGGTGACTACCCTCGGCCAGGGTGGCTGGAGAACCTGGCTTATTTGC

TGGAGAATGGCATCAAGGTTTCGCTTGTTTACGGTGATCGGGACTACGCA

TGCAACTGGTTCGGTGGTGAGCTCTCAAGTCTGGGAATCAACTACACTGA

CACCCACGAATTCCATAATGCCGGCTATGCAGGTATCCAGATCAATAGCA

GCTACATCGGTGGACAGGTGAGGCAGTACGGCAACCTCTCCTTCGCCCGC

GTCTACGAGGCCGGCCATGAGGTGCCATCGTACCAACCCGAGACTGCACT

GCAGATATTCCACCGTTCCCTGTTCAACAAGGATATCGCTACTGGAACCA

AGGACACGTCATCGCGCATGGACGGAGGCAAGTTTTACGGCACCTCGGGC

CCTGCGGACTCGTTTGGTTTCAAGAACAAACCTCCACCGCAGCACGTCCA

CTTCTGTCATATCTTAGACACCAGCACCTGCACCAAGGAGCAGATCCAGT

CAGTTGAGAACGGCACTGCCGCCGTACGCAGCTGGATCATTGTCGACTCC

AACTCGACCTCTCTGTTCCCCGAGGTAGTTGGCTCAGGGGAACCCACGCC

AACCCCTATGCCTGGAGGGGCTACTACACTATCTGCTCACGGGTTCTTGT

ATGGCGTGACATTATGGGCTGTTATTGTTGTAGCTGTTATAGAGCTGGCA

ATGTAA

A ruCBPS1 nucleic acid of 1989 (SEQ ID NO: 14) is shown in Table 5B. A disclosed ruCBPS1 open reading frame ("ORF") begins with an ATG start codon at position 1 (underlined in Table 5B).

TABLE 5B ruCBPS1 nucleotide sequence (SEQ ID NO: 14).

<u>ATG</u>GTGTCATTCTGCGGAGTGGCAGCCTGCCTGCTGACAGTTGCTGGCCA

TCTTGCGCAGGCTCAGTTCCCACCAAAACCGGAGGGAGTCACTGTCCTGG

AGTCGAAATTCGGCAGCGGTGCTCGCATCACTTATAAGGAGCCTGGCCTC

TGTGAGACGACAGAGGGCGTCAAGTCGTACGCCGGATATGTCCATCTGCC

TCCAGGCACGCTCAGGGACTTCGGTGTCGAGCAGGACTACCCTATCAACA

CCTTTTTTGGTTCTTTGAGGCAAGAAAGGACCCTGAAAATGCCCCTCTC

GGCATCTGGATGAACGGTGGCCCGGGTAGCTCGTCGATGTTTGGAATGAT

GACTGAGAACGGGCCTTGCTTCGTCAATGCAGACTCCAATTCTACTCGCC

TGAACCCTCATTCTTGGAACAATGAAGTCAATATGCTGTATATAGACCAG

CCAGTGCAGGTCGGTCTGTCCTACGACACTTTGGCCAACTTCACCAGGAA

TCTAGTCACGGATGAGATCACGAAACTGAAACCCGGAGAACCTATTCCGG

AACAGAATGCCACTTTCCTGGTAGGTACATATGCAAGCCGCAATATGAAC

ACCACTGCACACGGAACTAGGCATGCTGCCATGGCTCTCTGGCACTTCGC

CCAAGTCTGGTTCCAAGAGTTCCCAGGATATCACCCTAGGAACAACAAGA

TCAGCATTGCTACCGAATCCTACGGCGGCCGTTATGGCCCGGCCTTTACT

GCCTTCTTTGAAGAGCAGAACCAGAAGATCAAGAACGGCACATGGAAGGG

ACACGAGGGAACTATGCACGTGCTGCATCTCGACACCCTCATGATCGTCA

ACGGATGCATCGACCGTCTTGTCCAATGGCCGGCATATCCGCAAATGGCG

TACAACAACACATATAGCATCGAGGCAGTCAACGCCAGCATTCATGCAGG

AATGCTGGATGCCCTCTACCGCGACGGTGGCTGTCGAGACAAGATTAACC

ACTGCCGCTCCCTCTCTTCTGTGTTCGATCCTGAGAATCTCGGCATCAAC

TCAACCGTCAATGATGTCTGCAAGGATGCCGAGACATTCTGCTCCAATGA

TGTTCGCGATCCCTACCTCAAGTTCTCTGGCCGCAACTACTATGACATCG

GACAGCTTGACCCCAGCCCATTCCCAGCACCATTTTACATGGCCTGGCTA

AATCAGCCGCATGTGCAGGCAGCACTGGGTGTGCCACTTAACTGGACACA

GTCAAACGATGTTGTGTCTACCGCATTCCGTGCAATTGGTGACTACCCTC

GGCCAGGGTGGCTGGAGAACCTGGCTTATTTGCTGGAGAATGGCATCAAG

GTTTCGCTTGTTTACGGTGATCGGGACTACGCATGCAACTGGTTCGGTGG

TGAGCTCTCAAGTCTGGGAATCAACTACACTGACACCCACGAATTCCATA

ATGCCGGCTATGCAGGTATCCAGATCAATAGCAGCTACATCGGTGGACAG

GTGAGGCAGTACGGCAACCTCTCCTTCGCCCGCGTCTACGAGGCCGGCCA

TGAGGTGCCATCGTACCAACCCGAGACTGCACTGCAGATATTCCACCGTT

CCCTGTTCAACAAGGATATCGCTACTGGAACCAAGGACACGTCATCGCGC

ATGGACGGAGGCAAGTTTTACGGCACCTCGGGCCCTGCGGACTCGTTTGG

TTTCAAGAACAAACCTCCACCGCAGCACGTCCACTTCTGTCATATCTTAG

ACACCAGCACCTGCACCAAGGAGCAGATCCAGTCAGTTGAGAACGGCACT

TABLE 5B-continued ruCBPS1 nucleotide sequence (SEQ ID NO: 14).

GCCGCCGTACGCAGCTGGATCATTGTCGACTCCAACTCGACCTCTCTGTT
CCCCGAGGTAGTTGGCTCAGGGGAACCCACGCCAACCCCTATGCCTGGAG
GGGCTACTACACTATCTGCTCACGGGTTCTTGTATGGCGTGACATTATGG
GCTGTTATTGTTGTAGCTGTTATAGAGCTGGCAATGTAA

A disclosed ruCBPS1 nucleic acid (SEQ ID NO: 14) encodes a protein having 662 amino acid residues (SEQ ID NO: 15), which is presented in Table 5C using the one-letter amino acid code.

TABLE 5C

Encoded ruCBPS1 protein sequence (SEQ ID NO: 15).

MVSFCGVAACLLTVAGHLAQAQFPPKPEGVTVLESKFGSGARITYKEPGL
CETTEGVKSYAGYVHLPPGTLRDFGVEQDYPINTFFWFFEARKDPENAPL
GIQMNGGPGSSSMFGMMTENGPCFVNADSNSTRLNPHSWNNEVNMLYIDQ

TABLE 5C-continued

Encoded ruCBPS1 protein sequence (SEQ ID NO: 15).

PVQVGLSYDTLANFTRNLVTDEITKLKPGEPIPEQNATFLVGTYASRNMN
TTAHGTRHAAMALWHFAQVWFQEFPGYHPRNNKISIATESYGGRYGPAFT
AFFEEQNQKIKNGTWKGHEGTMHVLHLDTLMIVNGCIDRLVQWPAYPQMA
YNNTYSIEAVNASIHAGMLDALYRDGGCRDKINHCRSLSSVFDPENLGIN
STVNDVCKDAETFCSNDVRDPYLKFSGRNYYDIGQLDPSPFPAPFYMAWL
NQPHVQAALGVPLNWTQSNDVVSTAFRAIGDYPRPGWLENLAYLLENGIK
VSLVYGDRDYACNWFGGELSSLGINYTDTHEFHNAGYAGIQINSSYIGGQ
VRQYGNLSFARVYEAGHEVPSYQPETALQIFHRSLFNKDIATGTKDTSSR
MDGGKFYGTSGPADSFGFKNKPPPQHVHFCHILDTSTCTKEQIQSVENGT
AAVRSWIIVDSNSTSLFPEVVGSGEPTPTPMPGGATTLSAHGFLYGVTLW
AVIVVAVIELAM

The disclosed ruCBPS1 has homology to the amino acid sequences shown in the BLAST data listed in Table 5D, 5E and 5F. This data was analyzed by the program PAIRWISE BLAST.

TABLE 5D

TBLASTN results for ruCBPS1

| Gene Index/Identifier | Protein/Organism | Length (aa) | Identity (%) | Positives (%) | Expect |
|---|---|---|---|---|---|
| gi\|32410708 | *Neurospora crassa* strain OR74A | 1947 | 222/632 (35%) | 321/632 (50%) | 1e-90 |
| gi\|3046860 | *Schizosaccharomyces pombe* cpy1 gene for carboxypeptidase Y | 4308 | 137/481 (28%) | 204/481 (42%) | 6e-41 |
| gi\|18152938 | *Pichia angusta* carboxypeptidase Y (CPY) gene | 2214 | 141/520 (27%) | 228/520 (43%) | 4e-40 |
| gi\|4028157 | *Pichia angusta* carboxypeptidase Y precursor (CPY) gene | 2509 | 140/520 (26%) | 226/520 (43%) | 7e-40 |
| gi\|170828 | *Candida albicans* carboxypeptidase Y precursor (CPY1) gene | 1985 | 131/482 (27%) | 205/482 (42%) | 3e-36 |

TABLE 5E

BLASTX results for ruCBPS1

| Gene Index/Identifier | Protein/Organism | Length (aa) | Identity (%) | Positives (%) | Expect |
|---|---|---|---|---|---|
| gi\|15004616 | carboxypeptidase S1/ *Aspergillus oryzae* | 555 | 209/535 (39%) | 294/535 (54%) | 1e-98 |
| gi\|435818 | carboxypeptidase S1, CPD-S1/ *Penicillium janthinellum* | 423 | 159/498 (31%) | 234/498 (46%) | 6e-64 |
| gi\|995456 | preprocarboxypeptidase Z/ *Absidia zychae* | 460 | 147/506 (29%) | 219/506 (43%) | 8e-48 |
| gi\|3046861 | carboxypeptidase Y/ *Schizosaccharomyces pombe* | 1002 | 137/481 (28%) | 204/481 (42%) | 7e-42 |
| gi\|18152939 | carboxypeptidase Y/ *Pichia angusta* | 537 | 141/520 (27%) | 228/520 (43%) | 4e-41 |
| gi\|4028158 | carboxypeptidase Y precursor; vacuolar carboxypeptidase/ *Pichia angusta* | 541 | 140/520 (26%) | 226/520 (43%) | 7e-41 |
| gi\|7597001 | carboxypeptidase Y precursor/ *Candida albicans* | 542 | 131/482 (27%) | 206/482 (42%) | 2e-37 |

TABLE 5F

BLASTP results for ruCBPS1

| Gene Index/Identifier | Protein/Organism | Length (aa) | Identity (%) | Positives (%) | Expect |
|---|---|---|---|---|---|
| gi\|15004616 | carboxypeptidase S1/ *Aspergillus oryzae* | 555 | 210/537 (39%) | 296/537 (55%) | 2e-95 |
| gi\|435818 | carboxypeptidase S1, CPD-S1/ *Penicillium janthinellum* | 423 | 159/498 (31%) | 234/498 (46%) | 2e-60 |
| gi\|995456 | preprocarboxypeptidase Z/ *Absidia zychae* | 460 | 146/500 (29%) | 217/500 (43%) | 6e-47 |
| gi\|19115337 | carboxypeptidase y/ *Schizosaccharomyces pombe* | 1002 | 136/481 (28%) | 204/481 (42%) | 7e-41 | ruCBPS1' ruCBPS1' is a *T. rubrum* carboxypeptidase. Genomic DNA sequence of a ruCBPS1' nucleic acid of 2030 nucleotides (SEQ ID NO: 16) is shown in Table 6A.

TABLE 6A ruCBPS1' genomic nucleotide sequence (SEQ ID NO: 16).

ATGCGCTTTGCTGCTAGCATTGCCGTGGCCCTGCCAGTCATTCACGCGGC

GAGTGCTCAAGGCTTCCCTCCACCCGTTAAGGGCGTCACCGTGGTCAAAT

CCAAGTTCGACGAAAACGTAAAGATCACATACAAGGAGGTATGTGTTTAC

ATCATTTTCACATCCAGATCTTATATCCTTACAATAAATCTGGCTAACTC

ACTGGATAGAATGACATATGTGAAACCACTCAAGGAGTTAGATCATTCAC

CGGTCATGTCCACCTTCCTCCAGACAACGATGACTTTGGTGTCTACCGGA

ACTACTCCATCAACACATTCTTCTGGTTCTTTGAAGCTCGTGAAGACCCT

AAGAATGCTCCTCTCTCCATCTGGCTGAACGGTGGTCCGGGATCGTCATC

CATGATTGGACTCTTCCAGGAAAACGGTCCATGCTGGGTCAATGAAGACT

CTAAATCTACCACCAACAATTCATTTTCATGGAACAATAAAGTAAATATG

CTCTACATTGATCAGCCAAACCAAGTCGGTTTCAGTTATGACGTACCTAC

CAACATCACTTACTCTACCATCAATGATACAATATCTGTTGCGGACTTCT

CTAACGGTGTCCCTGCGCAAAATCTTTCTACGTTGGTTGGAACCGGCAGC

AGCCAGAACCCTTGGGCAACTGCCAATAACACTGTGAACGCTGCTCGTTC

TATCTGGCACTTTGCACAACTGTGGTTCCAGGAATTCCCTGAACACAAGC

CTAACAATAACAAGATCAGTATTTGGACAGAGTCCTATGGAGGAAGATAT

GGTCCCTCATTCGCCTCTTACTTCCAGGAACAGAACGAAAAGATCAAAAA

CCATACCATTACTGAAGAAGGAGAGATGCATATTCTGAACCTCGACACCC

TCGGTATCATCAACGGCTGCATCGATCTTATGTTCCAAGCAGAAAGTTAT

GCTGAATTCCCATACAACAACACCTATGGCATCAAAGCTTATACCAAGGA

GAAGCGTGACGCTATATTACACGACATCCACCGTCCTGACGGCTGCTTCG

ACAAGGTTACCAAGTGCCGTGAGGCCGCGAAAGAAGGAGACCCTCACTTC

TACAGCAACAATGCAACCGTCAACACAATCTGTGCGGATGCTAACTCTGC

CTGCGACAAATATCTAATGGATCCTTTCCAAGAGACCAATCTTGGTTACT

ATGATATTGCTCATCCTCTTCAGGATCCCTTCCCCCCACCATTCTATAAG

GGCTTCCTCAGCCAATCCAGCGTTCTATCTGACATGGGATCGCCAGTCAA

TABLE 6A-continued ruCBPS1' genomic nucleotide sequence (SEQ ID NO: 16).

CTTCTCCCAATACGCCCAAGCTGTGGGAAAATCATTCCATGGAGTTGGCG

ACTACGCTCGCCCTGATGTGCGCGGCTTCACCGGTGACATTGCTTATCTT

CTCGAGAGCGGAGTCAAGGTTGCTCTCGTCTATGGTGACAGAGACTACAT

CTGCAATTGGTTCGGTGGTGAGCAGGTCAGTCTTGGCTTGAACTACACTG

GCACCCAAGACTTCCACAGGGCAAAATATGCCGATGTCAAGGTCAACTCT

TCATACGTCGGAGGCGTAGTGCGTCAACATGGAAACTTCTCTTTCACCAG

AGTTTTCGAGGCCGGTCATGAAGTCCCTGGTTACCAACCCGAGACTGCCC

TCAAGATCTTTGAGCGCATCATGTTCAACAAGGATATTTCTACCGGTGAG

ATCGACATTGCTCAGAAACCAGACTACGGTACCACTGGAACTGAGTCTAC

GTTCCATATCAAAAACGATATCCCTCCTTCGCCTGAGCCGACCTGCTACC

TCCTCAGTGCTGACGGAACCTGTACCCCGGAGCAGCTTAATGCTATTAAG

CATGGAACTGCAGTTGTTGAGAACTACATTATTAAGAGCCCTGCTGCGTC

GAAGGGGAACCCTCCACCAACCACGACCTCATCTCCCACAGCAGCCCCTA

CCGCTGGAAGTGCCATGCTAAAGGCTCCTGTGGCAATGCTAGCAATATCA

GCTCTCACTGTCCTTGCTTTCTTCTTGTAG

A ruCBPS1' nucleic acid of 1959 (SEQ ID NO: 17) is shown in Table 6B. A disclosed ruCBPS1' open reading frame ("ORF") begins with an ATG start codon at position 1 (underlined in Table 6B).

TABLE 6B ruCBPS1' nucleotide sequence (SEQ ID NO: 17).

<u>ATG</u>CGCTTTGCTGCTAGCATTGCCGTGGCCCTGCCAGTCATTCACGCGGC

GAGTGCTCAAGGCTTCCCTCCACCCGTTAAGGGCGTCACCGTGGTCAAAT

CCAAGTTCGACGAAAACGTAAAGATCACATACAAGGAGAATGACATATGT

GAAACCACTCAAGGAGTTAGATCATTCACCGGTCATGTCCACCTTCCTCC

AGACAACGATGACTTTGGTGTCTACCGGAACTACTCCATCAACACATTCT

TCTGGTTCTTTGAAGCTCGTGAAGACCCTAAGAATGCTCCTCTCTCCATC

TGGCTGAACGGTGGTCCGGGATCGTCATCCATGATTGGACTCTTCCAGGA

AAACGGTCCATGCTGGGTCAATGAAGACTCTAAATCTACCACCAACAATT

TABLE 6B-continued ruCBPS1' nucleotide sequence (SEQ ID NO: 17).

CATTTTCATGGAACAATAAAGTAAATATGCTCTACATTGATCAGCCAAAC

CAAGTCGGTTTCAGTTATGACGTACCTACCAACATCACTTACTCTACCAT

CAATGATACAATATCTGTTGCGGACTTCTCTAACGGTGTCCCTGCGCAAA

ATCTTTCTACGTTGGTTGGAACCGGCAGCAGCCAGAACCCTTGGGCAACT

GCCAATAACACTGTGAACGCTGCTCGTTCTATCTGGCACTTTGCACAAGT

GTGGTTCCAGGAATTCCCTGAACACAAGCCTAACAATAACAAGATCAGTA

TTTGGACAGAGTCCTATGGAGGAAGATATGGTCCCTCATTCGCCTCTTAC

TTCCAGGAACAGAACGAAAAGATCAAAAACCATACCATTACTGAAGAAGG

AGAGATGCATATTCTGAACCTCGACACCCTCGGTATCATCAACGGCTGCA

TCGATCTTATGTTCCAAGCAGAAAGTTATGCTGAATTCCCATACAACAAC

ACCTATGGCATCAAAGCTTATACCAAGGAGAAGCGTGACGCTATATTACA

CGACATCCACCGTCCTGACGGCTGCTTCGACAAGCTTACCAAGTGCCGTG

AGGCCGCGAAAGAAGGAGACCCTCACTTCTACAGCAACAATGCAACCGTC

AACACAATCTGTGCGGATGCTAACTCTGCCTGCGACAAATATCTAATGGA

TCCTTTCCAAGAGACCAATCTTGGTTACTATGATATTGCTCATCCTCTTC

AGGATCCCTTCCCCCCACCATTCTATAAGGGCTTCCTCAGCCAATCCAGC

GTTCTATCTGACATGGGATCGCCAGTCAACTTCTCCCAATACGCCCAAGC

TGTGGGAAAATCATTCCATGGAGTTGGCGACTACGCTCGCCCTGATGTGC

GCGGCTTCACCGGTGACATTGCTTATCTTCTCGAGAGCGGAGTCAAGGTT

GCTCTCGTCTATGGTGACAGAGACTACATCTGCAATTGGTTCGGTGGTGA

GCAGGTCAGTCTTGGCTTGAACTACACTGGCACCCAAGACTTCCACAGGG

CAAAATATGCCGATGTCAAGGTCAACTCTTCATACGTCGGAGGCGTAGTG

CGTCAACATGGAAACTTCTCTTTCACCAGAGTTTTCGAGGCCGGTCATGA

AGTCCCTGGTTACCAACCCGAGACTGCCCTCAAGATCTTTGAGCGCATCA

TGTTCAACAAGGATATTTCTACCGGTGAGATCGACATTGCTCAGAAACCA

GACTACGGTACCACTGGAACTGAGTCTACGTTCCATATCAAAAACGATAT

CCCTCCTTCGCCTGAGCCGACCTGCTACCTCCTCAGTGCTGACGGAACCT

TABLE 6B-continued ruCBPS1' nucleotide sequence (SEQ ID NO: 17).

GTACCCCGGAGCAGCTTAATGCTATTAAGGATGGAACTGCAGTTGTTGAG

AACTACATTATTAAGAGCCCTGCTGCGTCGAAGGGGAACCCTCCACCAAC

CACGACCTCATCTCCCACAGCAGCCCCTACCGCTGGAAGTGCCATGCTAA

AGGCTCCTGTGGCAATGCTAGCAATATCAGCTCTCACTGTCCTTGCTTTC

TTCTTGTAG

A disclosed ruCBPS1' nucleic acid (SEQ ID NO: 17) encodes a protein having 652 amino acid residues (SEQ ID NO: 18), which is presented in Table 6C using the one-letter amino acid code.

TABLE 6C

Encoded ruCBPS1' protein sequence (SEQ ID NO: 18).

MRFAASIAVALPVIHAASAQGFPPPVKGVTVVKSKFDENVKITYKENDIC

ETTQGVRSFTGHVHLPPDNDDFGVYRNYSINTFFWFFEAREDPKNAPLSI

WLNGGPGSSSMIGLFQENGPCWVNEDSKSTTNNSFSWNNKVNMLYIDQPN

QVGFSYDVPTNITYSTINDTISVADFSNGVPAQNLSTLVGTGSSQNPWAT

ANNTVNAARSIWHFAQVWFQEFPEHKPNNNKISIWTESYGGRYGPSFASY

FQEQNEKIKNHTITEEGEMHILNLDTLGIINGCIDLMFQAESYAEFPYNN

TYGIKAYTKEKRDAILHDIHRPDGCFDKVTKCREAAKEGDPHFYSNNATV

NTICADANSACDKYLMDPFQETNLGYYDIAHPLQDPFPPPFYKGFLSQSS

VLSDMGSPVNFSQYAQAVGKSFHGVGDYARPDVRGFTGDIAYLLESGVKV

ALVYGDRDYICNWFGGEQVSLGLNYTGTQDFHRAKYADVKVNSSYVGGVV

RQHGNFSFTRVFEAGHEVPGYQPETALKIFERIMFNKDISTGEIDIAQKP

DYGTTGTESTFHIKNDIPPSPEPTCYLLSADGTCTPEQLNAIKDGTAVVE

NYIIKSPAASKGNPPPTTTSSPTAAPTAGSAMLKAPVAMLAISALTVLAF

FL

The disclosed ruCBPS1' has homology to the amino acid sequences shown in the BLAST data listed in Table 6D, 6E and 6F. This data was analyzed by the program PAIRWISE BLAST.

TABLE 6D

| TBLASTN results for ruCBPS1' | | | | |
|---|---|---|---|---|
| Gene Index/Identifier | Protein/Organism | Length (aa) | Identity (%) | Positives (%) | Expect |
| gi|32410708 | *Neurospora crassa* strain OR74A | 1947 | 246/632 (38%) | 337/632 (53%) | e−104 |
| gi|3046860 | *Schizosaccharomyces pombe* cpy1 gene for carboxypeptidase Y | 4308 | 137/480 (28%) | 215/480 (44%) | 1e−45 |
| gi|18152938 | *Pichia angusta* carboxypeptidase Y (CPY) gene | 2214 | 139/508 (27%) | 227/508 (44%) | 2e−42 |

TABLE 6E

BLASTX results for ruCBPS1'

| Gene Index/Identifier | Protein/Organism | Length (aa) | Identity (%) | Positives (%) | Expect |
|---|---|---|---|---|---|
| gi\|15004616 | carboxypeptidase S1/ Aspergillus oryzae | 555 | 221/567 (38%) | 310/567 (54%) | e-102 |
| gi\|435818 | carboxypeptidase S1, CPD-S1/ Penicillium janthinellum | 423 | 174/499 (34%) | 258/499 (51%) | 4e-77 |
| gi\|995456 | preprocarboxypeptidase Z/ Absidia zychae | 460 | 155/491 (31%) | 243/491 (49%) | 2e-58 |
| gi\|19115337 | carboxypeptidase y/ Schizosaccharomyces pombe | 1002 | 137/480 (28%) | 215/480 (44%) | 1e-46 |
| gi\|4028158 | carboxypeptidase Y precursor; vacuolar carboxypeptidase/ Pichia angusta | 541 | 139/508 (27%) | 226/508 (44%) | 2e-43 |

TABLE 6F

BLASTP results for ruCBPS1'

| Gene Index/Identifier | Protein/Organism | Length (aa) | Identity (%) | Positives (%) | Expect |
|---|---|---|---|---|---|
| gi\|15004616 | carboxypeptidase S1/ Aspergillus oryzae | 555 | 222/567 (39%) | 310/567 (54%) | 7e-98 |
| gi\|435818 | carboxypeptidase S1, CPD-S1/ Penicillium janthinellum | 423 | 174/499 (34%) | 259/499 (51%) | 1e-71 |
| gi\|995456 | preprocarboxypeptidase Z/ Absidia zychae | 460 | 156/491 (31%) | 244/491 (49%) | 2e-57 |
| gi\|19115337 | carboxypeptidase y/ Schizosaccharomyces pombe | 1002 | 137/480 (28%) | 215/480 (44%) | 4e-44 | ruPAP ruPAP is a *T. rubrum* prolylaminopeptidase. Genomic DNA sequence of a ruPAP nucleic acid of 1795 nucleotides (SEQ ID NO: 19) is shown in Table 7A.

TABLE 7A ruPAP genomic nucleotide sequence (SEQ ID NO: 19).

ATGCAAGCAGCAAAATTGTTGAGCCGGTACTGGCAAAATGTACCTGGTTA

GTGCAGCTAATCTTGAGTCACATCATGCATAGTTAACCGAGTATCACAAC

ACAATCTACTATTGCGTTTTTGCTAATGGCTACCATAGGAAGACTGAGGG

TATCTGAGCTCCTTTTCCATGTCCCTTTAGCTACTCAAACCCGTCTTCC

ACTTCGCTCCGGTTGTTCGCCAGGAGTGTGCAGCGGCGAATTCCAGGGTC

CTCTCTCGATGATAAAGACAGACAGCTACCCTGGATTGTTTTCCTGCAG

GGTGGACCAGGAGGAGCTTGCCCACAACCTCAGGAGGTAGGCTGGGTTGG

GCCATTGCTGGATCGAGGATTCCAGGTGAGTCTCCAGAATCGGGATGAGT

AACTGTAGAACACCTTGTTGAATTTCTTGATTAGATCCTTCTCCTTGACC

AGCGAGGAACAGGGCTTTCAACCCCTATAACCGCTGCGACGCTTGCTCTT

CAGGGAAACGCAGTAAAGCAAGCCGAATATCTTAGGCTATTCCGTGCCGA

TAATATCGTGCGAGACTGTGAAGCAGTGCGTAAACTATTGACTGCTTATT

ACCCTCCAGATAAGCAGAAATGGAGCGTCCTTGGCCAGAGTTTTGGAGGA

TTCTGTGCCGTCACGTATGTTTCTAAGTAGTGAGTAACTACTCCTTCAAA

TCCACCTGCTATAGATTGTCGTGCAAATCTAACCTTCATCATCTAGTCCT

TABLE 7A-continued ruPAP genomic nucleotide sequence (SEQ ID NO: 19).

GAGGGACTTAAAGAAGTCTTCACAACTGGTGGATTACCCCCTCTTGTGTC

AAAGCCTGATCCTGTGTACGAGAGGACCTACGGTAAGTTGGGATAGATTG

GGCTATTTTTAGTTTAATATACAGCTGACATCTACAGACAAGGTCCAGTC

CCGGAATAAAGTGTACTATTCCACTTTCCCCGAAGACGAAGATCGAGTGC

GGATTATACTCAAGCATCTCCAAACCCACGATGTTAAGCTCCCCGATGGC

TCACCGTTAACTCCGGAACGCTTTCTCCAGCTAGGAATTCATTTTGGAAT

GAAAGGTACGCCATACTTCGCAGGTGACTTCTCGTAACCAATGACTAACA

TATGCATATAGGGGGCATCGGCTTAGTTCATAGTATGATACCATCAATAA

CTTACATTATACTTATTCACTGACTAACAATGTCGAAATATCAGGCATAA

TTTTGAAGTGCATTAATGAACTGGAATACTTTGGCTTCCTCACACGACCT

ACTTTATCTCTGATTGAGAACGACACGAGTGCAGACAACGGCATTCTATA

TGCCATAATGCATGAATCTATCTACTGCCAAGGGTAAAACGTCTCTCCTG

ATCGAGTCAATATCAGAATCTAACGTGATACCGTAGGGAGGCCTCAAACT

GGGCTGCCGAAAGACTACTACCAAAGTTCTCTGGCTTCCGAGGCGCTCAT

AATCCTGATGGCATCTACTTCACTGGGGAGATGGTATACAAACACTGGTT

TGAGTCGTCCACAGAACTCGGCCAGCTCAAAGAGGTAGCCGATATTCTTG

CTTCCTACAATGACTGGCCGCAGTTGTATGATAAGGAACAGCTCGCGCGC

AACGAGGTGCCAGTGTATTCCGCTACATATGTCGAGGATATGTACGTGCA

TABLE 7A-continued ruPAP genomic nucleotide sequence (SEQ ID NO: 19).

CTTCAGCTACGCCAACGAAACAGCTGCCACTATTCACAATTGCAAACAGT
TCATCACCAACACGATGTACCACAACGGACTGCGTTCAGATTCCGCTGAA
CTTATTGCGCAGCTGTTTGCTCTTCGTGATGATACGATTGACTAG

A ruPAP nucleic acid of 1326 (SEQ ID NO: 20) is shown in Table 7B. A disclosed ruPAP open reading frame ("ORF") begins with an ATG start codon at position 1 (underlined in Table 7B).

TABLE 7B ruPAP nucleotide sequence (SEQ ID NO: 20).

<u>ATG</u>CAAGCAGCAAAATTGTTGAGCCGGTACTGGCAAAATGTACCTGGAAG
ACTGAGGGTATCTGAGCTCCTTTTCGATGTCCCTTTAGACTACTCAAACC
CGTCTTCCACTTCGCTCCGGTTGTTCGCCAGGAGTGTGCAGCGGCGAATT
CCAGGGTCCTCTCTCGATGATAAAGACAGACAGCTACCCTGGATTGTTTT
CCTGCAGGGTGGACCAGGAGGAGCTTGCCCACAACCTCAGGAGGTAGGCT
GGGTTGGGCCATTGCTGGATCGAGGATTCCAGATCCTTCTCCTTGACCAG
CGAGGAACAGGGCTTTCAACCCCTATAACCGCTGCGACGCTTGCTCTTCA
GGGAAACGCAGTAAAGCAAGCCGAATATCTTAGGCTATTCCGTGCCGATA
ATATCGTGCGAGACTGTGAAGCAGTGCGTAAACTATTGACTGCTTATTAC
CCTCCAGATAAGCAGAAATGGAGCGTCCTTGGCCAGAGTTTTGGAGGATT
CTGTGCCGTCACGTATGTTTCTAATCCTGAGGGACTTAAAGAAGTCTTCA
CAACTGGTGGATTACCCCCTCTTGTGTCAAAGCCTGATCCTGTGTACGAG
AGGACCTACGACAAGGTCCAGTCCCGGAATAAAGTGTACTATTCCACTTT
CCCCGAAGACGAAGATCGAGTGCGATTATACTCAAGCATCTCCAAACCC
ACGATGTTAAGCTCCCCGATGGCTCACCGTTAACTCCGGAACGCTTTCTC
CAGCTAGGAATTCATTTTGGAATGAAAGGCTAATTTTGAAGTGCATTAAT
GAAACTGGAATACTTTGGCTTCCTCACACGACCTACTTTATCTCTGATTG
AGAACGACACGAGTGCAGACAACGGCATTCTATATGCCATAATGCATGAA

TCTATCTACTGCCAAGGGGAGGCCTCAAACTGGGCTGCCGAAAGACTACT
ACCAAAGTTCTCTGGCTTCCGAGGCGCTCATAATCCTGATGGCATCTACT
TCACTGGGGAGATGGTATACAAACACTGGTTTGAGTCGTCCACAGAACTC
GGCCAGCTCAAAGAGGTAGCCGATATTCTTGCTTCCTACAATGACTGGCC
GCAGTTGTATGATAAGGAACAGCTCGCGCGCAACGAGGTGCCAGTGTATT
CCGCTACATATGTCGAGGATATGTACGTGCACTTCAGCTACGCCAACGAA
ACAGCTGCCACTATTCACAATTGCAAACAGTTCATCACCAACACGATGTA
CCACAACGGACTGCGTTCAGATTCCGCTGAACTTATTGCGCAGCTGTTTG
CTCTTCGTGATGATACGATTGACTAG

A disclosed ruPAP nucleic acid (SEQ ID NO: 20) encodes a protein having 441 amino acid residues (SEQ ID NO: 21), which is presented in Table 7C using the one-letter amino acid code.

TABLE 7C

Encoded ruPAP protein sequence (SEQ ID NO: 21).

MQAAKLLSRYWQNVPGRLRVSELLFDVPLDYSNPSSTSLRLFARSVQRRI
PGSSLDDKDRQLPWIVPLQGGPGGACPQPQEVGWVGPLLDRGFQILLLDQ
RGTGLSTPITAATLALQGNAVKQAEYLRLFRADNIVRDCEAVRKLLTAYY
PPDKQKWSVLGQSFGGFCAVTYVSNPEGLKEVFTTGGLPPLVSKPDPVYE
RTYDKVQSRNKVYYSTFPEDEDRVRIILKHLQTHDVKLPDGSPLTPERFL
QLGIHFGMKGIILKCINELEYFGFLTRPTLSLIENDTSADNGILYAIMHE
SIYCQGEASNWAAERLLPKFSGFRGAHNPDGIYFTGEMVYKHWFESSTEL
GQLKEVADILASYNDWPQLYDKEQLARNEVPVYSATYVEDMYVHFSYANE
TAATIHNCKQFITNTMYHNGLRSDSAELIAQLFALRDDTID

The disclosed ruPAP has homology to the amino acid sequences shown in the BLAST data listed in Table 7D, 7E and 7F. This data was analyzed by the program PAIRWISE BLAST.

TABLE 7D

TBLASTN results for ruPAP

| Gene Index/Identifier | Protein/Organism | Length (aa) | Identity (%) | Positives (%) | Expect |
|---|---|---|---|---|---|
| gi\|14329656 | *Aspergillus niger* papA gene for prolyl aminopeptidase A | 3752 | 151/307 (49%) | 190/307 (61%) | e-118 |
| gi\|32414442 | *Neurospora crassa* strain OR74A | 1449 | 212/477 (44%) | 285/477 (59%) | e-100 |
| gi\|604877 | *Aeromonas sobria* gene for prolyl aminopeptidase | 1740 | 175/420 (41%) | 239/420 (56%) | 4e-77 |

TABLE 7E

BLASTX results for ruPAP

| Gene Index/Identifier | Protein/Organism | Length (aa) | Identity (%) | Positives (%) | Expect |
|---|---|---|---|---|---|
| gi\|18307408 | prolyl aminopeptidase A/ Aspergillus niger | 442 | 266/442 (60%) | 334/442 (75%) | e−152 |
| gi\|14456054 | putative prolyl aminopeptidase/ Aspergillus nidulans | 365 | 211/366 (57%) | 263/366 (71%) | e−114 |
| gi\|22507295 | prolyl aminopeptidase/ Talaromyces emersonii | 300 | 181/301 (60%) | 226/301 (75%) | 4e−99 |
| gi\|1236731 | prolyl aminopeptidase/ Aeromonas sobria | 425 | 175/420 (41%) | 239/420 (56%) | 4e−78 |

TABLE 7F

BLASTP results for ruPAP

| Gene Index/Identifier | Protein/Organism | Length (aa) | Identity (%) | Positives (%) | Expect |
|---|---|---|---|---|---|
| gi\|18307408 | prolyl aminopeptidase A/ Aspergillus niger | 442 | 267/443 (60%) | 336/443 (75%) | e−157 |
| gi\|14456054 | putative prolyl aminopeptidase/ Aspergillus nidulans | 365 | 211/366 (57%) | 263/366 (71%) | e−116 |
| gi\|22507295 | prolyl aminopeptidase/ Talaromyces emersonii | 300 | 181/301 (60%) | 226/301 (75%) | e−102 |
| gi\|1236731 | prolyl aminopeptidase/ Aeromonas | 425 | 175/420 (41%) | 239/420 (56%) | 2e−78 | ruAMPP ruAMPP is a *T. rubrum* aminopeptidase P. Genomic DNA sequence of a ruAMPP nucleic acid of 2418 nucleotides (SEQ ID NO: 22) is shown in Table 8A.

TABLE 8A ruAMPP genomic nucleotide sequence (SEQ ID NO:22).

ATGCCGCCACCACCGGTTGACACGACCCAGCGTCTCGCAAAGCTGCGAGA

GCTGATGGCTCAGAACAAGGTCGATGTATATAGTATGCAATTCAGATACA

CCATTAAAGCTCCCTTGATAATAACAGTCGTATACTCATTCTTCTTTCTT

CTACTCCTCGCCTTAAAGTTGTGCCTTCGGAAGACAGCCATCAGTCGAGT

ACATTGCTCCATGTGATGGGCGTCGAGGTTAGACCTGTCCCTCCATAAAA

GAATACCTACCCGTAATACCAGCCGGCAGACGCTCATACGTATCACTGCA

GCTTTCATATCCAGCTTCACTGGCTCGGCAGGATGTGCCATCGTCTCTAT

GAGTAAAGCTGCTCTGTCTACAGACGGCAGATACTTCAGCCAAGCTGCAA

AACAGCTCGATGCCAACTGGATCCTGTTGAAGCGAGGTGTCGAGGGTGTC

CCAACCTGGGAAGAATGGTATATCTGCCCCTGGTATCGACTTTTCCGGTA

TAATGGTTGACAGGCTGGATATAGGACCGCTGAGCAGGCCGAGACACGGC

AAGGTTGTGGGTGTTGACCCGTCACTTATTACGGCAGGTGAGAATCTACA

GTATGCGTCTCTTACAAGTGTCATCGTGACTAACTGTATGTTATAGCGGA

TGCACGAAAGCTTTCTCAGACGTTGAAGACCACCGGAGGCTCCTTGGTTG

GAATTGATCAGAACCTGATTGATGCCGTCTGGGGAGATGAACGTCCTGCA

CGGCCTGCCAACCAAATTACGGTACAGCCTGTTGAGCGCGCGGGAAAGTC

ATTCGAGGAGAAAGTGGAAGACCTGCGAAAGGAATTGACTGCGAAGAAGA

CGTCTGCTATGGTTATTTGTATGACGCTAGATCTATTTTTGATCAAACAT

ATACTAACAAACGCAATATAGCCACCTTGGATGAGATTGCATGGCTCTTC

AACCTCCGTGGAAGCGAGTAAGTTTCTATATAAATGGTATCTTTCACTTT

ATACAAAAAGCCATGCTGACTGGTGTAGTATTCCATATAACCCCGTCTTT

TTCTCGTACGCAATTGTGACGCCCTCAGTTGCGGAACTCTATGTCGATGA

GAGCAAGCTGTCTCCAGAAGCCAGAAAACATCTCGAAGGCAAGGTCGTTC

TCAAGCCATACGAGTCCATCTTCCAAGCTTCCAAAGTCCTCGCCGAATCA

AAGGCATCGGCTAGCAGCGGTTCCTCTGGGAAGTTCTTGTTGTCTAACAA

GGCTTCGTGGTCTTTGAGCCTCGCCCTCGGTGGGGAACAGAACGTCGTTG

AGGTTCGAAGTCCCATCACTGACGCCAAAGCCATCAAGAACGAAGTTGAA

CTGGAAGGATTCAGAAAATGCCATATCCGAGACGGTGCAGCTCTGATCGA

GTACTTCGCCTGGCTTGAAAATGCATTGATCAAAGAAGGTGCCAAGCTAG

ACGAAGTAGATGGAGCCGACAAACTCTTCGAGATCCGCAAGAAATATGAC

CTCTTCGTCGGCAACTCCTTCGACACCATCTCTTCTACCGGTGCTAACGG

TGCTACCATTCATTACAAACCCGAGAAGTCAACTTGCGCTATCATTGACC

CGAAGGCTATGTACCTGTGTGACTCTGGTGGCCAATACCTTGATGGTACT

ACTGATACTACCCGAACTCTCCACTTTGGAGAGCCCACGGAGTTCCAGAA

GAAGGCTTATGCACTTGTTCTAAAGGGACATATCAGCATTGACAATGCCA

TTTTCCCCAAAGGAACCACCGGATACGCCATTGACTCGTTTGCTCGACAG

TABLE 8A-continued ruAMPP genomic nucleotide sequence (SEQ ID NO:22).

CATTTGTGGAAGGAGGGTCTGGATTACCTCCACGGCACCGGTCATGGTGT

TGGCTCATTTTTGGTACGGGGTTTCCTTTTTCTTTTTTTTTTCTTTTTTT

ATTTTTATTATTACTTCTCTTAGGCTAACACATTCTCTCTAAGAACGTCC

ATGAGGGACCTATGGGCATAGGAAGCCGTGCTCAGTACGCTGAAGTTCCT

CTCTCTGCCAGCAATGTTCTTTCCAACGGTAGGATTTCTGCATCTCATCT

TTCTTGAATCCTACTAATTGCAAAATAGAGCCTGGATATTATGAAGACGG

CAACTTCGGCATTCGTCTCGAGAGTAAGTTCAATGACTGCGTATTCTAGT

TTTTTCATACTGACGGCCTCTTTAGACCTCGTAATCTGCAAGGAGGTCCA

GACTGCACACAAATTCGGCGACAAGCCCTTCCTCGGATTTGAGTCCATCA

CCCTGGTACCTTTCTGCCAAAAACTCCTTGATGCTTCTCTCTTGACCGAA

GCTGAGAGAAAGTGGGTGAATGATTACCATGCGAAAGTCTGGGAGAAGAC

CAGTCCCTTCTTTGAGAAGGACGAGTTAACAACCGCCTGGCTAAAGCGCG

AGACACAACCTATTTAA

A ruAMPP nucleic acid of 1878 (SEQ ID NO: 23) is shown in Table 8B. A disclosed ruAMPP open reading frame ("ORF") begins with an ATG start codon at position 1 (underlined in Table 8B).

TABLE 8B ruAMPP nucleotide sequence (SEQ ID NO:23).

<u>ATG</u>CCGCCACCACCGGTTGACACGACCCAGCGTCTCGCAAAGCTGCGAGA

GCTGATGGCTCAGAACAAGGTCGATGTATATATTGTGCCTTCGGAAGACA

GCCATCAGTCGGAGTACATTGCTCCATGTGATGGGCGTCGAGCTTTCATA

TCCAGCTTCACTGGCTCGGCAGGATGTGCCATCGTCTCTATGAGTAAAGC

TGCTCTGTCTACAGACGGCAGATACTTCAGCCAAGCTGCAAAACAGCTCG

ATGCCAACTGGATCCTGTTGAAGCGAGGTGTCGAGGGTGTCCCAACCTGG

GAAGAATGGACCGCTGAGCAGGCCGAGACACGGCAAGGTTGTGGGTCGGA

TGCACGAAAGCTTTCTCAGACGTTGAAGACCACCGGAGGCTCCTTGGTTG

GAATTGATCAGAACCTGATTGATGCCGTCTGGGGAGATGAACGTCCTGCA

CGGCCTGCCAACCAAATTACGGTACAGCCTGTTGAGCGCGCGGGAAAGTC

ATTCGAGGAGAAAGTGGAAGACCTGCGAAAGGAATTGACTGCGAAGAAGA

GGTCTGCTATGGTTATTTCGAGTAAGTTTCTATATAAATGGTATCTTTCA

CTTTATACAAAAAGCCATGCTGACTGGTGTAGTATTCCATATAACCCCGT

CTTTTTCTCGTACGCAATTGTGACGCCCTCAGTTGCGGAACTCTATGTCG

ATGAGAGCAAGCTGTCTCCAGAAGCCAGAAAACATCTCGAAGGCAAGGTC

GTTCTCAAGCCATACGAGTCCATCTTCCAAGCTTCCAAAGTCCTCGCCGA

ATCAAAGGCATCGGCTAGCAGCGGTTCCTCTGGGAAGTTCTTGTTGTCTA

ACAAGGCTTCGTGGTCTTTGAGCCTCGCCCTCGGTGGGGAACAGAACGTC

GTTGAGGTTCGAAGTCCCATCACTGACGCCAAAGCCATCAAGAACGAAGT

TGAACTGGAAGGATTCAGAAAATGCCATATCCGAGACGGTGCAGCTCTGA

TABLE 8B-continued ruAMPP nucleotide sequence (SEQ ID NO:23).

TCGAGTACTTCGCCTGGCTTGAAAATGCATTGATCAAAGAAGGTGCCAAG

CTAGACGAAGTAGATGGAGCCGACAAACTCTTCGAGATCCGCAAGAAATA

TGACCTCTTCGTCGGCAACTCCTTCGACACCATCTCTTCTACCGGTGCTA

ACGGTGCTACCATTCATTACAAACCCGAGAAGTCAACTTGCGCTATCATT

GACCCGAAGGCTATGTACCTGTGTGACTCTGGTGGCCAATACCTTGATGG

TACTACTGATACTACCCGAACTCTCCACTTTGGAGAGCCCACGGAGTTCC

AGAAGAAGGCTTATGCACTTGTTCTAAAGGGACATATCAGCATTGACAAT

GCCATTTTCCCCAAAGGAACCACCGGATACGCCATTGACTCGTTTGCTCG

ACAGCATTTGTGGAAGGAGGGTCTGGATTACCTCCACGGCACCGGTCATG

GTGTTGGCTCATTTTTGAACGTCCATGAGGGACCTATGGGCATAGGAAGC

CGTGCTCAGTACGCTGAAGTTCCTCTCTCTGCCAGCAATAGCCTGGATAT

TATGAAGACGGCAACTTCGGCATTCGTCTCGAGAGTAAGTTCAATGACTG

CGTATTCTAGTTTTTTCATACTGACGGCCTCTTTAGACCTCGTAATCTGC

AAGGAGGTCCAGACTGCACACAAATTCGGCGACAAGCCCTTCCTCGGATT

TGAGTCCATCACCCTGGTACCTTTCTGCCAAAAACTCCTTGATGCTTCTC

TCTTGACCGAAGCTGAGAGAAAGTGGGTGAATGATTACCATGCGAAAGTC

TGGGAGAAGACCAGTCCCTTCTTTGAGAAGGACGAGTTAACAACCGCCTG

GCTAAAGCGCGAGACACAACCTATTTAA

A disclosed ruAMPP nucleic acid (SEQ ID NO: 23) encodes a protein having 625 amino acid residues (SEQ ID NO: 24), which is presented in Table 8C using the one-letter amino acid code.

TABLE 8C

Encoded ruAMPP protein sequence (SEQ ID NO:24).

MPPPPVDTTQRLAKLRELMAQNKVDVYIVPSEDSHQSEYIAPCDGRRAFI

SSFTGSAGCAIVSMSKAALSTDGRYFSQAAKQLDANWILLKRGVEGVPTW

EEWTAEQAETRQGCGSDARKLSQTLKTTGGSLVGIDQNLIDAVWGDERPA

RPANQITVQPVERAGKSFEEKVEDLRKELTAKKRSAMVISSKFLYKWYLS

LYTKSHADWCSIPYNPVFFSYAIVTPSVAELYVDESKLSPEARHKLEGKV

VLKPYESIFQASKVLAESKASASSGSSGKFLLSNKASWSLSLALGGEQNV

VEVRSPITDAKAIKNEVELEGFRKCHIRDGAALIEYFAWLENALIKEGAK

LDEVDGADKLFEIRKKYDLFVGNSFDTISSTGANGATIHYKPEKSTCAII

DPKAMYLCDSGGQYLDGTTDTTRTLHFGEPTEFQKKAYALVLKGHISIDN

AIFPKGTTGYAIDSFARQHLWKEGLDYLHGTGHGVGSFLNVHEGPMGIGS

RAQYAEVPLSASNSLDIMKTATSAFVSRVSSMTAYSSFFILTASLDLVIC

KEVQTAHKFGDKPFLGFESITLVPFCQKLLDASLLTEAERKWVNDYHAKV

WEKTSPFFEKDELTTAWLKRETQPI

The disclosed ruAMPP has homology to the amino acid sequences shown in the BLAST data listed in Table 8D, 8E and 8F. This data was analyzed by the program PAIRWISE BLAST.

TABLE 8D

TBLASTN results for ruAMPP

| Gene Index/Identifier | Protein/Organism | Length (aa) | Identity (%) | Positives (%) | Expect |
|---|---|---|---|---|---|
| gi\|32403169 | *Neurospora crassa* strain OR74A | 1845 | 339/630 (53%) | 433/630 (68%) | 0.0 |
| gi\|20453016 | *Drosophila melanogaster* aminopeptidase P gene | 12647 | 268/638 (42%) | 369/638 (57%) | e−127 |
| gi\|17571207 | *Drosophila melanogaster* (ApepP) on chromosome 2 | 12001 | 268/638 (42%) | 369/638 (57%) | e−127 |
| gi\|4583560 | *Drosophila melanogaster* Daminopep-p gene | 2358 | 268/638 (42%) | 369/638 (57%) | e−127 |

TABLE 8E

BLASTX results for ruAMPP

| Gene Index/Identifier | Protein/Organism | Length (aa) | Identity (%) | Positives (%) | Expect |
|---|---|---|---|---|---|
| gi\|25529603 | X-Pro aminopeptidase, cytosolic form/ *Drosophila melanogaster* | 613 | 268/638 (42%) | 369/638 (57%) | e−127 |
| gi\|4107172 | aminopeptidase P/ *Drosophila melanogaster* | 613 | 258/638 (40%) | 369/638 (57%) | e−124 |
| gi\|15384991 | Xaa-Pro aminopeptidase 2/ *Lycopersicon esculentum* | 654 | 268/674 (39%) | 365/674 (54%) | e−120 |
| gi\|8489879 | cytosolic aminopeptidase P/ *Homo sapiens* | 623 | 254/646 (39%) | 358/646 (55%) | e−119 |
| gi\|2584787 | Aminopeptidase P-like/ *Homo sapiens* | 623 | 254/646 (39%) | 357/646 (55%) | e−119 |

TABLE 8F

BLASTP results for ruAMPP

| Gene Index/Identifier | Protein/Organism | Length (aa) | Identity (%) | Positives (%) | Expect |
|---|---|---|---|---|---|
| gi\|30923284 | Probable peptidase C22G7.01c | 598 | 291/629 (46%) | 384/629 (61%) | e−156 |
| gi\|25529603 | X-Pro aminopeptidase, cytosolic form/ *Drosophila melanogaster* | 613 | 268/638 (42%) | 369/638 (57%) | e−124 |
| gi\|15384991 | Xaa-Pro aminopeptidase 2/ *Lycopersicon esculentum* | 654 | 268/674 (39%) | 365/674 (54%) | e−123 |
| gi\|8489879 | cytosolic aminopeptidase P/ *Homo sapiens* | 623 | 254/646 (39%) | 358/646 (55%) | e−122 |
| gi\|2584787 | Aminopeptidase P-like/ *Homo sapiens* | 623 | 254/646 (39%) | 357/646 (55%) | e−122 |
| gi\|4107172 | aminopeptidase P/ *Drosophila melanogaster* | 613 | 258/638 (40%) | 369/638 (57%) | e−121 |
| gi\|18777778 | cytoplasmic aminopeptidase P/ *Rattus norvegicus* | 623 | 253/645 (39%) | 353/645 (54%) | e−120 |
| gi\|18875372 | cytosolic aminopeptidase P/ *Mus musculus* | 623 | 250/645 (38%) | 354/645 (54%) | e−118 |
| gi\|15384989 | Xaa-Pro aminopeptidase 1/ *Lycopersicon esculentum* | 655 | 264/674 (39%) | 361/674 (53%) | e−117 | ruPLD ruPLD is a *T. rubrum* prolidase. Genomic DNA sequence of a ruPLD nucleic acid of 2344 nucleotides (SEQ ID NO: 25) is shown in Table 9A.

TABLE 9A ruPLD genomic nucleotide sequence (SEQ ID NO: 25).

ATCAACCTCACCTCTTCACCGTCTCACGCCCTTCGTCCCGTCCAACTCTT
CATTTCGCCCTCTCTATGATAACCAACAAACATCCGCTGTTATGTAATCG
AACCCGCCGTTAGCCATCCCTAGCCCCGCGTTTTCTCCCAGCATCAATAC
GACCGAAATGAAGACAGACGGGGAAGACGAGGCAAAACAATAACACATCA
ACAATTTAACCCGTTGCCGTCTTCTACCCATCTTGTCTACGCATCGTCCA
ACCTTTTCTTGCCCTATATCAGCCGAACTCGGCCATCATGGATATCCACG
TCGACAAATACCCGGCTAAGAGTCACGCCAGGCGCGTCGCCGAGAAGCTC
AAGGCCGCGGGGCACGGCTCTACCGGCATCATCTTCGTCGAAGGCCAAAA
GGAGCATATTATCGATGATAGCGACGAGCCGTTTCACTTCCGGTGAGCCG
TGGGAATACACTCGACTGGGCGGAATAAGCTAACAAAGGGTGTGATAGT
CAACGCCGAAACTTCCTCTATCTGTCCGGCTGTCTTGAGGCCGAGTGCTC
CGTTGCATACAACATCGAGAAAGATGAGCTTACATTGTTCATTCCACCAG
TCGACCCAGCCTCGGTTATGTGGTCCGGCCTCCCTCTTGAGCCCGCCGAA
GCCTTGAAGCAGTTCGATGTTGATGCCGTGCTCCTCACAACTGAGATAAA
CAACTATCTCGCGAAGTGTGGGGGCGAGAAGGTCTTCACCATTGCAGACA
GAGTTTGCCCGGAGGTCTCCTTCTCATCCTTCAAGCACAACGACACCGAT
GCCCTGAAGCTTGCCATCGAGTCCTGCCGTATAGTGAAAGACGAGTATGA
AATTGGTCTTCTCCGACGTGCTAATGAGGTCTCCAGCCAAGCTCATATTG
AAGTGATGAAAGCCGCAACCAAGTCAAAGAACGAGAGAGAGCTCTATGCT
ACTCTCAACTATGTCTGCATGTCTAATGGCTGCTCCGACCAGTCTTACCA
TCCAATTCTTGCATGTGGCCCCAATGCTGCCACTCTCCACTACACCAAGA
ACAACGGTGACCTAACTAACCCGGCTACCGGGATTAAGGACCAGCTCGTA
CTTATCGACGCTGGATGCCAGTACAAGGCGTACTGTGCAGATATCACTCG
TGCATTCCCCTTGTCCGGCAAATTCACCACGGAGGGCCGCCAGATCTATG
ATATTGCCTTGGAGATGCAGAAAGTCGCGTTTGGCATGATCAAACCTAAT
GTTTTGTTCGACGACATGCATGCTGCGGTCCACCGGGTTGCGATCAAGGG
GCTGCTCAAGATTGGCATTCTCACTGGCTCTGAGGATGAGATTTTCGATA
AGGGAATCAGCACTGCCTTTTTCCCACATGGTCTAGGCCACCATCTCGGC
ATGGACACTCACGATGTTGGAGGAAACCCTAACCCGGCTGACCCGAATCG
CATGTTTAAATACTTGCGTCTGCGAGGCACTGTTCCAGAGGGATCCGTCA
TTACAATTGAGCCCGGTGTAAGTGTTGAATCGAGTAGTTGCTCCGCCGAA
TGTTTCACATACATTTACTAACCCTTGCTCTAGGTCTACTTCTGCCGTTA
CATCATTGAGCCATTCCTTACTAACCCCGAGACCAGCAAGTACATCAACT
CCGAAGTTCTAGACAAGTACTGGGCTGTTGGAGGTGTACGTATCGAGGAC
AACGTCGTCGTCCGCGCCAATGGCTTTGAGAACCTGACCACGGTGCCAAA
GGAGCCCGAGGAGGTCGAACGCATTGTCCAGGAGGGTGCTAAATAATTAT

TABLE 9A-continued ruPLD genomic nucleotide sequence (SEQ ID NO: 25).

GTTTTTATTCAGTACACCGAGTGGTCGGACACACGCAGGAGCATGTACAT
ATTTATGATCTACCCAGTTGATTTGCTACCAAAAAAGAACCGACCACAGC
CCTATTTATTGATATTACATAGTAGGAATAAAGGCCACTTTGCCCACCGC
GAATAATAACAATAAGAAAAGCAACTACTCGTACAACCAGCCTAGAAAGC
TCTAGACCTCTTTCTCGCTGGGCCCTTGAATGCCGGGCTACTGGTGTTAT
CACGCTCCCTGGCCCTCTTCTCCTTCATGTCCAACACCCGATTAAGCAAA
TCGAAACTGAACTGGGGATGCTCAAGACACAATGCCTTGAACTGCTCTTC
AGCATCATGACGCAGCACATCACTCATCTTAGCCCAGAAGCGAGCAACCG
GTCCTCTGATAGCAGTGTCTTCCGGCGTGGTATGGCTGTACACGTATCTC
GCATACTCGATCTCACCCGTAGCACTACTCTCGATGCTACCAATCTTGTT
CTGAGCAAGCAGTTTGAGTTTTTCGTTTCCGAGCTTTTCGGCCA

A ruPLD nucleic acid of 1401 (SEQ ID NO: 26) is shown in Table 9B. A disclosed partial ruPLD open reading frame ("ORF") sequence was obtained as judged by the absence of an ATG start codon at position 1.

TABLE 9B ruPLD nucleotide sequence (SEQ ID NO:26).

CCGAACTCGGCCATCATGGATATCCACGTCGACAAATACCCGGCTAAGAG
TCACGCCAGGCGCGTCGCCGAGAAGCTCAAGGCCGCGGGGCACGGCTCTA
CCGGCATCATCTTCGTCGAAGGCCAAAAGGAGCATATTATCGATGATAGC
GACGAGCCGTTTCACTTCCGTCAACGCCGAAACTTCCTCTATCTGTCCGG
CTGTCTTGAGGCCGAGTGCTCCGTTGCATACAACATCGAGAAAGATGAGC
TTACATTGTTCATTCCACCAGTCGACCCAGCCTCGGTTATGTGGTCCGGC
CTCCCTCTTGAGCCCGCCGAAGCCTTGAAGCAGTTCGATGTTGATGCCGT
GCTCCTCACAACTGAGATAAACAACTATCTCGCGAAGTGTGGGGGCGAGA
AGGTCTTCACCATTGCAGACAGAGTTTGCCCGGAGGTCTCCTTCTCATCC
TTCAAGCACAACGACACCGATGCCCTGAAGCTTGCCATCGAGTCCTGCCG
TATAGTGAAAGACGAGTATGAAATTGGTCTTCTCCGACGTGCTAATGAGG
TCTCCAGCCAAGCTCATATTGAAGTGATGAAAGCCGCAACCAAGTCAAAG
AACGAGAGAGAGCTCTATGCTACTCTCAACTATGTCTGCATGTCTAATGG
CTGCTCCGACCAGTCTTACCATCCAATTCTTGCATGTGGCCCCAATGCTG
CCACTCTCCACTACACCAAGAACAACGGTGACCTAACTAACCCGGCTACC
GGGATTAAGGACCAGCTCGTACTTATCGACGCTGGATGCCAGTACAAGGC
GTACTGTGCAGATATCACTCGTGCATTCCCCTTGTCCGGCAAATTCACCA
CGGAGGGCCGCCAGATCTATGATATTGCCTTGGAGATGCAGAAAGTCGCG
TTTGGCATGATCAAACCTAATGTTTTGTTCGACGACATGCATGCTGCGGT
CCACCGGGTTGCGATCAAGGGGCTGCTCAAGATTGGCATTCTCACTGGCT
CTGAGGATGAGATTTTCGATAAGGGAATCAGCACTGCCTTTTTCCCACAT
GGTCTAGGCCACCATCTCGGCATGGACACTCACGATGTTGGAGGAAACCC

TABLE 9B-continued ruPLD nucleotide sequence (SEQ ID NO:26).

TAACCCGGCTGACCCGAATCGCATGTTTAAATACTTGCGTCTGCGAGGCA

CTGTTCCAGAGGGATCCGTCATTACAATTGAGCCCGGTGTCTACTTCTGC

CGTTACATCATTGAGCCATTCCTTACTAACCCCGAGACCAGCAAGTACAT

CAACTCCGAAGTTCTAGACAAGTACTGGGCTGTTGGAGGTGTACGTATCG

AGGACAACGTCGTCGTCCGCGCCAATGGCTTTGAGAACCTGACCACGGTG

CCAAAGGAGCCCGAGGAGGTCGAACGCATTGTCCAGGAGGGTGCTAAATA

A

A disclosed partial ruPLD nucleic acid (SEQ ID NO: 26) encodes a protein with a partial sequence having 466 amino acid residues (SEQ ID NO: 27), which is presented in Table 9C using the one-letter amino acid code.

TABLE 9C

Encoded ruPLD protein sequence (SEQ ID NO: 27).

PNSAIMDIHVDKYPAKSHARRVAEKLKAAGHGSTGIIFVEGQKEHIIDDS

DEPFHFRQRRNFLYLSGCLEAECSVAYNIEKDELTLFIPPVDPASVMWSG

LPLEPAEALKQFDVDAVLLTTEINNYLAKCGGEKVFTIADRVCPEVSFSS

FKHNDTDALKLAIESCRIVKDEYEIGLLRRANEVSSQAHIEVMKAATKSK

NERELYATLNYVCMSNGCSDQSYHPILACGPNAATLHYTKNNGDLTNPAT

GIKDQLVLIDAGCQYKAYCADITRAFPLSGKFTTEGRQIYDIALEMQKVA

FGMIKPNVLFDDMHAAVHRVAIKGLLKIGILTGSEDEIFDKGISTAFFPH

GLGHHLGMDTHDVGGNPNPADPNRMFKYLRLRGTVPEGSVITIEPGVYFC

RYIIEPFLTNPETSKYINSEVLDKYWAVGGVRIEDNVVVRANGFENLTTV

PKEPEEVERIVQEGAK

The disclosed partial ruPLD has homology to the amino acid sequences shown in the BLAST data listed in Table 9D, 9E and 9F. This data was analyzed by the program PAIRWISE BLAST.

TABLE 9D

| TBLASTN results for ruPLD | | | | | |
|---|---|---|---|---|---|
| Gene Index/Identifier | Protein/Organism | Length (aa) | Identity (%) | Positives (%) | Expect |
| gi\|14272360 | *Aspergillus nidulans* pepP gene for prolidase, exons 1-3 | 2632 | 199/348 (57%) | 249/348 (71%) | e-143 |
| gi\|32420910 | *Neurospora crassa* strain OR74A | 2562 | 235/457 (51%) | 324/457 (70%) | e-136 |
| gi\|3114965 | *Suberites domuncula* mRNA for prolidase, form 1 | 1688 | 157/464 (33%) | 235/464 (50%) | 4e-66 |
| gi\|22531161 | *Arabidopsis thaliana* X-Pro dipeptidase-like protein | 1672 | 160/477 (33%) | 242/477 (50%) | 2e-64 |

TABLE 9E

| BLASTX results for ruPLD | | | | | |
|---|---|---|---|---|---|
| Gene Index/Identifier | Protein/Organism | Length (aa) | Identity (%) | Positives (%) | Expect |
| gi\|14272361 | prolidase/ *Emericella nidulans* | 496 | 267/463 (57%) | 336/463 (72%) | e-153 |
| gi\|3114966 | prolidase/ *Suberites domuncula* | 501 | 157/464 (33%) | 235/464 (50%) | 1e-66 |
| gi\|22531162 | X-Pro dipeptidase-like protein/ *Arabidopsis thaliana* | 486 | 160/477 (33%) | 242/477 (50%) | 6e-65 |
| gi\|30582223 | peptidase D/ *Homo sapiens* | 493 | 152/452 (33%) | 231/452 (51%) | 2e-63 |
| gi\|20271451 | peptidase D/ *Homo sapiens* | 493 | 152/452 (33%) | 230/452 (50%) | 3e-63 |

TABLE 9F

BLASTP results for ruPLD

| Gene Index/Identifier | Protein/Organism | Length (aa) | Identity (%) | Positives (%) | Expect |
|---|---|---|---|---|---|
| gi\|14272361 | prolidase/ *Emericella nidulans* | 496 | 267/463 (57%) | 336/463 (72%) | e-158 |
| gi\|3114966 | prolidase/ *Suberites domuncula* | 501 | 158/466 (33%) | 235/466 (50%) | 6e-67 |
| gi\|22531162 | X-Pro dipeptidase-like protein/ *Arabidopsis thaliana* | 486 | 159/477 (33%) | 241/477 (50%) | 6e-64 |
| gi\|30584879 | *Homo sapiens* peptidase D | 494 | 152/452 (33%) | 231/452 (51%) | 2e-63 |
| gi\|15929143 | peptidase D/ *Homo sapiens* | 493 | 152/452 (33%) | 231/452 (51%) | 2e-63 |
| gi\|20271451 | peptidase D/ *Homo sapiens* | 493 | 152/452 (33%) | 230/452 (50%) | 4e-63 | caLAP2 caLAP2 is a *Microsporum canis* leucine aminopeptidase. A caLAP2 nucleic acid of 1730 nucleotides (SEQ ID NO: 28) is shown in Table 10A.

TABLE 10A caLAP2 genomic nucleotide sequence (SEQ ID NO: 28).

ATGAAGACACAGTTGTTGAGTCTGGGAGTTGCCCTCACGGCCATCTCTCA
GGGCGTTATTGCTGAGGATGCCTTGAACTGGCCATTCAAGCCGTTGGTTA
ATGCTGTGAGTATATACACAAGATCGATCGATCGTCCTCTTGTCCCTGTC
ACTTATCGCTCTACAGTAAGCAAAAATACTGGAGAATCATGTGCTGATGT
AAATGTATAGGATGACCTGCAAAACAAGATTAAGCTCAAGGATCTTATGG
CTGGCGTACAGAAACTCCAAGACTTCGCCTACGCTCACCCTGAGAAGAAT
CGAGTATTCGGTGGTGCTGGCCACAAGGATACCGTCGACTGGATCTACAA
TGAGCTCAAGGCTACCGGCTACTACGATGTGAAGATGCAGCCACAAGTCC
ACCTGTGGTCTCATGCTGAGGCAGCTGTCAATGCCAATGGCAAGGATCTC
ACTGCCAGTGCCATGTCCTACAGCCCTCCAGCCGACAAGATCACTGCCGA
GCTTGTCCTGGCCAAGAACATGGGATGCAATGCTGTATGTGCGCCCCTTT
TCCATTCTATATATCGACTGGTCGCTTGGAAATTCAGAAGAGCTGACAAT
TGCAAACAGACTGATTACCCAGAGGGTACCAAGGGCAAGATTGTCCTCAT
CGAGCGTGGTGTCTGCAGCTTTGGCGAGAAGTCCGCTCAGGCTGGCGATG
CAAAGGCTATTGGTGCCATCGTCTACAACAACGTCCCTGGAAGCTTGGCC
GGCACCCTGGGTGGCCTTGACAACCGCCATGCTCCAACTGCTGGAATCTC
TCAGGCTGATGGAAAGAACCTCGCTAGCCTTGTCGCCTCTGGCAAGGTTA
CCGTCACCATGAACGTTATCAGCAAGTTTGAGAACAGGACTACGTGAGTA
TTGTTCCATACTTTGGTCAACAATGATATATACACGTACTAACACTGCTC
TATAGCTGGAACGTCATTGCCGAGACCAAGGGAGGAGACCACAACAACGT
CATCATGCTCGGTTCTCACTCTGACTCTGTCGACGCCGGCCCTGGTATCA
ACGACAACGGCTCCGGTACCATTGGTATCATGACCGTTGCCAAAGCCCTC
ACCAACTTCAAGGTCAACAACGCCGTCCGCTTCGGCTGGTGGACCGCCGA

A disclosed caLAP2 open reading frame ("ORF") of 1488 nucleotides begins with an ATG start codon at position 1 (underlined in Table 10B).

TABLE 10A-continued caLAP2 genomic nucleotide sequence (SEQ ID NO: 28).

GGAGTTCGGCCTTCTCGGCAGCACTTTCTACGTCGACAGCCTTGACGACC
GTGAACTGCACAAGGTCAAGCTGTACCTCAACTTCGACATGATTGGCTCC
CCCAACTTCGCCAACCAGATCTACGACGGAGACGGCTCCGCCTACAACAT
GACTGGCCCCGCCGGATCTGCTGAAATCGAGTACCTGTTCGAGAAGTTCT
TCGATGACCAGGGAATCCCACACCAGCCCACCGCCTTCACCGGCCGCTCC
GACTACTCTGCCTTCATCAAGCGCAACGTCCCTGCCGGAGGTCTGTTTAC
TGGTGCTGAGGTCGTCAAGACCGCCGAGCAGGCTAAGCTATTTGGCGGCG
AGGCTGGCGTTGCTTATGACAAGAACTACCACGGCAAGGGCGACACTGTA
GACAACATCAACAAGGGTGCTATCTACCTCAACACTCGAGGAATCGCGTA
TGCCACTGCTCAGTATGCTAGTTCGCTGCGCGGATTCCCAACCCGCCCAA
AGACGGGTAAGCGTGACGTGAGCCCCGTGGCCAGTCTATGCCTGGTGGT
GGATGCGGACACCACAGCGTCTTCATGTAA

TABLE 10B caLAP2 nucleotide sequence (SEQ ID NO: 29).

<u>ATG</u>AAGACACAGTTGTTGAGTCTGGGAGTTGCCCTCACGGCCATCTCTCA
GGGCGTTATTGCTGAGGATGCCTTGAACTGGCCATTCAAGCCGTTGGTTA
ATGCTGATGACCTGCAAAACAAGATTAAGCTCAAGGATCTTATGGCTGGC
GTACAGAAACTCCAAGACTTCGCCTACGCTCACCCTGAGAAGAATCGAGT
ATTCGGTGGTGCTGGCCACAAGGATACCGTCGACTGGATCTACAATGAGC
TCAAGGCTACCGGCTACTACGATGTGAAGATGCAGCCACAAGTCCACCTG
TGGTCTCATGCTGAGGCAGCTGTCAATGCCAATGGCAAGGATCTCACTGC
CAGTGCCATCTCCTACAGCCCTCCAGCCGACAAGATCACTGCCGAGCTTG
TCCTGGCCAAGAACATGGGATGCAATGCTACTGATTACCCAGAGGGTACC
AAGGGCAAGATTGTCCTCATCGAGCGTGGTGTCTGCAGCTTTGGCGAGAA

TABLE 10B-continued caLAP2 nucleotide sequence (SEQ ID NO: 29).

GTCCGCTCAGGCTGGCGATGCAAAGGCTATTGGTGCCAATGGCAAGGATC

TCGTCCCTGGAAGCTTGGCCGGCACCCTGGGTGGCCTTGACAACCGCCAT

GCTCCAACTGCTGGAATCTCTCAGGCTGATGGAAAGAACCTCGCTAGCCT

TGTCGCCTCTGGCAAGGTTACCGTCACCATGAACGTTATCAGCAAGTTTG

AGAACAGGACTACCTGGAACGTCATTGCCGAGACCAAGGGAGGAGACCAC

AACAACGTCATCATGCTCGGTTCTCACTCTGACTCTGTCGACGCCGGCCC

TGGTATCAACGACAACGGCTCCGGTACCATTGGTATCATGACCGTTGCCA

AAGCCCTCACCAACTTCAAGGTCAACAACGCCGTCCGCTTCGGCTGGTGG

ACCGCCGAGGAGTTCGGCCTTCTCGGCAGCACTTTCTACGTCGACAGCCT

TGACGACCGTGAACTGCACAAGGTCAAGCTGTACCTCAACTTCGACATGA

TTGGCTCCCCCAACTTCGCCAACCAGATCTACGACGGAGACGGCTCCGCC

TACAACATGACTGGCCCCGCCGGATCTGCTGAAATCGAGTACCTGTTCGA

GAAGTTCTTCGATGACCAGGGAATCCCACACCAGCCCACCGCCTTCACCG

GCCGCTCCGACTACTCTGCCTTCATCAAGCGCAACGTCCCTGCCGGAGGT

CTGTTTACTGGTGCTGAGGTCGTCAAGACCGCCGAGCAGGCTAAGCTATT

TGGCGGCGAGGCTGGCGTTGCTTATGACAAGAACTACCACGGCAAGGGCG

ACACTGTAGACAACATCAACAAGGGTGCTATCTACCTCAACACTCGAGGA

ATCGCGTATGCCACTGCTCAGTATGCTAGTTCGCTGCGCGGATTCCCAAC

TABLE 10B-continued caLAP2 nucleotide sequence (SEQ ID NO: 29).

CCGCCCAAAGACGGGTAAGCGTGACGTGAGCCCCCGTGGCCAGTCTATGC

CTGGTGGTGGATGCGGACACCACAGCGTCTTCATGTAA

A disclosed caLAP2 nucleic acid (SEQ ID NO: 29) encodes a protein having 495 amino acid residues (SEQ ID NO: 30), which is presented in Table 10C using the one-letter amino acid code.

TABLE 10C

Encoded caLAP2 protein sequence (SEQ ID NO: 30).

MKTQLLSLGVALTAISQGVIAEDALNWPFKPLVNADDLQNKIKLKDLMAG

VQKLQDFAYAHPEKNRVFGGAGHKDTVDWIYNELKATGYYDVKMQPQVHL

WSHAEAAVNANGKDLTASAMSYSPPADKITAELVLAKNMGCNATDYPEGT

KGKIVLIERGVCSFGEKSAQAGDAKAIGAIVYNNVPGSLAGTLGGLDNRH

APTAGISQADGKNLASLVASGKVTVTMNVISKFENRTTWNVIAETKGGDH

NNVIMLGSHSDSVDAGPGINDNGSGTIGIMTVAKALTNFKVNNAVRFGWW

TAEEFGLLGSTFYVDSLDDRELHKVKLYLNFDMIGSPNFANQIYDGDGSA

YNMTGPAGSAEIEYLFEKFFDDQGIPHQPTAFTGRSDYSAFIKRNVPAGG

LFTGAEVVKTAEQAKLFGGEAGVAYDKNYHGKGDTVDNINKGAIYLNTRG

IAYATAQYASSLRGFPTRPKTGKRDVSPRGQSMPGGGCGHHSVFM

The disclosed caLAP2 has homology to the amino acid sequences shown in the BLAST data listed in Table 10D, 10E and 10F. This data was analyzed by the program PAIRWISE BLAST.

TABLE 10D

| TBLASTN results for caLAP2 | | | | | |
|---|---|---|---|---|---|
| Gene Index/Identifier | Protein/Organism | Length (aa) | Identity (%) | Positives (%) | Expect |
| gi\|600025 | *Saccharomyces cerevisiae* (s288c) RIF1, DPB3, YmL27 and SNF5 genes | 32421 | 182/477 (38%) | 254/477 (53%) | 8e−77 |
| gi\|469463 | *Saccharomyces cerevisiae* aminopeptidase Y gene | 2272 | 182/477 (38%) | 254/477 (53%) | 8e−77 |
| gi\|16033407 | *Bacillus licheniformis* leucine aminopeptidase precursor, gene | 2054 | 132/474 (27%) | 215/474 (45%) | 3e−27 |

TABLE 10E

BLASTX results for caLAP2

| Gene Index/Identifier | Protein/Organism | Length (aa) | Identity (%) | Positives (%) | Expect |
|---|---|---|---|---|---|
| gi\|1077010 | aminopeptidase Y precursor, vacuolar/ *Saccharomyces cerevisiae* | 537 | 182/477 (38%) | 254/477 (53%) | 9e−78 |
| gi\|6319763 | Aminopeptidase yscIII; Ape3p/ *Saccharomyces cerevisiae* | 563 | 182/477 (38%) | 254/477 (53%) | 9e−78 |
| gi\|31791596 | probable lipoprotein aminopeptidase LPQL/ *Mycobacterium bovis* | 500 | 188/485 (38%) | 269/485 (55%) | 3e−77 |
| gi\|15839805 | hydrolase/ *Mycobacterium tuberculosis* | 493 | 187/481 (38%) | 268/481 (55%) | 6e−77 |

TABLE 10F

BLASTP results for caLAP2

| Gene Index/Identifier | Protein/Organism | Length (aa) | Identity (%) | Positives (%) | Expect |
|---|---|---|---|---|---|
| gi\|6319763 | aminopeptidase yscIII; Ape3p/ *Saccharomyces cerevisiae* | 563 | 182/477 (38%) | 254/477 (53%) | 5e−78 |
| gi\|1077010 | aminopeptidase Y precursor, vacuolar/ *Saccharomyces cerevisiae* | 537 | 182/477 (38%) | 254/477 (53%) | 8e−78 |
| gi\|15839805 | hydrolase/ *Mycobacterium tuberculosis* | 493 | 187/481 (38%) | 268/481 (55%) | 1e−71 |
| gi\|31617182 | probable lipoprotein aminopeptidase LPQL/ *Mycobacterium bovis* | 500 | 188/485 (38%) | 269/485 (55%) | 2e−71 |
| gi\|15598135 | probable aminopeptidase/ *Pseudomonas aeruginosa* | 536 | 166/445 (37%) | 242/445 (54%) | 2e−65 | meLAP2 meLAP2 is a *Trichophyton mentagrophytes* leucine aminopeptidase. A meLAP2 nucleic acid of 1775 nucleotides (SEQ ID NO: 31) is shown in Table 11A.

TABLE 11A meLAP2 genomic nucleotide sequence (SEQ ID NO: 31).

ATGAAGTCGCAACTGTTGAGCCTAGCCGTGGCCGTCACCACCATTTCCCA

GGGCGTTGTTGGTCAAGAGCCCTTTGGATGGCCCTTCAAGCCTATGGTCA

CTCAGGTGAGTTGCTGTCAACAGATCGATCGATCGATCTACCTTCGTCCC

TGTCACCTATAACTCCACAGCAGGACCAAGAAAACACAAGTTTTCCGGGG

AATTCTTATGTGCTGATGTAAATGTATAGGATGACCTGCAAAACAAGATT

AAGCTCAAGGATATCATGGCAGGTGTGGACACTGTCGAGTGGATCTACAA

TGAGCTCAAGGCCACCGGCTACTACAATGTGAAGAAGCAGGAGCAGGTAC

ACCTGTGGTCTCACGCTGAGGCCGCTCTCAGTGCCAATGGCAAGGACCTC

AAGGCCAGCGCCATGTCGTACAGCCCTCCTGCCAACAAGATCATGGCCGA

GCTTGTCGTTGCCAAGAACAATGGCTGCAATGCTGTAAGTGCCATACACT

TCCTATACATCACATTCACTTTAGAATGAAGAGCGCGGGAGAACTGATTT

TTTTTTTTTTTTTTTTTTTTGTAACAGACCGATTACCCAGAGAACACT

CAGGGAAAGATAGTCCTCATTCAGCGTGGTGTCTGCAGCTTCGGCGAGAA

GTCTTCTCAGGCTGGTGATGCGAAGGCTATTGGTGCCGTTGTCTACAACA

TABLE 11A-continued meLAP2 genomic nucleotide sequence (SEQ ID NO: 31).

ACGTCCCCGGATCCCTTGCTGGCACTCTTGGTGGCCTTGACAAGCGCCAT

GTCCCAACCGCTGGTCTTTCCCAGGAGGATGGAAAGAATCTTGCTAGCCT

CGTTGCTTCTGGCAAGGTTGATGTCACCATGAACGTTGTCAGTCTGTTTG

AGAACCGAACCACGTAAGTAACTCAACGTCATATCCAGCATTAATCTTCA

GGAGTATATATACTAATTCGGTATCTCACAGCTGGAACGTCATTGCTGAG

ACCAAGGGAGGAGACCACAACAATGTTGTCATGCTTGGTGCTCACTCCGA

CTCCGTCGATGCCGGCCCCGGTATCAACGACAACGGCTCCGGCTCCATTG

GTATCATGACCGTTGCCAAAGCCCTTACTAACTTCAAGCTCAACAACGCC

GTTCGCTTTGCCTGGTGGACCGCTGAGGAATTCGGTCTCCTTGGAAGCAC

CTTCTACGTCGACAGCCTTGATGACCGTGAGCTGCACAAGGTCAAGCTGT

ACCTCAACTTCGACATGATCGGCTCTCCCAACTTCGCCAACCAGATCTAC

GACGGTGACGGTTCGGCCTACAACATGACTGGTCCCGCTGGCTCTGCTGA

AATCGAGTACCTGTTCGAGAAGTTCTTTGACGACCAGGGTCTCCCACACC

AGCCCACTGCCTTCACCGGCCGATCCGACTACTCTGCATTCATCAAGCGC

AACGTCCCCGCTGGAGGTCTTTTCACTGGTGCCGAGGTTGTCAAGACCCC

CGAGCAAGTTAAGCTGTTCGGTGGTGAGGCTGGCGTTGCCTATGACAAGA

TABLE 11A-continued meLAP2 genomic nucleotide sequence (SEQ ID NO: 31).

ACTACCATGGCAAGGGTGACACCGTTGCCAACATCAACAAGGGAGCTATC

TTCCTTAACACTCGAGCAATCGCCTACTCTGTGGCCGAGTATGCTCGATC

CCTCAAGGGCTTCCCAACCCGCCCAAAGACCGGCAAGCGTGCCGTCAACC

CTCAGTATGCTAAGATGCCTGGTGGTGGTTGCGGACACCACACTGTCTTC

ATGTAA

A disclosed meLAP2 open reading frame ("ORF") of 1488 nucleotides begins with an ATG start codon at position 1 (underlined in Table 11B).

TABLE 11B meLAP2 nucleotide sequence (SEQ ID NO: 32).

<u>ATG</u>AAGTCGCAACTGTTGAGCCTAGCCGTGGCCGTCACCACCATTTCCCA

GGGCGTTGTTGGTCAAGAGCCCTTTGGATGGCCCTTCAAGCCTATGGTCA

CTCAGGATGACCTGCAAAACAAGATTAAGCTCAAGGATATCATGGCAGGT

GTCGAGAAGCTGCAAAGCTTTTCTGATGCTCATCCTGAAAAGAACCGAGT

GTTCGGTGGTAATGGCCACAAGGACACTGTCGAGTGGATCTACAATGAGC

TCAAGGCCACCGGCTACTACAATGTGAAGAAGCAGGAGCAGGTACACCTG

TGGTCTCACGCTGAGGCCGCTCTCAGTGCCAATGGCAAGGACCTCAAGGC

CAGCGCCATGTCGTACAGCCCTCCTGCCAACAAGATCATGGCCGAGCTTG

TCGTTGCCAAGAACAATGGCTGCAATGCTACCGATTACCCAGAGAACACT

CAGGGAAAGATAGTCCTCATTCAGCGTGGTGTCTGCAGCTTCGGCGAGAA

GTCTTCTCAGGCTGGTGATGCGAAGGCTATTGGTGCCGTTGTCTACAACA

ACGTCCCCGGATCCCTTGCTGGCACTCTTGGTGGCCTTGACAAGCGCCAT

GTCCCAACCGCTGGTCTTTCCCAGGAGGATGGAAAGAATCTTGCTAGCCT

CGTTGCTTCTGGCAAGGTTGATGTCACCATGAACGTTGTCAGTCTGTTTG

AGAACCGAACCACCTGGAACGTCATTGCTGAGACCAAGGGAGGAGACCAC

AACAATGTTGTCATGCTTGGTGCTCACTCCGACTCCGTCGATGCCGGCCC

CGGTATCAACGACAACGGCTCCGGCTCCATTGGTATCATGACCGTTGCCA

AAGCCCTTACTAACTTCAAGCTCAACAACGCCGTTCGCTTTGCCTGGTGG

ACCGCTGAGGAATTCGGTCTCCTTGGAAGCACCTTCTACGTCGACAGCCT

TABLE 11B-continued meLAP2 nucleotide sequence (SEQ ID NO: 32).

TGATGACCGTGAGCTGCACAAGGTCAAGCTGTACCTCAACTTCGACATGA

TCGGCTCTCCCAACTTCGCCAACCAGATCTACGACGGTGACGGTTCGGCC

TACAACATGACTGGTCCCGCTGGCTCTGCTGAAATCGAGTACCTGTTCGA

GAAGTTCTTTGACGACCAGGGTCTCCCACACCAGCCCACTGCCTTCACCG

GCCGATCCGACTACTCTGCATTCATCAAGCGCAACGTCCCCGCTGGAGGT

CTTTTCACTGGTGCCGAGGTTGTCAAGACCCCCGAGCAAGTTAAGCTGTT

CGGTGGTGAGGCTGGCGTTGCCTATGACAAGAACTACCATGGCAAGGGTG

ACACCGTTGCCAACATCAACAAGGGAGCTATCTTCCTTAACACTCGAGCA

ATCGCCTACTCTGTGGCCGAGTATGCTCGATCCCTCAAGGGCTTCCCAAC

CCGCCCAAAGACCGGCAAGCGTGCCGTCAACCCTCAGTATGCTAAGATGC

CTGGTGGTGGTTGCGGACACCACACTGTCTTCATGTAA

A disclosed meLAP2 nucleic acid (SEQ ID NO: 32) encodes a protein having 495 amino acid residues (SEQ ID NO: 33), which is presented in Table 11C using the one-letter amino acid code.

TABLE 11C

Encoded meLAP2 protein sequence (SEQ ID NO:33).

MKSQLLSLAVAVTTISQGVVGQEPFGWPFKPMVTQDDLQNKIKLKDIMAG

VEKLQSFSDAHPEKNRVFGGNGHKDTVEWIYNELKATGYYNVKKQEQVHL

WSHAEAALSANGKDLKASASMSYPPANKIMAELVVAKNNGCNATDYPENT

QGKIVLIQRGVCSFGEKSSQAGDAKAIGAVVYNNVPGSLAGTLGGLDKRH

VPTAGLSQEDGKNLASLVASGKVDVTMNVVSLFENRTTWNVIAETKGGDH

NNVVMLGAHSDSVDAGPGINDNGSGSIGIMTVAKALTNFKLNNAVRFAWW

TAEEFGLLGSTFYVDSLDDRELHKVKLYLNFDMIGSPNFANQIYDGDGSA

YNMTGPAGSAEIEYLFEKFFDDQGLPHQPTAFTGRSDYSAFIKRNVPAGG

LFTGAEVVKTPEQVKLFGGEAGVAYDKNYHGKGDTVANINKGAIFLNTRA

IAYSVAEYARSLKGFPTRPKTGKRAVNPQYAKMPGGGCGHHTVFM

The disclosed meLAP2 has homology to the amino acid sequences shown in the BLAST data listed in Table 11D, 11E and 11F. This data was analyzed by the program PAIRWISE BLAST.

TABLE 11D

| TBLASTN results for meLAP2 | | | | |
|---|---|---|---|---|
| Gene Index/Identifier | Protein/Organism | Length (aa) | Identity (%) | Positives (%) | Expect |
| gi\|600025 | *Saccharomyces cerevisiae* (s288c) RIF1, DPB3, YmL27 and SNF5 genes | 32421 | 180/479 (37%) | 251/479 (52%) | 2e-70 |
| gi\|469463 | *Saccharomyces cerevisiae* aminopeptidase Y gene | 2272 | 180/479 (37%) | 251/479 (52%) | 2e-70 |

TABLE 11E

BLASTX results for meLAP2

| Gene Index/Identifier | Protein/Organism | Length (aa) | Identity (%) | Positives (%) | Expect |
|---|---|---|---|---|---|
| gi\|1077010 | aminopeptidase Y precursor, vacuolar/ *Saccharomyces cerevisiae* | 537 | 180/479 (37%) | 251/479 (52%) | 8e−71 |
| gi\|6319763 | aminopeptidase yscIII; Ape3p/ *Saccharomyces cerevisiae* | 563 | 180/479 (37%) | 251/479 (52%) | 8e−71 |
| gi\|15839805 | hydrolase/ *Mycobacterium tuberculosis* | 493 | 159/440 (36%) | 236/440 (53%) | 1e−63 |
| gi\|31791596 | probable lipoprotein aminopeptidase LPQL/ *Mycobacterium bovis* | 500 | 159/440 (36%) | 236/440 (53%) | 1e−63 |
| gi\|15598135 | probable aminopeptidase/ *Pseudomonas aeruginosa* | 536 | 158/445 (35%) | 237/445 (53%) | 1e−62 |
| gi\|1045225 | N-acetylpuromycin N-acetylhydrolase/ *Streptomyces anulatus* | 485 | 154/477 (32%) | 218/477 (45%) | 4e−48 |
| gi\|29831415 | putative aminopeptidase/ *Streptomyces avermitilis* | 315 | 95/244 (38%) | 131/244 (53%) | 2e−37 |

TABLE 11F

BLASTP results for meLAP2

| Gene Index/Identifier | Protein/Organism | Length (nt) | Identity (%) | Positives (%) | Expect |
|---|---|---|---|---|---|
| gi\|6319763 | aminopeptidase yscIII; Ape3p/ *Saccharomyces cerevisiae* | 563 | 179/479 (37%) | 248/479 (51%) | 9e−71 |
| gi\|1077010 | aminopeptidase Y precursor, vacuolar/ *Saccharomyces cerevisiae* | 537 | 179/479 (37%) | 248/479 (51%) | 9e−71 |
| gi\|31617182 | probable lipoprotein aminopeptidase LPQL/ *Mycobacterium bovis* | 500 | 159/440 (36%) | 236/440 (53%) | 2e−62 |
| gi\|15839805 | hydrolase/ *Mycobacterium tuberculosis* | 493 | 159/440 (36%) | 236/440 (53%) | 2e−62 | ruDPPIV ruDPPIV is a *T. rubrum* dipeptidylpeptidase IV. A ruDPPIV nucleic acid of 2326 nucleotides (SEQ ID NO: 34) is shown in Table 12A. A disclosed ruDPPIV open reading frame ("ORF") begins with an ATG start codon at position 1 (underlined in Table 12A).

TABLE 12A ruDPPIV nucleotide sequence (SEQ ID NO: 34).

ATGAAGCTCCTCTCGCTACTTATGCTGGCGGGCATCGCCCAAGCCATCGT

TCCTCCTCGTGAGCCCGTTCACCAACTGGTGGCGGCAACAAGCTGTTGA

CCTACAAGGAGTGTGTCCCTAGAGCTACTATCTCTCCAAGGTCGACGTCC

CTTGCCTGGATTAACAGTGAAGAAGATGGCCGGTACATCTCCCAGTCCGA

CGATGGAGCATTGATCCTCCAGAACATCGTCACGAACACCAACAAGACTC

TCGTGGCCGCAGACAAGGTACCCAAGGGTTACTATGACTACTGGTTCAAG

CCAGACCTTTCTGCTGTCTTATGGGCAACCAATTACACCAAGCAGTACCG

TCACTCTTACTTTGCCAACTACTTATTCTAGACATCAAAAAAGGGATCGT

TGACCCCTCTAGCCCAGGACCAGGCTGGTGACATCCAGTATGCTCAATGG

AGCCCCATGAACAACTCTATCGCCTATGTCCGTGAAACGACCTGTATAT

TABLE 12A-continued ruDPPIV nucleotide sequence (SEQ ID NO: 34).

CTGGAACAATGGCAAGACCAAGCGTATTACCGAAAATGGCGGCCCGGATA

TCTTCAATGGTGTCCCTGACTGGGATATACGAGGAAGAAATCTTCGGGGA

CCGGTTCGTCTTTGGTTCTCACCTGACGGTGAATACCTTGCGTACCTCCG

CTTTAACGAGACTGGAGTCCCGACCTACACTATTCCGTACTACAAGAACA

AGCAAAAGATTGCCCCTGCCTACCCAAGGGAGCTGGAGATCCGTTACCCT

AAAGTCTCTGCGAAGAACCCAACCGTGCAGTTCCACCTGTTAAACATTGC

TTCATCCCAGGAGACAACTATCCCAGTTACTGCGTTCCCGGAAAACGATC

TTGTGATCGGTGAGGTTGCTTGGCTCAGCAGTGGCCATGATAGTGTAGCA

TATCGTGCTTTCAACCGTGTCCAGGATAGAGAAAAGATTGTCAGCGTCAA

GGTTGAGTCCAAGGAATCCAAGGTTATTCGCGAAAGAGATGGCACCGACG

GCTGGATCGACAACCTTCTCTCATGTCATATATCGGAAACGTTAACGGCA

AGGAGTACTACGTCGATATATCTGATGCTTCTGGCTGGGCACATATCTAC

CTCTACCCGGTTGATGGAGGAAAGGAGATTGCACTAACAAAGGGAGAATG

GGAAGTCGTTGCCATTCTCAAGGTTGACACGAAGAAGAAGCTGATCTACT

TABLE 12A-continued ruDPPIV nucleotide sequence (SEQ ID NO: 34).

TCACCTCTACCAAATATCACAGCACCACTCGACACGTCTACTCTGTCTCG
TATGACACAAAGGTCATGACCCCTCTCGTCAACGATAAGGAGGCTGCGTA
CTACACTGCATCCTTCTCGGCCAAGGGTGGTTACTATATCTTGTCCTACC
AAGGTCCAAATGTTCCATACCAAGAACTTTACTCCACCAAGGACAGTAAG
AAGCCTCTCAAGACAATCACTAGCAATGATGCATTGCTCGAGAAGCTGAA
GGAGTACAAGCTCCCCAAGGTTAGCTTCTTTGAGATCAAGCTTCCATCTG
GTGAAACCCTTAATGTTAAGCAACGCCTACCACCTAACTTCAACCCACAC
AAGAAGTACCCCGTCCTCTTCACTCCGTATGGTGGCCCTGGTGCCCAAGA
GGTAAGCCAGGCATGGAATTCATTGGACTTCAAGTCCTACATTACATCTG
ACCCTGAGCTTGAATACGTTACCTGGACTGTTGACAACCGTGGAACCGGC
TACAAGGGCCGCAAGTTCCGCAGCGCCGTAGCTAAGCGTCTCGGTTTCCT
CGAAGCCCAGGACCAGGTCTTTGCTGCTAAGGAGGTGCTGAAAAACCGTT
GGGCTGATAAGGACCATATTGGAATCTGGGGCTGNAGCTATGGCGGCTTC
CTGACCGCTAAGACCCTCGAGACCGACAGTGGTGTATTCACTTTTGGTAT
CAGTACTGCTCCTGTCTCTGATTTCAGACTCTACGACAGCATGTACACTG
AGCGTTACATGAAGACCGTTGAACTAAACGCTGACGGCTACAGTGAGACC
GCCGTGCACAAGGTTGATGGCTTTAAGAACCTCAAAGGTCATTACTCATC
CAGCATGGAACCGGTGACGACAACGTCCACTTCCAAAACGCCGCTGTCCT
TTCCAACACCCTGATGAACGGCGGTGTAACTGCAGACAAGTTGACTACTC
AGTGGTTTACTGACTCGGACCACGGCATCAGATACGATATGGACTCCACT
TACCAGTACAAGCAGCTTTCTAAGATGGTCTACGACCAGAAGCAACGAAG
GCCAGAAAGCCCACCAATGCACCAATGGAGCAAGAGAGTTTTGGCTGCCC
TGTTGGTGAGAGGGCAGAGGAATGA

A disclosed ruDPPIV nucleic acid (SEQ ID NO: 34) encodes a protein having 775 amino acid residues (SEQ ID NO: 35), which is presented in Table 12B using the one-letter amino acid code.

TABLE 12B

Encoded ruDPPIV protein sequence (SEQ ID NO: 35).

MKLLSLLMLAGIAQAIVPPREPRSPTGGGNKLLTYKECVPRATISPRSTS

LAWINSEEDGRYISQSDDGALILQNIVTNTNKTLVAADKVPKGYYDYWFK

PDLSAVLWATNYTKQYRHSYFANYFILDIKKGSLTPLAQDQAGDIQYAQW

SPMNNSIAYVRXNDLYIWNNGKTKRITENGGPDIFNGVPDWVYEEEIFGD

RFALWFSPDEGYLAYLRFENTGVPTYTIPYYKNKQKIAPAYPRELEIRYP

KVSAKNPTVQFHLLNIASSQETTIPVTAFPENDLVIGEVAWLSSGHDSVA

YRAFNRVQDREKISVSKVESKESKVIRERDGTDGWIDNLLSMSYIGBVNG

KEYYVDISDASGWAHIYLYPVDGGKEIALTKGEWEVVAILKVDTKKKLIY

FTSTKYHSTTRHVYSVSYDTKVMTPLVNDKEAAYYTASFSAKGGYYILSY

QGPNVPYQELYSTKDSKKPLKTITSNDALLEKLKEYKLPKVSFFEIKLPS

GETLNVKQRLPPNFNPHKKYPVLFTPYGGPGAQEVSQAWNSLDFKSYITS

DPELEYVTWTVDNRGTGYKGRKFRSAVAKRLGFLEAQDQVFAAKEVLKNR

WADKDHIGIWGXSYGGFLTAKTLETDSGVFTFGISTAPVSDFRLYDSMYT

ERYMKTVELNADGYSETAVHKVDGFKNLKGHYLIQHGTGDDNVHFQNAAV

LSNTLMNGGVTADKLTTQWFTDSDHGIRYDMDSTYQYKQLSKMVYDQKQR

RPESPPMHQWSKRVLAALFGERAEE

The disclosed ruDPPIV has homology to the amino acid sequences shown in the BLAST data listed in 12C, 12D, and 12E. This data was analyzed by the program PAIRWISE BLAST.

TABLE 12C

TBLASTN results for ruDPPIV

| Gene Index/Identifier | Protein/Organism | Length (aa) | Identity (%) | Positives (%) | Expect |
| --- | --- | --- | --- | --- | --- |
| gi\|2351699 | *Aspergillus fumigatus* dipeptidyl - peptidase IV (Dpp4) gene | 2352 | 469/761 (61%) | 585/761 (76%) | 0.0 |
| gi\|2924304 | *Aspergillus oryzae* DppIV gene | 4771 | 448/769 (58%) | 568/769 (73%) | 0.0 |
| gi\|32422540 | *Neurospora crassa* strain OR74A | 2688 | 256/720 (35%) | 374/720 (51%) | e−114 |
| gi\|14330262 | *Aspergillus niger* dapB gene for dipeptidyl aminopeptidase type IV, exons 1-3 | 3989 | 224/637 (35%) | 333/637 (52%) | e−111 |
| gi\|1621278 | *Xenopus laevis* mRNA for dipeptidyl-peptidase IV | 3337 | 244/752 (32%) | 375/752 (49%) | e−100 |
| gi\|6978772 | *Rattus norvegicus* Dipeptidyl peptidase 4 (Dpp4) | 4835 | 246/742 (33%) | 373/742 (50%) | 8e−98 |

TABLE 12D

BLASTX results for ruDPPIV

| Gene Index/Identifier | Protein/Organism | Length (aa) | Identity (%) | Positives (%) | Expect |
|---|---|---|---|---|---|
| gi\|2351700 | dipeptidyl-peptidase IV/ *Aspergillus fumigatus* | 765 | 218/341 (63%) | 270/341 (79%) | 0.0 |
| gi\|2924305 | prolyl dipeptidyl peptidase/ *Aspergillus oryzae* | 771 | 213/344 (61%) | 270/344 (78%) | 0.0 |
| gi\|1621279 | dipeptidyl-peptidase IV/ *Xenopus laevis* | 748 | 118/349 (33%) | 186/349 (53%) | 8e−93 |
| gi\|535388 | dipeptidyl peptidase IV/ *Homo sapiens* | 766 | 125/375 (33%) | 191/375 (50%) | 3e−90 |

TABLE 12E

BLASTP results for ruDPPIV

| Gene Index/Identifier | Protein/Organism | Length (aa) | Identity (%) | Positives (%) | Expect |
|---|---|---|---|---|---|
| gi\|2351700 | dipeptidyl-peptidase IV/ *Aspergillus fumigatus* | 765 | 468/761 (61%) | 585/761 (76%) | 0.0 |
| gi\|2924305 | prolyl dipeptidyl peptidase/ *Aspergillus oryzae* | 771 | 448/769 (58%) | 568/769 (73%) | 0.0 |
| gi\|14330263 | dipeptidyl aminopeptidase type IV/ *Aspergillus niger* | 901 | 261/733 (35%) | 387/733 (52%) | e−114 |
| gi\|19114882 | dipeptidyl aminopeptidase/ *Schizosaccharomyces pombe* | 793 | 258/742 (34%) | 396/742 (53%) | e−106 |
| gi\|3660 | dipeptidyl aminopeptidase B/ *Saccharomyces cerevisiae* | 841 | 254/750 (33%) | 370/750 (49%) | 2e−95 |

One aspect of the invention pertains to isolated nucleic acid molecules that encode EXOX polypeptides or biologically active portions thereof. Also included in the invention are nucleic acid fragments sufficient for use as hybridization probes to identify EXOX-encoding nucleic acids (e.g., EXOX mRNAs) and fragments for use as PCR primers for the amplification and/or mutation of EXOX nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule may be single-stranded or double-stranded.

An EXOX nucleic acid can encode a mature EXOX polypeptide. As used herein, a "mature" form of a polypeptide or protein disclosed in the present invention is the product of a naturally occurring polypeptide or precursor form or proprotein. The naturally occurring polypeptide, precursor or proprotein includes, by way of nonlimiting example, the full-length gene product, encoded by the corresponding gene. Alternatively, it may be defined as the polypeptide, precursor or proprotein encoded by an ORF described herein. The product "mature" form arises, again by way of nonlimiting example, as a result of one or more naturally occurring processing steps as they may take place within the cell, or host cell, in which the gene product arises. Examples of such processing steps leading to a "mature" form of a polypeptide or protein include the cleavage of the N-terminal methionine residue encoded by the initiation codon of an ORF, or the proteolytic cleavage of a signal peptide or leader sequence. Thus a mature form arising from a precursor polypeptide or protein that has residues 1 to N, where residue 1 is the N-terminal methionine, would have residues 2 through N remaining after removal of the N-terminal methionine. Alternatively, a mature form arising from a precursor polypeptide or protein having residues 1 to N, in which an N-terminal signal sequence from residue 1 to residue M is cleaved, would have the residues from residue M+1 to residue N remaining. Further as used herein, a "mature" form of a polypeptide or protein may arise from a step of post-translational modification other than a proteolytic cleavage event. Such additional processes include, by way of non-limiting example, glycosylation (N-, O- and W types), myristoylation, phosphorylation, sulfation, N-terminus cyclisation, or C-terminus amidation. In general, a mature polypeptide or protein may result from the operation of only one of these processes, or a combination of any of them.

The term "probes", as utilized herein, refers to nucleic acid sequences of variable length, preferably between at least about 10 nucleotides (nt), 100 nt, or as many as approximately, e.g., 6,000 nt, depending upon the specific use. Probes are used in the detection of identical, similar, or complementary nucleic acid sequences. Longer length probes are generally obtained from a natural or recombinant source, are highly specific, and much slower to hybridize than shorter-length oligomer probes. Probes may be single- or double-stranded and designed to have specificity in PCR, membrane-based hybridization technologies, or ELISA-like technologies.

The term "isolated" nucleic acid molecule, as utilized herein, is one, which is separated from other nucleic acid molecules, which are present in the natural source of the nucleic acid. Preferably, an "isolated" nucleic acid is free of sequences, which naturally flank the nucleic acid (e.g., sequences located at the 5'- and 3'-termini of the nucleic acid) in the genomic DNA of the organism from which the nucleic acid is derived. For example, in various embodiments, the isolated EXOX nucleic acid molecules can contain less than about 5 kb, 4 kb, 3 kb, 2 kb, 1 kb, 0.5 kb or 0.1 kb of nucleotide sequences which naturally flank the nucleic acid molecule in genomic DNA of the cell/tissue/species from which the nucleic acid is derived. Moreover, an "isolated" nucleic acid molecule, such as a cDNA molecule, can be substantially free of other cellular material or culture medium when produced by recombinant techniques, or of chemical precursors or other chemicals when chemically synthesized. Particularly, it means that the nucleic acid or protein is at least about 50% pure, more preferably at least about 85% pure, and most preferably at least about 99% pure.

As used herein, the term "recombinant" when used with reference to a cell indicates that the cell replicates a heterologous nucleic acid, or expresses a peptide or protein encoded by a heterologous nucleic acid. Recombinant cells can contain genes that are not found within the native (non-recombinant) form of the cell. Recombinant cells can also contain genes found in the native form of the cell wherein the genes are modified and re-introduced into the cell by artificial means. The term also encompasses cells that contain a nucleic acid endogenous to the cell that has been modified without removing the nucleic acid from the cell; such modifications include those obtained by gene replacement, site-specific mutation, and related techniques. One skilled in the art will recognize that these cells can be used for unicellular or multicellular transgenic organisms, for example transgenic fungi producing EXOX.

A nucleic acid molecule of the invention, e.g., a nucleic acid molecule having the nucleotide sequence of SEQ ID NOs: 2, 5, 8, 11, 14, 17, 20, 23, 26, 29, 32, or 34 or a complement of this aforementioned nucleotide sequence, can be isolated using standard molecular biology techniques and the sequence information provided herein. Using all or a portion of the nucleic acid sequence of SEQ ID NOs: 2, 5, 8, 11, 14, 17, 20, 23, 26, 29, 32, or 34 as a hybridization probe, EXOX molecules can be isolated using standard hybridization and cloning techniques (e.g., as described in Sambrook et al., (eds.), MOLECULAR CLONING: A LABORATORY MANUAL $2^{nd}$ Ed., Cold Spring Harbor Laboratory Press, Cold Spring Harbor, N.Y., 1989; and Ausubel et al., (eds.), CURRENT PROTOCOLS IN MOLECULAR BIOLOGY, John Wiley & Sons, New York, N.Y., 1993.)

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to EXOX nucleotide sequences can be prepared by standard synthetic techniques, e.g., using an automated DNA synthesizer.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 nt in length, preferably about 15 nt to 30 nt in length. In one embodiment of the invention, an oligonucleotide comprising a nucleic acid molecule less than 100 nt in length would further comprise at least 6 contiguous nucleotides of SEQ ID NOs: 2, 5, 8, 11, 14, 17, 20, 23, 26, 29, 32, or 34, or a complement thereof. Oligonucleotides may be chemically synthesized and may also be used as probes.

In another embodiment, an isolated nucleic acid molecule of the invention comprises a nucleic acid molecule that is a complement of the nucleotide sequence shown in SEQ ID NOs: 2, 5, 8, 11, 14, 17, 20, 23, 26, 29, 32, or 34, or a portion of this nucleotide sequence (e.g., a fragment that can be used as a probe or primer or a fragment encoding a biologically-active portion of a EXOX polypeptide). A nucleic acid molecule that is complementary to the nucleotide sequence shown in SEQ ID NOs: 2, 5, 8, 11, 14, 17, 20, 23, 26, 29, 32, or 34 is one that is sufficiently complementary to the nucleotide sequence shown in SEQ ID NOs: 2, 5, 8, 11, 14, 17, 20, 23, 26, 29, 32, or 34 that it can hydrogen bond with little or no mismatches to the nucleotide sequence shown in SEQ ID NOs: 2, 5, 8, 11, 14, 17, 20, 23, 26, 29, 32, or 34, thereby forming a stable duplex.

As used herein, the term "complementary" refers to Watson-Crick or Hoogsteen base pairing between nucleotide units of a nucleic acid molecule. The term "binding" means the physical or chemical interaction between two polypeptides or compounds or associated polypeptides or compounds or combinations thereof. Binding includes ionic, non-ionic, van der Waals, hydrophobic interactions, and the like. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Fragments provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full length sequence. Fragments may be derived from any contiguous portion of a nucleic acid or amino acid sequence of choice. Derivatives are nucleic acid sequences or amino acid sequences formed from the native compounds either directly or by modification or partial substitution. Analogs are nucleic acid sequences or amino acid sequences that have a structure similar to, but not identical to, the native compound but differ from it with respect to certain components or side chains. Analogs may be synthetic or from a different evolutionary origin and may have a similar or opposite metabolic activity compared to wild type. Homologs or orthologs are nucleic acid sequences or amino acid sequences of a particular gene that are derived from different species.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 70%, 80%, or 95% identity (with a preferred identity of 80-95%) over a nucleic acid or amino acid sequence of identical size or when compared to an aligned sequence in which the alignment is done by a computer homology program known in the art, or whose encoding nucleic acid is capable of hybridizing to the complement of a sequence encoding the aforementioned proteins under stringent, moderately stringent, or low stringent conditions. See, e.g., Ausubel et al., CURRENT PROTOCOLS IN MOLECULAR BIOLOGY, John Wiley & Sons, New York, N.Y., 1993, and below.

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of EXOX polypeptides. Isoforms can be expressed in the same organism as a result of, for example, alternative splicing of RNA. Alternatively, isoforms can be encoded by different genes. In the invention, homologous nucleotide sequences can include nucleotide sequences encoding an EXOX polypeptide of species other than fungi. Homologous nucleotide sequences also include, but are not limited to, naturally occurring allelic variations and mutations of the nucleotide sequences set forth herein. Homologous nucleic acid sequences include those nucleic acid sequences that encode conservative amino acid substitutions (see below) in SEQ ID NOs: 2, 5, 8, 11, 14, 17, 20, 23, 26, 29, 32, or 34, as well as a polypeptide possessing EXOX biological activity. Various biological activities of the EXOX proteins. are described below.

A EXOX polypeptide is encoded by the open reading frame ("ORF") of an EXOX nucleic acid. A stretch of nucleic acids comprising an ORF is uninterrupted by a stop codon. An ORF that represents the coding sequence for a full protein begins with an ATG "start" codon and terminates with one of the three "stop" codons, namely, TAA, TAG, or TGA. For the purposes of this invention, an ORF may be any part of a coding sequence, with or without a start codon, a stop codon, or both. For an ORF to be considered as a good candidate for coding for a bona fide cellular protein, a minimum size requirement is often set, e.g., a stretch of DNA that would encode a protein of 50 amino acids or more.

The nucleotide sequences determined from the cloning of the fungal EXOX genes allows for the generation of probes and primers designed for use in identifying and/or cloning EXOX homologues in other species, as well as EXOX homologues from other fungi. The probe/primer typically comprises a substantially purified oligonucleotide. The oligonucleotide typically comprises a region of nucleotide sequence that hybridizes under stringent conditions to at least about 12, 25, 50, 100, 150, 200, 250, 300, 350 or 400 consecutive sense strand nucleotide sequence of SEQ ID NOs: 2, 5, 8, 11, 14, 17, 20, 23, 26, 29, 32, or 34; or an anti-sense strand nucleotide sequence of SEQ ID NOs: 2, 5, 8, 11, 14, 17, 20, 23, 26, 29, 32, or 34; or of a naturally occurring mutant of SEQ ID NOs: 2, 5, 8, 11, 14, 17, 20, 23, 26, 29, 32, or 34.

"A polypeptide having a biologically-active portion of an EXOX polypeptide" refers to polypeptides exhibiting activity similar, but not necessarily identical to, an activity of a polypeptide of the invention, including mature forms, as measured in a particular biological assay, with or without dose dependency. A nucleic acid fragment encoding a "biologically-active portion of EXOX" can be prepared by isolating a portion SEQ ID NOs: 2, 5, 8, 11, 14, 17, 20, 23, 26, 29, 32, or 34 that encodes a polypeptide having a EXOX biological activity (the biological activities of the EXOX proteins are described below), expressing the encoded portion of EXOX protein (e.g., by recombinant expression in vitro) and assessing the activity of the encoded portion of EXOX.

EXOX Nucleic Acid and Polypeptide Variants

The invention further encompasses nucleic acid molecules that differ from the nucleotide sequences shown in SEQ ID NOs: 2, 5, 8, 11, 14, 17, 20, 23, 26, 29, 32, or 34 due to degeneracy of the genetic code and thus encode the same EXOX proteins that are encoded by the nucleotide sequences shown in SEQ ID NOs: 2, 5, 8, 11, 14, 17, 20, 23, 26, 29, 32, or 34. In another embodiment, an isolated nucleic acid molecule of the invention has a nucleotide sequence encoding a protein having an amino acid sequence shown in SEQ ID NOs: 3, 6, 9, 12, 15, 18, 21, 24, 27, 30, 33, or 35. In addition to the fungal EXOX nucleotide sequences shown in SEQ ID NOs: 2, 5, 8, 11, 14, 17, 20, 23, 26, 29, 32, and 34, it will be appreciated by those skilled in the art that DNA sequence polymorphisms that lead to changes in the amino acid sequences of the EXOX polypeptides may exist within a population of various species. Such genetic polymorphisms in the EXOX genes may exist among individual fungal species within a population due to natural allelic variation. As used herein, the terms "gene" and "recombinant gene" refer to nucleic acid molecules comprising an open reading frame (ORF) encoding an EXOX protein, preferably a fungal EXOX protein. Such natural allelic variations can typically result in 1-5% variance in the nucleotide sequence of the EXOX genes. Any and all such nucleotide variations and resulting amino acid polymorphisms in the EXOX polypeptides, which are the result of natural allelic variation and that do not alter the functional activity of the EXOX polypeptides, are intended to be within the scope of the invention.

Moreover, nucleic acid molecules encoding EXOX proteins from other species, and, thus, that have a nucleotide sequence that differs from the fungal sequence SEQ ID NOs: 2, 5, 8, 11, 14, 17, 20, 23, 26, 29, 32, or 34 are intended to be within the scope of the invention. Nucleic acid molecules corresponding to natural allelic variants and homologues of the EXOX cDNAs of the invention can be isolated based on their homology to the fungal EXOX nucleic acids disclosed herein using the fungal cDNAs, or a portion thereof, as a hybridization probe according to standard hybridization techniques under stringent hybridization conditions.

Accordingly, in another embodiment, an isolated nucleic acid molecule of the invention is at least 6 nucleotides in length and hybridizes under stringent conditions to the nucleic acid molecule comprising the nucleotide sequence of SEQ ID NOs: 2, 5, 8, 11, 14, 17, 20, 23, 26, 29, 32, or 34.

In another embodiment, the nucleic acid is at least 10, 25, 50, 100, 250, 500, 750, 1000, 1500, or 2000 or more nucleotides in length. In yet another embodiment, an isolated nucleic acid molecule of the invention hybridizes to the coding region. As used herein, the term "hybridizes under stringent conditions" is intended to describe conditions for hybridization and washing under which nucleotide sequences at least 60% homologous to each other typically remain hybridized to each other.

Homologs or other related sequences (e.g., orthologs, paralogs) can be obtained by low, moderate or high stringency hybridization with all or a portion of the particular fungal sequence as a probe using methods well known in the art for nucleic acid hybridization and cloning.

As used herein, the phrase "stringent hybridization conditions" refers to conditions under which a probe, primer or oligonucleotide will hybridize to its target sequence, but to no other sequences. Stringent conditions are sequence-dependent and will be different in different circumstances. Longer sequences hybridize specifically at higher temperatures than shorter sequences. Generally, stringent conditions are selected to be about 5° C. lower than the thermal melting point $(T_m)$ for the specific sequence at a defined ionic strength and pH. The $T_m$ is the temperature (under defined ionic strength, pH and nucleic acid concentration) at which 50% of the probes complementary to the target sequence hybridize to the target sequence at equilibrium. Since the target sequences are generally present at excess, at $T_m$, 50% of the probes are occupied at equilibrium. Typically, stringent conditions will be those in which the salt concentration is less than about 1.0 M sodium ion, typically about 0.01 to 1.0 M sodium ion (or other salts) at pH 7.0 to 8.3 and the temperature is at least about 30° C. for short probes, primers or oligonucleotides (e.g., 10 nt to 50 nt) and at least about 60° C. for longer probes, primers and oligonucleotides. Stringent conditions may also be achieved with the addition of destabilizing agents, such as formamide.

Stringent conditions are known to those skilled in the art and can be found in Ausubel et al., (eds.), CURRENT PROTOCOLS IN MOLECULAR BIOLOGY, John Wiley & Sons, N.Y. (1989), 6.3.1-6.3.6. Preferably, the conditions are such that sequences at least about 65%, 70%, 75%, 85%, 90%, 95%, 98%, or 99% homologous to each other typically remain hybridized to each other. A non-limiting example of stringent hybridization conditions are hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C., followed by one or more washes in 0.2×SSC, 0.01% BSA at 50° C. An isolated nucleic acid molecule of the invention that hybridizes under stringent conditions to the sequences of SEQ ID NOs: 2, 5, 8, 11, 14, 17, 20, 23, 26, 29, 32, or 34 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In a second embodiment, a nucleic acid sequence that is hybridizable to the nucleic acid molecule comprising the nucleotide sequence of SEQ ID NOs: 2, 5, 8, 11, 14, 17, 20, 23, 26, 29, 32, or 34 or fragments, analogs or derivatives thereof, under conditions of moderate stringency is provided. A non-limiting example of moderate stringency hybridization conditions are hybridization in 6×SSC, 5×Denhardt's solution, 0.5% SDS and 100 mg/ml denatured salmon sperm DNA at 55° C., followed by one or more washes in 1×SSC, 0.1% SDS at 37° C. Other conditions of moderate stringency that may be used are well-known within the art. See, e.g., Ausubel et al. (eds.), 1993, CURRENT PROTOCOLS IN MOLECULAR BIOLOGY, John Wiley & Sons, NY, and Kriegler, 1990; GENE TRANSFER AND EXPRESSION, A LABORATORY MANUAL, Stockton Press, NY.

In a third embodiment, a nucleic acid that is hybridizable to the nucleic acid molecule comprising the nucleotide sequences of SEQ ID NOs: 2, 5, 8, 11, 14, 17, 20, 23, 26, 29, 32, or 34 or fragments, analogs or derivatives thereof, under conditions of low stringency, is provided. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (w/v) dextran sulfate at 40° C., followed by one or more washes in 2×SSC, 25 mM Tris-HCl (pH 7.4), 5 mM EDTA, and 0.1% SDS at 50° C. Other conditions of low stringency that may be used are well known in the art (e.g., as employed for cross-species hybridizations). See, e.g., Ausubel et al. (eds.), 1993, CURRENT PROTOCOLS IN MOLECULAR BIOLOGY, John Wiley & Sons, NY, and Kriegler, 1990, GENE TRANSFER AND EXPRESSION, A LABORATORY MANUAL, Stockton Press, NY; Shilo & Weinberg, *Proc Natl Acad Sci USA* 78:6789-6792 (1981).

Conservative Mutations

In addition to naturally-occurring allelic variants of EXOX sequences that may exist in the population, the skilled artisan will further appreciate that changes can be introduced by mutation into the nucleotide sequences of SEQ ID NOs: 2, 5, 8, 11, 14, 17, 20, 23, 26, 29, 32, or 34 thereby leading to changes in the amino acid sequences of the encoded EXOX proteins, without altering the functional ability of said EXOX proteins. For example, nucleotide substitutions leading to amino acid substitutions at "non-essential" amino acid residues can be made in the sequence of SEQ ID NOs: 3, 6, 9, 12, 15, 18, 21, 24, 27, 30, 33, or 35. A "non-essential" amino acid residue is a residue that can be altered from the wild-type sequences of the EXOX proteins without altering their biological activity, whereas an "essential" amino acid residue is required for such biological activity.

As used herein, the term "biological activity" or "functional activity" refers to the natural or normal function of the EXO proteins, for example the ability to degrade other proteins. Amino acid residues that are conserved among the EXOX proteins of the invention are predicted to be particularly non-amenable to alteration. Amino acids for which conservative substitutions can be made are well known within the art. One of skill in the art will recognize that each codon in a nucleic acid (except AUG, which is ordinarily the only codon for methionine) can be modified to yield a functionally identical molecule by standard techniques. Furthermore, individual substitutions, deletions or additions which alter, add or delete a single amino acid or a small percentage of amino acids (typically less than 5%, more typically less than 1%) in an encoded sequence are "conservative mutations" where the alterations result in the substitution of an amino acid with a chemically similar amino acid.

Another aspect of the invention pertains to nucleic acid molecules encoding EXOX proteins that contain changes in amino acid residues that are not essential for activity. Such EXOX proteins differ in amino acid sequence from SEQ ID NOs: 3, 6, 9, 12, 15, 18, 21, 24, 27, 30, 33, or 35 yet retain biological activity. In one embodiment, the isolated nucleic acid molecule comprises a nucleotide sequence encoding a protein, wherein the protein comprises an amino acid sequence at least about 45% homologous to the amino acid sequences of SEQ ID NOs: 3, 6, 9, 12, 15, 18, 21, 24, 27, 30, 33, or 35. Preferably, the protein encoded by the nucleic acid molecule is at least about 60% homologous to SEQ ID NOs: SEQ ID NOS: 3, 6, 9, 12, 15, 18, 21, 24, 27, 30, 33, or 35; more preferably at least about 70% homologous to SEQ ID NOs: 3, 6, 9, 12, 15, 18, 21, 24, 27, 30, 33, or 35; still more preferably at least about 80% homologous to SEQ ID NOS: SEQ ID NOs: 3, 6, 9, 12, 15, 18, 21, 24, 27, 30, 33, or 35; even more preferably at least about 90% homologous to SEQ ID NOs: 3, 6, 9, 12, 15, 18, 21, 24, 27, 30, 33, or 35; and most preferably at least about 95% homologous to SEQ ID NOs: 3, 6, 9, 12, 15, 18, 21, 24, 27, 30, 33, or 35.

An isolated nucleic acid molecule encoding an EXOX protein homologous to the protein of SEQ ID NOs: 3, 6, 9, 12, 15, 18, 21, 24, 27, 30, 33, or 35 can be created by introducing one or more nucleotide substitutions, additions or deletions into the nucleotide sequence of SEQ ID NOs: 2, 5, 8, 11, 14, 17, 20, 23, 26, 29, 32, or 34 such that one or more amino acid substitutions, additions or deletions are introduced into the encoded protein.

Mutations can be introduced into SEQ ID NOs: 3, 6, 9, 12, 15, 18, 21, 24, 27, 30, 33, or 35 by standard techniques, such as site-directed mutagenesis, PCR-mediated mutagenesis and DNA shuffling. Preferably, conservative amino acid substitutions are made at one or more predicted, non-essential amino acid residues. Single base substitutions are among the most common changes to human DNA. These base changes can occur in the coding or the non-coding regions of the DNA. If they occur in the coding region, they can be conservative or non-conservative substitutions. A "conservative amino acid substitution" is a new amino acid that has similar properties and is one in which the amino acid residue is replaced with an amino acid residue having a similar side chain. Non-conservative substitutions refer to a new amino acid, which has different properties. Families of amino acid residues having similar side chains have been defined within the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, hydroxyproline, phenylalanine, methionine, tryptophan), beta-branched-side chains (e.g., threonine, valine, isoleucine) and aromatic side chains (e.g., tyrosine, phenylalanine, tryptophan, histidine). Thus, for a conservative substitution, a predicted non-essential amino acid residue in the EXOX protein is replaced with another amino acid residue from the same side chain family. Alternatively, in another embodiment, mutations can be introduced randomly along all or part of an EXOX coding sequence, such as by saturation mutagenesis, and the resultant mutants can be screened for EXOX biological activity to identify mutants that retain activity. Following mutagenesis of SEQ ID NOs: 2, 5, 8, 11, 14, 17, 20, 23, 26, 29, 32, or 34, the encoded protein can be expressed by any recombinant technology known in the art and the activity of the protein can be determined.

The relatedness of amino acid families may also be determined based on side chain interactions. Substituted amino acids may be fully conserved "strong" residues or fully conserved "weak" residues. The "strong" group of conserved amino acid residues may be any one of the following groups: STA, NEQK, NHQK, NDEQ, QHRK, MILV, MILF, HY, FYW, wherein the single letter amino acid codes are grouped by those amino acids that may be substituted for each other. Likewise, the "weak" group of conserved residues may be any one of the following: CSA, ATV, SAG, STNK, STPA, SGND, SNDEQK, NDEQHK, NEQHRK, HFY, wherein the letters within each group represent the single letter amino acid code.

In one embodiment, a mutant EXOX protein can be assayed for (i) the ability to form protein:protein interactions with other EXOX proteins, other cell-surface proteins, or biologically-active portions thereof, (ii) complex formation between a mutant EXOX protein and a EXOX ligand; or (iii) the ability of a mutant EXOX protein to bind to an intracellular target protein or biologically-active portion thereof; (e.g. avidin proteins).

In yet another embodiment, a mutant EXOX protein can be assayed for the ability to regulate a specific biological function (e.g., proteolytic activity).

EXOX Polypeptides

A polypeptide according to the invention includes a polypeptide including the amino acid sequence of EXOX polypeptides whose sequences are provided in SEQ ID NOs: 3, 6, 9, 12, 15, 18, 21, 24, 27, 30, 33, and 35. The invention also includes a mutant or variant protein any of whose residues may be changed from the corresponding residues shown in SEQ ID NOs: 3, 6, 9, 12, 15, 18, 21, 24, 27, 30, 33, or 35 while still encoding a protein that maintains its EXOX activities and physiological functions, or a functional fragment thereof.

In general, an EXOX variant that preserves EXOX-like function includes any variant in which residues at a particular position in the sequence have been substituted by other amino acids, and further include the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above.

One aspect of the invention pertains to isolated EXOX proteins, and biologically active portions thereof, or derivatives, fragments, analogs or homologs thereof. Biologically active portions refer to regions of the EXOX proteins, which are necessary for normal function, for example, aminopeptidase activity. Also provided are polypeptide fragments suitable for use as immunogens to raise anti-EXOX antibodies. In one embodiment, native EXOX proteins can be isolated from cells, tissue sources or culture supernatants by an appropriate purification scheme using appropriate protein purification techniques. In another embodiment, EXOX proteins are produced by recombinant DNA techniques. Alternative to recombinant expression, an EXOX protein or polypeptide can be synthesized chemically using standard peptide synthesis techniques.

An "isolated" or "purified" polypeptide or protein or biologically-active portion thereof is substantially free of cellular material or other contaminating proteins from the cell or tissue source from which the EXOX protein is derived, or substantially free from chemical precursors or other chemicals when chemically synthesized. The language "substantially free of cellular material" includes preparations of EXOX proteins in which the protein is separated from cellular components of the cells from which it is isolated or recombinantly-produced. In one embodiment, the language "substantially free of cellular material" includes preparations of EXOX proteins having less than about 30% (by dry weight) of non-EXOX proteins (also referred to herein as a "contaminating protein"), more preferably less than about 20% of non-EXOX proteins, still more preferably less than about 10% of non-EXOX proteins, and most preferably less than about 5% of non-EXOX proteins. When the EXOX protein or biologically-active portion thereof is recombinantly-produced, it is also preferably substantially free of any constituent of the culture medium, e.g., culture medium components may represent less than about 20%, more preferably less than about 10%, and most preferably less than about 5% of the EXOX protein preparation.

The language "substantially free of chemical precursors or other chemicals" includes preparations of EXOX proteins in which the protein is separated from chemical precursors or other chemicals that are involved in the synthesis of the protein. In one embodiment, the language "substantially free of chemical precursors or other chemicals" includes preparations of EXOX proteins having less than about 30% (by dry weight) of chemical precursors or non-EXOX chemicals, more preferably less than about 20% chemical precursors or non-EXOX chemicals, still more preferably less than about 10% chemical precursors or non-EXOX chemicals, and most preferably less than about 5% chemical precursors or non-EXOX chemicals. Furthermore, "substantially free of chemical precursors or other chemicals" would include oxidation byproducts. One of skill in the art would know how to prevent oxidation, for example, by keeping chemicals in an oxygen free environment.

Biologically-active portions of EXOX proteins include peptides comprising amino acid sequences sufficiently homologous to or derived from the amino acid sequences of the EXOX proteins (e.g., the amino acid sequence shown in SEQ ID NOs: 3, 6, 9, 12, 15, 18, 21, 24, 27, 30, 33, or 35) that include fewer amino acids than the full-length EXOX proteins, and exhibit at least one activity of an EXOX protein.

Typically, biologically active portions comprise a domain or motif with at least one activity of the EXOX protein. A biologically active portion of an EXOX protein can be a polypeptide that is, for example, 10, 25, 50, 100 or more amino acid residues in length.

Moreover, other biologically active portions, in which other regions of the protein are deleted, can be prepared by recombinant techniques and evaluated for one or more of the functional activities of a native EXOX protein.

In an embodiment, the EXOX protein has an amino acid sequence shown in SEQ ID NOs: 3, 6, 9, 12, 15, 18, 21, 24, 27, 30, 33, or 35. In other embodiments, the EXOX protein is substantially homologous to SEQ ID NOs: 3, 6, 9, 12, 15, 18, 21, 24, 27, 30, 33, or 35, and retains the functional activity of the protein of SEQ ID NOs: 3, 6, 9, 12, 15, 18, 21, 24, 27, 30, 33, or 35, yet differs in amino acid sequence due to natural allelic variation or mutagenesis, as described in detail, below. Accordingly, in another embodiment, the EXOX protein is a protein that comprises an amino acid sequence at least about 90% homologous to the amino acid sequence SEQ ID NOs: 3, 6, 9, 12, 15, 18, 21, 24, 27, 30, 33, or 35, and retains the functional activity of the EXOX proteins of SEQ ID NOs: 3, 6, 9, 12, 15, 18, 21, 24, 27, 30, 33, or 35. As used herein, the term "biological activity" or "functional activity" refers to the natural or normal function of the EXO proteins, for example the ability to degrade other proteins.

Determining Homology Between Two or More Sequences

To determine the percent of similarity or homology of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are homologous at that position (i.e., as used herein amino acid or nucleic acid "homology" is equivalent to amino acid or nucleic acid "identity").

The nucleic acid sequence homology may be determined as the degree of identity between two sequences. The homology may be determined using computer programs known in the art, such as GAP. software provided in the GCG program package. See Needleman & Wunsch, *J. Mol. Biol.* 48:443-453 1970. Using GCG GAP software with the following settings for nucleic acid sequence comparison: GAP creation penalty of 5.0 and GAP extension penalty of 0.3, the coding region of the analogous nucleic acid sequences referred to above exhibits a degree of identity preferably of at least 70%, 75%, 80%, 85%, 90%, 95%, 98%, or 99%, with the CDS (encoding) part of the DNA sequence shown in SEQ ID NOs: 2, 5, 8, 11, 14, 17, 20, 23, 26, 29, 32, and 34.

The term "sequence identity" refers to the degree to which two polynucleotide or polypeptide sequences are identical on a residue-by-residue basis over a particular region of comparison. The term "percentage of sequence identity" is calculated by comparing two optimally aligned sequences over that region of comparison, determining the number of positions at which the identical nucleic acid base (e.g., A, T, C, G, U, or I, in the case of nucleic acids) occurs in both sequences to yield the number of matched positions, dividing the number of matched positions by the total number of positions in the region of comparison (e.g., the window size), and multiplying the result by 100 to yield the percentage of sequence identity. The term "substantial identity" as used herein denotes a characteristic of a polynucleotide sequence, wherein the polynucleotide comprises a sequence that has at least 80 percent sequence identity, preferably at least 85 percent identity and often 90 to 95 percent sequence identity, more usually at least 99 percent sequence identity as compared to a reference sequence over a comparison region.

Chimeric and Fusion Proteins

The invention also provides EXOX chimeric or fusion proteins. As used herein, a EXOX "chimeric protein" or "fusion protein" comprises a EXOX polypeptide operatively-linked to a non-EXOX polypeptide. An "EXOX polypeptide" refers to a polypeptide having an amino acid sequence corresponding to an EXOX protein (SEQ ID NOs: 3, 6, 9, 12, 15, 18, 21, 24, 27, 30, 33, or 35), whereas a "non-EXOX polypeptide" refers to a polypeptide having an amino acid sequence corresponding to a protein that is not substantially homologous to the EXOX protein, e.g., a protein that is different from the EXOX protein and that is derived from the same or a different organism. Within an EXOX fusion protein the EXOX polypeptide can correspond to all or a portion of an EXOX protein. In one embodiment, a EXOX fusion protein comprises at least one biologically active portion of a EXOX protein. In another embodiment, an EXOX fusion protein comprises at least two biologically active portions of an EXOX protein. In yet another embodiment, an EXOX fusion protein comprises at least three biologically active portions of an EXOX protein. Within the fusion protein, the term "operatively-linked" is intended to indicate that the EXOX polypeptide and the non-EXOX polypeptide are fused in-frame with one another. The non-EXOX polypeptide can be fused to the N-terminus and/or C-terminus of the EXOX polypeptide.

In one embodiment, the fusion protein is a GST-EXOX fusion protein in which the EXOX sequences are fused to the C-terminus of the GST (glutathione S-transferase) sequences. Such fusion proteins can facilitate the purification of recombinant EXOX polypeptides.

In another embodiment, the fusion protein is an EXOX protein containing a heterologous signal sequence at its N-terminus. In certain host cells (e.g., mammalian host cells), expression and/or secretion of EXOX can be increased through use of a heterologous signal sequence.

In yet another embodiment, the fusion protein is an EXOX-immunoglobulin fusion protein in which the EXOX sequences are fused to sequences derived from a member of the immunoglobulin protein family. The EXOX-immunoglobulin fusion proteins of the invention can be incorporated into pharmaceutical compositions and administered to a subject to inhibit an interaction between a EXOX ligand and a EXOX protein on the surface of a cell, to thereby suppress EXOX-mediated signal transduction in vivo. The EXOX-immunoglobulin fusion proteins can be used to affect the bioavailability of an EXOX cognate ligand. Inhibition of the EXOX ligand/EXOX interaction may be useful therapeutically for both the treatment of proliferative and differentiative disorders, as well as modulating (e.g. promoting or inhibiting) cell survival. Moreover, the EXOX-immunoglobulin fusion proteins of the invention can be used as immunogens to produce anti-EXOX antibodies in a subject, to purify EXOX ligands, and in screening assays to identify molecules that inhibit the interaction of EXOX with an EXOX ligand.

A EXOX chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended temmini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (See, e.g., Ausubel et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). A EXOX-encoding nucleic acid can be cloned into such an expression vector such that the fusion moiety is linked in-frame to the EXOX protein.

EXOX Agonists and Antagonists

The invention also pertains to variants of the EXOX proteins that function as either EXOX agonists (e.g., mimetics) or as EXOX antagonists. Variants of the EXOX protein can be generated by mutagenesis (e.g., discrete point mutation or truncation of the EXOX protein). An agonist of the EXOX protein can retain substantially the same, or a subset of, the biological activities of the naturally occurring form of the EXOX protein. An antagonist of the EXOX protein can inhibit one or more of the activities of the naturally occurring form of the EXOX protein by, for example, competitively binding to a downstream or upstream member of a cellular signaling cascade, which includes the EXOX protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the EXOX proteins.

Variants of the EXOX proteins that function as either EXOX agonists (e.g., mimetics) or as EXOX antagonists can be identified by screening combinatorial libraries of mutants (e.g., truncation mutants) of the EXOX proteins for EXOX protein agonist or antagonist activity. In one embodiment, a variegated library of EXOX variants is generated by combinatorial mutagenesis at the nucleic acid level and is encoded by a variegated gene library. A variegated library of EXOX variants can be produced by, for example, enzymatically ligating a mixture of synthetic oligonucleotides into gene sequences such that a degenerate set of potential EXOX sequences is expressible as individual polypeptides, or alternatively, as a set of larger fusion proteins (e.g., for phage display) containing the set of EXOX sequences therein. There are a variety of methods, which can be used to produce libraries of potential EXOX variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential EXOX sequences. Methods for synthesizing degenerate oligonucleotides are well-known within the art. See, e.g., Narang, Tetrahedron 39:3 (1983); Itakura et al., Annu. Rev. Biochem. 53:323 (1984); Itakura et al., Science 198:1056 (1984); Ike et al., Nucl. Acids Res. 11:477 (1983).

Polypeptide Libraries

In addition, libraries of fragments of the EXOX protein coding sequences can be used to generate a variegated population of EXOX fragments for screening and subsequent selection of variants of an EXOX protein. In one embodiment, a library of coding sequence fragments can be generated by treating a double stranded PCR fragment of an EXOX coding sequence with a nuclease under conditions wherein nicking occurs only about once per molecule, denaturing the double stranded DNA, renaturing the DNA to form double-stranded DNA that can include sense/antisense pairs from different nicked products, removing single stranded portions from reformed duplexes by treatment with $S_1$ nuclease, and ligating the resulting fragment library into an expression vector. By this method, expression libraries can be derived which encode N-terminal and internal fragments of various sizes of the EXOX proteins.

Various techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of EXOX proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique that enhances the frequency of functional mutants in the libraries, can be used in combination with the screening assays to identify EXOX variants. See, e.g., Arkin & Yourvan, *Proc. Natl. Acad. Sci. USA* 89:7811-7815 (1992); Delgrave et al., *Protein Engineering* 6:327-331 (1993).

Libraries can also be generated by DNA shuffling. DNA shuffling uses related genes from different species or genes that are related in their function, fragments them and reassembles them through recombination. It can then be determined if the recombined genes comprise usable or potentially interesting products. Any recombined gene found to be useful are again fragmented and reassembled to form new recombinant genes. As the various fragments of different species and genes are annealed and extended, diversity is created in the library. The process can be performed until a protein of interest is found. The important factors in creating recombined genes with DNA shuffling include the temperature at which annealing occurs, the similarity of the genes and the size of the DNA fragments.

Stemmer et al., Nature 370:389-391 (1994); Stemmer, Proc. Natl. Acad. USA 91:10747-10751 (1994); U.S. Pat. No. 5,603,793; U.S. Pat. No. 5,830,721; and U.S. Pat. No. 5,811,238, which are incorporated herein by reference, describe e.g., in vitro protein shuffling methods, e.g., by repeated cycles of mutagenesis, shuffling and selection as well as a variety of methods of generating libraries of displayed peptides and antibodies as well as a variety of DNA reassembly techniques following DNA fragmentation, and their application to mutagenesis in vitro and in vivo. Moreover, various applications of DNA shuffling technology are also known in the art. In addition to the publications noted above, see U.S. Pat. No. 5,837,458, which provides for the evolution of new metabolic pathways and the enhancement of bio-processing through recursive shuffling techniques, and Crameri et al., Nature Medicine 2(1):100-103 (1996), which describes antibody shuffling for antibody phage libraries. See also, WO95/22625, WO97/20078, WO96/33207, WO97/33957, WO98/27230, WO97/35966, WO98/31837, WO98/13487, WO98/13485 and WO989/42832.

Expression Vectors

Another aspect of the invention pertains to vectors, preferably expression vectors, containing a nucleic acid encoding an EXOX protein, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of used in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The production of a functional protein is intimately related to the cellular machinery of the organism producing the protein. E. Coli has typically been the "factory" of choice for the expression of many proteins because its genome has been fully mapped and the organism is easy to handle; grows rapidly; requires an inexpensive, easy-to-prepare medium for growth; and secretes protein into the medium which facilitates recovery of the protein. However, E. coli is a prokaryote and lacks intracellular organelles, such as the endoplasmic reticulum and the golgi apparatus that are present in eukaryotes, which contain enzymes which modify the proteins being produced. Many eukaryotic proteins can be produced in E. coli but these may be produced in a nonfunctional, unfinished form, since glycosylation or post-translational modifications do not occur.

Therefore, researchers have recently turned to eukaryotic yeast, mammalian and plant expression systems for protein production. For example, the methanoltrophic yeast P. pastoris has become a powerful host for the heterologous expression of proteins during the last few years and has been established as an alternative eukaryotic host for the expression of human proteins with high-throughput technologies.

As another example, plants are being utilized as expression hosts for large-scale heterologous expression of proteins and offer potential advantages of cost-effectiveness, scalability and safety over traditional expression systems. There are currently a variety of plant heterologous expression systems including transient expression, plant cell-suspension cultures, recombinant plant viruses and chloroplast transgenic systems. While proteins expressed in plants have some variations from mammalian proteins (e.g., glycosylation), there is currently no evidence that these differences result in adverse reactions in human patients. See, e.g., Julian et al., Nat. Rev. Gen. 4:794-805 (2003).

Another suitable heterologous expression system uses insect cells, often in combination with baculovirus expression vectors. Baculovirus vectors available for expressing proteins in cultured insect cells, e.g., SF9 cells include the pAc series (Smith et al., Mol. Cell. Biol. 3: 2156-2165 (1983)) and the pVL series (Lucklow & Summers, *Virology* 170: 31-39 (1989)).

Host cells of the invention can also be used to produce non-human transgenic animals in which exogenous sequences have been introduced into their genome. The transgenic animal is a non-human animal, preferably a mammal, more preferably a rodent such as a rat or mouse, in which one or more of the cells of the animal includes a transgene. Other examples of transgenic animals include, e.g., non-human primates, sheep, dogs, cows, goats, chickens, amphibians. Methods for generating transgenic animals via embryo manipulation and micro-injection, particularly animals such as mice, have become conventional in the art and are described, for example, in U.S. Pat. Nos. 4,736,866; 4,870,009; and 4,873,191; and Hogan, 1986. In: MANIPULATING THE MOUSE EMBRYO, Cold Spring Harbor Laboratory Press, Cold Spring Harbor, N.Y. Similar methods are used for production of other transgenic animals.

*Pichia pastoris* Expression System

One such eukaryotic yeast is the methanoltrophic *Pichia pastoris*. *P. pastoris* has been developed to be an outstanding host for the production of foreign proteins since its alcohol oxidase promoter was isolated and cloned: The *P. pastoris* transformation was first reported in 1985. The *P. pastoris* heterologous protein expression system was developed by Phillips Petroleum, see, e.g., U.S. Pat. Nos. 4,855,231, 4,857, 467, 4,879,231 and 4,929,555, each of which is incorporated herein by reference. This system is currently marketed by Invitrogen. Compared to other eukaryotic expression systems, *Pichia* offers many advantages, because it does not have the endotoxin problem associated with bacteria nor the viral contamination problem of proteins produced in animal cell cultures. Furthermore, *P. pastoris* can utilize methanol as a carbon source in the absence of glucose. The *P. pastoris* expression system uses the methanol-induced alcohol oxidase (AOX1) promoter, which controls the gene that codes for the expression of alcohol oxidase, the enzyme that catalyzes the first step in the metabolism of methanol. This promoter has been characterized and incorporated into a series of *P. pastoris* expression vectors. Since the proteins produced in *P. pastoris* are typically folded correctly and secreted into the medium, the fermentation of genetically engineered *P. pastoris* provides an excellent alternative to *E. coli* expression systems. Furthermore, *P. pastoris* has the ability to spontaneously glycosylate expressed proteins, which also is an advantage over *E. coli*. A number of proteins have been produced using this system, including tetanus toxin fragment, Bordatella pertussis pertactin, human serum albumin and lysozyme.

Tag Removal with EXOX Proteins

Several systems have been developed to allow for rapid and efficient purification of recombinant proteins expressed in bacteria. Most of these rely on the expression of the protein as a fusion protein with a glutathione-S-transferase (GST) domain, a calmodulin binding peptide (CBP) or a His-tag. For example, the expression of polypeptides in frame with glutathione S-transferase (GST) allows for purification of the fusion proteins from crude bacterial extracts under nondenaturing conditions by affinity chromatography on glutathione agarose.

Furthermore, this vector expression system generally incorporates a specific protease cleavage site to facilitate proteolysis of the bacterial fusion proteins, which is, depending on the vector used, a thrombin, enterokinase or Factor Xa protease cleavage site. Thrombin specifically cleaves target proteins containing the recognition sequence Leu-Val-Pro-Arg↓Gly-Ser (SEQ ID NO: 44). The enterokinase cleavage site is Asp-Asp-Asp-Asp-Lys↓(SEQ ID NO: 45). Like enterokinase, Factor Xa cleaves at the C-terminal side of its recognition sequence Ile-Glu-Gly-Arg↓ (SEQ ID NO: 46), and can therefore be used for removing all vector-encoded sequences from appropriately designed constructs. All of these enzymes are now commercially available in a high purity to avoid secondary cleavage arising from contaminating proteases. These enzymes are provided either in a kit often including all the tools for the enzyme capture, or biotinylated to facilitate removal of the enzyme from cleavage reaction medium. More recently Qiagen also developed the TAGZyme system for an efficient removal of N-terminal His tags from proteins which involves exopeptidases that cleave dipeptides sequentially from the N-terminus up to a "stop point" amino acid motif, which is either ↓Lys-Xaa-, ↓Arg-Xaa-, ↓Xaa-Xaa-Pro-Xaa-, ↓Xaa-Pro-Xaa-Xaa- or ↓Gln-Xaa-.

Although it is not always necessary to remove the short His affinity tag (whatever the number of His residues) from a recombinant protein after purification, there are some applications, such as structural analysis by X-ray crystallography or NMR, where removal of the tag is desirable. The same thing is also true for the residual residues Gly-Ser of the thrombin cleavage site or any supplementary residual N-terminal amino acid that could be still present and which could be related to the expression system used.

A more recent approach to affinity purification involves utilizing a condensation reaction between a carbonyl group and a molecule with two vicinal nucleophilic groups. Examples of amino acids with two vicinal nucleophilic groups includes, e.g., serine, threonine and cysteine. Purifying a protein or peptide involves forming a reversible covalent bond formed by between, e.g., an N-terminal cysteine, threonine or serine residue, and an appropriate resin. See Villain et al., Chem. & Biol. 8:673-679 (2001). Addition of a pair of residues, e.g., Thr-Pro, Cys-Pro or Ser-Pro, to the N-terminus of a recombinant protein, or of a protein (peptide) obtained by chemical synthesis, permits two-step purification: (1) purification by covalent capture; and (2) removal of the di-peptide tag. This method permits efficient recovery of recombinant protein in its mature form, without the di-peptide flag sequence.

Reverse Proteolytic Activity of EXOX Proteins

Another aspect of the invention pertains to methods of adding one or more amino acids to amino acids, peptides, oligopeptides, polypeptides or any composition with an accessible secondary amine, by using the reverse proteolytic activity of one or more EXOX proteins. As used herein, the term "reverse proteolytic activity" refers to enzymatic activity that catalyzes the addition of one or more amino acids to an amino acid, a peptide, an oligopeptide, a polypeptide or any composition with an accessible secondary amine. One of ordinary skill in the art will recognize that, under suitable thermodynamic conditions, proteolytic enzymes can have reverse proteolytic activity.

An example of a proteolytic enzyme with reverse proteolytic activity is trypsin, which is a pancreatic serine protease with substrate specificity based upon positively charged lysine and arginine side chains. Trypsin is widely used in the manufacture of human insulin from porcine insulin, which is similar to the human form except the last amino acid residue in the B-chain is alanine rather than threonine. Reacting porcine insulin with a threonine ester in the presence of trypsin yields a human insulin threonine ester by removing the terminal alanine and adding the threonine ester. Subsequent treatment of the human insulin threonine ester with trifluoroacetic acid hydrolyzes the ester to yield human insulin.

In some embodiments, the EXOX proteins are used to catalyze reverse proteolytic reactions. In some instances, the EXOX proteins are incubated with a polypeptide and one or more amino acids under conditions permitting the addition of the one or more amino acids to the polypeptide.

There are multiple utilities for using the EXOX proteins of the present invention as reverse proteolytic enzymes. For example, the reverse proteolytic activity of the EXOX proteins can be used in the synthesis of a polypeptide chain. The EXOX proteins can also be used as a coupling agent to add one or more amino acids to another amino acid, a polypeptide, or any composition with an accessible secondary amine.

Pharmaceutical Compositions

The EXOX nucleic acid molecules, EXOX proteins, and anti-EXOX antibodies (also referred to herein as "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

Encapsulation technologies are also widely applied in many industries. Examples include pharmaceuticals for controlled release of drugs; pigments in foods and beverages; antioxidants in foods; and controlled release of insect pheromones in agriculture. Capsules, microcapsules and microspheres are small spherical particles, which contain an active ingredient within the particle matrix or attached to the particle surface. For example, encapsulation in biodegradable alginate microparticles has been shown. Bioencapsulation technologies are intended to encapsulate cells, enzymes, and biologically active materials.

A pharmaceutical composition of the invention is formulated to be compatible with its intended route of administration. Examples of routes of administration include parenteral, e.g., intravenous, intradermal, subcutaneous, oral (e.g., inhalation), transdermal (e.g., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against contamination by microorganisms, such as bacteria, fungi or viruses. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, or sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound (e.g., an EXOX protein or anti-EXOX antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

A crude preparation of cell culture medium from *T. rubrum* or transgenic fungi producing EXOX, or EXOX purified from *T. rubrum* or transgenic fungi producing EXOX can be administered orally since the proteases are secreted. Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from, for example, Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit contains a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection. See, e.g., Chen, et al., *Proc. Natl. Acad. Sci. USA* 91:3054-3057 (1994). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

EXAMPLES

Example 1

Methods and Materials

Strains and Plasmids

A clinical isolate, *T. rubrum* CHUV 862-00, was used in this study. *E. coli* LE392 was used for the propagation of the bacteriophage λEMBL3 (Promega, Wallisellen, Switzerland). All plasmid-subcloning experiments were performed in *E. coli* DH5α using plasmid pMTL2I. Chambers et al., Gene 68:139-149 (1988). *P. pastoris* GSI 15 and the expression vector pKJ113 (Borg-von Zepelin et al., Mol. Microbiol. 28:543-554 (1998)) were used to express recombinant peptidases. It is known in the art that *P. pastoris* can be utilized to express a multitude of recombinant proteins.

*T. rubrum* Growth Media

*T. rubrum* was grown on Sabouraud agar and liquid medium (Bio-Rad, Munchen, Germany) or, to promote production of proteolytic activity, in liquid medium containing 0.2% soy protein (Supro 1711, Protein Technologies International, St. Louis, Mo.) as a sole nitrogen and carbon source. No salt was added in this medium. Those skilled in the art will recognize it is also possible to utilize growth media in which salt is added to the medium. A volume of 100 ml of liquid medium was inoculated with a plug of freshly growing mycelium in 800 ml.-tissue culture flasks. The cultures were incubated 10 days at 30° C. without shaking.

Genomic and cDNA Libraries

A *T. rubrum* genomic DNA library was prepared using DNA isolated from freshly growing mycelium. (Yelton et al., Proc. Natl. Acad. Sci. USA. 81:1470-1474 (1984). The DNA was partially digested with Sau3A and DNA fragments ranging from 12 to 20 kb were isolated from low-melting-point agarose (Roche Diagnostics, Rotkreuz, Switzerland) with agarase (Roche Diagnostics). These DNA fragments were inserted into bacteriophage XEMBL3 using an appropriate cloning system (Promega).

A *T. rubrum* cDNA library was prepared in a pSPORT6 plasmid (Invitrogen Life Technologies; Rockville, Md., USA) using the microquantity mRNA system and 500 µg of total RNA. The RNA was prepared from 10-day-old cultures in soy protein liquid medium (10×100 ml). The mycelium was ground under liquid nitrogen to a fine powder using a mortar and pestle, and the total RNA was isolated using an RNeasy total RNA purification kit for plant and fungi (Qiagen, Basel, Switzerland).

An *A. fumigatus* cDNA library was previously constructed with the CHUVI 92-88 strain grown 40 h at 30° C. in liquid medium containing 0.2% collagen as a sole nitrogen and carbon source (Monod et al., 1991). Total RNA was extracted as described (Applegate and Monod) and the mRNA was purified using oligo(dT) cellulose (Sigma, Buchs, Switzerland) according to standard protocols (Sambrook et al., 1989). A library was prepared with this mRNA using lambda phage gt11 (Promega) and the protocols of the manufacturer.

TABLE 13 shows *T. rubrum* and *A. fumigatus* genes encoding aminopeptidases.

| Gene | Genomic DNA (bp. from the ATG to the STOP codon) | cDNA:ORF length (bp.) from the ATG codon | aa number encoded from the ATG codon | Introns (bp of the genomic DNA from the ATG codon) |
|---|---|---|---|---|
| ruLAP2 | 1757 | 1488 | 495 | 3 introns (bp 106-231; 556-632; 917-982) 4 exons coding for 35, 108, 95, 257 aa |
| fuLAP2 | 1557 | 1497 | 498 | 1 introns (bp 85-144) 2 exons coding for 28, 470 aa |
| ruLAP1 | 1256 | 1122 | 373 | 2 introns (bp 157-226; 968-1031) 3 exons coding for 52, 247, 74 aa |
| fuLAP1 | 1298 | 1167 | 388 | 2 introns (bp 187-252; 1000-1064) 3 exons coding for 62, 249, 77 aa |

Lap Gene Cloning

Recombinant plaques ($10^4$) of the genomic library were immobilized on GeneScreen nylon membranes (NEN Life science products, Boston, Mass.). The filters were hybridized with $^{32}$P-labelled probe using low-stringency conditions. Monod et al., Mol. Microbiol. 13:357-368 (1994). All positive plaques were purified and the associated bacteriophage DNAs were isolated as described by Grossberger. Grossberger, Nucleic Acid Res. 15:6737 (1987). Hybridizing fragments from EMBL3 bacteriophages were subcloned into pMTL2I following standard procedures. Nucleotide sequencing was performed by Microsynth (Balgach, Switzerland).

Isolation of cDNA by Standard PCR

*T. rubrum* and *A. fumigatus* cDNAs were obtained by PCR using DNA prepared from 106 clones of the cDNA libraries. PCR was performed according to standard conditions using homologous primers derived from DNA sequences of the different peptidase genes (Table 13). Two hundred ng of DNA, 10 µl of each sense and antisense oligonucleotides at a concentration of 42 mM and 8 µl of deoxynucleotide mix (containing 10 mM of each dNTP) were dissolved in 100 µl PCR buffer (10 mM Tris-HCl pH 8.3, 50 mM KCl and 1.5 mM $MgCl_2$). To each reaction 2.5 units of AmpliTAQ DNA polymerase (Perkin Elmer, Zurich, Switzerland) were added. The reaction mixtures was incubated 5 mm at 94° C., subjected to 25 cycles of 0.5 mm at 94° C., 0.5 mm at 55° C. and 0.5 mm at 72° C. and finally incubated 10 mm at 72° C.

Production of Recombinant LAPs

Expression plasmids were constructed by cloning cDNA PCR products in the multiple cloning site of the *E. coli-P. pastoris* shuttle vector pKJ 113. The PCR products were purified using a PCR purification kit (Roche Diagnostics) and digested by restriction enzymes for which a site was previously designed at the 5' extremity of the primers (Table 14). *P. pastoris* GSI 15 (Invitrogen) was transformed by electroporation with 10 pg of plasmid DNA linearized by EcoRI or SmaI. Transformants selected on histidine-deficient medium (1 M sorbitol, 1% (w/v) dextrose, 1.34% (w/v) yeast nitrogen base (YNB) without amino acids, $4 \times 10^{-5}$% (w/v) biotin, $5 \times 10^{-3}$% amino acids (e.g. $5 \times 10^{-3}$% (w/v) of each L glutamic acid, L-methionine, L-lysine, L-leucine, L-isoleucine), 2% (w/v) agarose) were screened for insertion of the construct at the AOX1 site on minimal methanol plates (1.34% (w/v) YNB without amino acids, 4×10$^{-5}$% (w/v) biotin, 0.5% (v/v) methanol, 2% (w/v) agarose). The transformants unable to grow on media containing only methanol as a carbon source were assumed to contain the construct at the correct yeast genomic location by integration events in the AOX1 locus displacing the AOX1 coding region. These transformants were grown to near saturation (OD 20 at 600 nm) at 30° C. in 10 ml of glycerol-based yeast media (0.1 M potassium phosphate buffer at pH 6.0, containing 1% (w/v) yeast extract, 2% (w/v) peptone, 1.34% (w/v) YNB without amino acids, 1% (v/v) glycerol and 4×1% (w/v) biotin). Cells were harvested and resuspended in 2 ml of the same medium with 0.5% (v/v) methanol instead of glycerol and incubated for 2 days. After 2 days of incubation, the supernatant was harvested and tested for protein production on SDS-PAGE gels. Recombinant peptidase enzymes were produced in large quantities from 400 ml cell culture supernatant.

Table 14 describes materials used for the expression of the different LAPs in *P. pastoris*.

TABLE 14

| Gene | Oligonucleotide primers | Orientation | Encoded amino acid sequence |
|---|---|---|---|
| ruLAP2 | GT TG/T CGA CTT GTT GGT CAA GAG CCC TTC GGA TGG (SEQ ID NO: 47) | sense | (R)(L)VGQEPFGW (SEQ ID NO: 63) |
| | GT TGC/ GGC CGC TTA CAT GAA GAC AGT TGG GTG TCC (SEQ ID NO: 48) | antisense | GHHTVFM$_{STOP}$ (SEQ ID NO: 64) |
| fuLAP2§ | GT TC/T CGA GGC CCA GGA TGG GAC TGG AAG (SEQ ID NO: 49) | sense | (R)GPGWDWK (SEQ ID NO: 65) |
| | CGC AAA GG/T GCA CTC GCC CCG CGA (SEQ ID NO: 50) | antisense | SRGECTFA (SEQ ID NO: 66) |
| | TCG CGG GGC GAG/ TGC ACC TTT GCG (SEQ ID NO: 51) | sense | SRGECTFA (SEQ ID NO: 67) |
| | CTT A/GA TCT CTA CTG CTC AAC CCG GTC CTT (SEQ ID NO: 52) | antisense | KDRVEQ$_{STOP}$ (SEQ ID NO: 68) |
| ruLAP1 | GT TC/T CGA GGC ATT CCT GTT GAT GCC CGG GCC G (SEQ ID NO: 53) | sense | (R)(G)IPVDARA (SEQ ID NO: 69) |
| | CTT A/GA TCT TTA CTT AGC AAG CTC AGT GAC GAA GCC GAC (SEQ ID NO: 54) | antisense | VGFVTELAK$_{STOP}$ (SEQ ID NO: 70) |
| fuLAPI | GT TC/T CGA GGG GCT GTA GCT GCA GTG ATT (SEQ ID NO: 55) | sense | (R)GAVAAVI (SEQ IDNO: 71) |
| | CTT A/GA TCT TTA AAA CGG CGC AAA TGC CAA (SEQ ID NO: 56) | antisense | LAFAPF$_{STOP}$ (SEQ ID NO: 72) |
| ruDPPIV§ | CT TC/T CGA GTC GTT CCT CCT CGT GAG CCC CG (SEQ ID NO: 57) | sense | (R)(V)VPPREPR (SEQ ID NO: 73) |
| | G TTC CAT GGT/CAT GAC CTT TGT GTC ATA CGA GAC AG (SEQ ID NO: 58) | antisense | VSYDTKVM (SEQ ID NO: 74) |
| | GT TCC ATG GT/C ATG ACC CCT CTC GTC AAC GAT AAG G (SEQ ID NO: 59) | sense | VMTPLVNDK (SEQ ID NO: 75) |
| | CTT G/GA TCC TCA TTC CTC TGC CCT CTC ACC (SEQ ID NO: 60) | antisense | GERAEE$_{STOP}$ (SEQ ID NO: 76) |
| ruDPPV | CCO G/AA TTC TTT ACC CCA GAG GAC TTC (SEQ ID NO: 61) | sense | (E)(F)FTPEDF (SEQ ID NO: 77) |
| | GAG T/CT AGA CTA GTA GTC GAA GTA AGA GTG (SEQ ID NO:62) | antisense | HSYFDY$_{STOP}$ (SEQ ID NO: 78) |

| Gene | PCR product (with cloning sites)¶ | Vector |
|---|---|---|
| ruLAP2 | ruLAP2 (58-1485) SaII-NotI | pKJ113 XhoI-NotI |
| fuLAP2§ | fuLAP2a (49-460) XhoI-ApaLI fuLAP2b (461-1494) ApaL1-BglII | pKJ113 XhoI-BamHI |
| ruLAP1 | ruLAP1 (61-1119) XhoI-BglII | pKJ113 XhoI-BamHI |
| fuLAPI | fuLAP1 (46-1164) XhoI-BglII | pKJII3 XhoI-BamHI |

TABLE 14-continued

| | | |
|---|---|---|
| ruDPPIV[§] | ruDPPIVa (49-1266) | |
| | XhoI-RcaI | XhoI-BamHI |
| | ruDPPIVb (1267-2325) | |
| | RcaI-BamHI | |
| ruDPPV | ruDPPV (58-2178) | pPICZOA |
| | EcoRI-XbaI | EcoRI-XbaI |

*In parentheses are shown amino acids encoded by the restriction site sequences and added to the N-terminal extremity of recombinant enzymes.
¶The numbers in parentheses represent nucleoside posisions on LAP aad DPP cDNAs.
§FuLAP2 and ruDPPIV PCR fragments inserted end to end into E. coli-P. passoris shuttle vectors.

Purification of Recombinant LAPs

The secreted proteins from 400 ml of *P. pastoris* culture supernatant were concentrated by ultrafiltration using an Amicon cell and an Ultracel Amicon YM30 membrane (30 kDa cut-off) (Millipore, Volketswil, Switzerland). The concentrate was washed with 50 mM Tris-HCl, pH 7.5 and applied to a Mono Q-Sepharose (Amersharn Pharmacia, Dübendorf, Switzerland) column equilibrated with the same buffer. After washing the column with 50 mM Tris-HCl, pH 7.5, elution was performed with a linear gradient of 0-0.5 M NaCl at a flow-rate of 1 ml/min. The different fractions eluted from the Mono Q-Sepharose column were screened for enzymatic activity using Leucine-7-amino-4-methylcoumarin (Leu-AMC) as a substrate and LAP-containing fractions were pooled. After concentration in an Amicon ultrafiltration cell with an Ultracel Amicon YM30 membrane and washing with 20 mM Tris-HCl, pH 6.0, the LAP extract was loaded on a size exclusion Superose 6 FPLC column (Amersham Pharmacia) and elution was performed at a flow-rate of 0.2 ml/min using 20 mM Tris-HCl, pH 6.0 as eluant. The eluted active fractions were pooled The LAP enzyme was concentrated to a final volume of 0.4-1.0 ml in a Centricon concentrator with a 30 kDa cut-off (Millipore) at 4° C. prior to further functional characterization.

In an alternative purification scheme, each step of purification was performed at 4° C. The secreted proteins from 400 ml of *P. pastoris* culture supernatant were concentrated by ultrafiltration using an Amicon cell and an Ultracel Amicon YM30 membrane (30 kDa cut-off) (Millipore, Volketswil, Switzerland). The concentrate was washed with 100 ml of 20 mM sodium acetate, pH 6.0 and applied to a Mono Q-Sepharose (Amersham Pharmacia, Dübendorf, Switzerland) column equilibrated with the same buffer. After washing the column with 20 mM Tris-HCl pH 6.0 buffer, the enzyme was eluted with a linear gradient of 0-0.2 M NaCl at a flow-rate of 1 ml/min over 142 min. The different fractions eluted from the Mono Q-Sepharose column were screened for enzymatic activity using Leucine-7-amino-4-methylcoumarin (Leu-AMC) as a substrate (see below) and LAP-containing fractions were pooled. After concentration in an Amicon ultrafiltration cell with an Ultracel Amicon YM30 membrane and washing with PBS, the LAP extract was loaded on a size exclusion Superdex 200 FPLC column (Amersham Pharmacia) using 20 mM sodium acetate pH 6.0 buffer and elution was performed at a flow-rate of 0.2 ml/min. The eluted active fractions were pooled. The LAP enzyme was subjected to further characterization after concentration to a final volume of 0.4-1.0 ml in a Centricon concentrator with a 30 kDa cut-off (Millipore) at 4° C.

A fraction containing ruLAP2 activity elutes from MonoQ at 30-40 min (approx. 50 mM NaCl) and at 65-70 min with superdex 200=Peak 3. However, a large amount of LAP2 activity was not retained and eluted in the flow-through at 1 M NaCl. Therefore, after desalting this fraction with 20 mM sodium acetate, the sample was applied on the same MonoQ column with a wider gradient between 0 and 1 M NaCl over 142 min at 0.5 ml/min. A first peak of activity eluates at 7-15 min corresponding to 70-140 mM NaCl and a second peak elutes at 150-250 mM NaCl (with more activity content). The fraction at 70-140 mM NaCl elutes at 78-80 min on Superdex and was therefore pooled with peak 3 obtained above. The fraction at 150-250 mM NaCl gives two active fractions eluting respectively at 44-49 min (Peak 1) and 50-63 min (Peak 2) on Superdex.

Protein Extract Analysis

Protein extracts were analyzed by SDS-PAGE with a separation gel of 12% polyacrylamide Gels were stained with Coomassie brilliant blue R-250 (Bio-Rad). N-glycosidase F digestion was performed as previously described. Doumas et al., Appl. Environ. Microbiol. 64:4809-4815 (1998)

Western Blots

The membranes were first stained with Red-Ponceau and the major protein bands were marked with a needle. Immunoblots were performed using rabbit antisera and alkaline phosphatase conjugated goat anti-rabbit IgG (Bio-Rad) or peroxidase-conjugated goat anti-rabbit IgG (Amersham Pharmacia) as secondary labeled antibodies. Rabbit antisera to ruLAP1, ruLAP2, *A. oryzae* secreted alkaline protease (ALP) and *A. oryzae* secreted neutral protease (NPI) of the fungalysin family (Doumas et al., J. Food Mycol. 2:271-279 (1999)) were made by Eurogentec (Liege, Belgium) using purified recombinant enzyme.

Aminopeptidase Activity Assay

Aminopeptidase activity was determined using different fluorogenic aminoacyl-4-methylcoumaryl-7-amide derivatives of peptides and the internally quenched fluorogenic substrate Lys(Abz)-Pro-Pro-pNA for specific determination of aminopeptidase P activity. Stockel et al, Adv Exp. Med. Biol. 421:31-35 (1997). All substrates were from Bachem (Bubendorf, Switzerland). Substrate stock solutions were prepared at 0.1 M according to the recommendations of the manufacturer and stored at −20° C. The reaction mixture contained a concentration of 5 mM substrate and enzyme preparation (between 56 and 2,662 ng per assay depending on the cleavage activity of each enzyme for the substrates) in 25 µl of 50 mM Tris-HCl buffer adjusted at the optimal pH for each LAP (between 7 and 8). After incubation at 37° C. for 60 min, the reaction was terminated by adding 5 µl of glacial acetic acid and the reaction mixture was diluted with 3.5 ml of water. The released 7-amino-4-methylcoumarin (AMC) was measured using a spectrofluorophotometer (Perkin Elmer LS-5 fluorometer, Zurich, Switzerland) at an excitation wavelength of 370 nm and an emission wavelength of 460 nm. A standard curve made with synthetic AMC was used to assess the released AMC. The released diprolyl-p-nitroanilide was measured at an excitation wavelength of 310 nm and an emission wavelength of 410 nm. The LA activities were expressed in mnoles of released AMC or pNA/min/µg protein.

Table 15 details the hydrolytic activity of different LAPs toward various aminoacyl-MCA comparison (%) to Leu-MCA used as a standard.

TABLE 15

| Substrate | ruLAP2 | fuLAP2 | ruLAP1 | fuLAP1 | pkLAP |
|---|---|---|---|---|---|
| Leu-AMC | 100.0 | 100.0 | 100.0 | 100.0 | 100.0 |
| Ile-AMC | 6.4 | 1.8 | 7.4 | 13.2 | 6.3 |
| Val-AMC | 4.8 | 0.8 | 4.9 | 27.6 | 4.0 |
| Ala-AMC | 33.3 | 11.7 | 5.2 | 4.7 | 584.7 |
| Gly-AMC | 3.3 | 2.2 | 5.1 | 0.8 | 74.8 |
| Ser-AMC | 26.1 | 10.3 | 5.9 | 10.3 | 24.6 |
| Thr-AMC | 0.9 | 0.1 | 1.7 | 5.1 | 4.4 |
| Cys-AMC | 14.9 | 2.1 | 18.5 | 5.0 | 35.5 |
| Met-AMC | 119.7 | 89.5 | 41.3 | 116.9 | 46.1 |
| Asn-AMC | 114.6 | 73.5 | 6.8 | 29.4 | 33.9 |
| Gln-AMC | 49.9 | 37.0 | 2.3 | 44.9 | 50.7 |
| Asp-AMC | 3.8 | 0.3 | 0.0 | 0.8 | 0.9 |
| Glu-AMC | 3.7 | 1.1 | 0.0 | 0.0 | 4.7 |
| Lys-AMC | 4.6 | 2.3 | 9.1 | 7.7 | 70.1 |
| Arg-AMC | 1.9 | 2.3 | 12.3 | 53.9 | 174.8 |
| His-AMC | 0.6 | 1.9 | 0.1 | 0.8 | 17.6 |
| Phe-AMC | 17.1 | 8.9 | 4.6 | 163.7 | 184.4 |
| Pro-AMC | 21.4 | 7.4 | 1.4 | 12.0 | 7.9 |
| Hyp-AMC | 14.2 | 13.3 | 0.3 | 3.9 | 1.7 |
| Gly-Pro-AMC | 7.2 | 74.1 | 0.0 | 5.4 | 16.7 |
| Pyr-AMC | 0.0 | 0.0 | 0.0 | 0.0 | 0.0 |
| Lys(Abz) | 0.0 | 0.0 | 0.0 | 0.0 | 0.0 |
| Pro-PropNA | | | | | |

Effect of Various Chemical Reagents on Laps

Inhibitors and metallic cations were pre-incubated with the enzymes for 15 min at 37° C. Then, Leu-AMC at a 5 mM final concentration was added. After further incubation for 60 min, enzyme activity was measured as described above. The inhibitors and their concentrations tested purified LAPs were: 500 µM amastatin (Bachem), 40 µM benzamidine (Sigma), 500 µM bestatin (Bachem), 5 mM/1 mM EDTA (Sigma). 100 µM E-64 (L-trans-epoxysuccinyl-leu-4-guanidinobutylamide) (Bachem), 100 µM leupeptin (Sigma), 5 mM/1 mM ortho-phenanthroline (Sigma), 500 µM p-chloromercuribenzoic acid (Sigma), 100 µM pepstatin A (Sigma), 40 µM PMSF (Sigma), 20 µM TLCK (Roche Diagnostics), and 20 µM TPCK (Roche Diagnostics). CaC MgCl$_2$, MnCl$_2$, CoCl$_2$, ZnCl$_2$, NiCl$_2$, CuCl$_2$ were tested at concentrations of 0.5 mM and 1 mM.

Table 16 details the hydrolytic activity of different EXOXs in the presence of various protease inhibitors using Leu-MCA as a substrate for LAP. The activity is given as a percentage of the activity of control enzymatic reaction without inhibitor.

TABLE 16

| Inhibitor | ruLAP2 | fuLAP2 | ruLAP1 | fuLAP1 | pkLAP |
|---|---|---|---|---|---|
| EDTA 5 mM | 5 | 50 | 0 | 16 | 99 |
| EDTA 1 mM | 7 | 77 | 7 | 19 | 68 |
| orthophenanthroline 5 mM | 0 | 0 | 0 | 0 | 0 |
| orthophenanthroline 1 mM | 0 | 0 | 0 | 0 | 0 |
| Bestatin 500 µM | 55 | 88 | 0 | 11 | 24 |
| Amastatin 500 µM | 0 | 0 | 0 | 17 | 0 |
| p-chloromercuribenzoic acid 500 µM | 21 | 96 | 32 | 90 | 59 |
| E 64 100 µM | 34 | 71 | 103 | 190 | 93 |
| Leupeptin 100 µM | 113 | 61 | 233 | 149 | 86 |
| Pepstatin 100 µM | 45 | 73 | 160 | 14 | 64 |
| PMSF 40 µM | 79 | 84 | 78 | 156 | 58 |
| Benzamidine 40 µM | 89 | 91 | 85 | 77 | 75 |
| TLCK 20 µM | 96 | 120 | 68 | 80 | 113 |
| TPCK 20 µM | 79 | 87 | 68 | 95 | 108 |

Table 17 details the hydrolytic activity of different EXOs in the presence of various cations using Leu-MCA as a substrate for LAP. The activity is given as the percentage of the activity of control enzymatic reaction without any cation.

TABLE 17

| | ruLAP2 | fuLAP2 | ruLAP1 | fuLAP1 | pkLAP |
|---|---|---|---|---|---|
| CaCl$_2$ 0.5 mM | 126.6 | 110.0 | 151.7 | 54.9 | 177.4 |
| CaCl$_2$ 1 mM | 141.9 | 165.4 | 175.6 | 43.3 | 161.8 |
| MgCl$_2$ 0.5 mM | 121.2 | 97.6 | 129.9 | 68.5 | 130.1 |
| MgCl$_2$ 1 mM | 110.2 | 108.0 | 132.6 | 72.6 | 146.1 |
| MnCl$_2$ 0.5 mM | 77.5 | 84.3 | 120.7 | 25.9 | 157.6 |
| MnCl$_2$ 1 mM | 86.8 | 140.2 | 105.2 | 28.4 | 165.8 |
| CoCl$_2$ 0.5 mM | 591.2 | 378.0 | 210.2 | 104.3 | 876.1 |
| CoCl$_2$ 1 mM | 789.7 | 662.7 | 202.1 | 96.5 | 899.8 |
| ZnCl$_2$ 0.5 mM | 77.9 | 51.4 | 43.0 | 60.7 | 437.6 |
| ZnCl$_2$ 1 mM | 88.9 | 119.5 | 68.9 | 53.2 | 297.9 |
| NiCl$_2$ 0.5 mM | 130.5 | 98.4 | 74.8 | 51.7 | 1187.7 |
| NiCl$_2$ 1 mM | 147.9 | 149.3 | 58.1 | 37.2 | 1158.7 |
| CuCl$_2$ 0.5 mM | 50.9 | 68.9 | 40.1 | 25.8 | 1422.0 |
| CuCl$_2$ 1 mM | 34.7 | 73.6 | 13.7 | 17.0 | 1092.4 |

Optimal pH of Activity of EXOXs

The optimal pH for enzymatic activities was determined using the Ellis and Morrison buffer system. Ellis & Morrison, Methods Enzymol. 87:405-426 (1982). The buffer contained three components with different pKa values while the ionic strength of buffer remained constant throughout the entire pH range examined. The pH of the buffer was adjusted from 6 to 11 in half-pH unit increments with 1M HCl or 1M NaOH. The assay conditions for activity on Leu-AMC substrates was the same as above except that the Tris/HCl buffer was replaced by the Ellis and Morrison buffer (composition) at the pH values indicated.

Table 18 details characteristics of native and recombinant *T. rubrum* and *A. fumigatus* secreted aminopeptidases.

TABLE 18

| Gene | Gene length (nt) | Number of introns | Preprotein (aa) | Signal (aa) | Mature domain (aa) | Molecular mass of the polypeptidic chain of the mature enzyme (kDa) | Molecular mass of the native/ recombinant enzyme (kDa) |
|---|---|---|---|---|---|---|---|
| ruLAP1 | 1256 | 2 | 373 | 19 | 354 | 38,804 | 31-33/38-40 |
| fuLAP1 | 1298 | 2 | 388 | 17 | 371 | 41,465 | §NI/40 |
| ruLAP2 | 1757 | 3 | 495 | 18 | 477 | 51,487 | 58/58-65 |
| fuLAP2 | 1557 | 1 | 498 | 15 | 383 | 52,270 | §NI/75-100 |
| ruDPPIV | 2326 | 0 | 775 | 15 | 760 | 86,610 | 90/90 |

| Gene | Molecular mass of recombinant enzyme after deglycosylation (kDa) | Number of putative glycosylation sites | Calculated pI (mature domain)* | Yield of recombinant protein (µg/ml) | GenBank accession number |
|---|---|---|---|---|---|
| ruLAP1 | 38-40 | 3 | 6.39 (6.23) | 40 | AY496930 |
| fuLAP1 | 40 | 3 | 5.67 (5.67) | 80 | AY436356 |
| ruLAP2 | 52 | 4 | 7.32 (6.94) | 40 | AY496929 |
| fuLAP2 | 52 | 6 | 5.57 (5.46) | 100 | AY436357 |
| ruDPPIV | 84 | 4 | (8.05) | 10 | AY497021 |

§NI: means not determined
*The value in brackets corresponds to full-length polypeptide without prosequence Temperature Optima of Activity of EXOXs The optimal temperature conditions were determined by measuring the enzymatic activity their pH optima after incubating each of the LAPs with Leu-AMC (5 mM) at 20, 30, 40, 50, 60, 70 and 80° C. for 10, 30 and 60 min.

Proteolytic Assays

The proteolytic activity was measured using resorufin-labeled casein in phosphate buffer (20 mM; pH 7.4). The reaction mixture contained 0.02% substrate in a total volume of 0.5 ml. After incubation at 37° C., the undigested substrate was precipitated by trichloroacetic add (4% final concentration) and separated from the supernatant by centrifugation. The absorbance at 574 nm of the supernatant was measured after alkalinization by adding 500 µl Tris buffer (500 mM; pH 9.4). For practical purposes, one unit (U) of proteolytic activity was defined as that producing an absorbance of 0.001 per min.

Example 2

T. rubrum Secreted Proteolytic Activity

T. rubrum was grown at 30° C. in a medium containing 0.2% soy protein as a sole carbon and nitrogen source. After 14 days of growth, a concomitant clarification of the culture medium was noted and a substantial proteolytic activity (400 U ml$^{-1}$) detected using resorufin-labeled casein as substrate. This proteolytic activity was 15% and 85% inhibited by PMSF and ortho-phenanthroline. respectively, attesting that serine and metalloproteases were secreted by T. rubrum. Western blot analysis of culture supernatant revealed that T. rubrum, like M. canis, secreted endoproteases of the subtilisin family (MEROPS>S8) and of the fungalysin family (MEROPS>M36) similar to the alkaline protease ALP and the neutral metalloprotease NPI secreted by A. oryzae (See FIG. 1). In addition, a high activity on substrates such as Leu-AMC and Leu-pNA was detected in the T. rubrum culture supernatant.

Example 3

T. rubrum Secreted Aminopeptidase Activity

The nucleotide sequences of Microsporum canis endoprotease genes showed 50-70% similarity to homologous genes encoding the subtilisins and the fungalysins secreted by A. oryzae and A. fumigatus. In addition, the M. canis and Aspergillus genes showed colinear intron-exon structures. Therefore, DNA sequences available for A. oryzae and Sacharomyces cerevisiae genes coding for aminopeptidases were used to design probes for screening a T. rubrum genomic DNA library. Characterization of the T. rubrum secreted aminopeptidases in comparison to those secrets by the opportunist A. fumigatus was performed using recombinant proteins.

Example 4

Cloning of Genes Encoding T. rubrum and A. fumigatus Aminopeptidases

Tables 19A and 19B detail a pairwise comparison of various LAPs.

TABLE 19A

| M28E Enzyme | % Similarity or Identity[a] | | | |
|---|---|---|---|---|
|  | ruLAP1 | fuLAP1 | orLAP1 | Vibrio LAP |
| ruLAP1 |  | 72 | 72 | 41 |
| fuLAP1 | 50 |  | 70 | 39 |
| orLAP1 | 48 | 49 |  | 42 |
| Vibrio LAP | 22 | 21 | 23 |  |

TABLE 19B

| M28A Enzyme | % Similarity or Identity[a] | | | |
|---|---|---|---|---|
|  | ruLAP2 | fuLAP2 | orLAP2 | S. cer. aaY |
| ruLAP2 |  | 69 | 71 | 53 |
| fuLAP2 | 51 |  | 85 | 52 |
| orLAP2 | 49 | 72 |  | 53 |
| S. cer. aaY | 32 | 33 | 34 |  |

[a]The percent of similarity (top right-hand corner) and percent of identity (bottom left-hand corner values were obtained with the program Gap implemented in the GCG package of the Genetics Computer Group, University of Wisconsin, Madison.

FIG. 14 is an alignment of deduced amino acid sequences of aminopeptidases of the M28E subfamily. Putative signal sequence processing sites are underlined. A putative KR processing site in ruLAP1 is indicated by a solid triangle. The amino acids of the two $Zn^{++}$ binding sites in S. griseus aminopeptidase and conserved in the other LAPs are indicated by an open arrow The alignment was performed with the Pileup algorithm implemented in the GCG package of the University of Wisconsin and reformatted with Boxshade 3.2. AbispLAP1 is for LAP of Agaricus bisporus.

Figure 15:
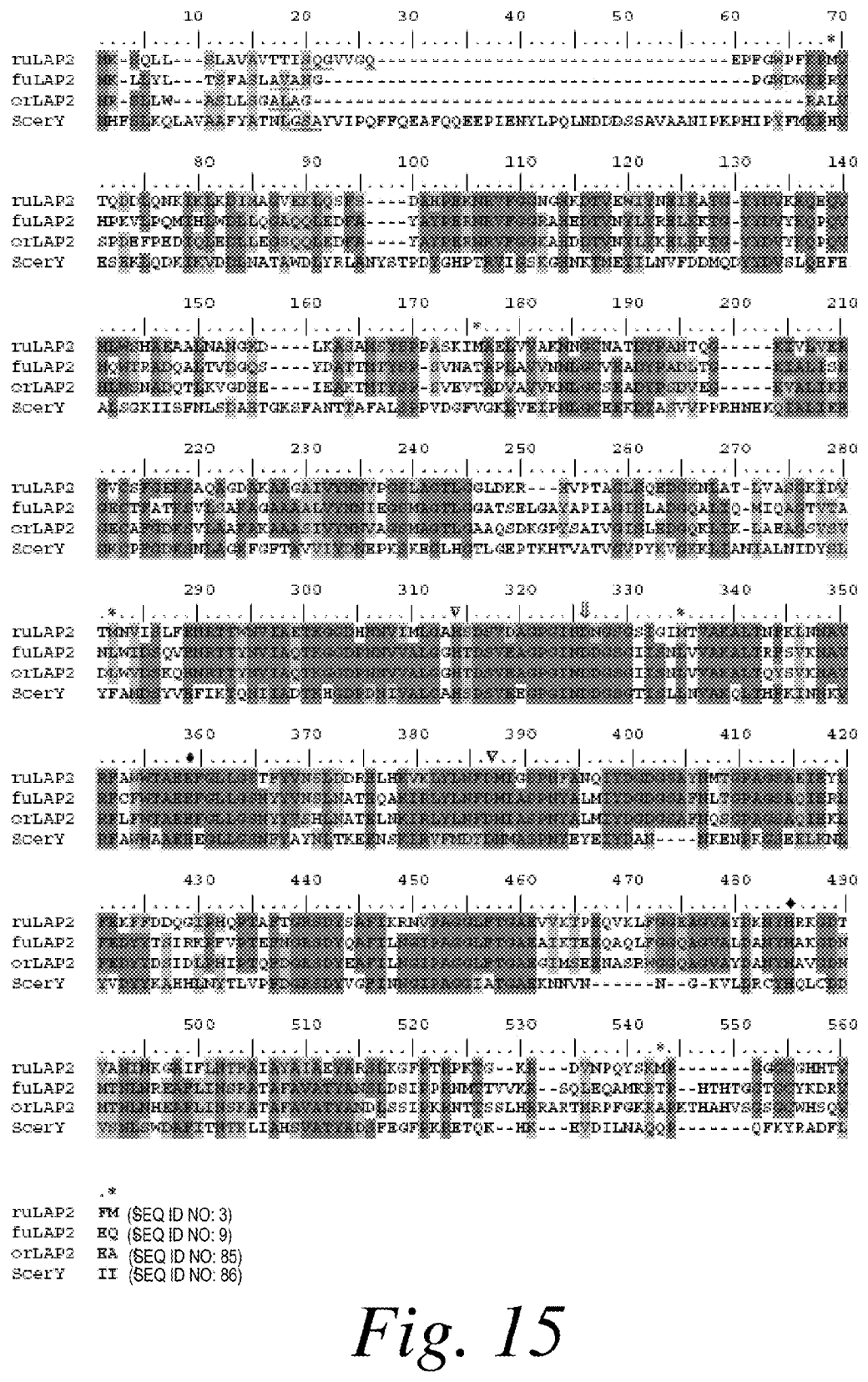

FIG. 15 is an alignment of deduced amino acid sequences of aminopeptidases of the M28A subfamily. Putative signal sequence processing sites are underlined. Two amino acid residues, His and Asp, conserved in the fungal LAPs and binding a first $Zn^{++}$ ion in S. griseus aminopeptidase are indicated by open triangles. Two additional residues His and Glu binding a second $Zn^{++}$ ion are indicated by solid diamonds, while the Asp residue bridging the two $Zn^{++}$ ions is indicated by an open arrow. The * represent methionine residues found only in ruLAP2. The alignment was performed with the Pileup algorithm implemented in the GCG package of the University of Wisconsin and reformatted with Boxshade 3.2.

The amino acid sequences GPGINDDGSG (SEQ ID NO: 36) and DM(Q/M)ASPN (SEQ ID NO: 37) were found in a A. oryzae secreted 52 kDa aminopeptidase (U.S. Pat. No. 6,127, 161) and the S. cerevisiae aminopeptidase. Nishizawa et al., J. Biol. Chem. 269:13651-13655 (1994). From these data, two consensus oligonucleotides (GGXATXAAYGAYGAYG-GXTCXGG (SEQ ID NO: 38) and TTXGGXGAXGCXAT-CATRTC (SEQ ID NO: 39) were used as sense and antisense, respectively, to amplify DNA from T. rubrum. A 220 bp PCR product was obtained and sequenced. The deduced amino acid sequence showed high similarity to the amino acid sequence of the A. oryzae and the S. cerevisiae aminopeptidases. This 220 bp PCR fragment was used as a probe for screening a λ phage EMBL3 T. rubrum genomic DNA library and a nucleotide sequence coding for a putative aminopeptidase (ruLAP2) was found. A nucleotide sequence coding for a similar secreted aminopeptidase (fuLAP2) was found in the A. fumigatus genome sequence (at website address www.TI-GR.com).

A 1200 bp fragment containing the nucleotide sequence of the gene encoding an A. oryzae 31 kDa aminopeptidase (U.S. Pat. No. 5,994,113) was obtained by PCR of A. oryzae genomic DNA using the oligonucleotides GCATTCCT-GUGATGCCCGGGCCG (sense) (SEQ ID NO: 40) and TTACTTAGCAAGCTCAGTGACGAAGCCGAC (antisense) (SEQ ID NO: 41). This fragment was used as a probe for a second screening of the T. rubrum genomic DNA library. A nucleotide sequence (EMBL) similar to those coding for the A. oryzae 30 kDa aminopeptidase and to another putative secreted aminopeptidase from the A. fumigatus genome sequence (at website address www.TIGR.com) was found in λ phage EMBL3 DNA of the T. rubrum genomic library. These T. rubrum and A. fumigatus putative aminopeptidases were called ruLAP1 and fuLAP1, respectively.

The identified nucleotide sequences of ruLAP1, ruLAP2, fuLAP1 and fuLAP2 each contain a 17-20 amino acid signal sequence. The intron-exon structure of the T. rubrum and A. fumigatus genes was determined by sequencing a PCR product using 5'-sense and 3'-antisense primers based on isolated genomic DNA (See Table 14) and total DNA from a pool of $10^8$ clones of the T. rubrum or A. fumigatus cDNA libraries as a target. The first of the three introns in ruLAP1 was in position similar to that of the unique intron of fuLAP2 (See Table 13). The genes ruLAP1 and fuLAP1 have similar colinear structures with two introns and three exons.

Example 5

Production of Recombinant T. rubrum and A. fumigatus Aminopeptidases

Figure 2:
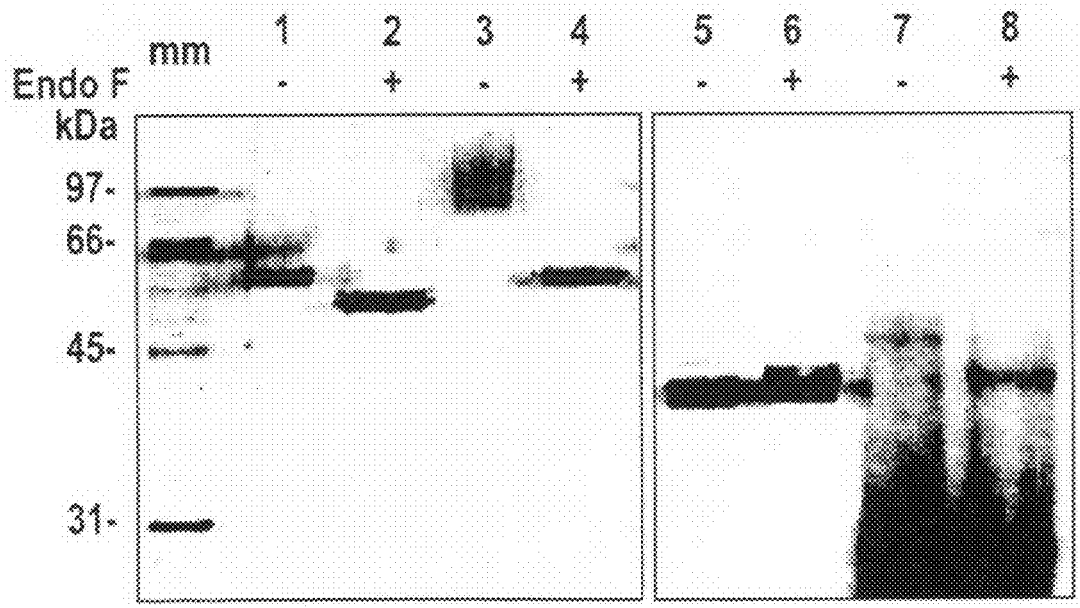
FIG. 2 is a photograph of a SDS-PAGE gel illustrating a protein profile of recombinant ruLAP2 (1, 2), fuLAP2 (3, 4), ruLAP1 (5, 6) and fuLAP1 (7, 8) produced in *P. pastoris*. 1 g of each purified recombinant LAP was loaded on a 10% SDS-PAGE gel. Lanes 2, 4, 6 and 8 show the proteins deglycosylated by N-glycosidase F treatment. The gel was stained with Coomassie brilliant blue R-250.

The T. rubrum and A. fumigatus cDNAs obtained by RT-PCR were cloned in pKJ113 (Borg-von Zepelin et al., 1998) and expressed in P. pastoris. Depending on the peptidase produced, about 10-80 µg/ml of active enzyme on Leu-AMC was obtained (See Table 18). Under identical culture conditions wild type P. pastoris did not secrete any leucine aminopeptidase activity into the culture medium. SDS-PAGE analysis of recombinant ruLAP2, fuLAP1 and fuLAP2 secreted by P. pastoris transformants showed a smearing band (FIG. 2). Upon treatment with N-glycosidase F, only a major band with a faster migration appeared on the gels attesting that, in contrast to ruLAP 1, these three LAPs were glycoproteins (FIG. 2). The apparent molecular mass of each deglycosylated recombinant LAP was close to that of the calculated molecular mass of the polypeptide chain deduced from the nucleotide sequence of the genes encoding the protease. The deduced primary structures (amino acid sequences) of each recombinant enzyme are provided in Table 18.

Example 6

Detection of ruLAP1 and ruLAP2 in T. rubrum Culture Supernatant

Figure 3:
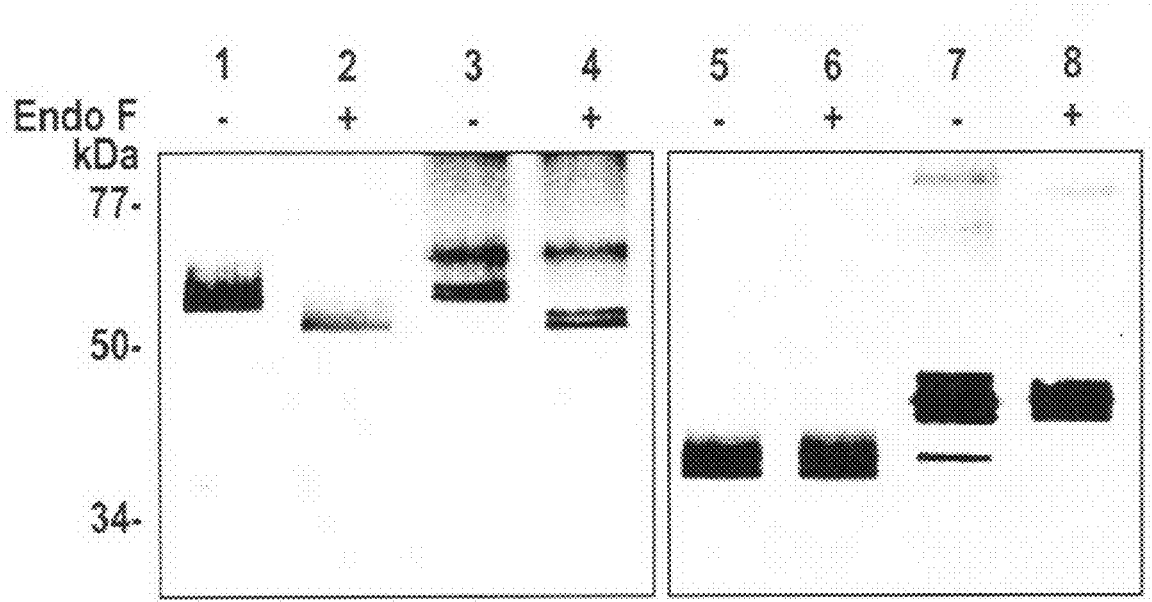
FIG. 3 is a photograph of a Western blot of *T. rubrum* culture supernatant and recombinant LAPs used as controls probed with anti-ruLAP2 (lanes 1-4) and anti-ruLAP1 antisera (lanes 5-8). In lane 1, 2, 5 and 6 the proteins of 0.25 ml of *T. rubrum* culture supernatant was precipitated with TCA before loading on the SDS-PAGE gel. 0.1 g of purified recombinant ruLAP2 (lanes 3, 4) and ruLAP1 (lanes 7, 8) was loaded as a control. N-glycosidase F was used for deglycosylation of proteins. The molecular mass of protein standards are shown in the left margin.
Figure 4:
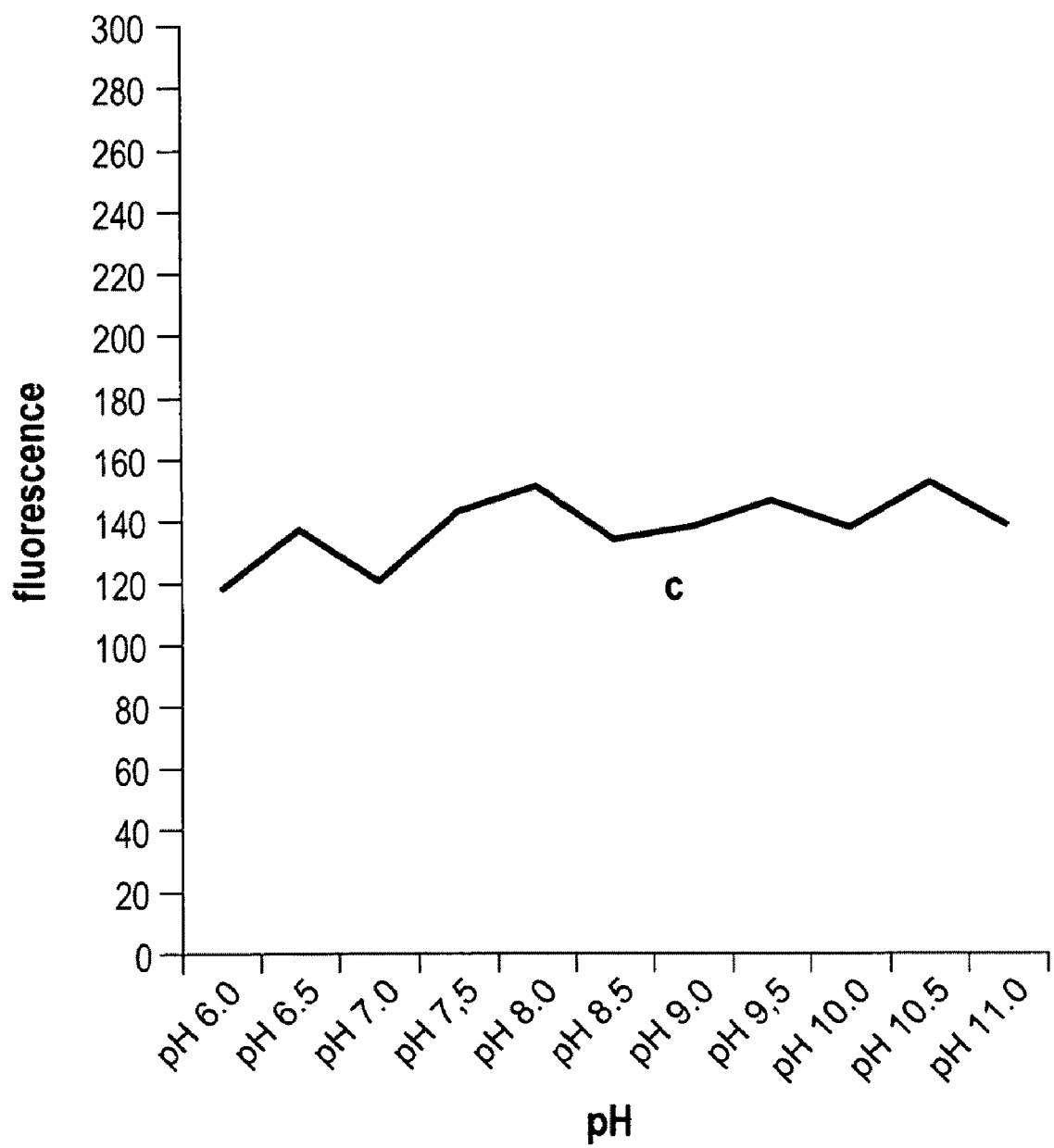
FIG. 4 is a graph of the enzymatic activity of *T. rubrum* AMPP (aminopeptidase P) at various pH values. It appears that AMPP has activity over a broad range of pH values, from pH 6 to 11.
Figure 5:
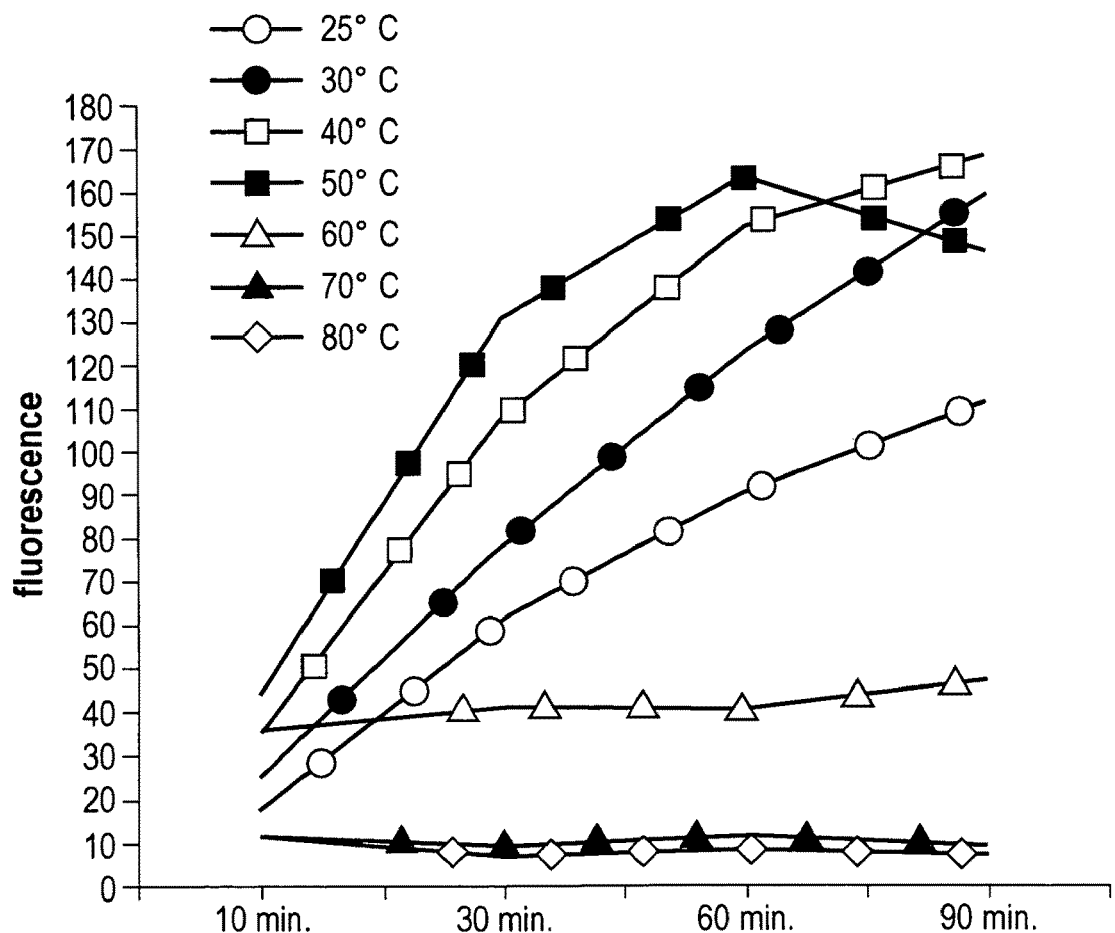
FIG. 5 is a graph of the enzymatic activity of *T. rubrum* AMPP at various temperatures. The enzyme exhibits activity at temperatures ranging from 25 to 60 C with an optimal temperature of 50 C.

Using anti-ruLAP1 antiserum, an accumulation of a LAP1 product with an electrophoretic mobility higher than that of recombinant ruLAP1 was detected in the T. rubrum culture supernatant (See FIG. 3).

Using anti-ruLAP2 antiserum, Western blot analysis of a T. rubrum culture supernatant revealed that T. rubrum secreted glycosylated LAP2 with the same electrophoretic mobility as that of the recombinant enzyme from P. pastoris (See FIG. 3).

Example 7

Properties of Recombinant LAPs

The aminopeptidases ruLAP1, ruLAP2, fuLAP1, fuLAP2, as well as the microsomal porcine kidney aminopeptidase (pkLAP) each efficiently hydrolyzed Leu-AMC. This substrate was used to determine the optimum temperature and pH of activity, and to further characterize the enzymes by measuring the effect of (i) various known peptidase inhibitors (See Table 16) and (ii) different divalent ions (See Table 17). Each LAP was capable of cleaving Leu-AMC at 20° C. and had a temperature optimum ranging from 40 to 50° C. The optimum pH was between 7.0 and 8.5 (See Table 18). A 10 min pre-treatment at 80° C. totally and irreversibly inactivated the enzymes.

The aminopeptidases tested were strongly or totally inhibited by amastatin (See Table 16) at a concentration of 500 µM. RuLAP1, fuLAP1 and pkLAP were also inhibited by bestatin, but this inhibitor had only partial inhibitory effect on both ruLAP2 and fuLAP2. Of the chelating agents tested, orthophenantroline totally inhibited the five enzymes at concentrations of 1 and 5 mM. FuLAP1, ruLAP2 and ruLAP1 were more sensitive to EDTA than the other LAPs. E64 and p-chloromercuribenzoate (cysteine protease inhibitors) blunted the activity of ruLAP2 indicating the presence of critical thiol residues for activity on the amino acid sequence of this enzyme. Leupeptin (serine/cysteine protease inhibitor), PMSF (serine protease inhibitor), benzamidine, TLCK and TPCK had no clear inhibitory effects on all the LAPs tested. Surprisingly, fuLAP1 and ruLAP1 exhibited some sensitivity to 0.1 mM pepstatin (aspartic acid protease inhibitor).

With the exception of fuLAP1, which exhibits a general sensitivity to divalent ions, Co ++ ions increased the activity of the LAPs from 200% to 900% at a concentration up to 1 mM. The four fungal LAPs showed variable sensitivities to divalent cations. For instance, fuLAP2 was activated by $Mn^{++}$ and $Ca^{++}$, while fuLAP1 was inhibited by the same ions. The microsomal pkLAP, highly activated by Zn, Ni and $Cu^{++}$ differs from the four fungal LAPs of the M28 family.

The hydrolytic activity of the enzymes toward different aminoacyl-AMC was compared to Leu-AMC used as a reference (See Table 15). Following the aminopeptidase tested, various preferences for the different aminoacyl residue were detected. For example, the aminopeptidase pkLAP differs from the four fungal LAPs by an extremely high efficiency towards Ala-AMC and Arg-AMC. ruLAP1 was clearly the most selective for Leu-AMC. However, some other preferential cleavage activities were observed with ruLAP2, fuLAP1 and fuLAP2. For instance Ser- and Pro-AMC were more efficiently cleaved by ruLAP2, whereas fuLAP1 appreciated Arg-, Val-, and Phe-AMC. Only ruLAP2 efficiently cleaved Asp- and Glu-AMC. None of these enzymes exhibited an aminopeptidase P activity since they were not able to cleave Lys(Abz)-Pro-Pro-pNA.

Example 8

Application of ruLAP2 Together with ruDPPIV in the Digestion of Gliadin Peptides Celiac disease (CD) is a digestive disease that damages the small intestine and interferes with absorption of nutrients from food. People who have celiac disease cannot tolerate a protein called gluten, which is found in wheat, rye and barley. When people with celiac disease eat foods containing gluten, their immune system responds by damaging the small intestine. The disease has a prevalence of ≈1:200 in most of the world's population groups and the only treatment for celiac disease is to maintain a life-long, strictly gluten-free diet. For most people, following this diet will stop symptoms, heal existing intestinal damage, and prevent further damage.

The principal toxic components of wheat gluten are a family of Pro- and Gln-rich proteins called gliadins, which are resistant to degradation in the gastrointestinal tract and contain several T-cellstimulatory epitopes. There is some controversy about the epitopes that effectively induce an immunological activation of HLA-DQ2 positive gut-derived and peripheral T cells (Vader et al., Gastroenterology 122:1729-1737 (2002)) because different in vitro systems have been used for these studies. The capacity of gliadin peptides to induce toxicity in an organ culture model of CD does not correspond to that of stimulating T-cells and vice versa. McAdam & Sollid, Gut 47: 743-745 (2000). Moreover, the binding of many gluten epitopes to HLA-DQ2 and HLA-DQ8 but not all is enhanced by deamidation of certain glutamine residues into glutamic acids through the action of the small intestinal enzyme tissue transglutaminase, which potentiates their ability to stimulate T-cells. Molberg et al., Nat. Med. 4:713-717 (1998). However, deamidation is not an absolute requirement for T-cell activation. Arentz-Hansen et al., Gastroenterology 123:803-809 (2002).

Other strategies for treating or preventing CD, with the ultimate hope being an alternative for the "gluten free" diet, have been suggested over the last years, including inhibition of T-cellactivation by compounds that block peptide binding to HLA-DQ2, inhibitors of tissue transglutaminase that prevent gluten deamidation (Sollid, Nat. Rev. Immunol. 2:647-655 (2002)) and peroral peptidase supplementation. This latter approach is considered to aid complete digestion of immunostimulatory peptides by involvement of bacterial prolyl endopeptidases which have broad tolerance for proline-containing peptides. Shan et al., Science 297:2275-2279 (2002); Hausch et al., Am. J. Physiol. Gastrointest Liver Physiol. 283:G996-G1003 (2002). A relatively large fragment of gliadin that is resistant to digestive enzymes degradation was identified. Furthermore, this peptide was shown to be a potent stimulator of different HLA-DQ2-restricted T cell clones derived from intestinal biopsies of CD patients stimulated with gluten, each of these clones recognizing a different epitope of the 33 mer. The prolyl endopeptidase, which has a preference for Pro-Xaa-Pro motif, is able to cleave the 33 mer gliadin peptide and the synergistic effect of brush border aminopeptidase rapidly decreases the T-cell stimulatory potential of the peptide.

Though there are stable homologs to this 33 mer in barley and rye, these gluten peptide motifs that are described as resistant to gastrointestinal degradation were used in our case as model substrates for different LAPs, either alone or in combination with ruDPPIV: PQPQLPYPQPQLPY (SEQ ID NO: 42)(14 mer) corresponding to fragment 82-95 of α/β gliadin AIV (P04724) or LQLQPF-PQPQLPYPQPQLPYPQPQLPYPQPQPF (SEQ ID NO: 43) (33 mer) corresponding to fragment 57-89 of gliadin MM1 (P 18573).

A N-terminal acetylated form of the 33 mer (Ac-33 mer) was also synthesized as control for the digestion experiments with exopeptidases to preclude any endoproteolytic cleavage by a contaminant enzyme.

The enzymes that have been evaluated include: ruLAP1 (aminopeptidase I of *Trichophyton rubrum*), ruLAP2 (aminopeptidase II of *Trichophyton rubrum*), or LAP2 (aminopeptidase II of *Aspergillus orizae*), fuLAP2 (aminopeptidase II of *Aspergillus fumigatus*), MicpKLAP (microsomal leucine aminopeptidase from porcine kidney, Sigma), CytpKLAP (cytosolic leucine aminopeptidase from porcine kidney, Sigma), and ruDPPIV.

Synthesis of the Peptides

Solid-phase synthesis was performed on a custom-modified 430A peptide synthesizer from Applied Biosystems, using in situ neutralization/2-(1H-benzotriazol-1-yl)-1,1,1,3,3-tetramethyluronium hexa fluoro-phosphate (HBTU) activation protocols for stepwise Boc chemistry chain elongation on a standard —O—$CH_2$-phenylacetamidomethyl resin. Schnölzer et al., Int. J. Peptide Protein Res. 40:180-193 (1992).

At the end of the synthesis, the peptides were deprotected and cleaved from the resin by treatment with anhydrous HF for 1 hr at 0° C. with 5% p-cresol as a scavenger. After cleavage, the peptides were precipitated with ice-cold diethylether, dissolved in aqueous acetonitrile and lyophilized. The peptides were purified by RP-HPLC with a $C_{18}$ column from Waters by using linear gradients of buffer B (90% acetonitile/10% $H_2O$/0.1% trifluoroacetic acid) in buffer A ($H_2O$/ 0.1% trifluoroacetic acid) and UV detection at 214 nm. Samples were analyzed by electrospray mass spectrometry with a Platform II instrument (Micromass, Manchester, England).

Conditions of Degradation Reaction:

Incubation was carried out at 37° C. in 50 mM Tris-HCl, pH7.2 supplemented with 1 mM $CoCl_2$ with a substrate concentration of 1 mg/mL and an E/S ratio of 1:20. The reaction was stopped by acidification with $CH_3COOH$ and the medium analysed by RP-HPLC on a $C_8$ column using a 2%/min $CH_3CN$ gradient in 0.1% TFA. All peaks were characterized by ESI-MS.

Figure 6:
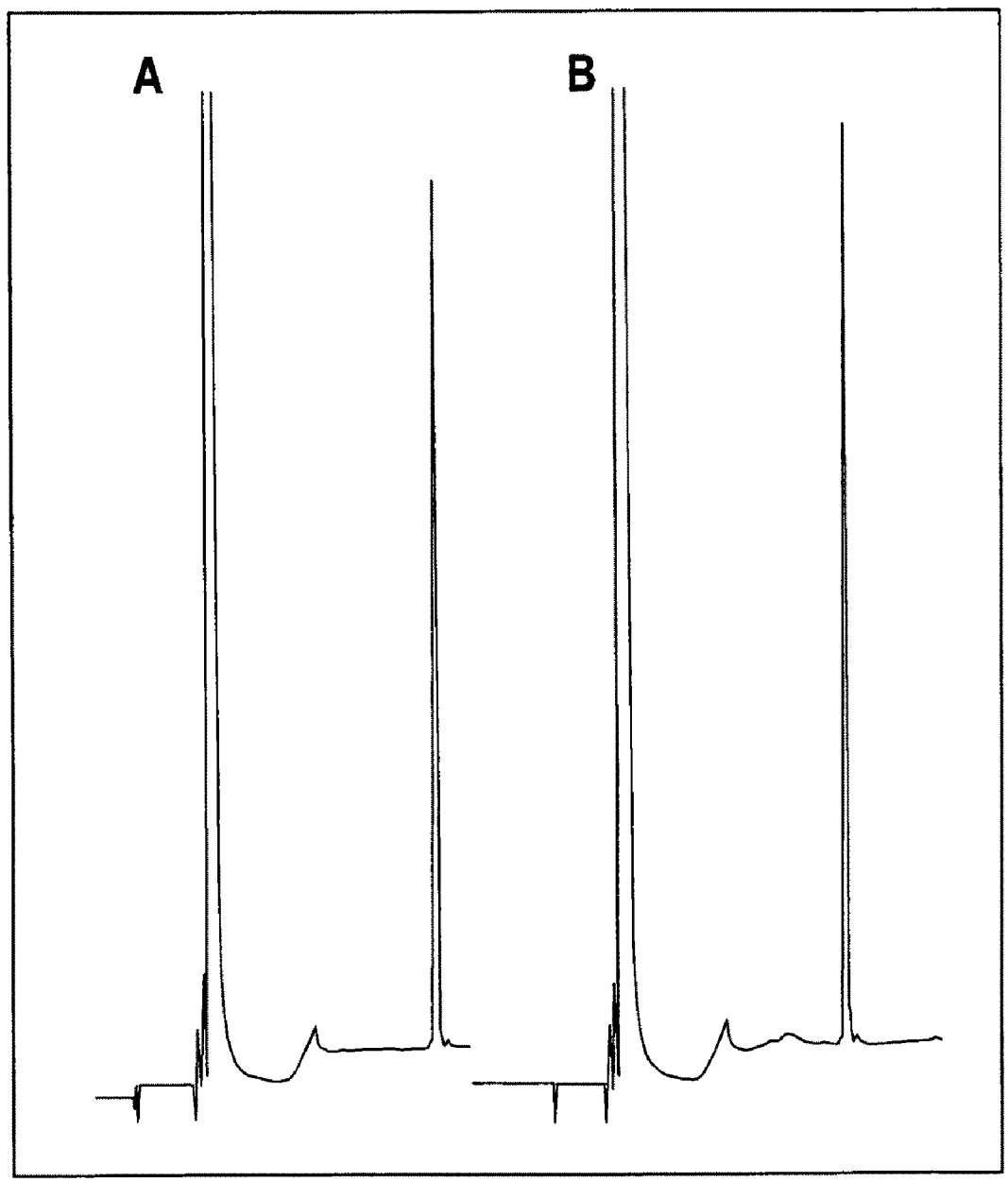
FIG. 6 is a graph showing the digestion of gliadin 14 mer (A) without ruLAP2 or (B) with ruLAP2 over 4 h at 37° C. with an E/S ratio (w:w) of 1/50.
Figure 7:
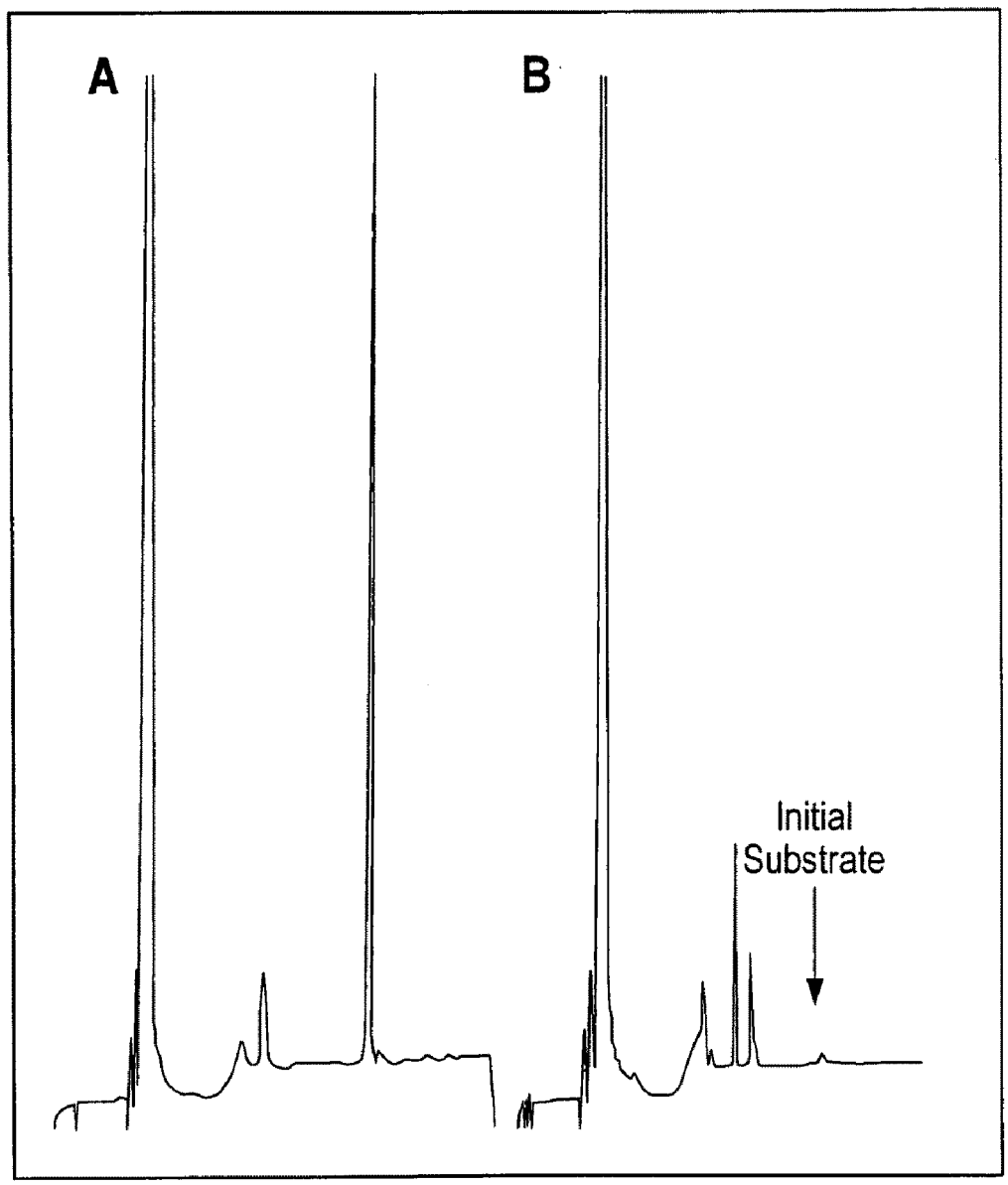
FIG. 7 is a graph showing the digestion of gliadin 14 mer (A) with ruDPPIV alone and (B) with a ruDPPIV/ruLAP2 cocktail.

Digestion of the 14 Mer:

As shown in FIG. 6, the 14 mer is not digested with ruLAP2 within 4 h. There is no change in the HPLC profile when compared with the control. In fact, digestion results only in the cleavage of the N-terminal Proline. On the other hand, supplementation with ruDPPIV results in a complete breakdown in amino acids and dipeptides, while ruDPPIV alone is not able to hydrolyse the peptide (FIG. 7).

Figure 8:
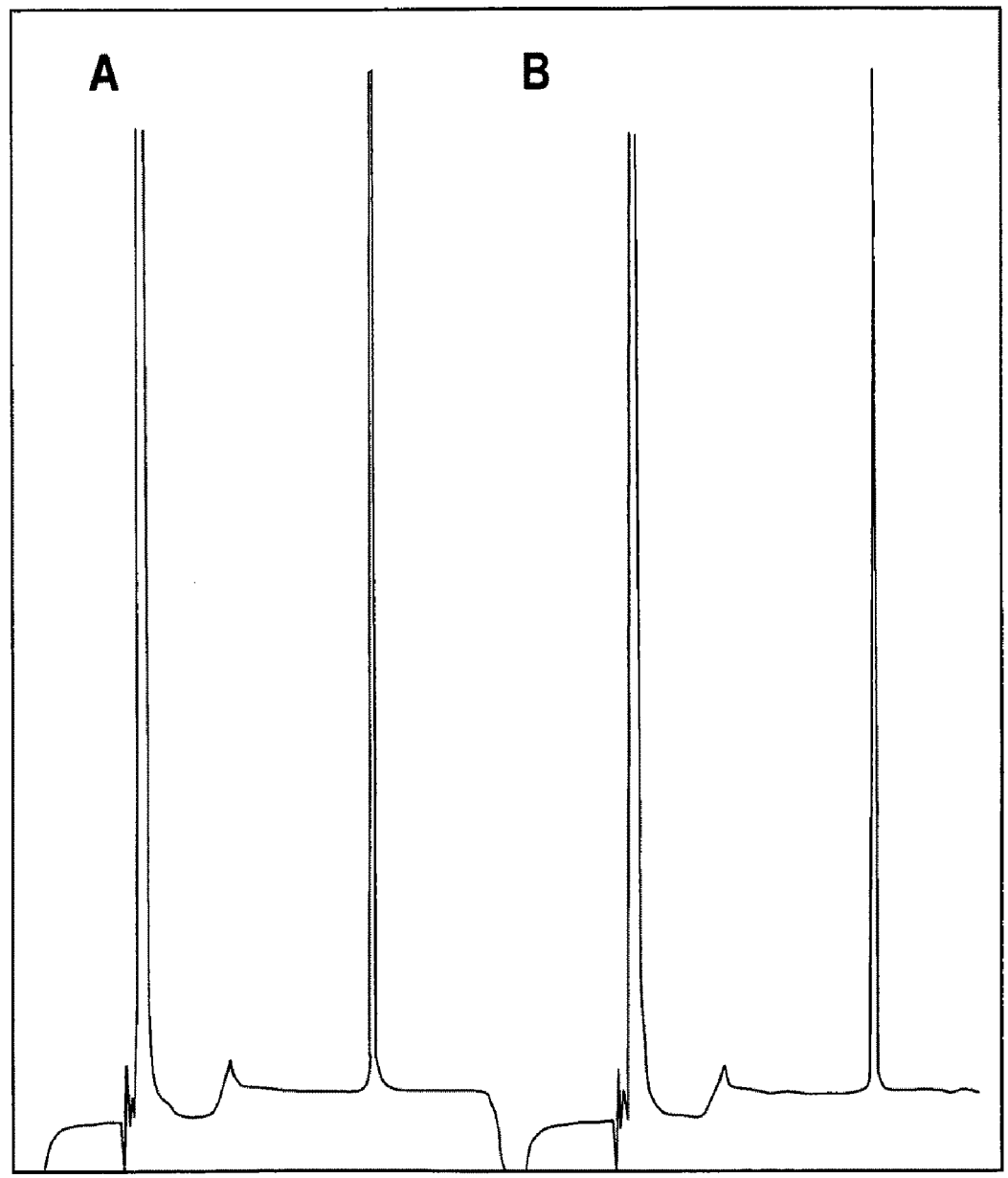
FIG. 8 is a graph showing the digestion of gliadin 33 mer with ruDPPIV over 4 h at 37° C. with an E/S ratio (w:w) of 1/50.
Figure 9:
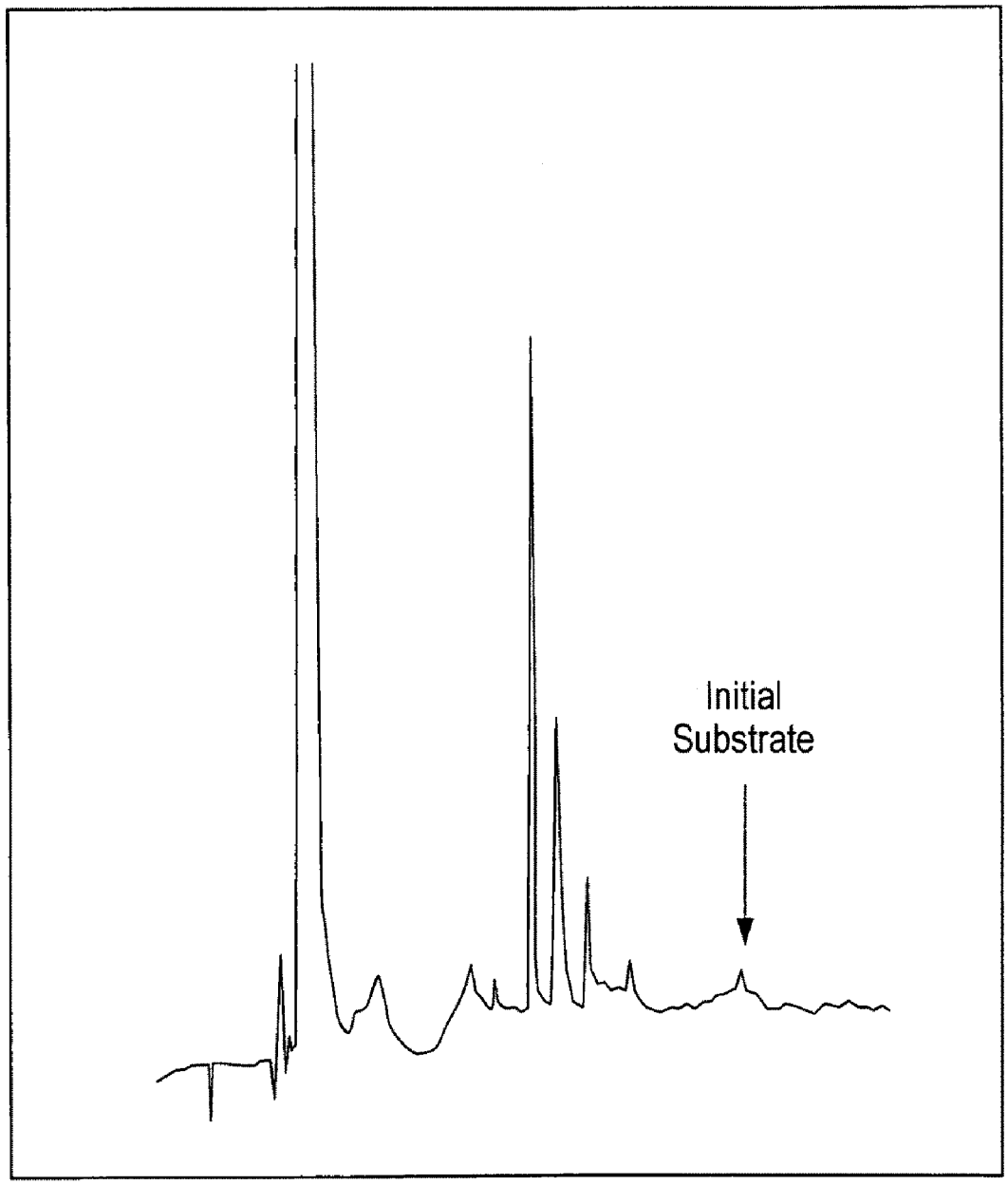
FIG. 9 is a graph showing the digestion of gliadin 33 mer with a DPPIV/ruLAP2 cocktail.

Digestion of the 33 Mer:

Digestion of the 33 mer with ruLAP2 alone results in partial degradation (less than 50%) of the peptide within 4 h (data not shown). This peptide is not a substrate for ruDPPIV (FIG. 8). However, when both enzymes are mixed, the 33 mer is totally digested (FIG. 9) into amino acids and dipeptides some of which could be identified by ESI-MS (Y, L, F, P, PY, and PF).

The same HPLC pattern is obtained when ruDPPIV is mixed with ruLAP2 or fuLAP2. However, with ruLAP1 some higher molecular weight compounds are still present, but represent less than 10% of the initial substrate.

On the other hand, incubation with microsomal porcine kidney aminopeptidase results only in a partial deletion of N-terminal Leu and C-terminal Phe (due to a carboxypeptidasic contaminant) and addition of DPPIV does not modify the profile. Cytosolic porcine kidney aminopeptidase is totally inactive towards the 33 mer.

The stability of the Ac-gliadin 33 mer in the digestion experiments with either LAP or DPPIV alone, or mixed together, confirms that a free amino group is required for the complete breakdown of the gliadin 33 mer by these exopeptidases.

Digestion with Other Enzymes:

Digestion with Pronase (E/S=1/25) over 20 h is only partial (less than 40%) and the addition of ruLAP2 (both enzymes at an E/S ratio (w:w) of 1:50) does not improve the hydrolysis. On the other hand, addition of DPPIV under the same conditions results in a complete breakdown of the peptide due to the complementary action of an aminopeptidase and dipeptidylpeptidase. Chymotrypsin alone or supplemented with ruLAP or DPPIV is not able to breakdown the peptide.

Example 9

Application of ruLAP2 in the Processing of Expressed Recombinant Proteins Fused with Another Protein or with a N-terminal Tag LAP2 was evaluated in the cleavage of the Gly-Ser from the N-terminus of proNPY and of a supplementary Ala from the N-terminus of the same peptide. In order to widen the applicability of LAP2 either alone or in conjunction with another exopeptidase in the processing of larger recombinant proteins, a G-CSF recombinant protein ($Cys^{17} \rightarrow Ser$, $Lys^{16,23,34,40} \rightarrow Arg$) with an N-terminal sequence Met-Thr-Pro-, was successively incubated with ruLAP2 and ruDPPIV to remove sequentially Met and Thr-Pro dipeptide from the 175 residue protein.

Figure 10A:
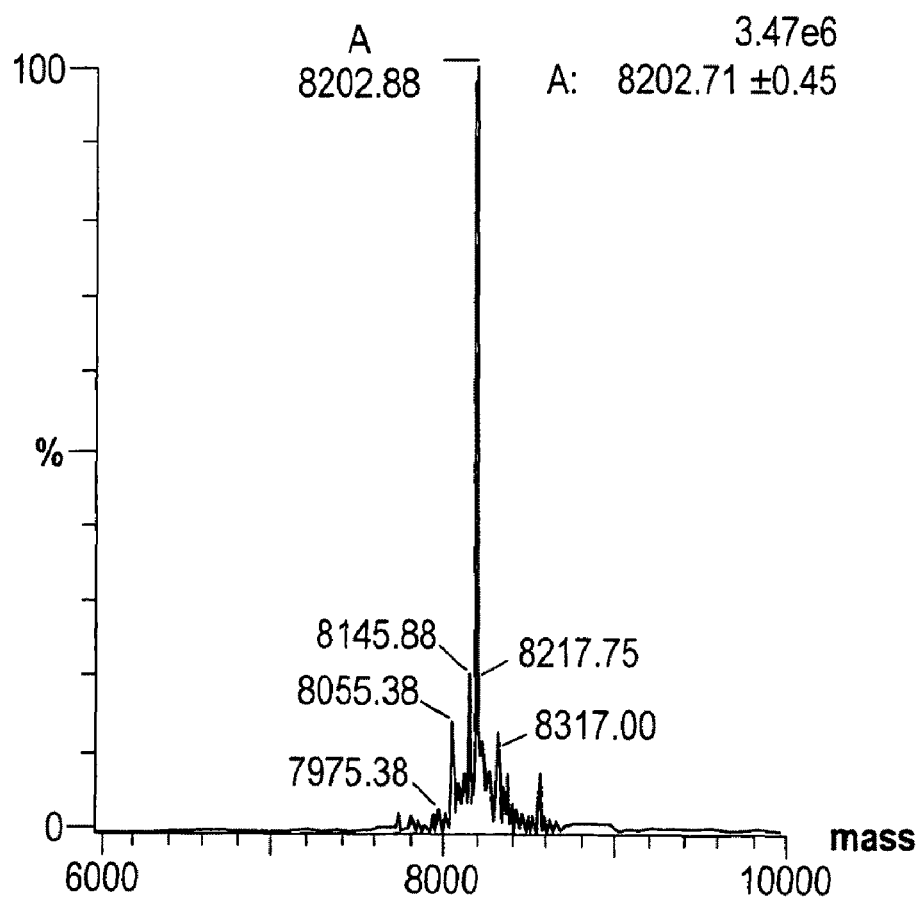
FIGS. 10A and 10B are mass spectrum of Gly-Ser-proNPY (A) before and (B) after digestion with ruLAP2.
Figure 10B:
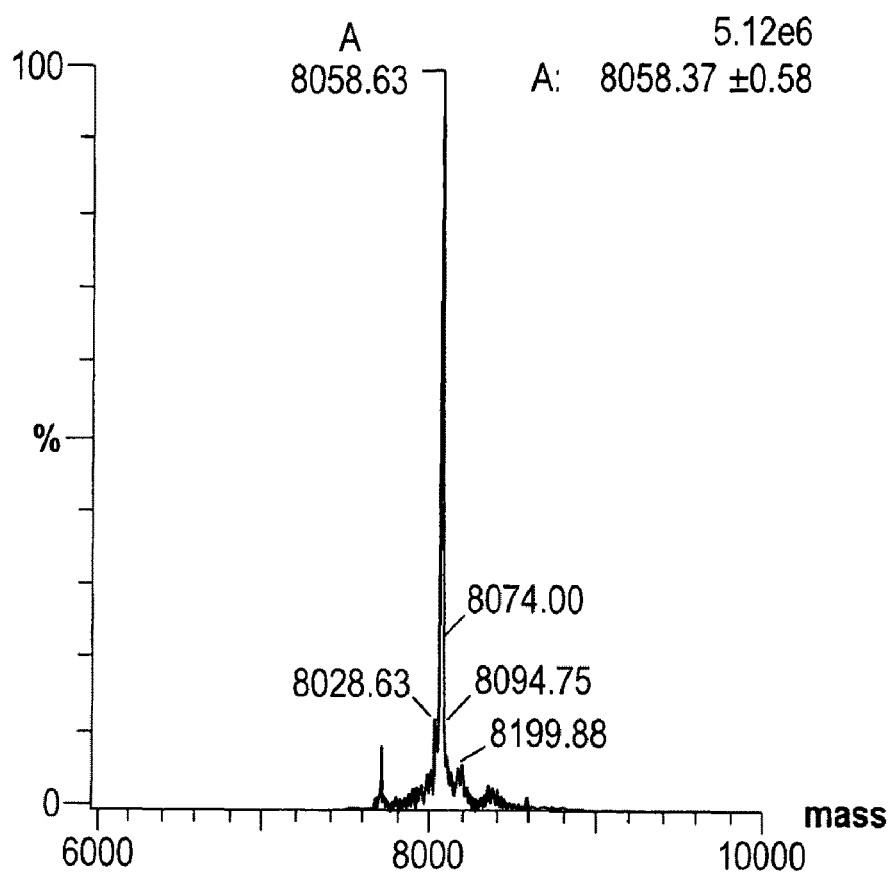

Digestion of Gly-Ser-proNPY with ruLAP2:

The peptide was incubated overnight at 37° C. and 1 mg/ml in a 50 mM Tris.HCl, 1 mM $CoCl_2$ buffer with ruLAP2 at an E/S ratio of 1:20 and 1:100 (w:w). The digested material was isolated by RP-HPLC and characterized by ESI-MS. As shown in FIG. 10, incubation with ruLAP2 results in the cleavage of the two N-terminal residues Gly-Ser with a theoretical loss of 144.1 amu (found 144.2). The same result is obtained at an 1:100 E/S ratio. Digestion halts when the enzyme reaches a Xaa-Pro-motif, which in case of proNPY is Tyr-Pro.

Figure 11A:
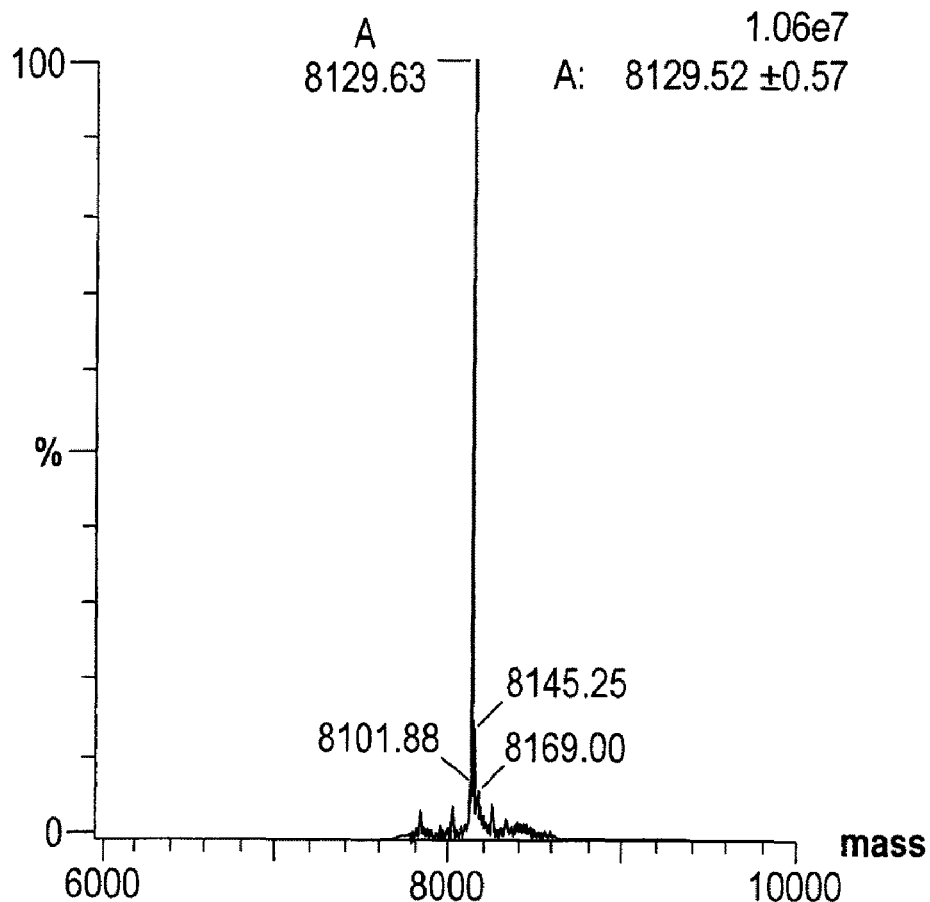
FIGS. 11A and 11B are mass spectra of Ala-proNPY (A) before and (B) after digestion with ruLAP2.
Figure 11B:
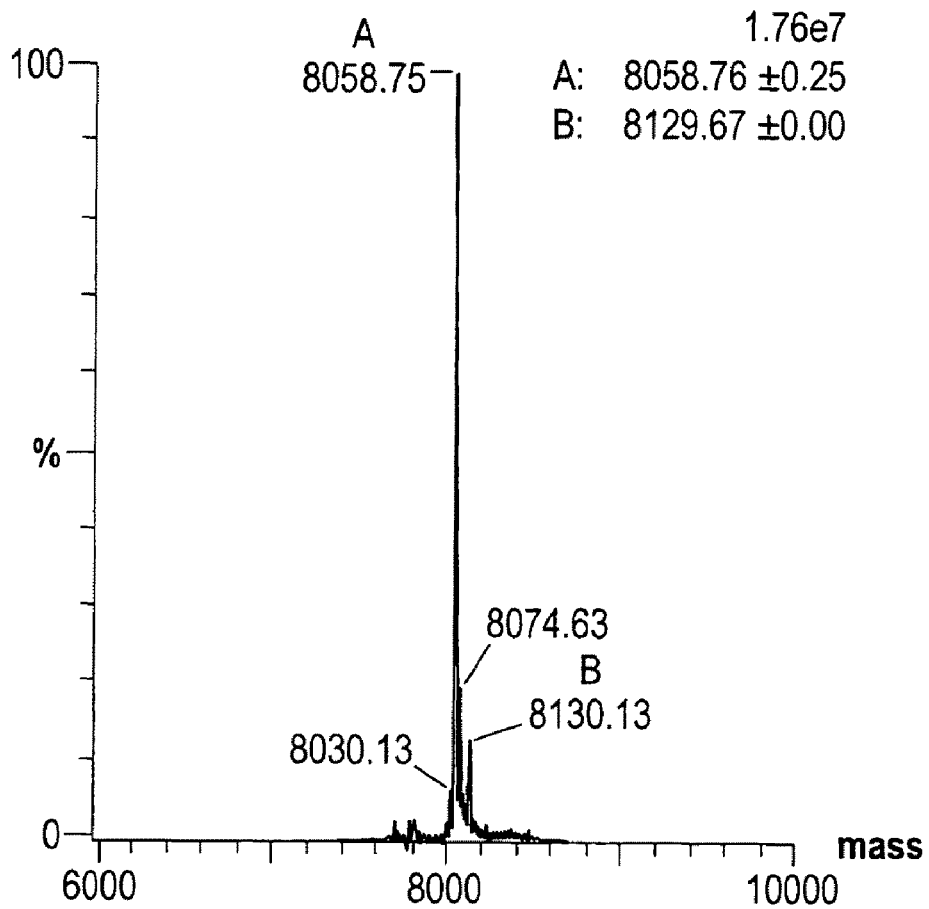

Digestion of Ala-proNPY with ruLAP2:

Conditions of incubation were the same as for Gly-Ser-proNPY. FIG. 11B shows that the N-terminal alanine was almost totally removed (molecular mass loss of 71 amu) from proNPY.

Successive Cleavage of Met and Thr-Pro from the N-terminus of G-CSF:

The mutant analogue of G-CSF known as TG47 used in these experiments is methionyl-[C17S, K16,23,34,40R] G-CSF with a theoretical mass of 18,894.90 for the refolded protein.

Figure 12A:
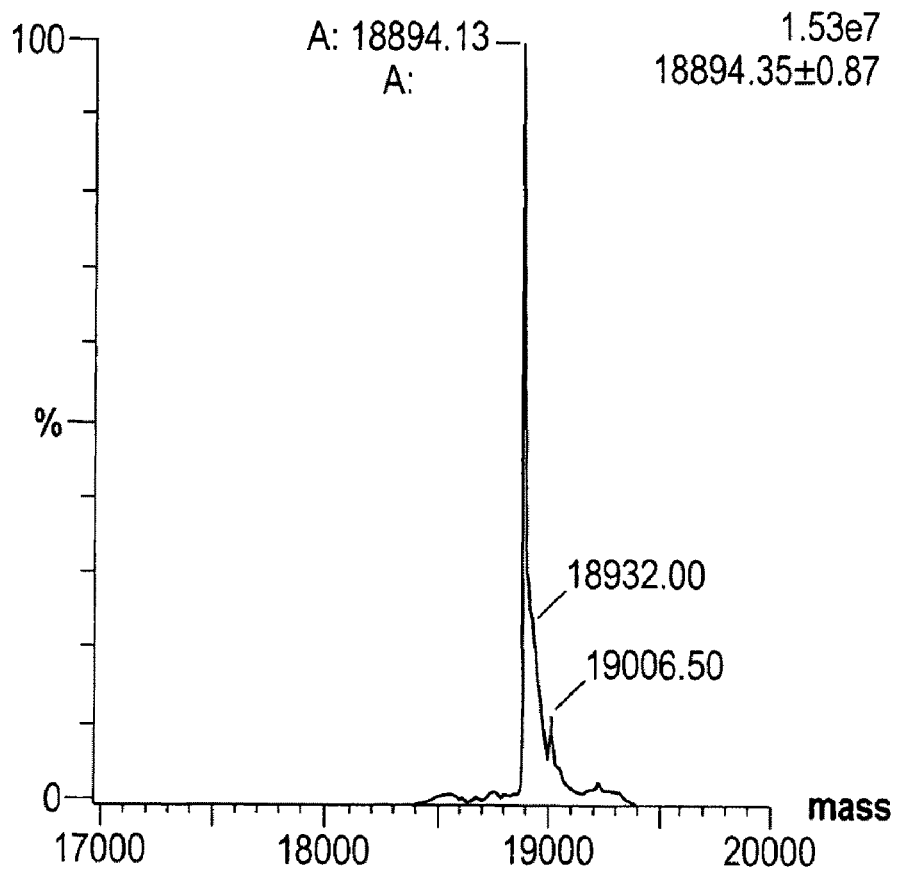
FIGS. 12A and 12B are mass spectra of TG47 (A) before and (B) after digestion with ruLAP2.

Digestion with ruLAP2:

Stock solution of G-CSF (1.9 mg/ml in PBS containing 0.1% Sarcosyl) was diluted 4 times in 50 mM Tris-HCl at pH7.2 supplemented with 1 mM $CoCl_2$, and incubated with ruLAP2 (E/S=1/20 and 1:100, w:w) for 15 h at 37° C. The solution was diluted with 30% (v:v) acetonitrile, acidified with acetic acid and the protein isolated by RP-HPLC for MS characterization. As shown in FIGS. 12A and B, the overnight incubation results in the complete cleavage of the N-terminal methionine with a theoretical mass loss of 131.2 amu. With an E/S ratio (w:w) of 1:100, traces of uncleaved material are still present after an overnight incubation.

Figure 12B:
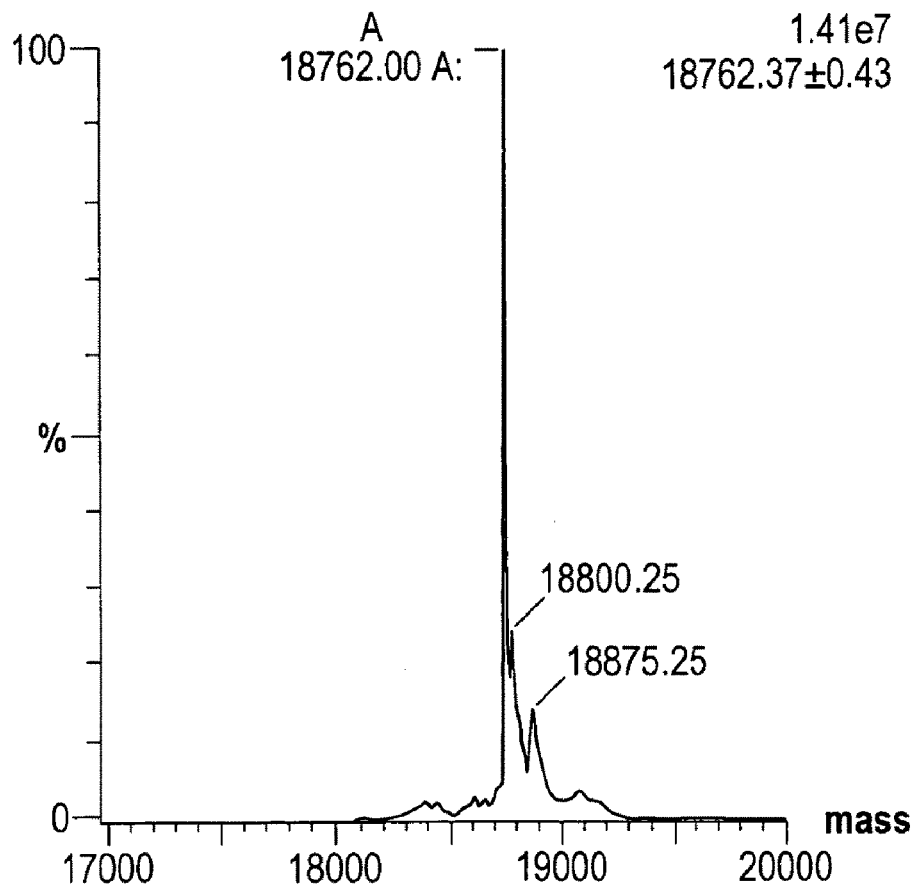

This experiment was repeated at a 2 mg scale in order to isolate the truncated material on a semi-preparative RP-HPLC column, by carrying out the digestion with a E/S ratio of 1:25 (w:w) at 37° C. over 15 h. The isolated material (0.8 mg) was characterized by ESI-MS (FIG. 12B, desMet-G-CSF, calculated molecular mass at 18,763.7 amu; measured molecular mass at 18,762.5).

Figure 13A:
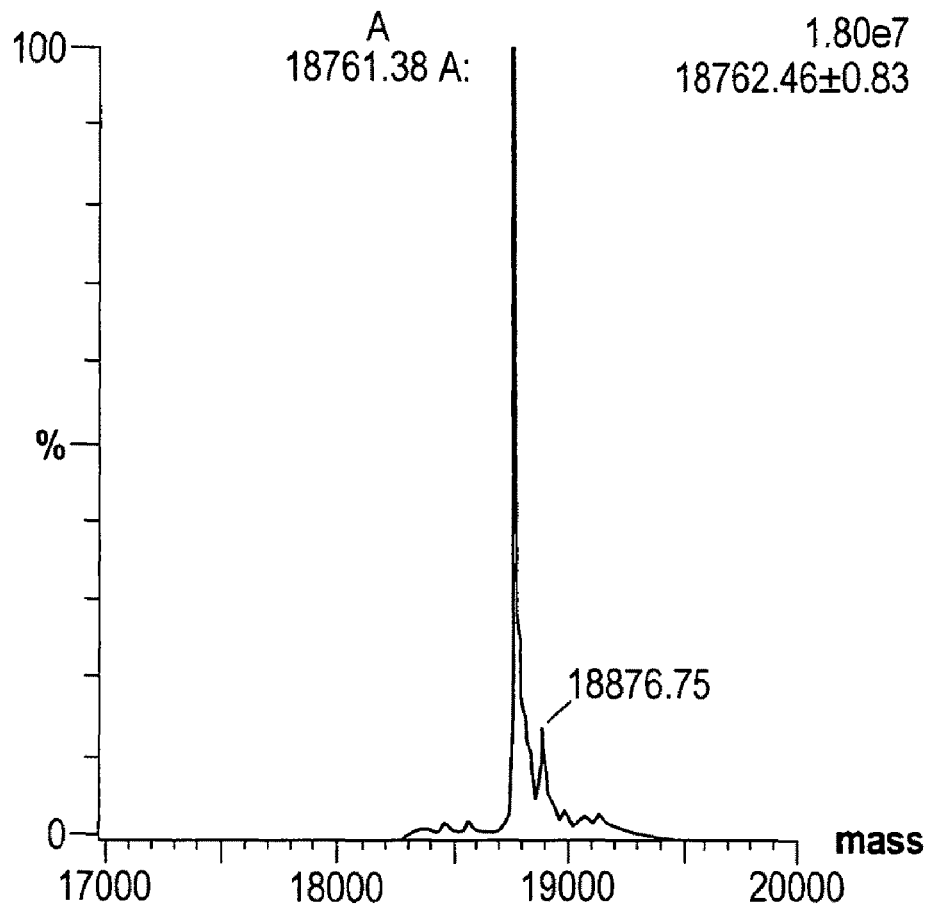
FIGS. 13A and 13B are mass spectra of desMet-G-CSF (A) before and (B) after digestion with DPPIV.
Figure 13B:
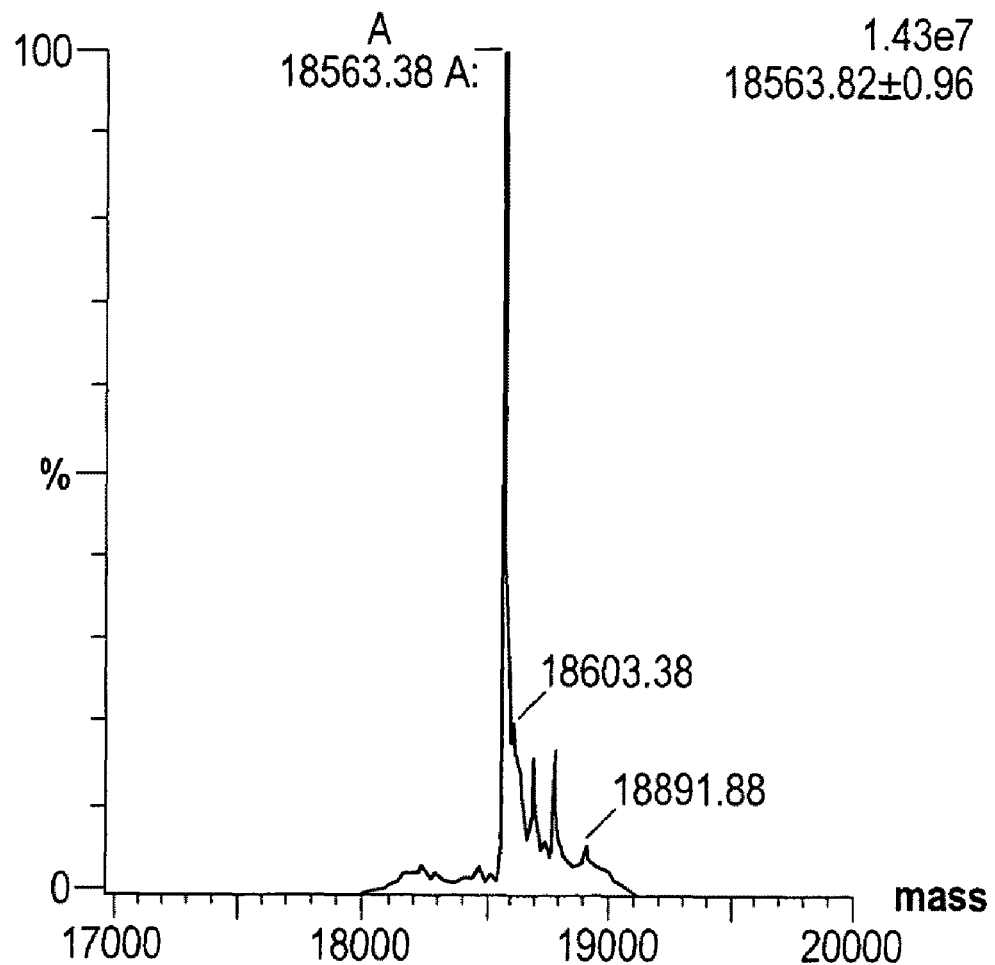

Digestion of desMet-G-CSF with DPPIV:

The freeze-dried material was suspended at a 1 mg/ml concentration in 50 mM Tris-HCl, pH 7.5 containing 0.1% Sarcosyl and incubated overnight at 37° C. with DPPIV at an E/S ratio of 1/20 (w:w). The protein was isolated by RP-HPLC as before and characterized by ESI-MS (FIGS. 13A and B). DPPIV digestion (FIG. 13B) results in the cleavage of the N-terminal dipeptide Thr-Pro (calculated molecular mass of 18,564.8 uma; measured molecular mass at 18,563). Traces of undigested material are still present in the reaction medium.

Thus, a sequential application of LAP2 and DPPIV results in the efficient removal of an N-terminal sequence from a recombinant protein. Digestion with ruLAP2 is halted when the enzyme reaches a "stop point" amino acid motif, such as Xaa-Pro-Xaa, or the Xaa-Pro motif, which may be specifically introduced as a LAP2 "stop point", is subsequently cleaved with DPPIV.

However, initial cleavage of the N-terminal residues is highly dependent on the sequence since the Met(His)$_6$ tag was not removed from Met(His)$_6$-proNPY by incubating with LAP and DPPIV.

OTHER EMBODIMENTS

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made to the invention without departing from the spirit and scope of the invention as defined by the claims. The choice of nucleic acid starting material, clone of interest, or library type is believed to be a matter of routine for a person of ordinary skill in the art with knowledge of the embodiments described herein. Other aspects, advantages, and modifications are considered to be within the scope of the following claims.

What is claimed is:

1. A method for removing an aminoterminal Xaa-Pro tag from a protein, wherein Xaa is any amino acid, comprising the steps of:
   (1) purification of the protein by covalent capture, and,
   (2) contacting the protein with a polypeptide comprising an amino acid sequence which is at least 95% identical to SEQ ID NO: 35, or a fragment thereof, wherein said polypeptide or fragment has dipeptidyl peptidase IV activity, wherein the DPPIV activity consists of cleavage of the aminoterminal Xaa-Pro tag of the protein such that the aminoterminal Xaa-Pro is removed.

2. The method of claim 1, wherein Xaa is an amino acid comprising at least two vicinal nucleophilic groups.

3. The method of claim 2, wherein said amino acid is selected from the group consisting of serine, threonine and cysteine.

4. The method of claim 1, wherein the polypeptide comprises the amino acid sequence set forth in SEQ ID NO: 35.

5. The method of claim 1, wherein the polypeptide consists of the amino acid sequence set forth in SEQ ID NO: 35.

6. The method of claim 1, wherein the polypeptide comprises an amino acid sequence comprising conservative amino acid substitutions of less than 5% of the amino acid residues of SEQ ID NO: 35.

7. The method of claim 3, wherein the polypeptide comprises the amino acid sequence set forth in SEQ ID NO: 35.

8. The method of claim 3, wherein the polypeptide consists of the amino acid sequence set forth in SEQ ID NO: 35.

9. The method of claim 3, wherein the polypeptide comprises an amino acid sequence comprising conservative amino acid substitutions of less than 5% of the amino acid residues of SEQ ID NO: 35.

10. A method of removing the amino terminus from a protein wherein the amino terminus consists of an aminoterminal Xaa-Pro tag, wherein Xaa is any amino acid, said method comprising contacting the protein with polypeptide comprising an amino acid sequence which is at least 95% identical to SEQ ID NO: 35, or a fragment thereof, wherein said polypeptide or fragment has dipeptidyl peptidase IV (DPPIV) activity, wherein said DPPIV activity consists of cleaveage of the aminoterminal Xaa-Pro tag, such that the amino terminus of the protein is removed.

11. The method of claim 10, wherein Xaa is an amino acid comprising at least two vicinal nucleophilic groups.

12. The method of claim 11, wherein said amino acid is selected from the group consisting of serine, threonine and cysteine.

13. The method of claim 10, wherein the DPPIV polypeptide comprises the amino acid sequence set forth in SEQ ID NO: 35.

14. The method of claim 10, wherein the polypeptide consists of the amino acid sequence set forth in SEQ ID NO: 35.

15. The method of claim 10, wherein the polypeptide comprises an amino acid sequence comprising conservative amino acid substitutions of less than 5% of the amino acid residues of SEQ ID NO: 35.

16. The method of claim 12, wherein the polypeptide comprises the amino acid sequence set forth in SEQ ID NO: 35.

17. The method of claim 12, wherein the polypeptide consists of the amino acid sequence set forth in SEQ ID NO: 35.

18. The method of claim 12, wherein the polypeptide comprises an amino acid sequence comprising conservative amino acid substitutions of less than 5% of the amino acid residues of SEQ ID NO: 35.

* * * * *